US011701391B2

(12) United States Patent
Elani

(10) Patent No.: US 11,701,391 B2
(45) Date of Patent: Jul. 18, 2023

(54) METHODS OF TREATING AN ISCHEMIC DISEASE

(71) Applicant: Dalia Elani, Petach-Tikva (IL)

(72) Inventor: Dalia Elani, Petach-Tikva (IL)

( * ) Notice: Subject to any disclaimer, the term of this patent is extended or adjusted under 35 U.S.C. 154(b) by 360 days.

(21) Appl. No.: 16/758,457

(22) PCT Filed: Oct. 24, 2018

(86) PCT No.: PCT/IL2018/051139
§ 371 (c)(1),
(2) Date: Apr. 23, 2020

(87) PCT Pub. No.: WO2019/082184
PCT Pub. Date: May 2, 2019

(65) Prior Publication Data

US 2020/0254025 A1 Aug. 13, 2020

Related U.S. Application Data

(60) Provisional application No. 62/576,094, filed on Oct. 24, 2017.

(51) Int. Cl.

| | |
|---|---|
| ***A61K 35/28*** | (2015.01) |
| ***A61P 9/10*** | (2006.01) |
| ***A01N 1/02*** | (2006.01) |
| ***C12N 5/077*** | (2010.01) |
| ***C12N 9/22*** | (2006.01) |
| ***C12N 15/113*** | (2010.01) |

(52) U.S. Cl.
CPC ............ *A61K 35/28* (2013.01); *A01N 1/0284* (2013.01); *A61P 9/10* (2018.01); *C12N 5/0669* (2013.01); *C12N 9/22* (2013.01); *C12N 15/113* (2013.01); *C12N 2310/20* (2017.05); *C12N 2510/00* (2013.01); *C12N 2800/80* (2013.01)

(58) Field of Classification Search
CPC ......... A61K 35/28; A61P 9/10; A01N 1/0284; C12N 5/0669; C12N 9/22; C12N 15/113; C12N 2310/20; C12N 2510/00; C12N 2800/80
See application file for complete search history.

(56) References Cited

U.S. PATENT DOCUMENTS

| | | | |
|---|---|---|---|
| 2011/0189768 A1 | 8/2011 | Danilkovitch et al. | |
| 2012/0014879 A1 | 1/2012 | Losordo et al. | |

FOREIGN PATENT DOCUMENTS

| | | |
|---|---|---|
| WO | WO 00/00504 | 1/2000 |
| WO | WO 2011/006914 | 1/2011 |
| WO | WO 2015/104322 | 7/2015 |
| WO | WO 2015/191545 | 12/2015 |
| WO | WO 2016/081924 | 5/2016 |
| WO | WO 2016/081926 | 5/2016 |
| WO | WO 2019/082184 | 5/2019 |

OTHER PUBLICATIONS

Al-Lamki & Mayadas in "TNF receptors: signaling pathways and contribution to renal dysfunction" (Kidney International, 2015 vol. 87, pp. 281-296, published online Aug. 20, 2014). (Year: 2014).*
International Preliminary Report on Patentability dated May 7, 2020 From the International Bureau of WIPO Re. Application No. PCT/IL2018/051139. (9 Pages).
International Search Report and the Written Opinion dated Dec. 31, 2018 From the International Searching Authority Re. Application No. PCT/IL2018/051139. (14 Pages).
Bao et al. "TNFR Gene-Modified Mesenchymal Stem Cells Attenuate Inflammation and Cardiac Dysfunction Following MI", Scandinavian Cardiovascular Journal, 42(1): 56-62, Published Online Jul. 12, 2009.
Choudhury et al. "An Exploratory Randomized Control Study of Combination Cytokine and Adult Autologous Bone Marrow Progenitor Cell Administration in Patients With Ischaemic Cardiomyopathy: The Regenerated-IHD Clinical Trial", European Journal of Heart Failure, 19(1): 138-147, Published Online Oct. 28, 2016.
Farhang et al. "CRISPR-Based Epigenome Editing of Cytokine Receptors for the Promotion of Cell Survival and Tissue Deposition in Inflammatory Environments", Tissue Engineering: Part A, 23(15-16): 738-749, Feb. 28, 2017.
Karantalis et al. "Use of Mesenchymal Stem Cells for Therapy of Cardiac Disease", Circulation Research, 116(8): 1413-1430, Apr. 10, 2015.
Kelly et al. "TNF Receptor-2, Not TNF Receptor 1 Enhances Mesenchymal Stem Cell-Mediated Cardiac Protection Following Acute Ischemia", Shock, 33(6): 602-607, Jun. 2010.
Kishore et al. "Tumor Necrosis Factor-Alpha Signaling Via TNFR1/p55 is Deleterious Whereas TNFR2/p75 Signaling is Protective in Adult Infarct Myocardium", Advances in Experimental Medicine and Biology. 691: 433-448, Published Online Oct. 22, 2010.
Kurrelmeyer et al. "Endogenous Tumor Necrosis Factor Protects the Adult Cardiac Myocyte Against Ischemic-Induced Apoptosis in a Murine Model of Acute Myocardial Infarction", Proc. Natl. Acad. Sci. USA, PNAS, 97(10): 5456-5461, May 9, 2000.
Moe et al. "In Vivo TNF-Alpha Inhibition Ameliorates Cardiac Mitochondrial Dysfunction. Oxidative Stress, and Apoptosis in Experimental Heart Failure", American Journal of Physiology—Heart and Circulatory Physiology, 287(4): H1813-H1820. Published Online Jun. 17, 2004.
Monden et al. "Tumor Necrosis Factor-Alpha is Toxic Via Receptor 1 and Protective Via Receptor 2 in a Murine Model of Myocardial Infarction", American Journal of Physiology—Heart Circulatory Physiology, 293: H743-H753, Published Online Apr. 6, 2007.
Tan et al. "Ablation of TNF-Alpha Receptors Influences Mesenchymal Stem Cell-Mediated Cardiac Protection Against Ischemia", Shock, 34(3): 236-242, Sep. 2010.

(Continued)

*Primary Examiner* — Catherine S Hibbert

(57) ABSTRACT

Methods of treating an ischemic disease in a subject are provided. Accordingly there is provided a method comprising administering to the subject a therapeutically effective amount of cells with reduced level of expression and/or activity of TNFR1, thereby treating the ischemic disease in the subject. Also provided is a method comprising treating with TNFalpha cells with reduced expression and/or activity of TNFR1 and administering to the subject a therapeutically effective amount of said cells, thereby treating the ischemic disease in the subject.

18 Claims, 11 Drawing Sheets

Specification includes a Sequence Listing.

(56) References Cited

OTHER PUBLICATIONS

Supplementary European Search Report and the European Search Opinion dated Jul. 26, 2021 From the European Patent Office Re. Application No. 18871526.2. (13 Pages).
Farhang et al. "CRISPR-Based Epigenome Editing of Cytokine Receptors for the Promotion of Cell Survival and Tissue Deposition in Inflammatory Environments", Advances in Tissue Engineering, XP055595238, 23(15-16): 1-48, Aug. 1, 2017.
Pan et al. "Enhancing Stem Cell Survival in an Ischemic Heart by CRISPR-dCas9-Based Gene Regulation",Medical Hypotheses, XP 29097483A, 83(6):702-705, Dec. 2014.
Communication Pursuant to Article 94(3) EPC dated May 10, 2023 From the European Patent Office Re. Application No. 18871526.2 (9 Pages).
Abarbanell et al. "Proinflammatory Cytokine Effects on Mesenchymal Stem Cell Therapy for The Ischemic Heart", The Annals of Thoracic Surgery, 88(3): 1036-1043, Sep. 3, 2009.
Wu et al. "Stem Cell-Based Therapies in Ischemic Heart Diseases: A Focus on Aspects of Microcirculation and Inflammation", Basic Research in Cardiology, 106: 317-324, Mar. 23, 2011.
Zeller et al. "Role of Tumor Necrosis Factor Receptor 1 in Sex Differences of Stem Cell Mediated Cardioprotection", The Annals of Thoracic Surgery, 87(3): 812-819, Mar. 2009.

* cited by examiner (2) Length 378.68 µm
(1) Length 707.66 µm
500 µm

20 µm (1) Length 1584.56 µm
(2) Length 440.56 µm
500 µm

50 µm (2) Length 323.09 µm
(1) Length 885.54 µm
500 µm

50 µm (1) Length 1579.85 µm
(2) Length 330.75 µm
500 µm

200 µm (1) Length 852.10 µm
(2) Length 452.06 µm
500 µm

200 µm

500 µm

200 µm (1) Length 4869.40 µm
(2) Length 1771.58 µm
500 µm

N
200 µm (2) Length 2029.58 µm
(1) Length 3996.65 µm
500 µm

N
200 µm (1) Length 2744.39 µm
(2) Length 1144.77 µm
500 µm

200 µm (1) Length 4142.77 µm
(2) Length 1012.40 µm
500 µm

N
200 µm

SEQUENCE LISTING

```
<160> NUMBER OF SEQ ID NOS: 47

<210> SEQ ID NO 1
<211> LENGTH: 233
<212> TYPE: PRT
<213> ORGANISM: Homo sapiens

<400> SEQUENCE: 1

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```

<210> SEQ ID NO 2
<211> LENGTH: 13361
<212> TYPE: DNA
<213> ORGANISM: Homo sapiens

<400> SEQUENCE: 2
ctcctccagc tcttcctgtc ccgctgttgc aacactgcct cactcttccc ctcccacctt 60
ctctcccctc ctctctgctt taattttctc agaattctct ggactgaggc tccagttctg 120
gcctttgggg ttcaagatca ctgggaccag gccgtgatct ctatgcccga gtctcaaccc 180
tcaactgtca ccccaaggca cttgggacgt cctggacaga ccgagtcccg ggaagcccca 240
gcactgccgc tgccacactg ccctgagccc aaatgggggga gtgagaggcc atagctgtct 300
ggcatgggcc tctccaccgt gcctgacctg ctgctgccac tggtgagacc agggacaaag 360
ggaagagtgg gctggtgggc gaggcacctt ccggctggcg tgggccctct ccgggagggg 420
gccgagcctc tcctgcccgg gcctggtcct ggcgccagcc tcaggcctgc aggtcctaac 480
ctcagccact gccagtgtgg ggttccccat tcatccgcct tttggagtag gggctgcgct 540
gaggcagggg aatgggagaa gtttgaaagg gagagagtaa aaggaagccc tggcccctga 600
cagcggtgga agtttgtggg cggccaaggg aatgtgggca ggagataggc ccagggtggg 660
gcagatttgg cggggaaaag aagggagtgg gagtaggaag attagtgctc ggggagtcca 720
gacggttctg aattctgtcc ctccggtcag ctggctggcc tggagggtgt tgggccgtgg 780
ggaggcgagg ctgcctgtgg aacttggtgg agcacaccct gtagggcagg attttggcgg 840
ctggtgaagt gggggagtga gttgaggagt ggggatgggc tggtgtggtg ggtttgggat 900
gctcatggtg ggaggtattt gagaatgggc tgggacactg gatggggcag ggcaacccag 960
tggacagtgt ccccagtgcc ctggccaagc cccggcctct cacctgggga cattctttac 1020
ccttttgcct gctgctaggc aggtagccgc tgtgggactg agccttccca gggagctagt 1080
cctaccccca cctggtcagt gtccctgggc ctgtcctcca gcttcccctc cccgctgctt 1140
ctcacagacc taaacaacaa tcccttggtt tcttattcta cagttcagtt tggggaagtt 1200
ggtagaaagt tgttttcgtc actggaaaat gtccctttct ctggcctcag ccttgtttca 1260
atgtatcctt gatcgtcctc cacgtcttgg tccgggaatc atcctgttca gatgtcctgg 1320
gcccatctag tcaggcagat tttccctgcc ctgcccggcc tctgaaggct gcgcctacct 1380
cccctctctt tagtgcctta tactcttcct ctcctaccat tcctttcttc cagcaatctc 1440
cccagactct cctcagactt ctcagagcct cttttttttga aatcttttct cgctaatcct 1500
ccttcccctc ctctctgctc cgctctggtc ccggccccag gtccccaggc agcacgtctc 1560
tggtcagggt ctcactcttc ttcttctgcc tcctcctgcc tccttagtcc cacccgctct 1620
tcccttcttc ccactgtcct tcccccacgg tctccccacc agccagctgc cctgacatcc 1680
tgcttctgtt ttctgtttgg gggcggcccc tggctccctc acatacctcc tgcatgaaca 1740
agagcagctt atataaccta accttccatg ccttcgtttc tttatctcca aaatgggtgt 1800
cacagtcttg acctcatact gttgttttga agattgaata gactgataca tgttaagtgt 1860
tcatttgatt tattaagtgt gcgctctggg ctagacactg tgataggtgc tgggattaca 1920
gcagagaaca aaatccctgc ccacagcttt gacagtccat caggggaata ggttgtagca 1980
aatagaaagc actcaataaa gtttttatat tgctgtgact agtagtaatt actgggtggc 2040
tacctgtgtt gggaaaacag agggtaaagg tagcctgaac aggtaaaggg aagtgcctgc 2100
gtcctggggt gcttcagccc aggtgggatt atgtctccta agggacagaa gcctggcctg 2160

-continued gagctggagg aaagggaaaa caaagggaat gcaacatcct tctgaatttc tcaccattca 2220
gtgggcaatg cagagctcac agtgtgtgtg tgtgtgtgtg tgtgtgtgtg tgtgtgagag 2280
agagagagag agagagagag aagtggggta ggggagtagg gaagaatgat acaggagaga 2340
ctgtggcaaa gcaaacagga ttttgctgct ctcaaagagc ttacagccta gtaaccaaga 2400
tggcttacag tgaaaaatga tttcagagca atcccgagga aaatatccac aaatgcattg 2460
tgatgtggtg tcctggagca ccagttggga ggaggaggaa ctggggaagg aggtgagcct 2520
tagtccactg cctttccttg cttagcaggt ctcagctcct gcgctcagct ccagaaaatt 2580
caggagcttc cccacgctgc ttcagtgtcc ttcactgtgc aactgcagca ctccctgtat 2640
agatctcagt gcctacaact gactgtcttt gactcaagtg agagctcttg agagcacgag 2700
ctgtgtatta tccacctcag catccctagc acccatacgg gacctgtcac attaactgtg 2760
ccccttaact atttgctgaa ggaattaagg aacaagagat gtgtcagatg ggatggcgga 2820
gggaaagcct catagaaaag tggatgtgga gctgacatct gaagtcactg cctgtcaggg 2880
tagctataaa ggagggaagc agagttggat actgatgtga ggaagaggag aggaatggag 2940
agatgggatt ttgtgttgat gggcagggtg gcaggaagcc agacaccttg gttcgggagt 3000
ggaaaaacca tgttgagaaa cactaagaaa tgtgaatggg agaattagag ggagtggggg 3060
agaggatgga ggaagagtgt tgaatatggt tccaggtgga ggaattcatt cattcgttta 3120
ttcagaagct gttctcctag ggcacattct gtgcccagac tgtgattaga agtgaggtga 3180
ggcatctcag atgggtgctg tggttcatgc ctgtaattcc agcacttcag gaggccgagg 3240
tgtgtggatt gcttgagtcc aggagttcga gaccagcctg ggcaacacag caaaaccctg 3300
tctctacaaa aaatacaaag attagcgggg catggtgggg cgtgcttgtc atcccagcta 3360
ttcgggagac tgagctcggg aggacggctt gggcccagga ggtggaggtt gtagtgagcc 3420
ctgaccacac cactacattc cgtcctggtg gtgaaggttg cagtgagcta tgattgtgcc 3480
actgcacttc accctgggtg acagagtgag accctgtttc aaaaaaaaaa aaaaaaaagt 3540
agtgaggcat ctgtggaagt cttcagatca tttccatgac catggaaatg ctgtttggag 3600
ccaggccctg gagatggaga ggaaggttca cacacttgtg cgtgcaagtt aaagcctgaa 3660
tgaagattta aaaagtgtgt aggacggatg ggagcaggag agaggctaga agacacttgc 3720
aataacccag gtgtgaggca acccaggaat gcggagagga ccgagagatc acagggggag 3780
gcctcgcaag atgaactgac acatgggatg gcggcaggga tagggatggg gccctgggga 3840
gagagcgtgg caagttctca gcattcgtcc gggaagtcga tggtgtgtca tttgtctagg 3900
tgaggagatg gatgaattcc gtctggggca tgttaagggt cagggaaatg gtcatgtgga 3960
agggtgcgcc taccaagctg gaggagaggt gctgcaactt ctttctgcct ttgtatcatt 4020
cagacacact gtgttcactc atcagtggtt ctcaaaagga gaggagcaca ccagactctt 4080
aagtaagggt gtgtgtgctt gtgtgtgggg aggtgggggg atggtctgaa aactctcccc 4140
cggagataaa tatattccta ccaggggtgc tgtctcctca cctccctctt tgggaatcac 4200
tggcttctac tagagtggaa gacagatgta tcattagatc gatcagttga tccatattta 4260
tctgctccca gtctggaggt ctggttctgg gagctgagag gacaccaggg gaggataaga 4320
cactttctga ccaagacatt ttttgatctc tcatcttata aggttcgtgg tcactttggg 4380
gagatcatat ctgtcaccca acataaccat attatgataa gagccaaaag tagatagggt 4440
cagttcacgt gcttcgagtt cacagggact atgggtctaa ggagccgggg tggaggaaac 4500
agacatcgtc aatggtggct tcacgggagg gagatgggat ctcaactggg cccttggagg 4560

-continued

```
agaagctgcc acgacctccc ccaacacctt gacattaaat gaacagacac atgaatgagg   4620
gggaaaggaa gactaattgg gtccctgcaa ggtggctgga tcggggtcag accacaaggc   4680
cgatctcagc gtcgcctccc cactctgcag ccccagcaca ggaagtcaca ctttaaagcc   4740
tcctctggcg gaaattgtgg gggagttgga ggggtgttgg gccacccccct caactgtctc   4800
tccacaggca ccccagcttc ctgcccttct gctccaggct ggagtctggg cctaaagagc   4860
tcacctcctg tttctcctgt tttgcttcat ttacgcaact gctgaggact gggcttactg   4920
gggccagctg gtgccagcag tggtgcccag tggtggggag tctgagggcc ctggctccta   4980
gggatcagag agggctgacc tggagcattc tgggggccag gggaagccta ggaagcaggg   5040
ctggttcttc catccggcat cccttcttgc ctgctccctc gttcctggaa gtgggtgttc   5100
agggctctgg aggctttcct gtattgccag tgggcttggg gagggtctgt ggagactcag   5160
aactggcctt gtttcctaag gattgtctgg ggaccccagg gaggccccca aacccagcac   5220
aactggtcag aaccagccag gctgtgggaa tgcggtgaac ccagggtggg agggcagcct   5280
tggcttgctt cctgctggga ctggggagtg ttgggggatg gagtgagagc tcacggaatg   5340
ggtttagctg ttggagactt gttgaactgg gaggaggagc tggggcgggg cctcagctaa   5400
aggccgctga ggggctagga ggagccaagt ggccctcagg gaagggaggg cacagacctg   5460
atgggcggaa gccagggtcg agggagactt cccttcggga tggaatgggg agagggaggc   5520
atttcccgga acatgtgggc caagtgggac aagggtctgt ggcctggctc tttgcatggg   5580
gaggggatgg atgggggttg agtggggatg ggaaggaggg acttggccat aggaagaagg   5640
gattagatgg agtcccactt gcatgcaggc tggtgccttc tgcctttctg ctgactcatg   5700
acccttgagg agctggggaa gctgctagtt ccctctcccc tccctaggtc tccctccctc   5760
tggcctgagt cactggggcg gagttgctgg gaaaagattt ccctttcccg gatctgactt   5820
aacccccaga gtgctggaaa gagaagggaa cacgtggcct gagaaagcct ctctccctcc   5880
ctccctccag ggaggctcat cccccactgg ccagaggtcc ctgaaaagct ccctttaagg   5940
ctgtctgggg ctggcgtccc ccagttcttc atcatgactc tgcctcaagc cccctggatg   6000
ggattcaaag taccagtgac cttaggtgct ccagtggctt cttcggggaa aggaaccaca   6060
ctttcaggac tgggaagttc ttcccatcac caccccaaac ccttcctgtt gccctggaag   6120
ccccagtcct gttctcagca gaggtggcac ggtgttggct ggtgcgggca ggggaaggtt   6180
gttgtcctct gagcaggggc acacgcctcc acctgcgggg gctgctgttg tgtttctgtg   6240
tgtggcttcc cctgtttgcg gctgaggctt gaacttccgg gcctgcacag cttacagctg   6300
cagcgtctcc ccgtggctga ctcagggtga ctggcctcct gctccgaaat gtggagttgg   6360
tgaggctggg tggctgtggg ctgcctgacc ctccttccct gccctagggt ttctgtgatc   6420
tggtgagtca gttgctcccc agtgtttaac agacattgag gacaccctct tatctttaca   6480
caaagtgtct cttatagtag aaaaaaaaaa tgaagcccag ggaaaaccag aaatgaagct   6540
ggcagagatc aaagtccaag ttagagctaa atattcactc ctggctttgc tttcctggca   6600
ctgatgccgg aacaggacaa gccatttagc tgctgtgggg ttggcctgag actgcaaagc   6660
acaccttcca gaatgccatg gtgtgcaggg ggctccagga ctccccagca cgccctcagc   6720
tctgacctga cagtcatcca agctgggtcg ctagccttgg ccagctctat ttgcctatgt   6780
cctgcacacc tttgcccact cctgcccccg tctcaacttt gtcccccgtc tacccatgca   6840
ggatccccaa cctttccctt ttactctcct ccccatttgt ccttgccaac cccgggtgtt   6900
```

-continued tgtaaatttt gaggtggagg ggatgggcca gggaatgtga gggcggaggc agattgaggt 6960
ttgatacaaa catgtaaata aacttccttc ttctgtccac tccccaggag tggtgctcac 7020
gggaacatca ctcgccccca ccgccagctg actttttcag aaagcttttc atggtgtaac 7080
atattcctgg gatgtgcata gatcctcatt gtttacctct gtgaatgttc gcaaagcgat 7140
cacacggtga acccagcacc cagatggaga aacaccgccc caatctttag ggctgcttgt 7200
tggaagaagg ggccatcact gaagtaacct gccaattccc aatcaaaaac acatcctttc 7260
aacatctgcc ctgtgtccag cactgttagc tgctgtgggg gatttcacag taaggataaa 7320
atacagggct gggctcacgc ctgtaatcct agcactttgg gaagccaagg tgggaggatc 7380
acttgagccc aggattttga gaccagtctg agcaacgtaa caagaccctg cctctactaa 7440
aaataaaaaa aaattagctg ggcatggtgg ttcacggccg tagtcccagc tattcaggag 7500
gctaaggtgg gaggactgct tgagcgtggg tggtggaggg tgcagtgatt gcatcactgc 7560
actccagcct ggacaacaga gcaagatcct gcctaaaaaa aaaaaaatac agcttagatc 7620
tggggcctac tagctttgag ttgagggaac aaaaatgaac acacaggaca actagagaac 7680
aattaagcat cagattgtat ggccccaact gtctaagttt caaggaagaa ctctaaactt 7740
agtgagtggc gtggcctggg cggaatgttt cactgaggaa ggacttgagc cagggaagtt 7800
ttagatctgc tacccctaag cttcccatcc ctccctctct tgatggtgtc tcctctatct 7860
gattcttccc caggtgctcc tggagctgtt ggtgggaata tacccctcag gggttattgg 7920
actggtccct cacctagggg acagggagaa gagagatagt gtgtgtcccc aaggaaaata 7980
tatccaccct caaaataatt cgatttgctg taccaagtgc cacaaaggta ggggcaagtg 8040
gaaacggtga atgccctcag gtctggggtg ctgcttcttt ctctgcttct tccagttgtt 8100
cttccctaac tttgctgtct ctcctgggct gggattttct ccctccctcc tctcctagag 8160
acttcaggga atcggccctg gctgttgtcc ctagcatggg gctccttcct tgtgttctca 8220
cccgcagcct aactctgcgg ccccattcac aggaacctac ttgtacaatg actgtccagg 8280
cccggggcag gatacggact gcagggagtg tgagagcggc tccttcaccg cttcagaaaa 8340
ccacctcaga cactgcctca gctgctccaa atgccgaaag ggtgagtgtg cacaggcagg 8400
agagtcaggc gggtcttgag tggtgtgtgg gtgcctgtct atgtgcaggc tggtgggtgt 8460
gggcaggaag gtgtgtgttt tggtgggaca ctgcatggat gtgagtgtgt attacagaga 8520
cacacactta ggggtatgtc aggaagggga tgcagggaca ggaggatgca ggactcatac 8580
cccatcttct cccctcacca gaaatgggtc aggtggagat ctcttcttgc acagtggacc 8640
gggacaccgt gtgtggctgc aggaagaacc agtaccggca ttattggagt gaaaaccttt 8700
tccagtgctt caattgcagc ctctgcctca atgggaccgt gcacctctcc tgtgagcgca 8760
gctctcctga ggccaagccc tctccccacc ccaggggttg gccccttccc catgcggtgg 8820
cacttccttt ccttccccct cctgtattct gtgggtctga caaccaactc ctctctggcc 8880
gcccccaccc tgtccctcgt cacttcctct gtcctgtggg gtgggggtgc aggcgcttct 8940
cctttagctg tgccgcactt ctccctacag gccaggagaa acagaacacc gtgtgcacct 9000
gccatgcagg tttctttcta agagaaaacg agtgtgtctc ctgtagtaag tgagtatctc 9060
tgagagctgc tgggcactgg atggtggcat gggttgggac gggtgactgg tgggaaccat 9120
tagctgggca acagatgcca ggatgcccca gagtgctcag ggtcctactg gctgagtagg 9180
agacacttcg ttaagacacc aggcagtcct tccccttgct cttcaaatct gaagaagtct 9240
ttgaggatgg aagatcatgc cccaagggct ggcagccctt ccaactcaga tatgtagatt 9300

-continued

```
cttggatcta cgatagctca ttggttctag gacatacact cttatagctc tgaaatcaaa   9360
cctcctataa ctggtgactc atcatggttg aattggcagc tctgtttgcg tctgggtagt   9420
aatgtaaaga aaagtgcctt ttattcttga tggcgtctta ggtttgatgc aatatggtat   9480
ttcctcatta gtcactgtcc aggcctcctt actcctggct ccacagaggc tgttcttgtc   9540
actcacttgc aaagaataaa ctctgagggc tctcagagtt tgaaccccag catagccact   9600
tactggctat gtgacgttgg gcaagtttct taacatctct gagcctgact tttcttttgg   9660
tgtttttttt tttttttttt ttttgagaca gggtttcact ctgtcaccca ggctggagtg   9720
cagtggtgca accgtggctc agcctccacc tccagggctc aagccatcct cttgccttag   9780
cctcctgagt agctgggatt agaggcacac accactacac ccagctaatg ttttactttt   9840
tgtagagaca gggtcctact atattgccca ggctggcctc ggactcctgg gctcaagcga   9900
tcttccgcct cagcctccca aagtgctagg attacgggca tgagccacca cgcctggcct   9960
gggccttaga tttcttatat ttaaagtaag cataatgaca ttcatttggt gaatttgtga  10020
gaaccaaaaa caaagaaaca aacaaaacct acaacacgtc tgacacaaaa ctatttattt  10080
tccattaatc ttcttttttt tttttttttt tttttttgac acagagtcct gctctgtcgc  10140
ccaggctgga atgcagtggc gcgatctcgg ctcactgcaa cctctgcctc ccagattcaa  10200
gcaattctcc tgcttcagcc tcccaagtag ctgggattac aggcacgtgc caccatgcct  10260
ggctaatttt tgtattttta gtagagatgg ggtttcacca tcttggtcag gctggtctca  10320
aactcctggt gatccacctg cctctgcctc ccaaagtgct gggattacag ccgtgagcca  10380
ctgcacccag ccggcttcat ctcttcttga aatcactttt ataccattct atgtggttct  10440
caccatgagc ttgagtggtg ggctaaagtg cctctccctg ctttcagctt cctgctggga  10500
actcactctc tcaagttcct tccagcacca ccccatagag ttcccatcac tccacactgt  10560
ccagtgacaa ctcccaacat ggaagatctg ctagttctac agggtgctct ctggctgccc  10620
cagtaacatg tgtttttaaa tttttcacat gcatgtttga ccccgactcc ccgaagtcag  10680
gtactgtaac tagcagtgtc atttaagaaa aagcccttta acctctcttt gccaaaggat  10740
tcttatcagc aaaacagtga tgaaacaaca atcccataac agctagctgg ctaccttctc  10800
aagcacttat taaatgaggc ataatgattt tgcttaatcc tcaatcctga gaggtgggcg  10860
atccctgtgg tgatgaggaa accgaggctt gggggttaat ggcttgccta gattcacact  10920
gctagccaag gaatgaactg gaatttacac cctgaccctg actgcttttc acattttcta  10980
cacagccttt tcaagatccc tgccaattct aaaattaaat gattctatga ttaactgtgt  11040
ttcattcttc tgcatcagtt cccaaaacaa attatatcaa gagacagcaa aaatatttgt  11100
aaagaaagga tgtccaacaa tctgtgtggt tgtttttctg tgttcctcca atggtagggc  11160
ctctgttcac cagtgccgtc tcttctttta gctgtaagaa aagcctggag tgcacgaagt  11220
tgtgcctacc ccagattgag aatgttaagg gcactgagga ctcaggtgag gagaagtgac  11280
ctggtgccca tgctcacctg ccctctccct cttcttgccc ccacccgtcc atccatccca  11340
cccatccatc tatccctgcg gcccccctct gcccgctcct ctgaccaaca cctgctttgt  11400
ctgcaggcac cacagtgctg ttgcccctgg tcattttctt tggtctttgc cttttatccc  11460
tcctcttcat tggtttaatg tatcgctacc aacggtggaa gtccaagctc tactccattg  11520
gtgagtgggg gctttgggag ggagagggag ctggtggggg tgagggagga catgggtggg  11580
tgcgatggac atgtgtggag ggaggtgagg agtgtcccct cagttcatac cgctggggac  11640
```

-continued

```
tctgggcaga aggtggccct ggatggctgg ggagatgtcg agctgcatca gtagctctct  11700

cgtccctggg gccacatagg ccctgaggca tgtcaccaca agtccccact gccagctgag  11760

tccagggtgc cagggctgag agaggaagtg aaatttatga tgctttcttt ctttttcctc  11820

agtttgtggg aaatcgacac ctgaaaaaga ggtgagatga aatgagagag ttactcccaa  11880

atgtccctga ccattcctta taattgccta atgctcagat cccctggaat catccttcac  11940

tttccggggg ctcgcctcat tccctctaag tcccaacccc cacgtagaat aaagagggcc  12000

ggggctggtt ttcgctgccg cactaatgtt gcgccacctt ctctctttca gggggagctt  12060

gaaggaacta ctactaagcc cctggcccca aacccaagct tcagtcccac tccaggcttc  12120

acccccaccc tgggcttcag tcccgtgccc agttccacct tcacctccag ctccacctat  12180

acccccggtg actgtcccaa ctttgcggct ccccgcagag aggtggcacc accctatcag  12240

ggggctgacc ccatccttgc gacagccctc gcctccgacc ccatccccaa cccccttcag  12300

aagtgggagg acagcgccca caagccacag agcctagaca gtgagtttct cccgcggctg  12360

gagacgagga ggctggggga gggccggggg agcgcgggag gcgctcccag aggggaccac  12420

gagaggcgga gggcgcggga tgcggggcgg ggcctggggt tgccgcccga ggctcaccgg  12480

cccgcgtccc cgcagctgat gaccccgcga cgctgtacgc cgtggtggag aacgtgcccc  12540

cgttgcgctg gaaggaattc gtgcggcgcc tagggctgag cgaccacgag atcgatcggc  12600

tggagctgca gaacgggcgc tgcctgcgcg aggcgcaata cagcatgctg gcgacctgga  12660

ggcggcgcac gccgcggcgc gaggccacgc tggagctgct gggacgcgtg ctccgcgaca  12720

tggacctgct gggctgcctg gaggacatcg aggaggcgct ttgcggcccc gccgccctcc  12780

cgcccgcgcc cagtcttctc agatgaggct gcgcccctgc gggcagctct aaggaccgtc  12840

ctgcgagatc gccttccaac cccacttttt tctggaaagg aggggtcctg caggggcaag  12900

caggagctag cagccgccta cttggtgcta acccctcgat gtacatagct tttctcagct  12960

gcctgcgcgc cgccgacagt cagcgctgtg cgcgcggaga gaggtgcgcc gtgggctcaa  13020

gagcctgagt gggtggtttg cgaggatgag ggacgctatg cctcatgccc gttttgggtg  13080

tcctcaccag caaggctgct cgggggcccc tggttcgtcc ctgagccttt ttcacagtgc  13140

ataagcagtt ttttttgttt ttgttttgtt ttgttttgtt tttaaatcaa tcatgttaca  13200

ctaatagaaa cttggcactc ctgtgccctc tgcctggaca agcacatagc aagctgaact  13260

gtcctaaggc aggggcgagc acggaacaat ggggccttca gctggagctg tggacttttg  13320

tacatacact aaaattctga agttaaagct ctgctcttgg a                     13361
```

<210> SEQ ID NO 3
<211> LENGTH: 2258
<212> TYPE: DNA
<213> ORGANISM: Homo sapiens

<400> SEQUENCE: 3

```
ctcctccagc tcttcctgtc ccgctgttgc aacactgcct cactcttccc ctcccacctt     60

ctctcccctc ctctctgctt taattttctc agaattctct ggactgaggc tccagttctg    120

gcctttgggg ttcaagatca ctgggaccag gccgtgatct ctatgcccga gtctcaaccc    180

tcaactgtca ccccaaggca cttgggacgt cctggacaga ccgagtcccg ggaagcccca    240

gcactgccgc tgccacactg ccctgagccc aaatggggga gtgagaggcc atagctgtct    300

ggcatgggcc tctccaccgt gcctgacctg ctgctgccac tggtgctcct ggagctgttg    360

gtgggaatat acccctcagg ggttattgga ctggtccctc acctagggga cagggagaag    420
```

-continued agagatagtg tgtgtcccca aggaaaatat atccaccctc aaaataattc gatttgctgt 480
accaagtgcc acaaaggaac ctacttgtac aatgactgtc caggcccggg gcaggatacg 540
gactgcaggg agtgtgagag cggctccttc accgcttcag aaaaccacct cagacactgc 600
ctcagctgct ccaaatgccg aaaggaaatg ggtcaggtgg agatctcttc ttgcacagtg 660
gaccgggaca ccgtgtgtgg ctgcaggaag aaccagtacc ggcattattg gagtgaaaac 720
cttttccagt gcttcaattg cagcctctgc ctcaatggga ccgtgcacct ctcctgccag 780
gagaaacaga acaccgtgtg cacctgccat gcaggtttct ttctaagaga aaacgagtgt 840
gtctcctgta gtaactgtaa gaaaagcctg gagtgcacga agttgtgcct accccagatt 900
gagaatgtta agggcactga ggactcaggc accacagtgc tgttgcccct ggtcattttc 960
tttggtcttt gccttttatc cctcctcttc attggtttaa tgtatcgcta ccaacggtgg 1020
aagtccaagc tctactccat tgtttgtggg aaatcgacac ctgaaaaaga gggggagctt 1080
gaaggaacta ctactaagcc cctggcccca aacccaagct tcagtcccac tccaggcttc 1140
acccccaccc tgggcttcag tcccgtgccc agttccacct tcacctccag ctccacctat 1200
acccccggtg actgtcccaa ctttgcggct ccccgcagag aggtggcacc accctatcag 1260
ggggctgacc ccatccttgc gacagccctc gcctccgacc ccatccccaa ccccccttcag 1320 aagtgggagg acagcgccca caagccacag agcctagaca ctgatgaccc cgcgacgctg 1380
tacgccgtgg tggagaacgt gccccccgttg cgctggaagg aattcgtgcg gcgcctaggg 1440
ctgagcgacc acgagatcga tcggctggag ctgcagaacg ggcgctgcct gcgcgaggcg 1500
caatacagca tgctggcgac ctggaggcgg cgcacgccgc ggcgcgaggc cacgctggag 1560
ctgctgggac gcgtgctccg cgacatggac ctgctgggct gcctggagga catcgaggag 1620
gcgctttgcg gccccgccgc cctcccgccc gcgcccagtc ttctcagatg aggctgcgcc 1680
cctgcgggca gctctaagga ccgtcctgcg agatcgcctt ccaaccccac ttttttctgg 1740
aaaggagggg tcctgcaggg gcaagcagga gctagcagcc gcctacttgg tgctaacccc 1800
tcgatgtaca tagcttttct cagctgcctg cgcgccgccg acagtcagcg ctgtgcgcgc 1860
ggagagaggt gcgccgtggg ctcaagagcc tgagtgggtg gtttgcgagg atgagggacg 1920
ctatgcctca tgcccgtttt gggtgtcctc accagcaagg ctgctcgggg gcccctggtt 1980
cgtccctgag cctttttcac agtgcataag cagttttttt tgtttttgtt ttgttttgtt 2040
ttgtttttaa atcaatcatg ttacactaat agaaacttgg cactcctgtg ccctctgcct 2100
ggacaagcac atagcaagct gaactgtcct aaggcagggg cgagcacgga acaatggggc 2160
cttcagctgg agctgtggac ttttgtacat acactaaaat tctgaagtta aagctctgct 2220
cttggaaaaa aaaaaaaaaa aaaaaaaaaa aaaaaaaa 2258

<210> SEQ ID NO 4
<211> LENGTH: 2102
<212> TYPE: DNA
<213> ORGANISM: Homo sapiens

<400> SEQUENCE: 4
ctcctccagc tcttcctgtc ccgctgttgc aacactgcct cactcttccc ctcccacctt 60
ctctcccctc ctctctgctt taattttctc agaattctct ggactgaggc tccagttctg 120
gcctttgggg ttcaagatca ctgggaccag gccgtgatct ctatgcccga gtctcaaccc 180
tcaactgtca ccccaaggca cttgggacgt cctggacaga ccgagtcccg ggaagcccca 240

-continued

```
gcactgccgc tgccacactg ccctgagccc aaatgggggga gtgagaggcc atagctgtct    300

ggcatgggcc tctccaccgt gcctgacctg ctgctgccac tggaacctac ttgtacaatg    360

actgtccagg cccggggcag gatacggact gcagggagtg tgagagcggc tccttcaccg    420

cttcagaaaa ccacctcaga cactgcctca gctgctccaa atgccgaaag gaaatgggtc    480

aggtggagat ctcttcttgc acagtggacc gggacaccgt gtgtggctgc aggaagaacc    540

agtaccggca ttattggagt gaaaaccttt tccagtgctt caattgcagc ctctgcctca    600

atgggaccgt gcacctctcc tgccaggaga aacagaacac cgtgtgcacc tgccatgcag    660

gtttctttct aagagaaaac gagtgtgtct cctgtagtaa ctgtaagaaa agcctggagt    720

gcacgaagtt gtgcctaccc cagattgaga atgttaaggg cactgaggac tcaggcacca    780

cagtgctgtt gcccctggtc attttctttg gtctttgcct tttatccctc ctcttcattg    840

gtttaatgta tcgctaccaa cggtggaagt ccaagctcta ctccattgtt tgtgggaaat    900

cgacacctga aaaagagggg gagcttgaag gaactactac taagcccctg gccccaaacc    960

caagcttcag tcccactcca ggcttcaccc ccaccctggg cttcagtccc gtgcccagtt   1020

ccaccttcac ctccagctcc acctataccc ccggtgactg tcccaacttt gcggctcccc   1080

gcagagaggt ggcaccaccc tatcaggggg ctgaccccat ccttgcgaca gccctcgcct   1140

ccgaccccat ccccaacccc cttcagaagt gggaggacag cgcccacaag ccacagagcc   1200

tagacactga tgaccccgcg acgctgtacg ccgtggtgga gaacgtgccc ccgttgcgct   1260

ggaaggaatt cgtgcggcgc ctagggctga gcgaccacga gatcgatcgg ctggagctgc   1320

agaacgggcg ctgcctgcgc gaggcgcaat acagcatgct ggcgacctgg aggcggcgca   1380

cgccgcggcg cgaggccacg ctggagctgc tgggacgcgt gctccgcgac atggacctgc   1440

tgggctgcct ggaggacatc gaggaggcgc tttgcggccc cgccgccctc ccgcccgcgc   1500

ccagtcttct cagatgaggc tgcgcccctg cgggcagctc taaggaccgt cctgcgagat   1560

cgccttccaa ccccactttt ttctggaaag gaggggtcct gcaggggcaa gcaggagcta   1620

gcagccgcct acttggtgct aaccccctcga tgtacatagc ttttctcagc tgcctgcgcg   1680

ccgccgacag tcagcgctgt gcgcgcggag agaggtgcgc cgtgggctca agagcctgag   1740

tgggtggttt gcgaggatga gggacgctat gcctcatgcc cgttttgggt gtcctcacca   1800

gcaaggctgc tcgggggccc ctggttcgtc cctgagcctt tttcacagtg cataagcagt   1860

tttttttgtt tttgttttgt tttgttttgt ttttaaatca atcatgttac actaatagaa   1920

acttggcact cctgtgccct ctgcctggac aagcacatag caagctgaac tgtcctaagg   1980

caggggcgag cacggaacaa tggggccttc agctggagct gtggactttt gtacatacac   2040

taaaattctg aagttaaagc tctgctcttg gaaaaaaaaa aaaaaaaaaa aaaaaaaaaa   2100

aa                                                                   2102
```

```
<210> SEQ ID NO 5
<211> LENGTH: 2374
<212> TYPE: DNA
<213> ORGANISM: Homo sapiens

<400> SEQUENCE: 5

ctcctccagc tcttcctgtc ccgctgttgc aacactgcct cactcttccc ctcccacctt     60

ctctcccctc ctctctgctt taattttctc agaattctct ggactgaggc tccagttctg    120

gcctttgggg ttcaagatca ctgggaccag gccgtgatct ctatgcccga gtctcaaccc    180

tcaactgtca ccccaaggca cttgggacgt cctggacaga ccgagtcccg ggaagcccca    240
```

-continued

```
gcactgccgc tgccacactg ccctgagccc aaatggggga gtgagaggcc atagctgtct    300
ggcatgggcc tctccaccgt gcctgacctg ctgctgccac tggtgctcct ggagctgttg    360
gtgggaatat accccctcagg ggttattgga ctggtccctc acctagggga cagggagaag    420
agagatagtg tgtgtcccca aggaaaatat atccaccctc aaaataattc gatttgctgt    480
accaagtgcc acaaaggaac ctacttgtac aatgactgtc caggcccggg gcaggatacg    540
gactgcaggg agtgtgagag cggctccttc accgcttcag aaaaccacct cagacactgc    600
ctcagctgct ccaaatgccg aaaggaaatg ggtcaggtgg agatctcttc ttgcacagtg    660
gaccgggaca ccgtgtgtgg ctgcaggaag aaccagtacc ggcattattg gagtgaaaac    720
cttttccagt gcttcaattg cagcctctgc ctcaatggga ccgtgcacct ctcctgccag    780
gagaaacaga acaccgtgtg cacctgccat gcaggtttct ttctaagaga aaacgagtgt    840
gtctcctgta gtaaagtcct gctctgtcgc ccaggctgga atgcagtggc gcgatctcgg    900
ctcactgcaa cctctgcctc ccagattcaa gcaattctcc tgcttcagcc tcccaagtag    960
ctgggattac agctgtaaga aaagcctgga gtgcacgaag ttgtgcctac cccagattga   1020
gaatgttaag ggcactgagg actcaggcac cacagtgctg ttgcccctgg tcattttctt   1080
tggtctttgc cttttatccc tcctcttcat tggtttaatg tatcgctacc aacggtggaa   1140
gtccaagctc tactccattg tttgtgggaa atcgacacct gaaaaagagg gggagcttga   1200
aggaactact actaagcccc tggccccaaa cccaagcttc agtcccactc caggcttcac   1260
ccccaccctg ggcttcagtc ccgtgcccag ttccaccttc acctccagct ccacctatac   1320
ccccggtgac tgtcccaact ttgcggctcc ccgcagagag gtggcaccac cctatcaggg   1380
ggctgacccc atccttgcga cagccctcgc ctccgacccc atccccaacc cccttcagaa   1440
gtgggaggac agcgcccaca agccacagag cctagacact gatgaccccg cgacgctgta   1500
cgccgtggtg gagaacgtgc ccccgttgcg ctggaaggaa ttcgtgcggc gcctagggct   1560
gagcgaccac gagatcgatc ggctggagct gcagaacggg cgctgcctgc gcgaggcgca   1620
atacagcatg ctggcgacct ggaggcggcg cacgccgcgg cgcgaggcca cgctggagct   1680
gctgggacgc gtgctccgcg acatggacct gctgggctgc ctggaggaca tcgaggaggc   1740
gctttgcggc cccgccgccc tcccgcccgc gcccagtctt ctcagatgag gctgcgcccc   1800
tgcgggcagc tctaaggacc gtcctgcgag atcgccttcc aaccccactt ttttctggaa   1860
aggaggggtc ctgcaggggc aagcaggagc tagcagccgc ctacttggtg ctaacccctc   1920
gatgtacata gcttttctca gctgcctgcg cgccgccgac agtcagcgct gtgcgcgcgg   1980
agagaggtgc gccgtgggct caagagcctg agtgggtggt ttgcgaggat gagggacgct   2040
atgcctcatg cccgttttgg gtgtcctcac cagcaaggct gctcgggggc ccctggttcg   2100
tccctgagcc tttttcacag tgcataagca gtttttttttg tttttgtttt gttttgtttt   2160
gtttttaaat caatcatgtt acactaatag aaacttggca ctcctgtgcc ctctgcctgg   2220
acaagcacat agcaagctga actgtcctaa ggcagggggcg agcacggaac aatggggcct   2280
tcagctggag ctgtggactt ttgtacatac actaaaattc tgaagttaaa gctctgctct   2340
tggaaaaaaa aaaaaaaaaa aaaaaaaaaa aaaa                                2374
```

<210> SEQ ID NO 6
<211> LENGTH: 455
<212> TYPE: PRT
<213> ORGANISM: Homo sapiens -continued

<400> SEQUENCE: 6

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415
```

-continued

```
Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 7
<211> LENGTH: 347
<212> TYPE: PRT
<213> ORGANISM: Homo sapiens

<400> SEQUENCE: 7

Met Gly Gln Val Glu Ile Ser Ser Cys Thr Val Asp Arg Asp Thr Val
1               5                   10                  15

Cys Gly Cys Arg Lys Asn Gln Tyr Arg His Tyr Trp Ser Glu Asn Leu
            20                  25                  30

Phe Gln Cys Phe Asn Cys Ser Leu Cys Leu Asn Gly Thr Val His Leu
        35                  40                  45

Ser Cys Gln Glu Lys Gln Asn Thr Val Cys Thr Cys His Ala Gly Phe
    50                  55                  60

Phe Leu Arg Glu Asn Glu Cys Val Ser Cys Ser Asn Cys Lys Lys Ser
65                  70                  75                  80

Leu Glu Cys Thr Lys Leu Cys Leu Pro Gln Ile Glu Asn Val Lys Gly
                85                  90                  95

Thr Glu Asp Ser Gly Thr Thr Val Leu Leu Pro Leu Val Ile Phe Phe
            100                 105                 110

Gly Leu Cys Leu Leu Ser Leu Leu Phe Ile Gly Leu Met Tyr Arg Tyr
        115                 120                 125

Gln Arg Trp Lys Ser Lys Leu Tyr Ser Ile Val Cys Gly Lys Ser Thr
    130                 135                 140

Pro Glu Lys Glu Gly Glu Leu Glu Gly Thr Thr Thr Lys Pro Leu Ala
145                 150                 155                 160

Pro Asn Pro Ser Phe Ser Pro Thr Pro Gly Phe Thr Pro Thr Leu Gly
                165                 170                 175

Phe Ser Pro Val Pro Ser Ser Thr Phe Thr Ser Ser Ser Thr Tyr Thr
            180                 185                 190

Pro Gly Asp Cys Pro Asn Phe Ala Ala Pro Arg Arg Glu Val Ala Pro
        195                 200                 205

Pro Tyr Gln Gly Ala Asp Pro Ile Leu Ala Thr Ala Leu Ala Ser Asp
    210                 215                 220

Pro Ile Pro Asn Pro Leu Gln Lys Trp Glu Asp Ser Ala His Lys Pro
225                 230                 235                 240

Gln Ser Leu Asp Thr Asp Asp Pro Ala Thr Leu Tyr Ala Val Val Glu
                245                 250                 255

Asn Val Pro Pro Leu Arg Trp Lys Glu Phe Val Arg Arg Leu Gly Leu
            260                 265                 270

Ser Asp His Glu Ile Asp Arg Leu Glu Leu Gln Asn Gly Arg Cys Leu
        275                 280                 285

Arg Glu Ala Gln Tyr Ser Met Leu Ala Thr Trp Arg Arg Arg Thr Pro
    290                 295                 300

Arg Arg Glu Ala Thr Leu Glu Leu Leu Gly Arg Val Leu Arg Asp Met
305                 310                 315                 320

Asp Leu Leu Gly Cys Leu Glu Asp Ile Glu Glu Ala Leu Cys Gly Pro
```

```
                325                 330                 335

Ala Ala Leu Pro Pro Ala Pro Ser Leu Leu Arg
            340                 345


<210> SEQ ID NO 8
<211> LENGTH: 302
<212> TYPE: PRT
<213> ORGANISM: Homo sapiens

<400> SEQUENCE: 8

Met Gln Trp Arg Asp Leu Gly Ser Leu Gln Pro Leu Pro Pro Arg Phe
1               5                   10                  15

Lys Gln Phe Ser Cys Phe Ser Leu Pro Ser Ser Trp Asp Tyr Ser Cys
            20                  25                  30

Lys Lys Ser Leu Glu Cys Thr Lys Leu Cys Leu Pro Gln Ile Glu Asn
        35                  40                  45

Val Lys Gly Thr Glu Asp Ser Gly Thr Thr Val Leu Leu Pro Leu Val
    50                  55                  60

Ile Phe Phe Gly Leu Cys Leu Leu Ser Leu Leu Phe Ile Gly Leu Met
65                  70                  75                  80

Tyr Arg Tyr Gln Arg Trp Lys Ser Lys Leu Tyr Ser Ile Val Cys Gly
                85                  90                  95

Lys Ser Thr Pro Glu Lys Glu Gly Glu Leu Glu Gly Thr Thr Thr Lys
            100                 105                 110

Pro Leu Ala Pro Asn Pro Ser Phe Ser Pro Thr Pro Gly Phe Thr Pro
        115                 120                 125

Thr Leu Gly Phe Ser Pro Val Pro Ser Ser Thr Phe Thr Ser Ser Ser
    130                 135                 140

Thr Tyr Thr Pro Gly Asp Cys Pro Asn Phe Ala Ala Pro Arg Arg Glu
145                 150                 155                 160

Val Ala Pro Pro Tyr Gln Gly Ala Asp Pro Ile Leu Ala Thr Ala Leu
                165                 170                 175

Ala Ser Asp Pro Ile Pro Asn Pro Leu Gln Lys Trp Glu Asp Ser Ala
            180                 185                 190

His Lys Pro Gln Ser Leu Asp Thr Asp Asp Pro Ala Thr Leu Tyr Ala
        195                 200                 205

Val Val Glu Asn Val Pro Pro Leu Arg Trp Lys Glu Phe Val Arg Arg
    210                 215                 220

Leu Gly Leu Ser Asp His Glu Ile Asp Arg Leu Glu Leu Gln Asn Gly
225                 230                 235                 240

Arg Cys Leu Arg Glu Ala Gln Tyr Ser Met Leu Ala Thr Trp Arg Arg
                245                 250                 255

Arg Thr Pro Arg Arg Glu Ala Thr Leu Glu Leu Leu Gly Arg Val Leu
            260                 265                 270

Arg Asp Met Asp Leu Leu Gly Cys Leu Glu Asp Ile Glu Glu Ala Leu
        275                 280                 285

Cys Gly Pro Ala Ala Leu Pro Pro Ala Pro Ser Leu Leu Arg
    290                 295                 300


<210> SEQ ID NO 9
<211> LENGTH: 12761
<212> TYPE: DNA
<213> ORGANISM: Mus musculus

<400> SEQUENCE: 9

cgctcttgca acaccacccc cgccactctc ccttcccctc ctaccttctc tctcccctca      60
```

-continued gcttaaattt tctccgagtt ttccgaactc tggctcatga tcgggcctac tgggtgcgag 120
gtcctggagg accgtaccct gatctctatc tgcctctgac tttcagcttc tcgaactcga 180
ggcccaggct gccatcgccc gggccacctg gtccgatcat cttacttcat tcacgagcgt 240
tgtcaattgc tgccctgtcc ccagccccaa tgggggagtg agaggccact gccggccgga 300
catgggtctc cccaccgtgc ctggcctgct gctgtcactg gtgagatggg agactggagg 360
ggagggtggg ttgctagcga ggcgccgggc aggagtgggc ttgtactagg ggtagagatg 420
ggggcagggg cttctgtgct ttagtttgac gccaggtttg ctgtgcctca cctggggctg 480
ccctgagatg tggaagggag aaatctgaga gggagagaat ctggcaagcc aagctggcaa 540
gcctgggccc ctgacagtca aggtcctggc ccgtgttggg ctgtggtcag gccagctgct 600
cggccagtgg agttagacgg agaagccttc tttctctggc cgaggttgaa cagcgtgggg 660
cagggtgttg gaagactggg tgctaggaga accgctttgg cgggacgagt ttgggaaagc 720
gtgcttggga gtggacccga aactggacaa agctgggcag ccttccggtc ccagacttct 780
ccctgagaca gcctctgacc ttctgccgcc tccatttctg cttccagaca agaggtccct 840
cctggcgtga ccctccttaa gtagctaata cctctttatc taggccatgt atcctcctgc 900
tccctcccca cagacccaaa agtcagtctc acggtttcca attccacagt tccaattggg 960
gaagttggta gcagcttgtt ttcgtcactg gaaaatgtac ttttctctgg cctcggccta 1020
gtgttcatgt tctcttgatt tctgtgtgtc cataattatt ctgtgtagat cctgggggct 1080
ccctggctgt ctgggtgggc tgtaccatcg gcgcagtgtt ctctgggtcc tgcctctccc 1140
tggcccagcg ttatccctga gacctgcctt tttctccctc ccctttcact cctcattctc 1200
ttctggtcag tctccagagc ctccttgcgg gggtggggtg ggggggtggg ggtggctcct 1260
ttgtgtctat tcccttccct ttctctacac accattctaa agcagtggtc ctagaaccct 1320
gcctgggtgt cacctcccct ctcctggtcc tgtcctgtct cccagtctct cctgggagac 1380
ttgtcaaggc tgcccctctg gctgttctcc aactccccca cccacttaat tcttttctct 1440
ttaggggtag atcacctgga tttagggctc agcccagcac ccttaccctc atgaacgcag 1500
gcatgtgatg tgactccccc gctttttgtt tcttttattt ccaaaatgtc tacaatgatc 1560
agtacctcat agttgttatt aagattgagt agatggattt gtgttaaata tttattcatt 1620
tccttccctg ctaggtccaa ttcagattag gtgaatgatc ccaaagggga gtaagaagta 1680
tgccacaaac agaaaggact cagcttggct tctctcttct catctctagc agtgatactc 1740
gtcactactc acgtcactac tcattgtgac ggtagatgtc acaataactg tcagagtgca 1800
gtggcccagc taggtagagg agagaggctg agccagttgt ggaggcccag gtgagggtgg 1860
gggcaccgtg aacagaagca gatcctgaag acaaggcaca cggaaggcta ctgaagtcta 1920
catggggctg gccactgcct tatcagtaca gagcacagtg cctgtgaggt gttcaggtag 1980
gacgaggtgc tgaggtcatg aggcagtgat ggccgtggca gggatgtggc aaggccaaga 2040
agactttgct atttttaaaa agtttcagta caggagtgga aatgacttta gaatactctg 2100
gaggaaaaga cgttccaagg ccttggtgat gtactatccc agaggcagaa ctgggggagg 2160
agggtgggct atatgccaac tgtcttcttg cttaatggcc tttgcctgtc tgctgggctg 2220
agcttgcctg catagaccct aaggctcata gtgtgttatc atctttggct catggagagc 2280
tcttgaaact gtgagctatg tcccatcccc agcacctatc caggccctga aaaagaaacc 2340
ttgaccgttg actaatggct taatcaattc aggaacaaga gattggtcag atgggaacaa 2400

-continued

```
ggcgggtgtt gcatagaaag gaggacttgg aactggtgtg cagaagccag gaggaggaag   2460
aacagaggag ttgggcgcct gggttggggg aatggagagg tgggactttg aagtcacaga   2520
agctgaacat ctcagctcgg ggtggagtgg ccatgttgag aaatgtgaca gagagagaag   2580
ggcactctgg cgtttgtgaa aaagaacctt gagccagtca ccttggggca tgcctgttat   2640
cctggaactt gggagatgga ggccagtgct cagatcgagg cccagttttg gctatatagg   2700
gagctggagg ccagcctgga tgactgagac tgtgtcttaa aaacaccaaa aagaaataaa   2760
gagtcatgct taaggaccta ggtgggggcc tgttttcctc tttccctccc tctctccctc   2820
ccttcctccc tccctccctc cctcctccct ccccttcctc ctttgctatc caccaagcag   2880
tctggccaga ctgtgttcca aagaacagtg agtttctcag atgtatgtgc tcatggaagg   2940
atttatccat ggaaatgatg tttgaagcca ggccctggag gtgcagagga agattcacac   3000
ccaggtggta caagttgaag cctgaatgta gataagaaac tatgtaggta gcctcagccc   3060
ctgcaaaggt ttgaggcagg cacatcactt gaaccagaag gttcgtggca gcctgagcca   3120
catagtgaag ccctgagaca ccactgtgga gtaggaagga gaaaggcagt tgtaaaaacc   3180
agggctccgg gtgtggggta aagggtggag aggttccaga aggactgact gatgagtctt   3240
agggctgttg cagagtttgc agcattggta ccaagaagtc ggtggtgtga catctaggca   3300
aggagcttgg tgagctcagc tgggggcagg ttaaagtagg tcactggctg gctaagtgga   3360
agtgtggttg tgctgtctgg agcagccctt ctcagccttt cttccagcta attccagctg   3420
catggctcgt cagctggact ctgcaggaga tgagcaaatg tggcagaatt gtcaccaggg   3480
acatgtgcac gagtgtgccc gtgtgtgggg aaggggatgc acagcttcta aaatacctcc   3540
cagaggcaga gtgtgtttga ggcaggggga tgctgcttcc ttccatccgg ctccctgact   3600
ggaaggcacc tcagtccctc aggtctgcag gcctggctct gggtgatgtg accaagacat   3660
gctctgatct cttaactcag agggtttgtg gtctgtctgg ggagattgta tctactcatt   3720
tgaaataact atagcttctg ataagagccc agagtagata tggatagttc gtgttattca   3780
accagaacag gcggctaggt atccgaggag cttgggtggg gagacatgaa tcatcgacgg   3840
ggggcttcgt gggtggaagg taggattgcg gcagcgtggc agcgctctct gaggaggtca   3900
caccgaagag ctcctcacca ccgtaggtct tgacattaag tggaacacag tttaacctaa   3960
tgtgcacgct gatgtggggc ttagtgagtg ggtccccaaa aggtggctgg gtcaagtttg   4020
accacagggt ccatttcatc ttcgctcccc tactcagcag ccccggcaca ggaagtcaca   4080
ctttaaggcc tctctaggcg gaagctgagg agtagttaga gaggccttgc cacctcctca   4140
gccatctctc ctctcctcag gcaccccccca gcatcctgcc cctcctctgc tccaggcatt   4200
caagtttggg ccaggacctg tgtcccttgt cccttgttgg cctcacaatg caactggtaa   4260
tagggtgcct attgaaagag ccagagggcc ctggaatccc tggagcatgt gagatgagag   4320
agctggctct gcacctgctc cttctctttt gttaccttgt ttttgttgag agtagacctg   4380
gctgtcctag aactcacatt gtagagcagg ctggccttga acccagggat ctgcctgcct   4440
ccacctctca gagtgcctgg attaatgtct agcttcctcc atctcttcta accttaagag   4500
ggctgtgatt tttgttccat agctacttga cctggggaga actggccctg tctcttaaag   4560
gttgtctagg gagcatccaa acccaatgca agtggccaga accaggcagg ctatgggaat   4620
gtggtgaact agggcgggag ggcaccctgg atttgattct tgttgggatt ggggagtgtc   4680
aggggctgcc aaaggcccag ggagccaggg agcagggatc ctgggaaagg ctttatcagc   4740
tgaagacgat gttgtttccc tttgaggagg gatcaaggca gctccaagtc caaaggaagg   4800
```

-continued

```
atgtcagaga tggaggaggt agatcctctg ggaggagctt actggcctga cagggaagcc   4860
aggggtcaga aagacttccc tttgggatgg gatggaagag ggaggcattt tcccgaaatc   4920
tgagcccagt gggacagggg ttcattgcct ggacgaatgg tctgagtggg ggtgggtgag   4980
agagagagag agactgtgca cccaggaggg agcagatggg gttccacttg ctgctggttg   5040
gcttttctgc tgattcacag cccttgttga gccgggaagc tgcagttccc tgtccactgt   5100
cctagatctc cctccctggc ctgagtcact ggggcggagc tgctgggaaa agatttccct   5160
ttcccggatt tgacttaacc cccagagttc tgcaaaggaa ggacacgtga ccaaagaaac   5220
aggctccttc tctggaggct cgtccatcgc tggttgagac tcgcccccac ccccaccccc   5280
gcaaggccgt tcttggcctg gagcccacat ctacctcttc ctgacactgc ctgatctgtt   5340
ggtttggctt caggttctct gatggggttg gaagtaccac tgaccttagg tgctccaagc   5400
atttcttctt cggggaaagg aaccacactt tcatgattgg gaagttctta tcataactaa   5460
cccttcctgt caccctggaa gcctctgtgt gtcgtgaggg gtgggggtgc acccctgcct   5520
gagagattgc tggtgtgctt tctgtgtgtg gcttcttggg tctatggctg aggcaagggg   5580
cttcctggcc cgtgcagctg ctgtgccgag gaggtagcac ttctagtaac agcagctgac   5640
agcagggtgc aagctgccag cctctttcca aacggagctt tgggggttgc agagccccca   5700
aaggcagctg tgagtctagg tgttaggtct ctcctgaatg tgatctgatt ggtcagttgc   5760
ttctgcatct gtcttgaaga cctccgctat cttgacgtaa caacgctatg cgaggggggg   5820
aggggagatg aaagaaggaa ggctgaggga aacccaaaac cgggagagat caaagagcaa   5880
ggtctacatt gaaactaaga gggctttgcg ctctccatac tgaagctgtt tacatacaag   5940
aaagccagtt ggttgctatg agctttgcca agattataaa gccagccctc tagaatgccc   6000
tgctttggga ctcctggcac atcctcagct cctgaattga gggtcatctt gaatcagatc   6060
accaatctct ggtcaactct agtacatgac acatttgtct ttggtcttac ttaatccttg   6120
tcgcgcctgc atgctcggag ttcttccttt tgtttctgtc ccgcaatggt gcttgggaga   6180
gcattatccc caggtgcgca ttcatatctg ggtgtttgag tgtgcacgga ggtcagaggt   6240
catcctcagg tgtttgcttc ccatcagttg gactaggttg cttagacaga gatcatcagg   6300
ggcctacctg gtgggctccc ctccatcacc gggaatacaa gcccgtacct ggctttttat   6360
gtaggtgatg gtgctcgatg tcaggtcctc acgtcgcaca gctgacactt tcctgaacca   6420
tcttcatgac agccctccct tcaacttgat ttcccccccc cagtagtact ttttgaatta   6480
ctgtcatgga atccaaagag gtttgtagat cctaatggct cacctctagg aagtgtccac   6540
aaacaggctt agtgtgaaac ccgtacccag atatagaaat gccaaatgag tagtaggatt   6600
gattgtctgt tggaaaaaca ggctgtaacg gaaacagcct gctacttctg gctaacattt   6660
cttggtcggg cagagggcat tgcagtgctt ctgtgtgaga cctggagctc caccctcagc   6720
cctgcagaca cacggggaaa ctaaacattc cttgaccggc tctcttgtga tcagcactgg   6780
gagccgcttc agggaactga acgggataaa atgcagctgg ggcctgagac ctaattgctc   6840
agttgtagaa acaaatgcta gcatacagag ccaccagaga ccaagaaaat actagactgc   6900
acagtcgcca ccatctaggg gagagtgtcc ctagggggtg gggggaatgt gaacttgtct   6960
ctctctctct ctctctctct ctctctctct ctctctctgt gtgtgtgtgt gtgtgtgtgt   7020
gtgtgtgtgt gtgtgttcaa tttgttgcta cctctaaggc cccacccctg acagtatttc   7080
ctctttctga ttgttccctc aggtgctcct ggctctgctg atggggatac atccatcagg   7140
```

-continued ggtcactgga ctagtccctt ctcttggtga ccgggagaag agggatagct tgtgtcccca 7200
aggaaagtat gtccattcta agaacaattc catctgctgc accaagtgcc acaaaggtag 7260
gagaaagtga gagcagagaa ttgtcttgag atttcttttg cttttttttt ttttttttt 7320
ttgagacagg gtttctctat acccctgtct gtcctggaac tcactttgta gaccaggctg 7380
gcctcgaaca cagaaatctg cctgcctctg cctcccgagt gctgggatta aaggcgtgcg 7440
cctccacgcc ccggcttctt ttgcttgttt ctgatgttcc ccgaccttgg tccctgggag 7500
tccccttatt ttgctgcccc actccctgcc cccgacttgg gttttgccct ttagttctcc 7560
actacagcct gaccctaacc ctatctacag gaacctactt ggtgagtgac tgtccgagcc 7620
cagggcggga tacagtctgc agggagtgtg aaaagggcac ctttacggct tcccagaatt 7680
acctcaggca gtgtctcagt tgcaagacat gtcggaaagg taagccttgg gattgggcca 7740
gggctataga aggtgcatgg tgtgtgaaga cgtgcgaaca tgtgtgtgtg tccgtgggtg 7800
ttggccagga ggtcaggatt tcgaatctgc tcgtgagtgt ggcggtagta tgcatgcgtg 7860
cacatgcaag ctcgggcctg tgtgcgtagg aggagtgtct gttacaaaga cgaatgccat 7920
gtggcagagc cagggggcgt caagatttgt gtgggaaaag ggatgtgaga ctcacacacc 7980
atttccttcc ctcttcagaa atgtcccagg tggagatctc tccttgccaa gctgacaagg 8040
acacggtgtg tggctgtaag gagaaccagt tccaacgcta cctgagtgag acacacttcc 8100
agtgcgtgga ctgcagcccc tgcttcaacg gcaccgtgac aatcccctgt gagcaccggt 8160
cacccaagtc ctctcccctc cccgggagca ccctgccccc ctcctctgcc ccccacccta 8220
tcctgtctgt gtgtctgagc tcctatgtgg cacctgcatt cccgccctcg tccctccctc 8280
gggccctcag actgcaggca cgcgctctta gtcttaaccg ctttcccaca ggtaaggaga 8340
ctcagaacac cgtgtgtaac tgccatgcag ggttctttct gagagaaagt gagtgcgtcc 8400
cttgcagcca gtgagtatct gccaagtgct tggggttcag gggtgggtga gcagctgtgg 8460
ctgaggggcc ccagcagggt caaaggtggg atcctacagc cggatgagca gaagacacta 8520
caagacatca gacagccctt tccctttctc caggacgtta ggggataagc aatagggctt 8580
agcgggtaaa gcgcttgcag caaacgtctg gcaacctgag ttcaagctct ggaaccccgt 8640
cttgtaaagg tgacaggaga gaatatcagg tgcacaacgt catcctctga ctgccacaca 8700
cacgtgctat agctcgcatg cctcttcagt gctgggcagt tagatccgag cgcgctgttc 8760
ttgactgcac tctggtgcat cttactgttg atggtatctt aggtttggct cgcacaagct 8820
ctaccgctgg ggatcccttc ttcccaggct ccctgacaga cttcctcatt cctgtggctc 8880
cgcatgggct gctcttatac atttgcttcc agagaagact ctcatagttg acctgacttg 8940
ggggttaaat cccaacttac ctttttcctg gctctgcaac cttgggcaag ttcttacctc 9000
tctacgcctt atgtttctta acctttaggg taaggagagt gggggtggag atgtggatca 9060
acggtagagc actggcctag cgtattggag gctctgggtt agatccccaa aacagacagc 9120
taaaccaaca atctatagga ctgtctgaac caaagctgtc tactttctat tttttttcc 9180
acgcagtttc atctcaaaag agctcatgtg cccatgtgtt caccctgtca tgaggtagac 9240
aaaacctcct ttccctgttc tgctgagaac gcatgttcct ctgccgtccc cctgccccca 9300
cccagtgtag ttttctcatc ccctctgccc tgtgacagct ctcaatggct gccccaatga 9360
gagacatcct aaaacctccc gtgcccttga ggcctgccgt ctccaaagtc aagtgctgta 9420
agcagccgga ccattggctg ggaagccctc cagcgtctca tatgagtcct ctttctgggc 9480
acgcggcttc atcagcttaa agcaaagacc ggctggtttc attcagctcc tggtggttgg 9540

-continued

```
cgttgctgct ttagagtcag tgctgaggca ggggcatcat gatcagagca tactgtgcaa   9600
gcacagtagc tcacctcgca gcccctgaga ggccaaagga aagggtgtgg agaggggtca   9660
aaagtgagcc ctcagggacc taacttatac tagtccccat gtcccagtat gctgggacca   9720
agccttcaac acatggaccc agcaggacat ttcagatcca tgccctaccg gcaaacacaa   9780
tgataaaccc agtctactac agctgccgtc taccgtgcca tgtcagggcc aagtacttga   9840
tcccagaagg aggtgtcatg agcgccatga gatgctggac cagaaaagtg aagtgactta   9900
tttctgtcat gttgccagtc aatgactgga atggaatttt tactcttgac tataaaggcc   9960
ttttaaattt tatttttaaa atactgattg attgttgaat ccgggctctt cgcatgctat  10020
tcacgtgctc taccatggag ccaaaatacc ctcagccctt cgaccgtttg attttatttc  10080
atttcatttt atttatttct ttttactcag ggtctcactg agtagccttg gctggcctgg  10140
gactaggtgg accaggctgg ccttgaactc ctaaatatct gcctgcttta gcctcccgac  10200
cactgggatg tgtcaccatg cctggcattt aaaaaatact ttaagaatta tttattttca  10260
ttctatgtgt atgagtgttt tgccagcatg catatatgtg tactgtgtac attgctcagt  10320
atcctcagag gccagaagag ggcgttagat accctggaac tggagttaca gatggccgtg  10380
agctgccatg tggggtgatg actgtgtcaa actcatcaag atggccgact tgccctctct  10440
ctccctttcc cctccctttc ctctctagtc tctttctgga caggatctcc tgttgcccag  10500
gctgaccctg accttgctgg gtagccatgg gtggccttaa accgatcctt tcgtcacttc  10560
ctgccaagtg ctgagatcac gtgcatccac ttctgctcct gcctgtccac acagccttcc  10620
cgggctccca tcagcttgta aactgttgta cggtgtggac tgtctcgttc ttccccacca  10680
gctctcaagg cgggttgaag agatagcaaa accatttgca aagcaaagaa ctgcaggcag  10740
ccttcctgct aaccggtgcc ttctcttctt tcagctgcaa gaaaaatgag gagtgtatga  10800
agttgtgcct acctcctccg cttgcaaatg tcacaaaccc ccaggactca ggtgaggggg  10860
ggtggcttgg tgccagctca ccgagctggc tggctgactc catgacctcc ctccaccccc  10920
accctttacc ccccagcccc ctagtctctg ctgtggcctc acactgagca acctctctgg  10980
tctgcaggta ctgcggtgct gttgcccctg gttatcttgc taggtctttg ccttctatcc  11040
tttatcttca tcagtttaat gtgccgatat ccccggtgga ggcccgaagt ctactccatc  11100
agtaagtagg actttgggga tatagggtgt tggtggagat acgggagggg ttcgggtggg  11160
caagttggag ggaaatgagg ggtggcctct cttcatggtt aaggactcta ggctgagtgg  11220
ccctggatgg tgggagggaa gccatactga tatccgtaat tctcttgtcc ctggggccac  11280
atagaccctg gggcatgaca ccacaagtcc ccaaggtcag cgttgaaagg gaagtgaaat  11340
tcatgacacc ttgtttcttt gttctccagt ttgtagggat cccgtgcctg tcaaagaggt  11400
gagaagggac gactccagct tccctgacta ctccttccaa cgcctgatac ctaaattact  11460
tggaatgagg gcggtgggct cccttagctc ctctgtcccc acccccataa agaataaagc  11520
gcccgaaggg agtccttttc tttactccca ctaatgctat gctttctttc tttcaggaga  11580
aggctggaaa gcccctaact ccagcccccct ccccagcctt cagccccacc tccggcttca  11640
accccactct gggcttcagc accccaggct ttagttctcc tgtctccagt acccccatca  11700
gccccatctt cggtcctagt aactggcact tcatgccacc tgtcagtgag gtagtcccaa  11760
cccagggagc tgaccctctg ctctacgaat cactctgctc cgtgccagcc cccacctctg  11820
ttcagaaatg ggaagactcc gcccacccgc aacgtcctga cagtgagttg ggttcctgct  11880
```

-continued

```
ggggcattac tcctggaggg agtcgggcag ggtggagggc acaaaggcag gctgctgctg  11940
gaagtgcacg gtccttgtcc ccagatgcag accttgcgat tctgtatgct gtggtggatg  12000
gcgtgcctcc agcgcgctgg aaggagttca tgcgtttcat ggggctgagc gagcacgaga  12060
tcgagaggct ggagatgcag aacgggcgct gcctgcgcga ggctcagtac agcatgctgg  12120
aagcctggcg gcgccgcacg ccgcgccacg aggacacgct ggaagtagtg ggcctcgtgc  12180
tttccaagat gaacctggct gggtgcctgg agaatatcct cgaggctctg agaaatcccg  12240
ccccctcgtc cacgacccgc ctcccgcgat aaagccacac ccacaacctt aggaagaggg  12300
acttgaactt caaggaccat tctgctagat gccctactcc ctgtgggtga aaagtgggca  12360
aaggtctcta aggggaaggc tcgagctggt agccacttcc ttggtgctac caacttggtg  12420
tacatagctt ttctcagccg ccgaggactg cctgagccag ccacttgtga gtggcaggga  12480
gatgtaccat cagctcctgg ccagctgagg gtgccaaaga caggattgta gaggaaaggc  12540
acaatgtatc tggtgcccac ttgggatgca cagggcccaa gccaagcttc tcagggcctc  12600
ctcagtgggt ttctgggcct tttcacttt tgataagcaa tctttgtatc aattatatca  12660
cactaatgga tgaactgtgt aaggtaagga caagcataga aaggcggggt ctccagctgg  12720
agccctcgac tcttgtaaat acactaaacg tctaaaaatg a                     12761
```

<210> SEQ ID NO 10
<211> LENGTH: 2186
<212> TYPE: DNA
<213> ORGANISM: Mus musculus

<400> SEQUENCE: 10

```
cgctcttgca acaccacccc cgccactctc ccttcccctc ctaccttctc tctcccctca     60
gcttaaattt tctccgagtt ttccgaactc tggctcatga tcgggcctac tgggtgcgag    120
gtcctggagg accgtaccct gatctctatc tgcctctgac tttcagcttc tcgaactcga    180
ggcccaggct gccatcgccc gggccacctg gtccgatcat cttacttcat tcacgagcgt    240
tgtcaattgc tgccctgtcc ccagccccaa tgggggagtg agaggccact gccggccgga    300
catgggtctc cccaccgtgc ctggcctgct gctgtcactg gtgctcctgg ctctgctgat    360
ggggatacat ccatcagggg tcactggact agtcccttct cttggtgacc gggagaagag    420
ggatagcttg tgtccccaag gaaagtatgt ccattctaag aacaattcca tctgctgcac    480
caagtgccac aaaggaacct acttggtgag tgactgtccg agcccagggc gggatacagt    540
ctgcagggag tgtgaaaagg gcacctttac ggcttcccag aattacctca ggcagtgtct    600
cagttgcaag acatgtcgga aagaaatgtc ccaggtggag atctctcctt gccaagctga    660
caaggacacg gtgtgtggct gtaaggagaa ccagttccaa cgctacctga gtgagacaca    720
cttccagtgc gtggactgca gcccctgctt caacggcacc gtgacaatcc cctgtaagga    780
gactcagaac accgtgtgta actgccatgc agggttcttt ctgagagaaa gtgagtgcgt    840
cccttgcagc cactgcaaga aaaatgagga gtgtatgaag ttgtgcctac ctcctccgct    900
tgcaaatgtc acaaaccccc aggactcagg tactgcggtg ctgttgcccc tggttatctt    960
gctaggtctt tgccttctat cctttatctt catcagttta atgtgccgat atccccggtg   1020
gaggcccgaa gtctactcca tcatttgtag ggatcccgtg cctgtcaaag aggagaaggc   1080
tggaaagccc ctaactccag ccccctcccc agccttcagc cccacctccg gcttcaaccc   1140
cactctgggc ttcagcaccc caggctttag ttctcctgtc tccagtaccc ccatcagccc   1200
catcttcggt cctagtaact ggcacttcat gccacctgtc agtgaggtag tcccaaccca   1260
```

```
gggagctgac cctctgctct acgaatcact ctgctccgtg ccagcccccca cctctgttca   1320

gaaatgggaa gactccgccc acccgcaacg tcctgacaat gcagaccttg cgattctgta   1380

tgctgtggtg gatggcgtgc ctccagcgcg ctggaaggag ttcatgcgtt tcatggggct   1440

gagcgagcac gagatcgaga ggctggagat gcagaacggg cgctgcctgc gcgaggctca   1500

gtacagcatg ctggaagcct ggcggcgccg cacgccgcgc cacgaggaca cgctggaagt   1560

agtgggcctc gtgctttcca agatgaacct ggctgggtgc ctggagaata tcctcgaggc   1620

tctgagaaat cccgccccct cgtccacgac ccgcctcccg cgataaagcc acacccacaa   1680

ccttaggaag agggacttga acttcaagga ccattctgct agatgcccta ctccctgtgg   1740

gtgaaaagtg ggcaaaggtc tctaagggga aggctcgagc tggtagccac ttccttggtg   1800

ctaccaactt ggtgtacata gcttttctca gccgccgagg actgcctgag ccagccactt   1860

gtgagtggca gggagatgta ccatcagctc ctggccagct gagggtgcca aagacaggat   1920

tgtagaggaa aggcacaatg tatctggtgc ccacttggga tgcacagggc ccaagccaag   1980

cttctcaggg cctcctcagt gggtttctgg gcctttttca cttttgataa gcaatctttg   2040

tatcaattat atcacactaa tggatgaact gtgtaaggta aggacaagca tagaaaggcg   2100

gggtctccag ctggagccct cgactcttgt aaatacacta aacgtctaaa aatgaaaaaa   2160

aaaaaaaaaa aaaaaaaaaa aaaaaa                                          2186
```

<210> SEQ ID NO 11
<211> LENGTH: 454
<212> TYPE: PRT
<213> ORGANISM: Mus musculus

<400> SEQUENCE: 11

```
Met Gly Leu Pro Thr Val Pro Gly Leu Leu Leu Ser Leu Val Leu Leu
1               5                   10                  15

Ala Leu Leu Met Gly Ile His Pro Ser Gly Val Thr Gly Leu Val Pro
            20                  25                  30

Ser Leu Gly Asp Arg Glu Lys Arg Asp Ser Leu Cys Pro Gln Gly Lys
        35                  40                  45

Tyr Val His Ser Lys Asn Asn Ser Ile Cys Cys Thr Lys Cys His Lys
    50                  55                  60

Gly Thr Tyr Leu Val Ser Asp Cys Pro Ser Pro Gly Arg Asp Thr Val
65                  70                  75                  80

Cys Arg Glu Cys Glu Lys Gly Thr Phe Thr Ala Ser Gln Asn Tyr Leu
                85                  90                  95

Arg Gln Cys Leu Ser Cys Lys Thr Cys Arg Lys Glu Met Ser Gln Val
            100                 105                 110

Glu Ile Ser Pro Cys Gln Ala Asp Lys Asp Thr Val Cys Gly Cys Lys
        115                 120                 125

Glu Asn Gln Phe Gln Arg Tyr Leu Ser Glu Thr His Phe Gln Cys Val
    130                 135                 140

Asp Cys Ser Pro Cys Phe Asn Gly Thr Val Thr Ile Pro Cys Lys Glu
145                 150                 155                 160

Thr Gln Asn Thr Val Cys Asn Cys His Ala Gly Phe Phe Leu Arg Glu
                165                 170                 175

Ser Glu Cys Val Pro Cys Ser His Cys Lys Lys Asn Glu Glu Cys Met
            180                 185                 190

Lys Leu Cys Leu Pro Pro Pro Leu Ala Asn Val Thr Asn Pro Gln Asp
        195                 200                 205
```

```
Ser Gly Thr Ala Val Leu Leu Pro Leu Val Ile Leu Leu Gly Leu Cys
    210                 215                 220

Leu Leu Ser Phe Ile Phe Ile Ser Leu Met Cys Arg Tyr Pro Arg Trp
225                 230                 235                 240

Arg Pro Glu Val Tyr Ser Ile Ile Cys Arg Asp Pro Val Pro Val Lys
                245                 250                 255

Glu Glu Lys Ala Gly Lys Pro Leu Thr Pro Ala Pro Ser Pro Ala Phe
            260                 265                 270

Ser Pro Thr Ser Gly Phe Asn Pro Thr Leu Gly Phe Ser Thr Pro Gly
        275                 280                 285

Phe Ser Ser Pro Val Ser Ser Thr Pro Ile Ser Pro Ile Phe Gly Pro
    290                 295                 300

Ser Asn Trp His Phe Met Pro Pro Val Ser Glu Val Val Pro Thr Gln
305                 310                 315                 320

Gly Ala Asp Pro Leu Leu Tyr Glu Ser Leu Cys Ser Val Pro Ala Pro
                325                 330                 335

Thr Ser Val Gln Lys Trp Glu Asp Ser Ala His Pro Gln Arg Pro Asp
            340                 345                 350

Asn Ala Asp Leu Ala Ile Leu Tyr Ala Val Val Asp Gly Val Pro Pro
        355                 360                 365

Ala Arg Trp Lys Glu Phe Met Arg Phe Met Gly Leu Ser Glu His Glu
    370                 375                 380

Ile Glu Arg Leu Glu Met Gln Asn Gly Arg Cys Leu Arg Glu Ala Gln
385                 390                 395                 400

Tyr Ser Met Leu Glu Ala Trp Arg Arg Arg Thr Pro Arg His Glu Asp
                405                 410                 415

Thr Leu Glu Val Val Gly Leu Val Leu Ser Lys Met Asn Leu Ala Gly
            420                 425                 430

Cys Leu Glu Asn Ile Leu Glu Ala Leu Arg Asn Pro Ala Pro Ser Ser
        435                 440                 445

Thr Thr Arg Leu Pro Arg
    450
```

<210> SEQ ID NO 12
<211> LENGTH: 42218
<212> TYPE: DNA
<213> ORGANISM: Homo sapiens

<400> SEQUENCE: 12

```
gcgagcgcag cggagcctgg agagaaggcg ctgggctgcg agggcgcgag ggcgcgaggg      60

cagggggcaa ccggaccccg cccgcaccca tggcgcccgt cgccgtctgg gccgcgctgg     120

ccgtcggact ggagctctgg gctgcggcgc acgccttgcc cgcccaggtg ggtgactcgc     180

gcggcccacg ggggacagcc gccccgcatg tccacccggc tggtgcgcag ccttcgggtg     240

cccgggccgc gctctcccgg ggcgctgtca cgggctggga ggctgggagt cccagtcgcc     300

gccccccatc cgcatcagac acgcgcgcct ctggggaccc gctggggact ccgggcccgg     360

cacacgtgcg ctcggggcac aactctggcc cccgaagccc ctcttacccg cgtcgtgaca     420

ggggcgcacc ctggttcctc cgcgagcgca ggccggggca tttggggctg agcagcgggt     480

cctgggcaga cccccgctag acccgggacc cctcttccct caccccggcg actgccgcga     540

cagcccttcc ctcccacgcg gtggagaagg ggctgtgccg gggcgctgcc ccactgccca     600

cgccgggcac cctcttcaaa agacttcctt ttcctctggg cgacggtttt ccgatttctt     660
```

-continued agaaatacca gggtcctgtg tctgaagagc aggaccaggt gtgtgtcagg tccactgagg 720
gcacagctgg agggcgagct gcctgtctgc ttcctccgat gcgtccgggg gctactgcag 780
agtctgtttt ctgcggcctc tggggacagg gcaagcgagg gaggtctggg ctggtaatcg 840
agcaaggcaa atgaagtctc cgggggccgc aggaaaatgg agacagcaga aaccctaggg 900
ctcctattca atatgaacgt cactcccaca gtagcaacgg gcgtacaagg gactgtgcac 960
cctttgcctg tttttgactg tctcctggtc tggtaacata ggataacccc atttttgttt 1020
tactgtctcc atggtttggt aagataagat aaaccatttt ttagagaagg aaaactgagg 1080
ctcagagaac ttgtatttca tggaagggtc tggggggaac tcttcctcca aagggggcct 1140
ctcctgcctt cggcccctgt gccctgaggc tgcggggaag gtgggcgttc atccttcctc 1200
agagccgccc ctgatggaca catggcccat ctgcccccat ctgacatctt gaccgaggag 1260
gaaggtggga ggtggcactg gcttctgtgg tgacataagg tgacttgttg atctgaggcc 1320
agagagtcca gttcttgtgg gtggaagatg ggggctgtca gactagaatt gactcaccga 1380
cagtgggtgt caggagtggg tcctggagaa ctgccccaga gtaagtcctg ggtggccttt 1440
gggtcaggag agtccccact ctagggccga gtgtgaatgg ggacgaccgt ggtccccagc 1500
ttgactttgg ggtcatgcca tatactctgg cctcagaggg ggtcttcctg ccgctgagct 1560
tgggcctgcc tgggtgaact ctggggtcat gtgagcccct ggatgggaga ggggtgtcag 1620
gcacagggct cagcaggaca ccaggctgca gtcctggagt agctggagga ggttccctcc 1680
cacttccttc ccttcctgac cagctcctgc ggcagctcat attccctcct ccctcatccc 1740
tgctccccac gaccccaccc ggactattgc cgcagccttg tagctggtct cccggccctg 1800
ccccctctcc cgctgatcct tggcagagag acccttctca agcatgaggc acctctctgt 1860
ttgcctgggg agcctcctgt ggctcccaat ggttgaggca gaaactcccc tggagatccc 1920
aggccagagt aaggtacctg aactcttcct cgcgcctccc tgcacatgtg ctcccccgcc 1980
tctgtagaac tgatgatggt catcgtgtgt gtcattgtgc aaaaagcatt gtccgtgcca 2040
tcccctctcc aagggacact tcttacccct atccttcaag gccttctgca aatgccattc 2100
tctccaggaa agcctttccg cattctcagt tggatttgat cttctcttcg aactcccagg 2160 ccctttttgtt ccctttgagg acagattgca ttctgctttt taatctagct gtgttttatc 2220
cccctcagtg gatggaaggt gtcttcaggg ccagaactgt gggttcctct tccttctcat 2280
cagtagcatc gccatagctc ctgatttctg aacacccact aaacaccagg cactgggcta 2340
ggtactttgt cacaaaattt cactgaaacc tcccttacag caactcccaa gaggtgggtg 2400
gtgccgtttg tctttagaga tgtggaaact gaggcgtttc ccaggatcac agagctgggg 2460
gccggggagc tgggggtggg atttgaatgc aggtctgcct gattcccaag ctcctttcac 2520
tgcaccctcc ccgtgcccgt atctgcactc atgctcccag ccaggccctc acacacagtg 2580
ggttctcagg atggaagtca actgagctgc agaagaagcc cccaggagac ctgagctagc 2640
catggacgca gccgactcac tgccagcagg gcttttgccc cgtttaaaag tcttatttgc 2700
cagctggtat ggaaaacatc attcattcat ttagccattt attcatttga caaagaaatg 2760
ccagtaaacc tggcagtagg tgagtgcttg gtgccctctg atggggatga gcagggtctg 2820
ggctgtctgg ggaggaggat gaggggtctc tgcctgatgg gcctggccca cctacccctg 2880
gaagtcttgg tgctgaggtg ccactatttg cctcctcatc acccagggcc tggggccagt 2940
ttgggttagg ggagaggttg ggggctccca ggctggatgt caaagaggag ttgggtgatc 3000
tggggtacct gctggccctg gggctcttc cctccttcca ccacgtctct gtctctttgc 3060

-continued cctctgtctg aaatcccagt ggggaccctg tgtgttgact gagggtgtgg tctgttggtc 3120
aggcacgtct tcagagggca atgggtaggt ggccaggcac cctgaggcag ggccattcat 3180
tcattcattc attccccaaa gttcatggac acacctagtc caagcccagc ccagtgcctg 3240
gctctgggga cctcaagatg actccagctc caatcctcta ggagctacac taccaatagg 3300
tcacagacct cacagacctg ggctctgtcc caactgccct tatgagctta gctgagctag 3360
taagcctatg ttctcatctg tggttgtgga aagtattccc tgcctggcct ttgtcacaga 3420
gccatgggtg tgaaaggctg agaacctgcc gggcattctt acgtcagagg tgaccctgcc 3480
atcctggcac ctggcacagt ggctccccgt agcactgtcc ctccccacgg ctgggtgacg 3540
ctttatggtc cttactatgc aatgttttct ggaggagtag cagggacggt tgtgcgtggg 3600
aaggggaaga gttttgccgg agccatggca tgtatgttac acccgactct acaccaactc 3660
acttcttact tttttctga gatggagtct tgctctgttg ctcaggctgg agtgcagtgg 3720
cgacatctct gctcactgca gtctccatct gcctcttggg ttcaaacgat tctcctgcct 3780
cagcctccag agtagctggg actacaggca tgcaccacca tgcccaacta attttttttt 3840
tttttgtatt tttagtagag tcggggtttc accatattgc ccaggatggt cttggacccc 3900
tgacctcaag tgatcctccc gcctcagcct cccaaagtgc tgggattaca agcatgtgcc 3960
actgtgcctg gcccgttctc acttcttctt cttttttct atttaatttt tttttattga 4020
gatagagtct tactctgtca cccaggctgg agtgcagtgg cccaatctct gctcactgca 4080
acctccacct cctgggttca agcaattttc ccacctcagc ctcccaagta gctgggatta 4140
caggtgtgtg ccaccatgcc cggctaattt ttcctttttt tttttttttt tagtagagac 4200
cgggttttgc catgttggcc aggctggtct cgaactcctg aactcaagtg atccacctgc 4260
ctcggcctcc cgaagtgctg ggattatagg cgtgagccac cccacccagc cccattctca 4320
cttttaagcc atgcttttct gtcctcagat gtgctgcaca cacacctgct ccagggcctt 4380
tgcacttgct ttccccatca cctccaatac tcctcctgct gacgtctctt ggtctccttc 4440
cctcgcttcc ttctgctgaa gtagacaatc ctgcctgtag gtgctccctg ccaggcactc 4500
tcactccctg acctgctttg tattcctgta taatgctctt gacctattct atttatttca 4560
cttttattat gtcttcccac aagattgtaa gtaccgtgag gacagggact cattcaccac 4620
tgtagactct agcctagaag agggttttc agtcagtgcc tctgacttta attctttgtt 4680
gtggggctgt cccgtgagct gtaggatgtt tagcgacatc cctggcctct acttattgga 4740
tggcagtagc gccaccctcc ctcgtgacaa aaatatctcc agatattgct aagtgtcctt 4800
tggggttggg ggattgcccc tgattgagaa ccactggcct aggacagtgc ctggcacata 4860
gtaagtgttc aaaaaatatt catctgacct tgaccttgat aatggccctg ttttacagat 4920
gagacggggg tttgaaaagt cagtggtggc agggtggggt tctgtttgcc tccatctctt 4980
ggggtatttt tctgggctcc tcttcccatt gagtggtgtc tgctgaggtt aggggtcctc 5040
tccccaaatt gctcaccccc tcgacatccc tcgtgtagtg agggatgggg ccactcactg 5100
acggtgactc agggccccag aatgcatgtg atttacccag aagcgggcaa ggagggaagc 5160
tggggtttgg ggtgccgggg atgaacagga acaaaggaga ggcgctgtgg ctccccgttc 5220
tggaccctcg tctggccaca gggaagcagc actgatgact ctggggaaag gccccggcct 5280
ctgaatcaga taaacctcaa gtcgctgctc tgctgtttta ctggctgtgt gacctgggca 5340
agtctttcta tccctcggag cctctgtgtt cttatctgta aaatgggagt aatcctagcc 5400

-continued

```
tcacgggctg gctgtcagga ttaaaagtgc tttctaatcc tggcattggc agctatttga   5460
gccattggtg gctttgcagg tctgacccga ctctctgggc catggggtgg tgctcgggcc   5520
taggtgggga cccctgtgga gtcagactgt ctgctctgag ccccagggcc ctgaagcttg   5580
ggtggcagcc ctgcagttgc ccagagttcc tgtctaagtg gctttgttgc ccatcatctc   5640
agaaagcaac ttctttcctc cctgcctttt cctgtctgtg cttctgcccc agtgcccccct  5700
ggctgggctc tcaaacccac tgcttgacag cctggtctta ggacactgta ttgtggcaaa   5760
ggctgtgggg tcaggatatc ccctcccctc cctttgccac cccttttagt gagtaacagg   5820
tgctgtgtgt tttggggatg agtgaagggt acatttggtg aagcacagag agagtgcaca   5880
aggcttcagt ttgcaagatg ggcacgggaa gattccaggc catctccaaa acctcttcca   5940
tctccaacct ctgtgctgct gaaggttctg tttacttgtg accctgagaa ggggatgccc   6000
tatgggggct cttctgagat catgctgtcc attttcctgc ctccaagtga cttctaagac   6060
agcatggctc tgaggaagga gcactgactt gggtgttggg agatcacagt tcccatctga   6120
gcaccgtcac tggcttgctg tgctaccttg cttgggttac ttaacctctc tgggcctaag   6180
catccctatc tatgaaacct aacaaccctg gttccaatgc tttcctagaa tattggggaa   6240
gtgtcggctt tgagtatact tgacaaaggc cacagattgg gggtggggta tataaaagtc   6300
tacaggaagg agagcccagg actccccact gtcaatatct tggttcccca gcttctcttc   6360
ttcttgctga cctcaatctc acttgctttg ggtggattga tttcctgact caggctccag   6420
ggccatcaag aattcacggc tgcctttcag ccttcatgaa ggacatggtg gagctcctta   6480
ggcagaactg ggtttgtgg atgtcctgcc tctctgcccc ttggtaccta ggtggcacct   6540
tttcaagttc gggagctaga tcctttcccc ttccccacac tgtaggaaag tccttactgt   6600
aggcaggcgc tgcagagcct gctgtctggg aacccacagg ttcaaggaag ccttgagcag   6660
gaagggcgtt ttcctggaag aagccctttg tcgctggtaa tgggtgcagg ctgctctgac   6720
ccggttctga gtcctgcccc cttccaggcc tagggctttg ggccttgatc acctctgctg   6780
agtagctgac tgcggggctg gggctctgat gctcaggacc cacctctctg ggacccacag   6840
tctttttcca ctgtggcgtg tagtgatgtc acaggtggca gtgatgtcac tgtggtttga   6900
ggtacttggc tgtgagcccc ggaggaggaa gtgtctgttc gctgatgggg ggttggaaga   6960
gatcattgac ttctgcccca agcgtgagcc ccaagtgtgc agggggggagt gcgggggggag  7020
ggctgttggc ggcgcatccc agggctctgg ctctgccctt gcatctagcc tgtctttcct   7080
gtgggctgtg acaagccact ctgcatctct gagactccat ttcttcttct tcttcttctt   7140
cttcttcttc ttcttcttct tctccttctc cttctccttc tccttctcct tctccttctc   7200
cttctccttc tccttctcct tctccttctc cttctccttc tccttctcct tctccttctt   7260
cttctgatgg agtctgactc cgttgcccag gctggagtgc agtggcgtga tcttggctca   7320
ctgcaacctc tgcctcccag gttcaagcta ttctccagcc tcaaccttcc aagtaactgg   7380
gattacaggc atgcaccacc acacccggct agtttttgta tttttagtag agatggggtt   7440
tcaccatgtt ggccaggctg gtctcgaact cctgacctca agtgatctgc ccgccttggc   7500
ctcccaaagt gctggaatta caggcgtgag ccactgcgcc cagcttccat ttcttctttg   7560
aaaagtagga ggggttggaa ttgtcaccct ggaggttcat ggttgctaga ttattgattc   7620
tgttgctgga ttcaggagac ctgttagctg gctagttcac agcaagtatt gggtgtttgg   7680
agggggggctg cagagcccct tctcaggccc caggagggcc agctgccctc cctacccccct  7740
cttttggaca ctagtgggca tgttctgctg ggaaaacaga cagtgtaacc tgacttcgag   7800
```

-continued

```
ggctgcaggc tgaatctctt tcagatgtac tggctccttg agaggcctag cagatctcta   7860
ctctgtgggt ccctttcgga gctggggctc aggtttgacc cagccactct gaccggagac   7920
agcgcagaaa tcaccaggag catttgtttg ttttcctttg ctgtccagac agtggcccac   7980
cgtctgcttc agtctgagcg tggccctgca ctagtgagac tgatgtggcc acaggttcag   8040
agaatcagtg cgcctgagtg ggagagcaga gcgggagggg atttggaggc aggcgggctg   8100
tggacaggga ggggggagga catcttccga gctgtcagcg ggaggccttc ttgaaggtct   8160
ttcaggagca aggccagagg ccgtgggagt gggcggggcc tggggctggg agtcaggggt   8220
ctgaggcctc atcttggccc ggcctctgct tccgggagaa cttggccaat tcccttctcc   8280
tttctgaacc ttggtggccc cagctgtcac ttgagattag caaggacctc cctggtccca   8340
gcaggagtga gtggctttgg gcagggggtg gagtgcagat tgcactgcca cgtcacccag   8400
ctcagaaggc ccaggtgtgg tccagctgtg gacttgattg tgaactcctg gggaagggct   8460
ctggtccttt gcctcagtta gcgggacccc caccagtgcc ctgggtgccc ctgctggccc   8520
ctcctctcgc tgaccccagc cccagtttct ggctgcaact cacagaggcc ccaggctcct   8580
gtggccccat caccagcagc tcctgctgtc atttcctgag cctcgcaagc ccctaatcct   8640
gctccttcct gtcctggccc ccagctccct caagccccac tcctgcatcc cattctccct   8700
ggacatcacc cctcccaccc cttggctcaa tttccttcct gtcgtggctt ggtcctttgg   8760
tcattgccct ggtcttttct tgtccccttc ctgattctgc ccttctccag gcccacacgg   8820
ggaacctcct aaccgctgag ccctgaaagg taggcgggtt taggatgagt ggctacaggg   8880
aggagaatgg tgtggggaga gagatatgga ggaaagaata ttaggggaca ggccgggcac   8940
ggtggctcac gcctgtaatc ccagcacttt gggaggccaa ggcgggcgga tcacttgagg   9000
tcaggagttg gagaccaccc tggccaacat ggtgaaaccc tgtctctact gaaaaaaaaa   9060
aaaaaaatta gccaggcgtg gtggtgtgca cctgtagtcc cagctacttg ggaggctgag   9120
gtatgagaat cacttgaacc ccagaggcgg aggttgccgt gagctgagat cgcaccattg   9180
cactccagtc tgggtgacag aacgagaccc tgtctcaaaa aagcaaaaca aaacaaaaca   9240
aaaaccgaat attagaggac aatgttagga ctgtcccagc tgtcctagct ggagccaaag   9300
gtttgttggg gacagtgaca gcagcacacg aggctgtaag tttagggcca gtttatggag   9360
gagtagtacc aattacattg agaaaactgt agcaactata atttgggagg aatttctaa    9420
atactttaca tgtgttattt aatcttccca tcagccccag gaggtatgtg catttatcag   9480
tcccattcta cagatgaaaa gactgaggtc tatgaactcc tttatttaaa aacaaaacaa   9540
aacccccctca aggctgcctg ctaagagggg aggagtgtgg attcaagcca gcatccttat   9600
tccagtgtcc atgctctcag ccaccacaca cacactccta tcaggagttg gggcagtggg   9660
gagccattat agtttttgag caagagagtg acagggcaaa gatcactgtg gcctcagtgt   9720
gaagcacaga tgagatggag agactggagg cagggaggcc catgaggagg ctgtcaacat   9780
ggttcaggtg acagctctgg gttggtgaag aagcagagaa caggaaggaa ggggcgagag   9840
gcttgaggga ggaggaggaa gcctttggac tgggccgtgg atatagggtg ggaacatagg   9900
aggtgaggag catgctctct ccacctgctt tttgcaacat gcggcctctc tggccttagc   9960
tctgcctgtc ctgagccctg agccctgagc ccaatggacc gattctgttt ttttttgag   10020
atggagtctt gctcttgttg cctaggctgg agtgcagtgg tgtgatcttg gctcactgca  10080
acctctgcct tctgagttca agcgattctc ccacctcagc ctcccaagta gctgggacta  10140
```

-continued caggcgtgcc ccaccacgcc tggctaattt tttgtatttt ttttagtaga gatggtgttt 10200
cgccatgttg gcccggctgg tcttgaactc ctgacctcag gtgatccacc tgccttggcc 10260
tcccagagtg ctgggattac aggcgggagc caccgtgccc ggccccagtg gactgattct 10320
ggtcagtgtc aaccccattt gtccctggag cttttgcagt cggtcacagg gccagcccgg 10380
tcctggtcac cgctggctgg ttaccccggc tgggttgggc aggagtctgg gcagggctgg 10440
ttgctcatct caggtatgaa attggctgca cccccactag tgtgggggag caggattcca 10500
gggcctgcct ggcgctgcta cccctgtgcc tccagacccc tcgagctcct cccagacctt 10560
tggcttcgtt gactgtgagg tgaaaacaaa agggctgctc tctgtcactt cccctagggg 10620
cgggcagatg ctggcagggc acagagagcc gagggctaag agctgacatt tagcctggct 10680
actcaggaga ctgaggcagg agaatcgctt gaacctggga ggcggagttt gcagtgaacc 10740
gagatcgcgc cattgcactc cagcctgggt gacagggtga gattctgtct ccaaaaaaaa 10800
aaaaaaaaga agagctgaca tttagcgggt gcttcttggg tgcaatgcgc aagagaccga 10860
tgcattaact acacagagtg cccttccttg tcacagctac ctgggggcag gggaacatca 10920
tccccatttt acagaagagg cctttgaagc acagagatta actgacgtac ttagggtttt 10980
gcagctcact agaggcagag ccaagactcc accccaggtg gccaggctcc tgagcgctat 11040
gcctacctca ccctccaatg aggtggtggt ggaggagacc gtgagccgct gtcacctgaa 11100
cactggtgca ctcagtctgc tgctctgagg acgccgcccc ctctctttgt aagtccattt 11160
cctgcccatt tctcatgcta gctccagctc atttcaacta attgaaaatt aaaactttgc 11220
ttctgttgag caattcggca tcgatgagac gccagctgtg ggctgtgtgc tggctgtgtg 11280
tagggtgatg agtagcagaa gcacgggtga cactgagctc tttccactgc cgggcacggt 11340
gccaagcacg ccacgtatac tgacttcatg aatcataaag ccctgtgaag ggggcactgt 11400
ttctgtcgcc attttataga tgataaagtg gaggtggggg aatggcagaa ctgggatcaa 11460
agcccacgtg tctgtgtctg gctcagcgcc catacaaggg tgtcaaggtt gcggggaggc 11520
acgagggaac caataattaa ccaaaactgg tcgggtgtgg gcagtataga gatgcacccg 11580
ggttgtcaca ggagccccta ggagggacct ctgacctccc tgaaatgatg gcagagggaa 11640
ctcttgaaag aagctgagaa gtcagcactg ccaggtcggg ggtggcgggt caggacgttt 11700
gggcagaggc agcagcagta cggcatggga gaagggggcg gaggagccag gtgctgcttt 11760
gtgttgtgac agcaacaggt gagtgatgaa tacaggtggg agatgctggc aggggctaag 11820
gaggttgcgc aggtggtggc agccgctgga agcttttaag gagagtcagg cttgattgta 11880
ggaagggggc ttaggtccat ctgaaaggga cagaaggctg ggaaccaaga ccaaggagcc 11940
tgcagctggc aggagatgct gagggcagcg aggaggaggg gtcgtgggag atggagcagg 12000
cgacatcagc aggccccttg gagggtgacg gtgggagagg ctggggcgtc tctcattaga 12060
ctcagggttc cttgcaggca gggaccatgc ccggcgtctt tgtaccctgg catttagcac 12120
aaagcctggc tccaagaacc ggataccagc ccagtcttcc tgtctgcccc cagctcattt 12180
ctaaagcaac atcacaggca gcgagtcggg agtgggatgt gtcacccccg ggttgcctgc 12240
ctgtgatgtg gtcagtcctt cctaacgcag atgccattcc tctccgtgac ggcagacggg 12300
cctccgctgt cactggccct ggcgttgctg tgacgacctg gcctgatgta gctgcaccct 12360
gcagtccatg ggctcctgt gaacccccaa ggttgagacc caaatgcctc tgctgcctcc 12420
caccacgccc taggggcccc gcgacccgcc atgcaaatga cgtggtttcc gcattgcttg 12480
aagagggttt cctctgtgtg gggtccctg ggtccttggg cagatacctc tgcccctccc 12540
cacagctttg gcccctgccc taagaccctg gagacccttt tgcctgggag agtcactgaa 12600
ccacctgccc ctgctcacag tgtgttcaca gaagagtcac tcccctctgt gggctccttg 12660
tctgtaaaat gagggagcag gacaagatca cagggtacaa aactgtcaga gggcacagag 12720
gctgatgttg ctgccatcag ctcctggagt gccgctcact ggctgcatga ccttggacaa 12780
tttgcacgaa atctcccaag cctcaatgtc tgcatctgta aaatggatca tcctgacctc 12840
attgcgttag tgctaggata aaataaagag aaggtatatg aacgtgccca gcactgtgcc 12900
tgcacacagt aggtactttt cctggatctg aacagtctct gttcttccag ctctgtgtaa 12960
aggcttgatc tcgaccccta aagcctgaag cttctccctg tggccacctc cccaccgcat 13020
catcttccgt tctcagcggg tagatccctg cccagggggg accccctggg gaaggctggg 13080
agcatgacct cttcccaagg gtacggcatc taaaagggat ctccggaaca ttgaaaagcc 13140
atgaaggccg ggcacagcgg ctcacgcctg taatcccagc actttgggag gctgagggag 13200
gaggatcgct taaggccagg agttcaagac cagtctggac aacatagcaa gacccggtct 13260
ctttctataa atgaaaaaat aataataaag ccatgaagat ccccaaagaa ggctgtgcta 13320
atggcggccg gaagagcaga gggcaccaca gatgccgtgc tttcagcttt ttccttctcc 13380
tccaggcctc ccttctttcc ttcctctctc gctatttata aataagagaa ggcattgagg 13440
gcccccacct cgggtacttg cagggccttg gcctgggaac aggacaagca gcaagtcagt 13500
tgacccgggg ttgctcaatt ccccaagagc tgacgcaaac tccagaatca gacctgccct 13560
ggccacctgg ccctgcccct taccagctaa gggctccagc agagtcctag tcttgagcga 13620
atcttatacc tgcagccctg tccaccagct gtgcttcctg agtcctccag ggtgaggggg 13680
cgtggggtca gaagagaggg gacggtgtgc agggagggtg gaacctgact gaccgggtca 13740
gccttactct tccagcgggg tcttttcttc ctggagctcg gccctcggca gctctcagaa 13800
gctcaccttc ttgcaggctc tcacagccgc atcgtcctct ggctgggctg ctcacagacc 13860
ccggcccctg ggttttgtcc actcacccag actctgtttt ggggtcacat tacccttcca 13920
gtgttcctct gagcaaagtc cctgtgagtt agcccaaggt ccctgtcaag gaggaccaca 13980
tctggcctgt tgcactcttc tcctttgccc caccgaagcc tctgtcacac tgtcacagca 14040
gcgggcctgc catggtctcc ccatgtaagg cttcctgagg aacgggcctg gtgccagcct 14100
gggggtgaac tgccagcccc aggagtcaca ggtcagcttc cccacactta ccctggaggc 14160
aggatggagg ccccctcctt tgcaaggccc acacgggcca tctaacaccc cactaaagcc 14220
gggcagttcg ctgccctggg gtgtgttctc gccttgccag ttcttggcta aaaccaaggc 14280
aggaagagcc cagttcccat gttctgtaac atgggtctat gaccagggcc tttgcaggcc 14340
ccttgcagcg cccccatgga gcccccagga gtctgggaga agatgatgaa cccaagtgag 14400
gacctcccca ggggcctttg ctcctcacaa gaaccccctgg aggagacagg gcaaggagta 14460
ccactcccat tttacaggtg acaatgccga ggctcagaga aagtccatga cacccccaaa 14520
tcccccggac ccactaccct gacctcctgg cggtgcacag agcatgccac gcacctctcc 14580
atatgcacat agaccctcta acctaagtca gcgccccttc tacaaggccg gtgtccagca 14640
cacctgggaa aggggacatt tctggccctt tcctctcaga agtcgcctgc tcgagctgcc 14700
ctccctgggg ggaaggggat gggggcagaa gctgagcatg gaagcccctg ctaatccacc 14760
ctctgctctc tccagaggcc caggaccagc ccaactctgc cccacatccc agcccccacc 14820
tcccagctcg tgctgtttct ccacctctca tgtggatggg ccacacacca cccagcaccc 14880

-continued ctgaggtctg gtgagggact gagccttcga cacccatcct taagaaccca gggctggtcc 14940
ttttgcttag agcatcaacc aggcccacac tctcatttta caggcagaga aactgaggca 15000
cagagaacct ggttactgcc cacagcagag gagacacttg agtgaggaca cagaggatct 15060
ttggggtagg ggcgggcctt ggggttgaga cccagtcttc ctggccaggg aggaaacaca 15120
ggactggagg tgaggaggcc tctttgaggc tagtttcttc atctgtaact tgggaataac 15180
aataggactg gcctcagggg gaccagggga ggattcagag aggctatgat gctgggacag 15240
ctcttcgtga tgactggcat gaagcaggct tctagtagat gctctactgc tgctttcgtt 15300
ctcaccctca cccacccgct ctgggcccac tgccctgacc tcctgaccaa gcactgagtg 15360
tgccaagggc atctccctgt ctccccggcc ccgcaccttg tgtcaccctt ttccttagct 15420
cttaccacca ccttgaattc tctattgaac gtgcatgtgt ctccccagct aagatgacaa 15480
cttcccgggg gcagggattt gatttgttca atgctactgt ttacccagca cctacaacac 15540
tgggtgctca gcacgtctgt tgaatgaatg aatgaatgaa tcactgcttt cacctttgcc 15600
cctgactttc tccatggacc acggacaagt gacttgatct ccctgagctg tgaaatgggg 15660
ccattcacac cagcttttta gggtggaact aggattttat acagtgcctg ccatctggcc 15720
tggcacatag tagttgctta gcaaatatcc cattgttttc cttcctcccc agagggccaa 15780
agccaagacc tggaggagca acagggtggg ggtctaaccc ctgggtgaca gagacagctc 15840
ccatctggga tggaggctgc atggtgggag gagctgctga ggttgggcca ttcagctttg 15900
gggcccttgg agtcctgggt ctgtgtggag ggggaaggga agctctctgg gccccaagag 15960
aagggaggca ggattggggg tggcaaggat tgcagctctt ctgggatagc cttgggcaca 16020
ctgctttgtc tccctgagca cctgcgaatg tcagtgagaa gaccagacag tgggtctaac 16080
acgcacagtt gcccctggga ggtagcaggt gctcggtacc gatgagctac cgctaactgc 16140
aggtgctacc tgtcttagag gagggagccc aatctggagg aggggaaatg ggagctgtgg 16200
acccagatgg gaggcggctc agagactgtg ggtgggccct gatgagcttc ttatccatag 16260
tcctctatcc gcttgccgcc atcctggccc tggcatggcc caaagtctct gggagacgag 16320
gggaggtggc tttgcctttt tccatctctg ttatctcatc tgtgaaatgg gcacaatcag 16380
acctgcctca ccaattggaa tatagattta ggtgcagttt tctttttttct ttccttttat 16440
ctattctctc tctctctctc tctctctctc tatgtatata tgtatagcta tctattgata 16500
ttttctatca tccatctatt tatcttgtat ctactttcta ttatctctat catctattta 16560
tctaatctat catctatcta gctatctttc tattttatct atctatctat ctgtttgtct 16620
gtctgtttta tctatctagc tattttatct attttatcta tctatctatc tatctatcta 16680
tctatctatc tatctatcta tctatctatt ctatctacct atctatctat ctatctatct 16740
atctatctag ctagctagct agctagctat ctattctatc tacctaccta tctatctatc 16800
tagctatcta tctattctat ctacctatct atctatctat ctatctatct acctacctac 16860
ctacctacat atctatccat cctctccgat tccctcacca ctgggtctca gattccctgc 16920
ctgttaaata aatggtcagt taaccctcaa cagtgatttt caatttttca cttgaggccc 16980
ccatatttttg gaagattgta gtttgctgaa cacgctgact gaatcaagta ctatccaact 17040
tatttcctca ttttaacatg tcaaagatcc cctgtggggt gagtggggtg tgaattggag 17100
cctccccaat ccaaggcaca ggaactggaa gcttctgtag ccctgcattt cctagagaat 17160
gcttgccatg ttttggggac ctcctggggg gcccctgtac tgaccagagg ccggctccca 17220
gggctgtggt ttgggcccag ccccctgctc ctggggactg ctgctgtgga gggagtgacc 17280

```
ttttgttctg ctttgccaag gggctttctg ttcctcattg tttagccatg acaaggctgt  17340
ggattttttt tttttttct gtccaagaga ataaacaggc ctgagattgc tcaagggagc  17400
cgacccccctc tgccagctac tgggggctgg aggctcacag agccagggag gaagtcctac  17460
cccctctgcc ggctaccggg ggggctggag ccacacagag ccagggagga agtccaggga  17520
cggtcactca cagcaaagcc tcagacaaga gaggaacctg gaggggagga ggtgggaggc  17580
caccactcag ccggcctggg ggccatggga gtccagctgc ctgccgttag tggccaggag  17640
ccctcgtcca ttgcggctct tgagagccca aacttggcca cggcagggct ctttcccatc  17700
aggccctttg agccctgatg ggaaaccctt ccccagccag ggtgggattt cttgctgccg  17760
cctggagccg ccctggccct gtggttctca ggccctggag gagtgagggg ctcccctggt  17820
taccccaagg gcactcgtgg ggatgaagcc cgcgggatgc aggattccca cgagacctgt  17880
gctggccact gtgcggggtg gggggctgcc agggaagagg tgcagcccct gcctgcctca  17940
gggatgcgat ctgagggaag aggcagctgt gtctgggagg ccgttcggtc ggagggggat  18000
aggcacagcc cctgcccttg gggaagcgcc cagcagcagc cttcagggaa ggcagtttgg  18060
gggtttgccg agggccagga agaccctctg ccgcagttag tattcgatgg aatggcttgt  18120
gcagagggag ctgcagaagc tgccatttct ctgggttagg ggctcccaca gcctttggat  18180
gccgggtctc ggccatgagc cccctccgcc acccctcccc caggtcacct tgctcaatcc  18240
aggaggccgg atgatcagag tgtgttctgc aaaggagcgt gagaatcact ggggagattt  18300
ccttttctt tttctttctc tttttttaat ggtacagctt cctgggccca cccctgagat  18360
tctgcacttg tttggggagt gggtgttggc ttcatgacag gcacccctgg gtgctttgga  18420
cacaggcagt gagctccccc cacactgtgt gaacccctga gaaggcttct ccttttgtct  18480
agggtgcctg ggagtctgct ccagcagcaa accggggagg ggaggggtac tgggaccgag  18540
tgtgtgtggc agcaccgtgt ccaggcaaac tgaggctcca gacgggggtt acttcttcag  18600
accctgttat gcagcatggt tcccactgcc cgtgcccaga attcaccata gctgatgggc  18660
ctggggtggg cctccggggc aggccagggt ggaaagtgca tctgtgtttg agctttgcgg  18720
ccctggcgct ggagttagat ccctacagga aaggacattg taacccagcc cgtggttgag  18780
actagcagct gctgagcacc tacgccctgc taggctgtgg ggcaacagca aagggtaacc  18840
cccagcctgc agcctcaggg gggcttccca tctagcgagg ggcccaggga ggccatgagg  18900
agagccatga gggaggaagg tggggactct gggcctgagt gactccttca gggtggggtg  18960
cgggcaggga gccttcagga gggagggtac tgcctgagca gggctcttaa gggacacgtg  19020
gaatttgtta caggaagcac caggccattc caggcataga aatcagctgg ggtgcaaagg  19080
cctgggggtc agaagagtgg cagattgctc catggcagga agccccagct cctctgggtc  19140
gttcccgctg agggattcca gctgttggca ccgaggggtg cagccagggc agggtggtgc  19200
tgcctgccag gctgaggtgg gagacagctg ggtttctagc cctgcttgtc actcgctata  19260
ggtgcagcca aacgctcagc aggcccaaac tctgggcagt cctgactccc aggcagtgct  19320
gtgaggaagg ggaggaggag gcacactgaa cccacctgct acgttggctg gtggaaattt  19380
ggccaggtct gcactggccc agcggtgctg ggtgtcgtga ctggtgtctg ctctgactgg  19440
cttgctgaca gctgaagtcc aggataggtc catggccacg ttgtgctggt ttgttaaata  19500
tttttagtat ctcccctgct cctatatgtt aggtactgga gtccagagag gttaaggcac  19560
ttgcctaagg ccacacagcc gctaagtggt ggagtgagga tttgaaacca gttctttctg  19620
```

-continued actccctgta tccttatcta tggagaggcc ccatgactcg ttcactaaag gttatggatc 19680
tcgatcttgt actggccaca tgactgcagc tggcagtaca gtggggagtg cgccagccct 19740
ggctctgacc tcctagaact gccctttgtt catttccagg tgacgcatct gtgggggccc 19800
ctgaaggact tggggtgtgt gtgtacaccc tctttgcttg tacagatgtg ttcacaccca 19860
tgtttgccta catgtgaatg tctccattct gagcttgctc tcagcctggt agaggtggct 19920
aattaatgct tgtccctgaa agcccggact gccaacccca gtctttcagg agagagggca 19980
ggactcaggg gcttgctccc gggggtcctg ggaaggcaca atggtgacag tgctgcagct 20040
ctgcactcct ggagggtcac tcagagaccc gagagaggag ggctctgcgt ctgctcctct 20100
gtccagggct gtagcttctc tgggtgcctt tgcttttctc ttttctcccc tctttttttt 20160
ttttttcga gatggagttt tgctctgtca attaggctgg aagtgcagtg gcatgatctc 20220
agctcactgc aacctcctcc tcccaggttc aggggattct cctgcctcag cctccagagt 20280
agctgggatt acaggcacac gccactatgc cgggataatt ttgtattttt agtagagaca 20340
gggttttgcc ttgttggcca ggctggtctc gaactcttga cctcaagtga tccacctgct 20400
tcggcctccc aaagtgctgg gattacaggt gtgagccacc acacctggcc ctctctctct 20460
tttcattcat cacattgttc atctcttccc ggaggcatcc agcacagtct ttgagactgt 20520
gagctgtgaa gtcagacagg acccaggtcc aaacccttct ctgtcactta ccaggtctgg 20580
gaccttgggc aggtgacctg ccctctcagg cctcggtttc ctgttctata aaatggctgc 20640
agtagggaaa ccgtctccat cttcattggg tggttgggaa gtcttgctga gaccacacac 20700
ctgtctcagg tagggtcttc cagaagcaga gcctgaggca gggatctttg tgaaagtgat 20760
ttgctaggga gggctcccag gagaagcagg cagggcaggt caggggaggg ggcttagcag 20820
ggacgttgtt caccagcttc agcccaacac cacgggggtg gctctggacc atgaattgta 20880
ccagggtggg tcccaccttg aggctgtgga gcattcatta tcagccaaca cccacagcag 20940
ctgggggagc ggtgccctgc tggcagcagg ggtctgagtg gggtgcaaca gcacccacca 21000
attcgagcag cagaaacgct tagaacagtg cctggtacct aggcagtgct tcaaaaatgg 21060
caacgattgt catggtcata accaacattc agctgatgag tgccggctct acggtgggtc 21120
ccatgtgaga gattgagggt ctagagatga caaggctgcc acctctgctg tctgcatcac 21180
atgagtgtgt gtgtacacat gtgtgtgcat acatacccac agggggtgga aggacaagca 21240
agtaaccatt ccagaacaat gagatgactg ttagaggggt cataacccac gtttagagag 21300
agccgagagg aggaggagga ggagcttgaa ttagccttgg gtagtcaggg agggcttccc 21360
agaggtggca gcactcatct tgaaagacaa agggatgttt caggtgcagg agggaaggag 21420
aggtatcttc cttcctcagc agagggcagc tttgtgctga gaacccccgt tctctgtgac 21480
caaggccact gtcttctgga tatctgtccc atgcagtgtt aggggtcacc cagcactgga 21540
gaaggccagc agagtcagtg cttctgcctg cagacatgac tagggtacac tgaggtgggg 21600
aggcagggga ggtaaaagaa ggcacgagct ctccttcctg taccctgctc caggggagaa 21660
aacctcccca gccatcatca gtgcagactg gcagggggag ggccaaacat ttgcagggcg 21720
gggacctggg catcaggcat ggcagaaccc aggggcggcc ctgttgatgg cagtcttccc 21780
ttcttccttc caggtggcat ttacacccta cgccccggag cccgggagca catgccggct 21840
cagagaatac tatgaccaga cagctcagat gtgctgcagc aaatgctcgc cgggtgaggg 21900
cagccacggg ggcactcggg gcccatgccc tggaggagcg tgtgtgtaca ggggctgggg 21960
cgcaagagca tagcccttga ttcttactga actcctagtt ctatgcactg gcccatgctc 22020

-continued

```
cctgctgctt ctgggcctgt gaacatgctg ttccctcttc ctggcacact tcccaactcc  22080
ctttccctga ttaactccaa cttgcccttt agacctcagc tgaagatgtc ccctcttcca  22140
ggaaggctgc ctgccccata ctgcccagcc ggtggaggag ggggaggagg agcctaaatt  22200
agctcctggg ggagtcaggg agggctgcct ggaggaggca gcactcagct tgaaagacaa  22260
gtgctgcctc ctttgagctc tcactggcct ctgatgttcc catggaagct ctttccttgc  22320
tgtgggatta tagcccggtc ctgcttcctg ttgcctccac tgtgtgctcc tctagggcag  22380
agattgtggc ttgttttctg ctgaatcccc agcacgtggc gcaatgccat gtaggtgctc  22440
agtgcatatt tgactgactc tgtgaatgct tacccatttc acagatggta gacctgaggc  22500
ccagccacag ttggtggagc taggtagcct gactcctggt gccctccatc tattcatttg  22560
tgtctgtatt cattcatgtc atgattataa ggtatctgct gtgtgttcta agtgctggga  22620
atacacagag agcagggcag acaaaaccct tgccctcgtg gagtctgcat tttaacggtg  22680
gatgcagaca gatacattag gagatgtgtg gtcctgtcta tctgtaagtg ctgtagaaag  22740
acaaggtcag gtaaggcggg ggagacagaa cgggacatac tgttttacac agggtggtct  22800
gggaaggtct ctctgaggag gtgacatttg ggcagagccc tgcaggaggt gagggagcag  22860
gtcatgcatg tatacaggga acagtgtgcc aggaggaagc aacagcatgt gcgaaggcct  22920
tgaagtcgga gcctgtttgg tgagttggag gaacagcagg gccagcatgt gtggcccagg  22980
atgagcgaag gcgagtacgg taggggagga ggaggaagga gtgagcaggg accatggtaa  23040
ggagtttaga ttttattctg tctgggagcc aatggagggc tttgagccgt taccttgaga  23100
tgtaggtggg catatgagta cctgtcaccg tccctagcca ttttaagaca tcctagggaa  23160
agtgactctc ttctttcttt tattaactgg aagggtctct ttaagaagtt actagagagg  23220
ctgaggtggg cggaccaccg gaggccagga gtttgagacc agcctggcca acatggtgga  23280
acccgtctct actaagaata caaaaaaata gctgggcata atggcaggca cctgtaatcc  23340
cagctacttg ggaggctgag gcaggagaat tgcttgagcc tgagaggcag aggttgcagt  23400
gagccgagat tgtgccactg cactctagcc tgggccacag agtgagattc tgtctcaaaa  23460
aaaaaaaaaa aaaaaaaagc agctactgag tcaacttttt tttaaggttt ccgttggtgt  23520
tctctgtccc tggaatgcct gctttccagg cccatgccct tgtccttgat aggataccag  23580
ggactacatt cttactacct gttcccccta tcattcatgc ccctagctgg agaatattag  23640
ccatctatca agaaggaaga aactggcaag ctagttctta ctaaagtgtg attgactgat  23700
aatagggctc cagtggtgga ggttcaagca tctggaaaga gcagagagga atctattttt  23760
gagcagaagg ggttcagaaa tgacgtgata gctggtacaa tactagatgg gagatgattc  23820
tgaggaattg gaactccaca gaatagcctt cccagctggg ctttagaact ctggactttg  23880
tggggacagt ggatgagccc agggtcctgg cagaaggctc gcccagctga gacctctggc  23940
ccttgtttcc tcaggccaac atgcaaaagt cttctgtacc aagacctcgg acaccgtgtg  24000
tgactcctgt gaggacagca catacaccca gctctggaac tgggttcccg agtgcttgag  24060
ctgtggctcc cgctgtagct ctggtgagta ggttcagaga aaaagggggc ccttacaccc  24120
ctgcctccaa cttcccccgg caactccagc ctctttggct tccagctgtc tggagttacc  24180
ccaggctggt tgttggaagt ggcacaggtg cagctgttta cccctaccac tggcattttc  24240
ctcctctgtc tcaccaaagc ctcttcacag ccccacgggg caggcggtgg gagaactgtg  24300
cccacgtgag ggttgaggag gtggtgcgtg ggagagtggt gcgcatgctc gtgctgcgag  24360
```

gagcaggact gcggggagga gcgaaactgc tgggaagagc gggactgcgg ggaagagcgg 24420
gacttcgggg aggagcggca ctgcggggag gagcaggact gcagggagga gcgggactgt 24480
ggggaggagc gggacttcgg ggaggagcgg gactgcgggg gacgagcgcg actgcggggg 24540
acgagcagga ctgcggagag tagcgggact gcggagagta gcgggactgc ggagagtagc 24600
aggactgccg gtcctgcccc tggactctgg ccggtgttgt gtgtgcccca tgctgaggcg 24660
gtccgccagc ctcctggaga tccgctgtct gagagtgctg ggctgtctgg gagggcagcg 24720
tgggtgtggc ggaggcaggc gtgaccgttt gccgccctct cgctgctcta gaccaggtgg 24780
aaactcaagc ctgcactcgg gaacagaacc gcatctgcac ctgcaggccc ggctggtact 24840
gcgcgctgag caagcaggag gggtgccggc tgtgcgcgcc gctgcgcaag tgccgcccgg 24900
gcttcggcgt ggccagacca ggtacggggt ggggctcagg tccttgggga cgcccatggg 24960
cctctccttt gtagacatcc ttgcagtgtc acgggcatca acccattaat tagtccagca 25020
gggagcactg ttagtggtgg ccaggtgcct gctacccatc cgtctgtcca cctgtccacc 25080
gttcattctt cctgccagca ctcccgatta ggcacctctt atgtactgga accaggagac 25140
ccagagatgg atcagaccaa gccctaagct aggaaagtta tgtgatgctg caagatgaac 25200
tcacataact ctacagccca atcccgtgca tgtgtgtaca ggaatctgtg tgtgtgcatg 25260
tgtgtacagg catctgtgtg tgtgtgtgtg tgtgtgtgtg tgtgtaaggg gtggaggtgc 25320
agacagagct ccttgggccc ctcagacctc tcctagggct ctagtgccaa ggcccagctg 25380
tcccgcagag tgtctgagtg gttgacaagt tcggattgtt ccctgaagga actgaaacat 25440
cagacgtggt gtgcaagccc tgtgccccgg ggacgttctc caacacgact tcatccacgg 25500
atatttgcag gccccaccag atgtgagtag ctgagtcctt tggttctgga ggagcaggga 25560
ggggctgtcc ctgggtgact gtgggtccag gacacagagc agctcaccaa ccaccattgt 25620
ccagactgct ttatctgagg gtggctccca ggataaatgg catggtgggc aggaccttgc 25680
cctggaaggc aggactgggt gggtgcatgg ggaggtgggg gagggctagg agggggtggt 25740
cctcagagag ggcacacatc gtcactctcc tatcctgcct gctggggccc gtgaatgagc 25800
ccagccaccc cagccactct gtcccctgct gcctcctgac caagcctcct cctcctccag 25860
ctgtaacgtg gtggccatcc ctgggaatgc aagcatggat gcagtctgca cgtccacgtc 25920
ccccacccgg agtatggccc caggggcagt acacttaccc cagccagtgt ccacacgatc 25980
ccaacacacg cagccaactc cagaacccag cactgctcca agcacctcct tcctgctccc 26040
aatgggcccc agccccccag ctgaagggag cactggcgac ttcgctcttc cagttggtaa 26100
gtcgcaagaa gtctcattca ttcactcctt ctgtctgcct gtctttctgt ctctctttct 26160
tcctctccca tggttttact gagagcccac ggggggctgg accctgtgcc ctgtcctggg 26220
atacaggtgg cagtgagact gctttctccc cacacctggt gctatcattc aaaatcccta 26280
agtgcgtggg ctggatgcag tggctcaagc ctgtaatccc agtgctttgg gaggccaagg 26340
aggctggagg attgcttgag gctaagagtt tgaggtcagt ctgggtaaca cagcgagact 26400
ccatctctat aaaaaaatta aaaaattatt tgggtgggat ggtgcctatt gtcccagcta 26460
ctcaggaggc tgaggtggga ggatcacatg agcccaggaa tttgaggctg cattgagctc 26520
tgatcgtgcc actgcactcc agcctgggca atgagtgagg tcctatctca aaaacaaaac 26580
aaaaccaaac aaaacccctg gataggggag aggtggggtc agcaattcac ctgaatatgc 26640
agatggtctc cttgctgctg tttctgatga gcccattagg ctaagaagac agcgggctgg 26700
gccaggtcac ctccaggggc ttccattctg ggtagaact gcatcaggcc agaggtctca 26760
aactagtggc ccttaggctg aatgaggcac acagacatga ttgctttgta attggatttg 26820
agaatctccg gcctagactc gcccctcatt tgcaatgacc cgaagcacct tgggtccctg 26880
gcttgcctgg ctggcccctg gtacatttga gtttgttttc tgtagctgtc tgagcttctc 26940
ttttctttct aggactgatt gtgggtgtga cagccttggg tctactaata ataggagtgg 27000
tgaactgtgt catcatgacc caggtgaaaa gtaagagtcc atccttcctt ccttcatcca 27060
cttgttcagg aagcttttgt ggggtgcctc ctgtgagtcc agcactgggc acagccttag 27120
gggtcagaca gagctggata tgggggtcct tgttctgtag gagcttaagg cctggggtga 27180
aggtacctct gctaacttaa ttactaaaag gcaagaggtg atcagggttt tctaaagggt 27240
aggaggagtt caggattcct atccaggaag cctgggggat tcgggcttcc tgcagcaggt 27300
ggtctctgag ctgggtaaga tcttgatggg tggagtctgt gcagggaagg acacgcatcc 27360
tcagtggagg cgcggatggt atagatgggg gactggagaa tggttgggat ggtggcaggt 27420
ggagttgggt gggggcttct gtggaccttg tctggtaggc gattggtccc cacagggctg 27480
ggcctctctg ctggttctat ggggccccat actgccctcc tacttaggac agatgtgcct 27540
gaggaagtca atctcttact tgtcccctct cctctttata gagaagccct tgtgcctgca 27600
gagagaagcc aaggtggtga gtgtctccac tgccctctcc ccctcttccc ctggtctcct 27660
tcccggcgtg ctgggctgtc acagaggaag cagtgaattc tgtcattggt ctgtccagtg 27720
tcaggaggtg tgcagagccc tgggaggtgg aggaaaggcc ggggagtcag gcagccctcc 27780
atgggctaag agaggctgtg agtgtgaaat gctccggcag agagcagatg ccttcgtggc 27840
gttcgtggca ggcacgtggt cgtggaccca cagcgcaacc ttgggcagat gtgaaattgc 27900
tctatggcta cttccttacc atgagatggg ggttgtgtct gctcgatcca gcctgcaggg 27960
tggtgccatt cggtcagctg acaatgatgt ttctccttgc ctccattgtg tttacagagc 28020
actttctcag agagcagtgg ttttcaaact gaattctggg atagcccagt gtcccacaga 28080
gggcccttgg gcgtggggga agtggtcatc tctcaggttt gaggtagagg ctgtggggct 28140
gggccctggg tcctcccaaa gcaactcacc tttgatctgt tttataaagt agggcctgcg 28200
aaggcttttt gttagagaca gaccaacagt gtgtcatatc atagtatttc attcattctc 28260
catcaggaag gcatttggct gcaagtaacc ccaaacctac aggtgacttt agaaaaaatg 28320
gctttatttt tcttgcattg taagaagtca aggggttggt gtctgctgga atggcctcca 28380
ctatcccctt gcatggtgcc agcaggaccc caggctctgt catctttagt gtgttgactt 28440
ttgttctctt gtttgtggcc tcatgtcata agatggtaat catcacttca tatgtcacct 28500
ctaagtttga ggtgggaaga aggggcaggt ggccaggtca gccatggtgc ccttatcagt 28560
aaatcggatg ccttcccaga agccctgggt agacttcttt catctcactg accagacagt 28620
gtcacatgac cacccctagc tgcgagggaa gctgggaaag agggtgtttt gcttttccag 28680
cctctatgga ggaggaggac aagggagggg ggttggaagt gggtatgggg tgagccagaa 28740
catacgtctg tcacagcctt gcacctggta ggcagggcag gttttttacc caatttgaca 28800
gatgagaaaa cagagtctga tgagttttct cgacctcagg ggcaggtaga gaaagaactt 28860
ctcaacctca tggatatttg agacaacatc ttacttaagg gaggccaagg tgggaggatt 28920
gcttgagtct aggagttcaa gaccagcctg ggaaacacag tgagacccta tccctaaaca 28980
aaattaaata aaataaatat ttttaaaaag gatcttggct gggcacggtg gctcactcct 29040
gtaatcccag cactttggaa ggccgaggta gatggatcac ttgaggtcag gagttcaaga 29100

-continued

```
ctagtctggc catcatggta aaaccccatc tctactaaaa acagaaaaat tagccaggcg  29160
tggtggcacg tgcctgtagt ctcagctact cgggaggctg aggcaggaga gtcgcttgaa  29220
cccgggcagt ggaggttgca atgagctgag atcacaccac tgctctccag cctgggcaat  29280
agagcaagac tccatctcaa aagaaaaaat aaaataaaat aaataaataa aatatcttac  29340
ttagttgtgg gggctgtccc gtgctattca gcagcatctt tggtctttat ttacttacat  29400
gccagcctca ttcccactcc agtggtgaca atcaaaaatt ctccagacat caccaagtgt  29460
cccctggagg gcaaaatcac ccctagtgga gaaccactgc tcgagggaac agctcagccc  29520
tgggcagccc aatacccgaa gcttacacca ggtgtttgga atcagataga ttgatttcat  29580
cccctgattt tggtgacaag aaaagagatg cagggaggaa aactgagttg ctcaaggtcg  29640
caccgcagtg tgtctctgga ctcccatctc agtgctcttt gccctgccct acagtatttc  29700
agtggggagg aaattttctc attccccggc gagcgagttt cactgctccc tttctccagc  29760
ttcaattcag tgacactgac ggttgccgcc tggtggcgtg cgtagagcag gtgtctcccc  29820
caagctcttc cgcagcagcc cagctgtcac cttccctttc cccaccaagc gtttcccaat  29880
cctctgtgca ctgaagatgt cctgggtgtg gcctagcagc ctctgcttcc cttttccatt  29940
ttttttttct ttctttcttt ttttttttt gagacagcta tgtcgcccag gctgcagtgc  30000
agtggcgccc tcttggctca ctgcagcctc cgcctcccgg gttcgagtgg tcatcccacc  30060
tcagcctccc aagtagatgg gactatgggc atgcgccacc atgcctggct aatttttata  30120
tttttagtag agacggggtt ttgccatgtt ggccaggctg gtctcaaacc cctgacctca  30180
agtgatctgc ccacctcggt ctcccaaagt actgggatga gaggcataag ccaccacgcc  30240
tggccccttt cctttcactg ttgctctcag tgttcactga atgtgagtga ctcaagtatc  30300
tgttgagtgc cccagtggtg tgtctagtgc agaaaaaaac ccccaaaccc tgatttgtgg  30360
tgtttgctaa tttctgtggt ataaacactc acactgtagc cagtttccaa ctcccaagac  30420
cttcctgaat atggagttgg gaggaaatct gcacaggcct gagcttatcc cagcacagcc  30480
ctggctgagc cctgccaggc tctttgtgac tgagtcccca cgcatccctg tggggcaggg  30540
agcatcatca cccccatttt acagaggagg aaactgagac tctgggaggt tccatttttc  30600
ctgtaggatt agatcattag gtgagtggca tagcccaggt ttgaatcagg tttatgcctg  30660
tgtcccacgc tactcctcaa ccagcagcta ctcctgataa gaggccagtg gagagtcctc  30720
ttgagctggg ctgctgggct tagagtgtgg actcagcacc cacctgctcc tcctgccaca  30780
gaaagaacgt ccagggcatg ggagacagtg gcgttccttt gtttagaaaa caccaacatg  30840
tggccgggcg ccatggctca cgcctgtaat cccagcactt tgggaggccg aggggggcgg  30900
atcacgaggt caggagatcg agaccatcct ggctaacaca gtgaaacccc atctctacta  30960
aaaataaaaa aaattagccg ggcgtggtgg cgggcgcccg tagtcccagc tactccggag  31020
gctgaggcag aatagcgtga acccgggagg tggagcttgc agtgtactga gatcgcacca  31080
ctgcactcca gcctgggcga tagagcgaga ctccatctca aaaaaaaaaa aaaaaaaaac  31140
caatatgtga gcttacccac aatcaccccc atggacacgg acacactcat gcacggaccc  31200
acgtctgata acaggtgcga acatttatcg ggtgttgaac ggatgccagg cactgtgccc  31260
agcgttcttt attctcacag ccatgctgcc acacgcaggc agtatgattc ttgtccccca  31320
ttatatggcc caagaatcat gggcccagag aagttagtaa ctttcccagt gtggcacagc  31380
taatgatcac ggcctgggac acgaacctag gagtgtctct cctcgccacc ccagcgcaca  31440
cactcactac gtcactcaca gatatgcaca catgccccca acatagacac acgtgtgcac  31500
```

gcttcacacc ctcacgcctg tagacacagg tgtgtgagcc ttgtgaacac acaaacagac 31560
ggacacagca ggaacctgga ggacctggcc cgtggctctg ctgggtctct gcttctgccc 31620
agcagggctg ggccaggagg ggccgggagc tgagggtgct ggctggctgg ctggctggct 31680
ggaattctgt tttttttttt ttttttgaga aagagtcttg ctttgtcgcc caggctggag 31740
tgcagtggca caatcttggc tcactgcaag ctccgcctcc cgggttcaca ccattctcct 31800
gcctcagcct cccaagtagc tgggactaca ggcacccacc agctcgccca gctaattttt 31860
tgtattttta gtagagacgg ggtttcacct tgttagccag gatggtctca atctcctgac 31920
ctcgtgattc ggtgaccacc tcggcctccc aaagtgctgg gattacaggt gtgagccact 31980
gcgcccggcc ctgggatcct gtgttttgaa tgaggctcct cagtactcgg ctctactggg 32040
gtcccagccc aaggaatagg actcagcctg cttctgtgcc acctggggct gcttgaactt 32100
tgcgacttgt ggcttgggag gagggaggtg gccgtgacct ttgggggttt ttgttctgcc 32160
tggctgtagc caccagcaga gggggtgggg cacaggccag aaaaacccct tttgtggggt 32220
tgtgaggagt gacaattggc tgcttctcct ccccttccag gctcagagca gggctggggg 32280
gcagttgtgg gcagtgacca gggtcagacc acctgggcgg aggttcagca tgaacttgca 32340
atgccctcca tctctccaaa actgggggac ccagcccagg gagggtgtgg gggttcctgg 32400
ggaagctggt ctaggcttct gctcctgcca cggaccagct gtgtgatgct gggcacagga 32460
tgcactttct ctgggcctcc gtggcctctt ggggatggct tgcacgagat ccctccagtc 32520
ctgagtgaga ggctgtggcc ttggggaatt aagggtgcag gtggcgctca ggtgtccgag 32580
aagccatggg agccgggggc tgcagggatt ggacagagag gaccctggta ctcgcatctg 32640
ttctcagacc acatctggaa ttgtagctcc ctctggaggg aggcaggagg tctcagcctt 32700
tcttgggggg cggtggcacc tgcgctgctc gctccacccc tgctctcacc tcccgctgca 32760
gtgctggcga gccccatcag cccttcactc atctctaccc tccttctttc tgcctgggac 32820
acttgttttc atcctgggca ggccaggggc cagggcagct gttgggaatg tggcctgtgc 32880
catctccttt tttgctggga tcagaaaaca atcgcttaga attccaaggc aagggtgtga 32940
gcgcctggcc agccagtggg aacagacaac agcctgggag aggaatttcc agcctctctt 33000
cagtgtgcgt gtctggaaat ggggaccttg ccttgagcct ccagagttga aaccccagac 33060
acccaggaaa ggccctttgg gatttagccc agccacagta tgtcctaacc gtgaccttgg 33120
gcaagtaact caatctctcc gtgcctcagt ttccacaaag caaggataac actgggttgt 33180
tggaagaatc aatatagata ttgtctggag ggatgtaggt acagtgcatg gcattgggtg 33240
gcactcaaat gtcagctaat aatattatta ttattctacg ggaagaagac atcaggggaa 33300
gttgcagagc agcctgtggg cggactctgg aacaagaggc tgaggcagtg cagcagaggg 33360
tctcagacgt gagcgctctc tgccccggaa tgattgactg agcgcaaagg tctgcacgct 33420
ttctctgtaa agggccagat ggtaggaatt tcaggctttg tggactgtat ggtctcagtg 33480
acagctactc aaacctgcct ctgtagcaag aaagcagcta catgcataga cagcacacac 33540
ccaactgaga gtggtgtgtt cctatctaat tgtgctactg gacacccaaa cttgagcttc 33600
ccaccattcc atgtgccgca aattattctt tttttttgag atggagtttc actcttgttg 33660
cccagcctgg agtgcagtgg ctcgatctcg cctcaccaca acctctgcct cccaggttca 33720
agcgattctc ctgcctcagc ctcctgagta gctgggatta caggcatgag ccaccacgcc 33780
agctaatttt gtatttttag tagagacggg gttttgccat gttggtcagg ctggtcccca 33840
actcccttcc tcaggtgatc cgcctgcctc agcctcccaa agtgttggga ttacaggcat 33900
gagccaccaa gcctggccac aaattattct taaacatttt tttttcaacc atttaaaaca 33960
tgaaaaccag tggggtgtgg tggtgcacgc ctggtatccc agcactttgg gaggccaggg 34020
taggaggatg gcttgagccc aggagtacaa gaccagcctg ggtaacatag cacaaccctg 34080
tctctacaaa caatcgacaa caaaaaaatt agccaggagc agtgacacgt gcctgtggtc 34140
tcagctactc aggaggttga ggcaggagga tcacttgagc ctggaaaatc gagggctata 34200
gtcagctatg attgtgccac tccactcctg cctgagcaac agggtgagac cctgtctcaa 34260
aaaaaaaaaa aaaaaaaaaa agtgaaaacc attcttagtg gcaggctgta ctgggcctct 34320
gggcaatcat ttgcctagtt ctgatttaac aaactcttgt atggagttta ctatgtaata 34380
ggcattgttt taagcacttt acaaatattc agccatctaa tcttcacaac aaccctatga 34440
ggtaggctat tattctccct ttatagagta aaaaaaaaaa aaaaggcaca gagaggttaa 34500
gtaacttgtc caaggtcaca cagcaagtga gtggtagagt catgatttgc acttgtgtgg 34560
cctgggttta gagtccacac tcttggttgc taggctgggc catgtctccc tgtgcagatg 34620
gggtgaagga aagctgcttt ccttctactc ccttatgcaa aataaggatg aaaatcctgc 34680
cccacctcta agactatttg gtgaacaggg ccaggtattc tctgccctca taggacactc 34740
tagtagagca gctgggtgct aataacagaa acacagaaac cacggagaat cacacctccc 34800
aaaaagtgcc gtgtgtggaa agaacgtgca agggtgggca gaaacgtcac gtaaactgag 34860
aagtgctgat ggcaggaggt gtggatggca gtgggaagga agaggggaag aaagagctgg 34920
ctggtgggct gactgctctc ccctaccacc ccctgcccat ccagcctcac ttgcctgccg 34980
ataaggcccg gggtacacag ggccccgagc agcagcacct gctgatcaca gcgccgagct 35040
ccagcagcag ctccctggag agctcggcca gtgcgttgga cagaagggcg cccactcgga 35100
accagccaca ggcaccaggc gtggaggcca gtggggccgg ggaggcccgg gccagcaccg 35160
ggagctcagg taagaggtgg gagcacacct ggcttcttcc caagcctcct tggtctttct 35220
cacctggttt ctgtcttagc catctcctcc tgagcctccc cgcagggtgg gacgaggcct 35280
gagccacagg gaacttcctt cggttcgctg aacctaagtt ccctcccgcc tttgcccatg 35340
ctgggcctat cacctcaaaa tcctcccttc tgtgggacaa ccccagcttg tccaagtccc 35400
tggtatctgg gggaggagtt ttcctgaaac cttctccctg ctaccacccc cagctggcct 35460
ggctgctcct ccgggctcac catgccctgg cctccctttc acaggactgt cagactgcat 35520
gtacagacat tgtcttctcc tgtctcccac gccaggctgt gggacacctg gtgagcctgg 35580
atcatctcat tcatccctgt atctgcaggc ccaacacggc ccagctactg ataattaatc 35640
ataacaatcg cttctactta tggaaggcta cggaacagca ggcactgtac tgggcacttt 35700
acatgcataa aactgacctg catgtcaatg ctaagagata gttcctgttg ttatcccatt 35760
ttacagatga ggaaactgag ccccagagag gttaaacagc ttcttcaagg gcacatggct 35820
agtaaacaga agagccagac tcacccctag gctgtcgggc tccagagccc tgggattgga 35880
agatgaatga agaaatggtg gctccagggc tccactcact gcagtttgtt gctgggtctc 35940
tttaggtctg aggcactggg actgtgggga ttgtgtccca tttatgcagg ctgcattgtg 36000
ccctggacct ggtctatgac agatgtcact cctggttggc atctctaggg cccacactgg 36060
aggggcccct gtacagggtc tgctggcctg tgcctctctc cctcttacct ggcagtgcca 36120
gccagtgaga attcagggaa tgaccatgaa cttgggtcag tctgagatcc ttgcctggcc 36180
actctggtgc cataagaatt tgggtgggat gcttaaccct gccaagcctt ggttttttca 36240

-continued

```
cctagaggtg agctatagcg cctccttgcc agggctggtg agagatgggt gacattgtgc  36300
ccagctgggc accagaccag ggccaggctc cctctgggcc gcctccaggt ggggactgat  36360
ggctgcagcc cccaccacgc agccctcctc cagctcactc acccccagct gctccccagc  36420
tcactgcgcc cctgcctctt gcctgcactc atgccacccc tgcctgccac acctgttcct  36480
acctgccccc aactgcccac aggagctgac gtggccattt ctgtctgccc catcatagcc  36540
cccagcctcc tcggtgggag gtctcatcag tgcccctcac tccatcctga gaactcccta  36600
tgggagggcc tgggccagtg cctggaagag atcaggggcc ctacacactg ttgaatgaat  36660
gaatgaatga gtgcgctcca attataaact cttagtcttt gcccagttct tggattcgtc  36720
tgattttttt tttttaaatg gggtctcgct cgtcgcctag gctggagtgc agtggcgcag  36780
tcttggctga cttatctgct caccgcagcc tccgcctccc aggttcaagt gatcctccca  36840
cctcagcttc ccgagtaggc gggattacag gcatgtgcca tcacgcctgg ctaacttttg  36900
tacttttagt agagatggag tttcaccatg ttggccagac tggtctcgaa atcctgacct  36960
caggtgatcc atctgcctcg gcctcccgaa gggctgggat tacaggcgtg agccaacatg  37020
cgcagcccat ctttctgatt tcttagctac acctggtgtg gctccctcct tgggccaggg  37080
tggagccctg accatgtctg ccctcccctc tcccctctgc cccttctgct ctgtgctcct  37140
tctcccgagt cccccagccc gtgtccctgg cctctgtctt ctctttctct ccctcccacc  37200
cctaacacct ccctccactg tgggaacctg taaaccccag ggttgtgccc cttcatggtc  37260
ccccatccac ccccgcaatg tctcatgctc gatatacaaa ggccatggtg actttgggtg  37320
acatttgggt gctgtggagg ctcagggtgg aaatttcctt ccggccttgt gatttcaacc  37380
ctcctccccc accacatgct tggggctgtt ttgagcacag caggttgcca gctccatcca  37440
cctcccggct accctatccg agtagttgga gttagggaga accaggctgg ggtgagggca  37500
ctcagcaggc ccctgcagca acagcagcag caactctcat tttctgaggg ggctacttac  37560
tgtatgccag tcccttcata ttcatctcag caaacccacc gtccagtgcc tccccaacca  37620
gttagaaaac tcagttgccc acaggggctg ggcaggaagg tgaggcaaac cttgggctgt  37680
ccttggccgg atctcctgca tctggctccc aagggaagcc ataaatccag atttttaaat  37740
gtaaacgcct gaattttaaa tgttggtaat caattcactt aaaaacatca ccaccaccac  37800
caccaccacc accaacaaaa aaacccgtag acttgtccct gttacaggca ctaggaacac  37860
agcagggaac aatcaaaaag tccctggtct ggccaggcaa ggtggctcat gcctgtaatc  37920
tcagtacttc aggaggccaa ggcaggagga tcacttgagc ccaggagttc gagactagcc  37980
tgggcaacat agcaagaccc ccgtctctac taaaaaaata aaaaaaaaag tccctaccct  38040
cctgggttca gagtctggtt ggggacccca ggagctgggg gctctggaga tcaggagatc  38100
acagaaatgg ggagggaccc agagagtggt ggataggatg ggaagtaaat gtctctagag  38160
agggaggcca gggggtggag ggcgcttcgt ggaggaggtg gcctttgagc taaggcctga  38220
gcactagaga agagctctct aggctgaggg agcggcctgt gcaaaggccc aggggacctg  38280
aagggctcaa ggggctgtag cagggggtgg ggaatgtggc tggaaggaac cccatcaagg  38340
tcttggagcg gcaggagagg gggtgggaga aggcaggctc cagatcagac agggcctggt  38400
aggctgtagc aaggactgtg ggtttttgag cccccaagga agtgatctgc caggttcaag  38460
ggccagctct ggctgctgat gggaaacaga tttcagaggg gtggggttga agccaggaca  38520
gatggaggct gttcacaccc atccagatgg gagtgagggg aggcttccat agcccaccat  38580
```

-continued

```
gcagcagcag ggcagggtga cccttgcaga agtcatcttt tgtttttgtt tgtttttgag  38640
atggagtttg gctctttcgc ccaggctgga gtgaagtgac gtgatttcgg ctcactgcaa  38700
cctccgtagc ctgggttcaa gctattctcc tgcctcagcc tcccgagtag ctgggattat  38760
aggcacctgc caccataccc ggctaatttt ttttttgta ttttgagtag agacagagtt  38820
tcaccatgtt ggccaggctg gtctcaaact cctgacctca ggcgatccac ctgccttggc  38880
ctcccaaagt gctgggatta caggcgtgag ccaccctgcc tggtccagaa gtcatctttt  38940
gaagggagac aaggcaggaa tgatggatgg gtgtgtgata tgagagaaag atgggtccga  39000
ggctctgggc ccaagcagct gggtggatgg cagcaatggg aactgtgatg agcaggagag  39060
gttttggatg cgagatggga gtagaatcaa gagttaagtt ggaggctgag cacggtggct  39120
cacacctgta atctcagcgc tttgcgaggc tgaggtaggc agattctttg aggtcaggtg  39180
ttcgagacca acccaggcaa cctggcgaaa ccctgtctct acaaaaaatt agcagggtgc  39240
ggtggcctgt agtcccagct attcaggagg ctgatgtggg aggatcactt gaggccggga  39300
ggcagaggtc acagtgagtt gagggagtga cacagcactc ttttgagacc ctgtctcaaa  39360
aaaaaaaaaa aaaaagacag aagagacagg gtctcactat gttgcccagt ctggtcttga  39420
actcctgggc tcaagcgatc ctacaaactt ggcctcccaa gtagacatct gttttatata  39480
attggctcct cccatctctg gggtgattgg ggctgggtag gtagtgatgc tattcttatt  39540
cggcagaggg gaaaatgagg cacatgcagg ttaagtgact tgctcaaggt cacacagcag  39600
agctgggcta gaatcttggt ctcggctcct ggcccagtgc tctttcccat gtgtctgaat  39660
ctgcatcttg ggcaggggtc cctgggcccc actcctggac ccccggactg acccccaccc  39720
catcttgtgc ttagcagatt cttcccctgg tggccatggg acccaggtca atgtcacctg  39780
catcgtgaac gtctgtagca gctctgacca cagctcacag tgctcctccc aagccagctc  39840
cacaatggga gacacagatt ccagcccctc ggagtccccg aaggacgagc aggtcccctt  39900
ctccaaggag gaatgtgcct ttcggtcaca gctggagacg ccagagaccc tgctggggag  39960
caccgaagag aagcccctgc cccttggagt gcctgatgct gggatgaagc ccagttaacc  40020
aggccggtgt gggctgtgtc gtagccaagg tgggctgagc cctggcagga tgaccctgcg  40080
aaggggccct ggtccttcca ggccccccacc actaggactc tgaggctctt tctgggccaa  40140
gttcctctag tgccctccac agccgcagcc tccctctgac ctgcaggcca agagcagagg  40200
cagcgagttg tggaaagcct ctgctgccat ggcgtgtccc tctcggaagg ctggctgggc  40260
atggacgttc ggggcatgct ggggcaagtc cctgactctc tgtgacctgc cccgcccagc  40320
tgcacctgcc agcctggctt ctggagccct tgggtttttt gtttgtttgt ttgtttgttt  40380
gtttgtttct ccccctgggc tctgccccag ctctggcttc cagaaaaccc cagcatcctt  40440
ttctgcagag gggctttctg gagaggaggg atgctgcctg agtcacccat gaagacagga  40500
cagtgcttca gcctgaggct gagactgcgg gatggtcctg gggctctgtg cagggaggag  40560
gtggcagccc tgtagggaac ggggtccttc aagttagctc aggaggcttg gaaagcatca  40620
cctcaggcca ggtgcagtgg ctcacgccta tgatcccagc actttgggag gctgaggcgg  40680
gtggatcacc tgaggttagg agttcgagac cagcctggcc aacatggtaa aaccccatct  40740
ctactaaaaa tacagaaatt agccgggcgt ggtggcgggc acctatagtc ccagctactc  40800
agaagcctga ggctgggaaa tcgtttgaac ccgggaagcg gaggttgcag ggagccgaga  40860
tcacgccact gcactccagc ctgggcgaca gagcgagagt ctgtctcaaa agaaaaaaaa  40920
aagcaccgcc tccaaatgcc aacttgtcct tttgtaccat ggtgtgaaag tcagatgccc  40980
```

agagggccca ggcaggccac catattcagt gctgtggcct gggcaagata acgcacttct 41040
aactagaaat ctgccaattt tttaaaaaag taagtaccac tcaggccaac aagccaacga 41100
caaagccaaa ctctgccagc cacatccaac cccccacctg ccatttgcac cctccgcctt 41160
cactccggtg tgcctgcagc cccgcgcctc cttccttgct gtcctaggcc acaccatctc 41220
ctttcaggga atttcaggaa ctagagatga ctgagtcctc gtagccatct ctctactcct 41280
acctcagcct agaccctcct cctcccccag aggggtgggt tcctcttccc cactccccac 41340
cttcaattcc tgggccccaa acgggctgcc ctgccacttt ggtacatggc cagtgtgatc 41400
ccaagtgcca gtcttgtgtc tgcgtctgtg ttgcgtgtcg tgggtgtgtg tagccaaggt 41460
cggtaagttg aatggcctgc cttgaagcca ctgaagctgg gattcctccc cattagagtc 41520
agccttcccc ctcccagggc cagggccctg cagaggggaa accagtgtag ccttgcccgg 41580
attctgggag gaagcaggtt gaggggctcc tggaaaggct cagtctcagg agcatgggga 41640
taaaggagaa ggcatgaaat tgtctagcag agcaggggca gggtgataaa ttgttgataa 41700
attccactgg acttgagctt ggcagctgaa ctattggagg gtgggagagc ccagccatta 41760
ccatggagac aagaagggtt ttccaccctg gaatcaagat gtcagactgg ctggctgcag 41820
tgacgtgcac ctgtactcag gaggctgagg ggaggatcac tggagcccag gagtttgagg 41880
ctgcagcgag ctatgatcgc gccactacac tccagcctga gcaacagagt gagaccctgt 41940
ctcttaaaga aaaaaaaagt cagactgctg ggactggcca ggtttctgcc cacattggac 42000
ccacatgagg acatgatgga gcgcacctgc cccctggtgg acagtcctgg gagaacctca 42060
ggcttccttg gcatcacagg gcagagccgg gaagcgatga atttggagac tctgtggggc 42120
cttggttccc ttgtgtgtgt gtgttgatcc caagacaatg aaagtttgca ctgtatgctg 42180
gacggcattc ctgcttatca ataaacctgt ttgtttta 42218

<210> SEQ ID NO 13
<211> LENGTH: 3682
<212> TYPE: DNA
<213> ORGANISM: Homo sapiens

<400> SEQUENCE: 13
gcgagcgcag cggagcctgg agagaaggcg ctgggctgcg agggcgcgag ggcgcgaggg 60
cagggggcaa ccggaccccg cccgcaccca tggcgcccgt cgccgtctgg gccgcgctgg 120
ccgtcggact ggagctctgg gctgcggcgc acgccttgcc cgcccaggtg gcatttacac 180
cctacgcccc ggagcccggg agcacatgcc ggctcagaga atactatgac cagacagctc 240
agatgtgctg cagcaaatgc tcgccgggcc aacatgcaaa agtcttctgt accaagacct 300
cggacaccgt gtgtgactcc tgtgaggaca gcacatacac ccagctctgg aactgggttc 360
ccgagtgctt gagctgtggc tcccgctgta gctctgacca ggtggaaact caagcctgca 420
ctcgggaaca gaaccgcatc tgcacctgca ggcccggctg gtactgcgcg ctgagcaagc 480
aggaggggtg ccggctgtgc gcgccgctgc gcaagtgccg cccgggcttc ggcgtggcca 540
gaccaggaac tgaaacatca gacgtggtgt gcaagccctg tgccccgggg acgttctcca 600
acacgacttc atccacggat atttgcaggc cccaccagat ctgtaacgtg gtggccatcc 660
ctgggaatgc aagcatggat gcagtctgca cgtccacgtc ccccacccgg agtatggccc 720
caggggcagt acacttaccc cagccagtgt ccacacgatc ccaacacacg cagccaactc 780
cagaacccag cactgctcca agcacctcct tcctgctccc aatgggcccc agccccccag 840

-continued ctgaagggag cactggcgac ttcgctcttc cagttggact gattgtgggt gtgacagcct 900
tgggtctact aataatagga gtggtgaact gtgtcatcat gacccaggtg aaaaagaagc 960
ccttgtgcct gcagagagaa gccaaggtgc ctcacttgcc tgccgataag gcccggggta 1020
cacagggccc cgagcagcag cacctgctga tcacagcgcc gagctccagc agcagctccc 1080
tggagagctc ggccagtgcg ttggacagaa gggcgcccac tcggaaccag ccacaggcac 1140
caggcgtgga ggccagtggg gccggggagg cccgggccag caccgggagc tcagattctt 1200
cccctggtgg ccatgggacc caggtcaatg tcacctgcat cgtgaacgtc tgtagcagct 1260
ctgaccacag ctcacagtgc tcctcccaag ccagctccac aatgggagac acagattcca 1320
gcccctcgga gtccccgaag gacgagcagg tccccttctc caaggaggaa tgtgcctttc 1380
ggtcacagct ggagacgcca gagaccctgc tggggagcac cgaagagaag cccctgcccc 1440
ttggagtgcc tgatgctggg atgaagccca gttaaccagg ccggtgtggg ctgtgtcgta 1500
gccaaggtgg gctgagccct ggcaggatga ccctgcgaag gggccctggt ccttccaggc 1560
ccccaccact aggactctga ggctctttct gggccaagtt cctctagtgc cctccacagc 1620
cgcagcctcc ctctgacctg caggccaaga gcagaggcag cgagttgtgg aaagcctctg 1680
ctgccatggc gtgtccctct cggaaggctg gctgggcatg gacgttcggg gcatgctggg 1740
gcaagtccct gactctctgt gacctgcccc gcccagctgc acctgccagc ctggcttctg 1800
gagcccttgg gtttttttgtt tgtttgtttg tttgtttgtt tgtttctccc cctgggctct 1860
gccccagctc tggcttccag aaaaccccag catccttttc tgcagagggg ctttctggag 1920
aggagggatg ctgcctgagt cacccatgaa gacaggacag tgcttcagcc tgaggctgag 1980
actgcgggat ggtcctgggg ctctgtgcag ggaggaggtg gcagccctgt agggaacggg 2040
gtccttcaag ttagctcagg aggcttggaa agcatcacct caggccaggt gcagtggctc 2100
acgcctatga tcccagcact ttgggaggct gaggcgggtg gatcacctga ggttaggagt 2160
tcgagaccag cctggccaac atggtaaaac cccatctcta ctaaaaatac agaaattagc 2220
cgggcgtggt ggcgggcacc tatagtccca gctactcaga agcctgaggc tgggaaatcg 2280
tttgaacccg ggaagcggag gttgcaggga gccgagatca cgccactgca ctccagcctg 2340
ggcgacagag cgagagtctg tctcaaaaga aaaaaaaaag caccgcctcc aaatgccaac 2400
ttgtcctttt gtaccatggt gtgaaagtca gatgcccaga gggcccaggc aggccaccat 2460
attcagtgct gtggcctggg caagataacg cacttctaac tagaaatctg ccaatttttt 2520
aaaaaagtaa gtaccactca ggccaacaag ccaacgacaa agccaaactc tgccagccac 2580
atccaacccc ccacctgcca tttgcaccct ccgccttcac tccggtgtgc ctgcagcccc 2640
gcgcctcctt ccttgctgtc ctaggccaca ccatctcctt tcagggaatt tcaggaacta 2700
gagatgactg agtcctcgta gccatctctc tactcctacc tcagcctaga ccctcctcct 2760
cccccagagg ggtgggttcc tcttccccac tccccacctt caattcctgg gccccaaacg 2820
ggctgccctg ccactttggt acatggccag tgtgatccca agtgccagtc ttgtgtctgc 2880
gtctgtgttg cgtgtcgtgg gtgtgtgtag ccaaggtcgg taagttgaat ggcctgcctt 2940
gaagccactg aagctgggat tcctccccat tagagtcagc cttccccctc ccagggccag 3000
ggccctgcag aggggaaacc agtgtagcct tgcccggatt ctgggaggaa gcaggttgag 3060
gggctcctgg aaaggctcag tctcaggagc atggggataa aggagaaggc atgaaattgt 3120
ctagcagagc aggggcaggg tgataaattg ttgataaatt ccactggact tgagcttggc 3180
agctgaacta ttggagggtg ggagagccca gccattacca tggagacaag aagggttttc 3240
caccctggaa tcaagatgtc agactggctg gctgcagtga cgtgcacctg tactcaggag 3300
gctgagggga ggatcactgg agcccaggag tttgaggctg cagcgagcta tgatcgcgcc 3360
actacactcc agcctgagca acagagtgag accctgtctc ttaaagaaaa aaaaagtcag 3420
actgctggga ctggccaggt ttctgcccac attggaccca catgaggaca tgatggagcg 3480
cacctgcccc ctggtggaca gtcctgggag aacctcaggc ttccttggca tcacagggca 3540
gagccgggaa gcgatgaatt tggagactct gtggggcctt ggttcccttg tgtgtgtgtg 3600
ttgatcccaa gacaatgaaa gtttgcactg tatgctggac ggcattcctg cttatcaata 3660
aacctgtttg ttttaaaaaa aa 3682

<210> SEQ ID NO 14
<211> LENGTH: 461
<212> TYPE: PRT
<213> ORGANISM: Homo sapiens

<400> SEQUENCE: 14

Met Ala Pro Val Ala Val Trp Ala Ala Leu Ala Val Gly Leu Glu Leu
1 5 10 15

Trp Ala Ala Ala His Ala Leu Pro Ala Gln Val Ala Phe Thr Pro Tyr
20 25 30

Ala Pro Glu Pro Gly Ser Thr Cys Arg Leu Arg Glu Tyr Tyr Asp Gln
35 40 45

Thr Ala Gln Met Cys Cys Ser Lys Cys Ser Pro Gly Gln His Ala Lys
50 55 60

Val Phe Cys Thr Lys Thr Ser Asp Thr Val Cys Asp Ser Cys Glu Asp
65 70 75 80

Ser Thr Tyr Thr Gln Leu Trp Asn Trp Val Pro Glu Cys Leu Ser Cys
85 90 95

Gly Ser Arg Cys Ser Ser Asp Gln Val Glu Thr Gln Ala Cys Thr Arg
100 105 110

Glu Gln Asn Arg Ile Cys Thr Cys Arg Pro Gly Trp Tyr Cys Ala Leu
115 120 125

Ser Lys Gln Glu Gly Cys Arg Leu Cys Ala Pro Leu Arg Lys Cys Arg
130 135 140

Pro Gly Phe Gly Val Ala Arg Pro Gly Thr Glu Thr Ser Asp Val Val
145 150 155 160

Cys Lys Pro Cys Ala Pro Gly Thr Phe Ser Asn Thr Thr Ser Ser Thr
165 170 175

Asp Ile Cys Arg Pro His Gln Ile Cys Asn Val Val Ala Ile Pro Gly
180 185 190

Asn Ala Ser Met Asp Ala Val Cys Thr Ser Thr Ser Pro Thr Arg Ser
195 200 205

Met Ala Pro Gly Ala Val His Leu Pro Gln Pro Val Ser Thr Arg Ser
210 215 220

Gln His Thr Gln Pro Thr Pro Glu Pro Ser Thr Ala Pro Ser Thr Ser
225 230 235 240

Phe Leu Leu Pro Met Gly Pro Ser Pro Pro Ala Glu Gly Ser Thr Gly
245 250 255

Asp Phe Ala Leu Pro Val Gly Leu Ile Val Gly Val Thr Ala Leu Gly
260 265 270

Leu Leu Ile Ile Gly Val Val Asn Cys Val Ile Met Thr Gln Val Lys
275 280 285

-continued

```
Lys Lys Pro Leu Cys Leu Gln Arg Glu Ala Lys Val Pro His Leu Pro
    290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
        355                 360                 365

Asp Ser Ser Pro Gly Gly His Gly Thr Gln Val Asn Val Thr Cys Ile
    370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
            420                 425                 430

Gln Leu Glu Thr Pro Glu Thr Leu Leu Gly Ser Thr Glu Glu Lys Pro
        435                 440                 445

Leu Pro Leu Gly Val Pro Asp Ala Gly Met Lys Pro Ser
    450                 455                 460
```

<210> SEQ ID NO 15
<211> LENGTH: 34503
<212> TYPE: DNA
<213> ORGANISM: Mus musculus

<400> SEQUENCE: 15

```
agtcaccagc tagagcgcag ctgaggcact agagctccag gcacaagggc gggagccacc     60

gctgccccta tggcgcccgc cgccctctgg gtcgcgctgg tcttcgaact gcagctgtgg    120

gccaccgggc acacagtgcc cgcccaggtg ggtgactctt ggggtcacgg gggacagctg    180

cgcatcacaa agtgcccatt ccagctactg ctactgcaca attccgggac agcatgagag    240

gccatcacgt ccccagcaga cacgcgccac gcgcctctgg ggacccactg gggacccgag    300

gtctggcccg ttgggatcct ggggtggtac tcggttcccg acagccttat gttccagaaa    360

tacccagtgg ctttctccgc gagcttgatc agggctcgaa taacacccag cagggctcag    420

gaacactgtt catccttgcg aaatcccttc tgtcccgcgg tctcgaggcg ggaaggacca    480

gggccactgc cccattgctt gagcgggttg tgtcgtctga agacttcctt ctctgcgcca    540

tggtctgtct ctttcttaga aaccctggga ttactagatg ttggcggggc caggagtcta    600

agtaagcgcc tagtataaga gaccgatggg gagtgagtca cttctctgtc actagattgc    660

ttccatggat ccgccttgct gtgttcaggg gacgtttcag aatgttctca gtgtagtggc    720

agagagggca gctaccccaa ggaacctcgg gaaaatggac cgattaaaga tcccagtatc    780

cggtattcac attgcccccc tccccccccc ttcctgcctc cattgatcga agacagggta    840

aaaaaaggca gattacaggt acggaaaaat gaggaggctc agagaaatta cctttttttga    900

aggatttaaa gggagcttgc tgcactgaca tgcctttgct tggttccatg tatgctctct    960

gcctcctgag cccaccttga tggacagggt gtgcttacct gactgcaggg gagtagagtg   1020

gaaggtggct tctgttgcgt ccggaggtga tattcaatgg tcctgggatg caaaggaatg   1080

gactcatcct tggtgggtgt aggtcctcag ggaggtgtca aggatggact ctgggtcagg   1140
```

-continued

```
acagtcccag ttctgagggc ggagtgtgaa tgtgcatggt tgtggtcagg agcctgagtg   1200
gggattgtgc tctgagctcc aaggaaggat aggtctttgg gcactgagct ggggtctgtc   1260
cctggggaca gacagagcac aggagcttct gtaccggatg ggacacgcaa ggctttgtgg   1320
gatccacagt ggtttggctg aaggtgtttc cctcagactt ccttccatac ctgaccagtc   1380
ccaggtcagc ttagaccttc tactactgtt gcgtggactc ttagctagtc tgcctgtgtt   1440
ctaactccca caaatcctcc tttgacagag agaccttgct caagcccaga cacctctatc   1500
tgggaagcct ttgtagctcc tagtggtgga ggcagaaccc ttccttacct tcaaggtatt   1560
ccaggccaga tggacatatc tgtgttgcct gctcacatga acctatgctc tgtgaagctg   1620
atgactaggt gtctaccact gtgcgtgtat gacccctgca cacacattgt ccatattaca   1680
gatctctcaa cacttctgag tcttttgtaa atgccaggtc accagaaagg cctgtacaca   1740
tccccccacc tagacatgac ctgctctata gagcacagat tccatgctac tttttattct   1800
ctgtccctca agggtagaag ggacccttaa cacagaactg tgcaagcctt ctcttgattg   1860
attccaaaga agctcctggt ttgggacact caagtgccag atactgtgtt gggcactttg   1920
tcacagatta gcactgaaac ttcccttcca gctgtttcta caaggtgggt accgttgttc   1980
cactgaaagg tgtggggatg ggtgacaagc tgtggcgtat gccaggacca cagaactggg   2040
aggtgatggg gtgagatttg aaggcaagtt gctagcctga ctcccaacat tctttctcca   2100
gacattctct tacctgtatt cccacttcta tccctattgt gggactcaga gatattgtgt   2160
gtagtgggtc tgggcagcag agagagccct gaggatattt gagtaggttc caggggcagc   2220
aaacttactt tacccttcta ttcagtcttt catttatttg gcagataaat aggtgtgaaa   2280
cagggtaggt gagcacttgt tctggtctta cttaacctga tatgtatggc ctccctgtcc   2340
ctgggactct caggactgag gactgctgtt tgctgctcga gccagagtct gtagcatccc   2400
aggctgaccc tggagtggat taggtacctg cagtactgct gaacctgaga gctctttact   2460
tctttcctcc tatctctgtc ttgtgttcgt tggctggcat ccttctgggg catctgtatt   2520
gtgactgagg atgtggcttg gtattgggac ctttagatgg cggtggttag gtggtcaggt   2580
accctgatat agagccatcc atccatcaac tctcttggca tttgtccatg catgcttcac   2640
acactgccca ctggacagct ctaggaaact acctccagaa ccccagaagc cacatggcca   2700
gaaggtcaca cacttcagag acttgggttt tgctcagaac tgctcttgtt acagttacat   2760
gggatacatt cgcttttgtc gtggtaatag agaatttgcc tggctttttt tttttaatga   2820
tgatggtgtc tcctgtagcc caggctggcc ttcaggtcac tatgttgttt aggatgacct   2880
tgaagtccag atcttttttg cacatctcca gagctaggat tacagctgtg tgccatcaac   2940
acctgacgta tgtagctctg gacttgtgtc tctgcatgct gggcagcgct ttaccagctg   3000
ggctacatcc tgaggccttc tctggcatgc ttgggttgaa gaaagtcctg gtccctggcc   3060
cagtggcttc ctgaaacatt tgtccatctc taaggttgag tgacactttg acatgttttg   3120
gcctttgcta cccaatacta gccagcgtag ctttgtaggg aaagagaaga gttcacccag   3180
ggtgtctttg tggggaagaa gagagatgtt tgccaccatg cctggtatat atatatatac   3240
atttcttgtt gctcttgctg acagcttaat cacaacactc agggtggtac aggcaggatt   3300
atcaattcaa ggccatcctt cggtacatga agggtttgag ataaccctgg acttcatgaa   3360
accaactaaa agaaaacaaa aaaactgaaa acatttgcta aatgtcagag atatttggct   3420
gacctttgtt gtgactcgtg actccgtttt acagccaaat gtgtcaggtt ggtgggcaga   3480
tcggggttct ggtggcccgc ctctttcaaa gtgtgtctgg gcttgttccc actgctgtat   3540
```

cagatctgat gagctggaga ccctctcctg aaagagctca cacttcctac ctctactcat 3600
cctgggttat gatgatgcca tcccagtggt ggtggctcag ggccttggag tgggcaagga 3660
gggaagttga gggttggcac tgggagcaga agtgaggtgc atatgctata cccccaattt 3720
cagacaacat gagacaccag ctcccttggt cagggcccaa ggcctgatca cacagatgtc 3780
agccttcagc cttcctctgt tgtgatcaga gcctccctca ttcctttgta cagtggaaac 3840
acacccatgg tgatggcaag gactaaggct ttgaagtcac tggtgtctgt cctgatttgg 3900
ttatattcag tgttcacagc taggaggaac tcaggcaccc atcagtggga gccataggtc 3960
cccaaagctt aggcagcaga tattcaattg ccccaagttc ctgtttgagt gaatttgctg 4020
cctggtaccc ccaaaccaac gttcttcctg tcaccttttc ctgctgtact tcctgcccca 4080
tatcccctgg ctgggcccct cagatcactt gtctgacttg ggtctgggac cctgtgtagg 4140
aagcaaaagc tatatggtca gggagtcacc atcttactct ttcagtggcc ggtgctaaat 4200
gtcacttggg gatgatgagg aatatgcatg atgaagttga aaggagcaca gaaggctcta 4260
gctctgtgct tgtcaatttc taaatcatgg ccccttaggc atcatggggg ggtcacctaa 4320
gaccatcttg tatatcagat atttacatta tgatttataa cagtagcaaa attacagtta 4380
taaagtggca aaaaatataa ctttatggtt tggggtcacc acaacatgag gaatggtatt 4440
aaagggtcac agcattaaga agattgagaa cccctattct agctcatccc tacatgccag 4500
gaggtctctc tcttaaatct cttccatctg catttgtgta tatttatgag tgtgagagag 4560
agagagacac agagatggag agacagagag agacagagaa agatcttgct tacttaagac 4620
ccaagatggg aaagccatct tctgaactga agctgtctaa ttccctatgc ccaagtgact 4680
tctaagacag tacaacctgg gccagacggt ggtggcgcac gcctttgatc ccagcacttg 4740
ggagggagag gcagatggat ctctgagttc gaggccagcc tggtctacag agtgagttcc 4800
aggacagcca gggctataca gagaagctct gtctcggaaa aaaaaaaaac aaaaacaaaa 4860
acaaacaaac aaaaacaaaa acaaaaaaag acagtacaac cttgaggagg aatcacagcc 4920
tgagtgttag tagaacagag tttaatggct tgctgtgtgt cctttccatt tatttaatct 4980
ctctgagcct aagtcttcca gcaacactaa tctcaatgtt ctcccagaag gagtggagct 5040
ggcagctaca tgagccatga gaaaaaaaga gctgatgtct ttaccccttc cttccttcct 5100
tcctccctcc ctccctccct ccctccctcc ctccctccct ccctccctcc ctcccttcct 5160
tccttccttc cttccttcct ttttgtatgt atgagcagtg tgcctccaca tgggtaggga 5220
tgtttgtctg tatgtaggtg catgtctctg tctgaattga tattagatgt cttccttgac 5280
cactctacag tttacttgat tgaggtgagt ctctcactga gcttggagtt ggtctagcta 5340
gccagcttgt tctgggatct ctgtttctac accctacccc agcccctgtg ctgggtttat 5400
agttagctgc ctcatttatg tgggctctgg agggtcctag ctgtggtcct taggcttgta 5460
ggcaagtgtt gttccccgga gccatctctc cagtccttct tgatcatttt attcccattt 5520
cttttggtta gaattatttc cctgtcttag gccccccttgg caagatttaa tggctgcccc 5580
tcaggttgct cgaagctggg gtgctgctgt ctcaggcagg cctggaagtc ttgggtttcc 5640
tgctcctgtc ccctagtgcc tttgatatgt caacagtgag gcatgccccc agatgctgag 5700
gaagtcagac ttgcgtaaca gccagcatga ccagctagta gcctccacgc tcaagtaagc 5760
ccaagtggga agggtgtttc ctcaaagaag ctttttgtca ctcattagag gggacgcctt 5820
atttggtact gattctggcc tgacagtatg tctctttgtc ctaggatgca gggcaggggc 5880

-continued

```
tttggggttt gggacccacc tcttatgtag gacaggggct ctgcagctct gggacctacc   5940
actctgatac ctacacacat ctttttccac cacggtactt tgtgatgtca tagctgacag   6000
tgacaccatt gtggtttgga ctgcttggct gtgagcaaga gaagaggaag caggcttagc   6060
ttaccagcag gaggttgagg aagagagtgt ccttgcaccc ccagtgtgag ccatgctagg   6120
gctcaggtgt gaaggtagct ggtgtgttcc aacctgtagc tctgtctgac ccttgccagc   6180
ttgaatagga tgatggaaga ctgactgaca tcttgaaggt catccacacc catcctgttt   6240
cttttgggtt ttttgtgtgt gtgtgtgtgt gtgtgtgtgt gtgtgtgtgt gtgtgtgtgt   6300
gtgtgtgtgt gtgatgtttt gttctattga aacagggtct tgctttgtag cttttggtca   6360
gcctggaact tgctttgtac accaggctgg ccttgaactc atagagatcc acaaatctct   6420
ggttccccag tgctgggatt aaaggtttat gccactacac caggctccat ttcttcttta   6480
tggaggtgga ggggttaggt ttgtggatgc tatgttgttc ctcatttaag aaggcctgca   6540
cccagcccac ccgttcagtg tgggaggctg caagaggtca cacagtctga gtaggtgtgc   6600
tctcctgttt aaactggaaa gtgacagcat ccagtgacct gctcaggggt gctgggtcct   6660
tgagaggtct tgggaaccat actgttctct ttgggagcct gggcctgggg tgacccagcc   6720
cctctgtcaa gacacgagga agacttccca ctcaccacca ctcaaggtgt ttgtcaggga   6780
ggccagtgca ggttgtctgg ttttgatctt gggccatagc aacctggagt tcagaaaact   6840
gagtcagtct gaagttgaaa accgagtgag aagagacttg cgggtagtct tgcaggccat   6900
gtacaaagac atcttttttt gtcctctggg gacagggcag aggctgtaga tcctgagttc   6960
tgacgtctgg tatgacttcc actttgggct ggaccaagtt gggcctccag ttcccttgcc   7020
tgttctgaat ctccattgct ccaagtctga cttctcaaag ccagcattgg aatccaggcc   7080
tgcagctgtt ggacagtggg tgggaagctc agtagcttgg agcagaggat ggcgtgtaac   7140
tggactggac agtggatctc tgaggaaggg ctctggaatg ttgactcgag tttcaggacc   7200
cctgccaatg ccctagctat gccctgtgcc tggcctccca ctgctgaccg acagcccagc   7260
ttctggctac tgctcacaga gccaaggttc ttaatgaggc tgtgaccagc tgcttgctct   7320
ctggctgcct atgcctctgg ccatgagcct gggtcctgct gcttcctgct ttctctggca   7380
ggagtccagc cctctccagt cttagcccct caggcctcca ctcttgcctc tcggtggctt   7440
ggtcctgtgg tcacatcctc accttgtcta gtcacccata tgattctccc tgaattctgc   7500
cctcctgcaa gagttcacag ggaacttttc tggccttgag tcccatagca tggcagacta   7560
gaaatgagtg gatgccaggt agaggctgga gggactggga gcaggctaga cccagtatct   7620
gggcaggaag tgtgctagaa tcaacaaaga ctcatgaggc tgtgtatctg cagccagttt   7680
gtgaaagaag taatagcaac tgcattaaac aattattggg gccagttgtg gtggattgaa   7740
caggcaatcc cttgggtggt ggaagcagga agatggagag agttccaggc cagcactgtc   7800
tcaaaaagaa aatgtagttt gcaaaacacc ttattgtgtg ttatgttatg taattttttt   7860
ttaccagacc cagacagtat gttgtcagat tcattctatg gagaaaaggg ttgggggagg   7920
aataatcttt ttttttattt gaaaatacag tgaacagggc tggtgctggg gcaatggttc   7980
aggagttagg gacagaaact gctcttacag aggaccttgg tttaatgccc accactgaaa   8040
cagcggttca ttaccatctg gaactgatat cctggggcac cagccgcaca cacgtacatt   8100
taagaaaaac actcatacac ataaaattaa aaataatagc aacaacaata gatgggctag   8160
ggaggtcagg atcacttgct gctcttgcag aatccggggt tctactccca acacctacat   8220
ggcaattaaa tgtctgtaac tccagttcca ggggatcggt tgcccattct ggcctcttca   8280
```

```
ggcaccaggc acatacatcg cgcatagaca aacatgtaga caaagcattc atacaggtaa   8340
aaatgaattt atcttttaaa atgtaacaat gtaactaaca atgtaaatgt aaaaatgtaa   8400
caaatataaa agcaaaaatg caacaaacag gctggggata caattgtgca agaaagaatt   8460
tattacattg tgtaataaat taataatcca actgattaat taaaaaataa agctccaaag   8520
aaaaataatt ccttcaagat gcctgctaat tagggattta ggctgagttc aaagccatac   8580
ttccatactt ttgtctgttg tcaactaaca cactcttgcc ataagaagat gaggcgacaa   8640
ggagccatcc atagtttgga ggcaaggagg gagcctgggg cagagagtag gtggactgat   8700
catctggcct ttgtgtggag gttcagaaag tctagagtca gggaggctca ctgggaggct   8760
gcagtggtga ctcaggtgaa gtagggagga cagcagagga gggacggaga gggggaggac   8820
caagcgatga gaaagctgga ggtaaggcat attttcccgt gtccccatct tccatagagg   8880
tttactgctc atcctgagct ggttgacttg ttttggtcat taaattgcct gaccttgaaa   8940
ctgctatgta tccgagggtg aacttctgat cctcctggtt ctctgcctca gttgctggaa   9000
ttacagatat gcaccaccat actgtctgtt tgtttgtttg ggtttttttgt ttgtttttgt   9060
ttgtttttgt ttgtttgttt taatgcagcg ctaggcatgg aaccaggccc ttcaggtgtg   9120
ttagacatcc tctctaccaa ctaatcttca ttctagcctt ctctgggtca cagtcagcca   9180
caggatcagc cttgccataa tcaccctggt cgcctactct gactggagtg gatttgaaac   9240
tgagctgagg tctgtaatgt ctcctgagag ccaggcatgt gccatgatta acccagcagg   9300
tgaatgagaa gaaccggatg ctgcacatgg cttcggcagg tgtctaacaa atagtttcag   9360
tgataatcaa caaaagcaaa aggtctaatt tcagagtggg tctgatgcac tgaatgtaag   9420
aagcccttcc attttcagcc agtggggcag caggccaata ctcttgccag aggagatgag   9480
agggtcaggc cttcttgtgc atggtactac tgttcacccc aaccaaagcc cagcttccat   9540
ccataggctg cagaggctac cacccagatg tgatggtggt tggttgtggc cactacctgg   9600
gctgtgatct gaaggctgcc cttcagtttc tggggatatt gccttggcca tttcttgacc   9660
agttctcatg tgagccaaac acagctcagt gaataggaaa ttagaacttt cacttttgtt   9720
gattagcgtt gcatctattt attagacacc taccccagcc atgtgcagca cccagttctt   9780
ctcattcacc tgcttggtta atcatgacac tatgtatggt gggcatggct ccgtttccat   9840
tttgtagatg ccaaaaccaa gatggaagaa taagagaagg aaagtcaaac caggttctgg   9900
ctcaaaggga gatcacagta gggtgtcagg gaacacacaa gttgaacaga gttaactcaa   9960
atatgctcta acctgggaaa tatacaaaca gtcctaggtt gtcagaggag ccttctggag  10020
ggatgacttc catctggggt tcaggggttt atatgagaaa gaggtgatgg tgggatgagt  10080
ctgaagaagc tggggggtct gctctgcaga atacgtggtc agaggtagca gcaggagtca  10140
gggtgcagaa gaggagtacg ggagtcgtgt gctttgcgtc aggtggcaga tgaaagctgg  10200
cagcagaagc tggagaagtt tcattccagc ctgaggacag ctgaataagg agggccagtc  10260
ctggaagtag gaagatggct taggtctgtc tgcaaaggga aatatgctag acaccaacag  10320
tgaggaaact agctggcagg agttgtccag gtattaagga gagccagttg gagatgaaga  10380
aacccatatc aaagggcctc agggtaatag cagagagggt gaggcattct ctgtcgttga  10440
actgagtatt atttgggggc agagcccttg gcatgtagcc tggagcctag ccctaagaac  10500
aggatcccag cgtgggtttc ctgtctgctg cagctcactt ctaaagcaca tcacaggcag  10560
cagtttgaag gagggatgtc tcacccctgg gccatctacc tgtgatgtgg ttggtccttc  10620
```

-continued

```
ctgacgccaa tgctctttgt ttccatgatg gttggcaggc ctggtcgcct aggccttgcg  10680
tcgctatgac agcctagctt gatgtggctg taccgccata gtccatgggc tcctataaac  10740
ctccaagatc aagacttaaa tgcacccccc ccacaccttc catgcaaatg atgtggtctc  10800
tctagtgctt gaagatagag cttccggctg agtggagggt ccttgggcag acacctctgt  10860
ctcatttgac ctgggatgtg gtggcccttt tgcctggaaa catcatcaaa ctcttcacca  10920
ctctgtaaag ccagacaaaa atcatagggc atgaaatatc tcagtcagta aagtagacca  10980
gcacacgctt gggatcacag cactggggaa gtggacaggc agatccccgg gttcactcag  11040
tggccagtct agacaaatta gtgaggcccg ggccagtgag agaccttgta ttgaaaccga  11100
gatggacaat gcactaagaa gagctgacat ctgacgtgca catgcgcact cgcaagcaca  11160
cacacacaca cacacacaca cacacacaca cacacacaca cacacacact tgtacccccca  11220
tatgcacaca caggacagct gtgtgttctt gcacatactt atacatgtgt acctgcatac  11280
acacagaaag gtacacatgt tcatgtgcac ctgaacacac acaaacagtt gtgcacacac  11340
acctctactc agacacacaa agaacacaag ttataaaact gactgatgta gctgtgatga  11400
gttcccagtc tgcacctaca ctgtatctcc tggatctttc acttctacag tgatggtgaa  11460
atggactctg tcttagttac tttttgattt ctgtgaagag acaccatgac taagacaatt  11520
cataaaagaa agcatttgac tgggggctag cttacagttt cagagggtga gtccatggct  11580
gtcgtggcag ggagcatgac aggcaggcag gtagacatgg cgcttgaaca atagctgaga  11640
acttacatct gattctcaag caggaggttg aggaagggag aatgggaagg agggagacac  11700
ctcctggcat gggcttttga aaccttgaaa cccacccccc atgtcacacc tccttcaaca  11760
aggccacacc tccaaatcct tcccagacaa gagacaaaac ttttgaatgt ataagtttat  11820
ggaagctatt cttatccaag ccaccgaagg cttgtactga cttcatttgt ttggttcaga  11880
gaaaaaggtg gggaaatata tacaaatgct ccagaatggc acttcacaca gtaggtactt  11940
tttctggata taagccttac tagtctttct agcttatata aatggtgatt ctagtgggta  12000
tatactcttt accacaagct gggagttctt ccaatgccac cttccctatc ttgctctata  12060
cctgcctcag tgatagatct atacctaggg tctattattc tttcacctct cagtctgtcc  12120
atctctacat ccatctatct ttccatctat ctatttaccc atccatctac ccactcatca  12180
tttcatccat ccatccatcc atccatccat acatccatcc atccatacat ccatccatac  12240
atacatacat acatcctttc tcccatctct ccatccattc attcctcttt ccatttctct  12300
ttccctccct ctatttctgc atccatccat ctccatctct ccctccctcc aatttttcat  12360
ccatccactt ctccatctat cctcttttca gtctttgcct accaggtaca gtaggtggtt  12420
cattcttacc ataggtttcc agttctgacc tggagccttg tttgcttttt gttgttttgc  12480
ttgtatgttt gtttgtttct ttgtttctag acagagtttc tctatgtagc cctggctgtc  12540
ctagaactct ctatgtagac cagattagcc ttgaacccac ggagaacctc aggcctccac  12600
caacttagct ctgggattaa aggcatatgc cactccacta ctccctgctg gaggctttat  12660
cttctgagca actggctcac acaaacatgc tgacagcatc aagtgaagtt ggattcattt  12720
cctcatttct cagtgtctga tctccatgca ctgggggtgg gggtgaatct gtgtctctct  12780
aatttaaagt aaaagactag tcctccccag ccttgggaat ctccggactt gtgaaccctc  12840
tctagtgccc ccattcccac ccccatccct ctgcagtccc tgtagtggcc ctgaggccca  12900
gcccccaaga ctatgttttg gggctttggg tacctccctt tgcaggagtg accttttgtt  12960
ctgcattacg caggggcttt ctgttcctca ttgtttagtc ctgacagaga ttgtggtttt  13020
```

-continued

```
tttttctttc ttctgtccaa gggaataaac aggcctggag gttgttgagg gaggcatggg  13080
cccctttgcc agctgctggg actgggatta cacatagcag caggagaaag gaccagaaag  13140
tttattctta gtgaagctgg ggacaaggag gccccccttga tgatgggtgg atcagtgaga  13200
cagtccaact tggctgagtc aaggcccttt cccatcaggc cctcttcgtc tggaaggaag  13260
ttgtttctag ccaaaacagt gtttctctgg gccactagaa gctgcccagg ccacagctca  13320
gttaccacca cccaagggat atacctaccc cagggctggc agggcaagtg ttcccatgag  13380
atgcacacac cgacagcccg tgtgtggagc cggaggctgc tgtttgagga agtagaggag  13440
ggtgaagaga aggttcttag ttaatgagac aaatagtttc cccaggaagg ctagtctggg  13500
agttttattg gggacactca ggccttctgt gtcagttagc attctttgga gtgatggata  13560
caaatgagct atgacactga tttctggggt ccaaggctcc cctaattctg ctgtgtacct  13620
tcctcactcc tttctcccaa cttaccttac tttctccatg ggataggata ctcagaccac  13680
attgagtaga gcagaggagt ctctaatccc caggaagagt tctttcttat tttatctttc  13740
ctctttatga gcagtgtggc tccccagccc agagactctc ccccccttaga tgtgaaaggg  13800
tcagccagcc attgatgtac cctttgatgt gtttgttaca ttagcagttc tcatctgaac  13860
acaacacact gggtccgagc ggttccacgt gtgagatgtt tattgggagg ggggcgcagg  13920
ggagaaggtg acagcagaaa gagaagggga aaaagagaga gagggcctcc ttagaagtgg  13980
gaacaaaaca cccttggaag gagttacaga gacaaagttt ggagctgaga ttaaagggtg  14040
gaccatgtag agactgcctt atccagggat ccaccccata atcagcatcc aaacgctgac  14100
accattgcat acactagcaa gattttatcg aaaggaccca gatgtagctg tctcttgtga  14160
gactatgccg gggcctagca aacacagaag tggatgccca cagtcagcta atggatggat  14220
cacagggctc ccaatggagg agctagagaa agtacccaag gagctaaagg gatctgcaac  14280
cctataggtg gatcaacatt atgaactaac cagtaccccg gagctcttga ctctagctgc  14340
acatgtatca aaagatggcc tagtcggcca tcactggaaa gagaggccca ttggacacac  14400
aaactttata tgccccagaa caggggaatg ccagggccaa aaagggggag tgggcaggta  14460
ggggagtggg ggtgggtggg tatgggggac ttttggtata gcattggaaa tgtaaatgaa  14520
ctaaatacct aataaaaaat ggaaaaaaaa aaaggaaaaa aaaagagata ttaaggaaaa  14580
gtaaaaaaaa aaaaagagag agagagaggg agggctgttc cccttattta tatgaaaaaa  14640
atgacgtaac acaggtaaag gtgggaggtg agccaagtgg attctgggaa tatgctgcag  14700
gtcgcgctgt cacctatgtg atgtcatagg tttgggaggt cctgatgcaa agacccttga  14760
ccttgagaac agtcagtgag gtcccagaca gtgtggaaca cccttatttg tgtgctcaga  14820
ctcaactggt tgttttgtca agaaatggaa cggggaagtg ccaggatatt gtgtgtaggc  14880
atgtgcgcat gcgcttggat gtgtgtgcag ctgtccagag ggagctgcag tggctttttc  14940
agactgggta ctcagcatgg ttctgcgact tccctcaccc agctgtctgc atgaccttcc  15000
tgaaaaggat tgccttgatg gaggaactca gagataggcc agggcagcag atgcatctat  15060
gttcaagctt cttggccctg gtgcccaggg ggaggctctc gcctcaagga aatgacatta  15120
gaattattac cttactcagg gtagcaacta ttgattactc ttttctgtct ggctctggat  15180
agggtagctc gcactgcagc ctccaatggg ccctcatctg gggttactgg gtgagcatga  15240
agacaaggca gggggctggc tgtattgggt tgcttatcca gggcacggtg tgcacagtcg  15300
cctgaagagg gaagcactct gtgtggactt ttggccaaag gcgcaagagg cagctagggt  15360
```

-continued

```
actgtggcag gtccagaaga gccaaagact gtccacagca tagaacccca gtcccttgag  15420
tcatggcttc tggtggcttt cagctgttat cactgagtgg ctgagcaaag agaaacatga  15480
taggctcaga ggtcactcag tgcacagcac taggcaaggt agggtgatgc tctccagaca  15540
cagctgggga tgggaagggg aaagacagaa agcagagcca ctgcccacag atcatgggag  15600
tttgtgcagt ctatacagac caaatgagcc taatagtaag gtcggcatct tctctgattg  15660
gcttgtttgc agtggctttt cagagactga tccatgcctt tgctgtgcta attgttggat  15720
attttatgta tctctcttgc tcccatagaa ttgagtcagg aaccgatgtc cagagagata  15780
gggacacttg attgactatg accatacagc ttctggatgg aagaataaga aaagaagacc  15840
acatctctct aactctccac ctttatctga ggagtcaggg gattcatttg ggttactggt  15900
ttaataaaca tttattaagc tcctgctgac catatgacgg cagctgctgg tacaatcaag  15960
agtgcggagc agccttcctc tttaacctag aaccacccct tggtcatttc caggtgacat  16020
cagcagaggc tgcaagggtg ttgagtgtgt gttcacaccc tctttgctct tgtagatcca  16080
ctcccatgtt tgctcatgag ttcacatttg tgcagaaatg gctaattcat gcttgtccct  16140
aaagtttcca attgctgttc caccttctgg aagaaaggct ggggcttagg caggtctctg  16200
aggtactggg atagacccag tggtgacagt tgctgctgct gtacacttct gagaactgag  16260
gacctcttgg agatctgagg gagggctctg tgtttctcac agttggttct gtgccatgtt  16320
gggtgttttt ttgtttttttg ttttttctcc tccccatttg tctccctttc ataattattt  16380
atttaattaa aaaatgtgag tactcctgag tatatgtatg tgaaccacac acattcagga  16440
gtatgcagaa cttagaaggg agcgtcaggt tacctggaac tggagtgaca gacagttgtg  16500
agctgccatg ttggtgctgg gaactgatcc caagttgtct ccaagaatag taagtgcccc  16560
taaccactgc gctatctctg gagctcctcc tccccatcct ccccatcgct ccctgctttc  16620
ctggtctctc cctggaagtg cttagcccag tcattgaaat catggcctag agagacagac  16680
aggacccagg ctcaaatctc tgtcactgcc ttaggtgggt aacctgtgct cgttatgcct  16740
gtttcctttc tatacaatgg tcggagtcca acatggctgg ttgttagaga actgaatgca  16800
ataatacatc catctcaggt ccaggctctg gaagcacagc ctgaggcatg gcttcttgta  16860
acaggagaag gctctcaggc aagagggtgg ggtggcagga tgtggcagca gggtcacatg  16920
ttttccagcc aaaacctatg agtgttggtc ttgggttgag gccaaggtac tgcctttgag  16980
ttggagactt gtcggccagt gctgaggcta ttctcctggc agttggagtc tgagcatggc  17040
taggagcccc cactggtcca aaccttctaa gcccataggt gtaaggcagc actgatgtga  17100
ggaggtgcac aggtttgttt tcattctgta ttaacttcct gaggcagctc tgccatggcc  17160
tgtgtcagaa gcttgggtct agaggtggcg cagccattat ctgtgtcata ggtggcagca  17220
tatggacaca tgtatgtaca cctgtgtgca tatgcatgga tgtgagtgca aggacacacg  17280
gtgccaattc agaacaatga catgaaggtc agaaggggcc atgtctatat tcagagagaa  17340
cccagaggag gaagagccta cattaggccc aggagagtag agggtacttc tgggagaagg  17400
aagacctcag ccacaaggac agagggacag atggacagac atcctaaaaa gagaagcttt  17460
gtgtggaggt ccttgtcaca gtgagtcaag ccactgtctt aaaaaaacta catcttctca  17520
gagccttgct gggtctcacc cagcaggcag gagggaagcc ctaaagtaac ccacttcctg  17580
gcccagcaaa ctgcagacac aagcgtgcca cgctgaagag gaaggccaag aagggaaaaa  17640
gcctgggctc tactctctca agccttcctc gtcctccaac gcaaaaaccc atccatgagg  17700
cctggtgaca ggtatgctgg agcccagagt catactgatg gctgcctccc ttgttccctt  17760
```

-continued

```
ccaggttgtc ttgacaccct acaaaccgga acctgggtac gagtgccaga tctcacagga  17820
atactatgac aggaaggctc agatgtgctg tgctaagtgt cctcctggtg agaggcagct  17880
gctggggctt tggaaggtgg tgccatggag ggagtgcttg tctgggaatg agggccttca  17940
gctctcactg gctgctttat acatgctagg gttcatgatt catcttgccc tgggctcttg  18000
catgtgctgt gccctccact gagcacactt ctcagtgtct tctcctggtt actgcctacc  18060
tacattttga ccctatcctc ttgtccagga agcctcctca atactgcaat gatgtcctag  18120
tacttttcat agccccacta tgtgctatgt ctacccctat tgagtagtga gtgtagcttg  18180
gtccctgtgg agttccaagc acacggctgg cctatattga tgtcctgtac ttaattgtca  18240
agtaaatgaa tggatagcca tatcatagat ggcggatctg agccctggcc tcattggcga  18300
ggactgagta gctggccccc agtgctgagt agacaatcaa gtgtatgcat tcaattaagt  18360
cgtatttata atgcatctac tctgtgctca atctgctgag aggaaagcca cacaaacacg  18420
ggatacagca ggctgggaag taagtgcaaa gccctaaagc aggggcctgt tttaatgggt  18480
ccaaagaagc ttgaggctgg tgtttgttgc ccagagtgaa agaagagtgt gatggaagat  18540
gggtatgaag gggtgagggt tggtgagatg gctctgtatg taaaggcact tgctgtgcaa  18600
gcctgagaac ctgaaccaat ggtggaagga gaaaacaggt tacacacaca caccaccacc  18660
accaccacca ccaccaccat cgtaataata tacatttgat taagcgagat gagtggtgtc  18720
accatgaaga attcagattt catttactgg aggctttgag tcctgtgctt gtgacccagt  18780
gggcaggaac acagggcaat gtcatcctcc acagtcacag ccaggggaca gtggcttttc  18840
tagtgacgag cagagtgtct ttacgaagtt acaagcttag agtagcagga acagaggaga  18900
cgagctggtt ccagaagaga aaaccttaaa gatttgtcct gttactcttc tatcctccag  18960
gctcttagga gccctatgcc cttggcactg acaggctacc agacatgacg cccttatagc  19020
cacttatatt tagtacatca ggatagagaa ttttaaccaa ctatcaagaa gacaggagct  19080
agcaaaccca ttctccctta agtattcttg actgttaata ggtttttcga gtggtggtgt  19140
ttcaactacc tggagagagc agagggaaga tatgttcaga ggtagagaga tagctagggc  19200
caccagacat gcttcatccc aggggcttcc tggcaagggt cttctgctga gacctctggt  19260
ccttgcttcc tcaggccaat atgtgaaaca tttctgcaac aagacctcgg acaccgtgtg  19320
tgcggactgt gaggcaagca tgtataccca ggtctggaac cagtttcgta catgtttgag  19380
ctgcagttct tcctgtacca ctggtgagtg gcatgagcac tgtgatccca acatcttccc  19440
cagtcactcg ccgtccagca agtaaggtgg atggggttac cctgggccag ccgttttcgt  19500
cttccaggac ttgagttgcg ggagactgct ttttttaaaa tattttttta ttacatattt  19560
tcctcaatta catttccaat gctatcccaa aagtccccca caccctcccc cccactcccc  19620
tacccaccca ttcccatttt ttggccctgg tgttcccctg tactggggca tataaagttt  19680
gcctgtccaa tgggcctctc tttccagtga tggccaacta ggccatcctt tgatacatat  19740
gcagctagag ttaagagctc cggggtactg gttagttcat aatgttgcac ctacagggtt  19800
gcagatctct ttagctcctt ggatactttc tctagctcct cccttggggg ccctgtgatc  19860
tatccaatag ttgactgtga gcatccactt ctgtgtttgc taggccccag cctagtctca  19920
caagagatgg ctatatcacg gtccttgcac caaacgcttg ctagtgtatg caatggtgtc  19980
atcgtttgga ggctaattat gggatggatc cctggatatg gcagtctcta gatggtccat  20040
ccttttgggg agactgcttt ttttcaactt gtatgtagtt atgtgattgg aacctgggac  20100
```

-continued ttcatgcagg tgatgcaaac actttttttt tttttttgg tttttgaga cagggtttct 20160 ctgtgtagcc ctggctgtcc tggaactcac tttgtagacc aggctggcct cgaactcaga 20220
aatctgcctg cctctgcctc ccaagtgctg ggattaaagg cgtgcgccac cacgcctggc 20280
tgatgcaaac actttttaac agaactacat caatccccag atattttttt tattaaaggt 20340
gtattaatta attaattaat taattaatta attaacttac ttattttggt ttttcaagac 20400
agcatttctc tgtgtatcct cggctgtcct ggaagtcact ctgtagacca ggctggcctc 20460
gaactcagag atctgcctga ctctgtatcc caagtgctag gactaaaggc gtgcgccgcc 20520
ccaacccaat aagatttatt tatttttatt gtatgtatat gggtattttt actggcatgt 20580
agtcaggatc tattttgcct tgagtcagga tctctctagg tagctcagaa tggctttgaa 20640
gttatgaact gcctaactca gcttcctgag tagctgagaa tacagacctg aactcccaga 20700
aaatgttttc agttcagatt tttttgtttg tttggttttt gttgttattg tatttgttta 20760
tttggttttg gtttttataa gatagggatg tgtgtgtgtg tgtgtgtgtg tgtgtgtgtg 20820
tgtgtgtata tagtcttggc tgttttgaaa ctgaactaac tctgtagacc aggctggcct 20880
tgaactcata gagctccaac tgcctctgcc tcctgagtgc tgggattaga gatgtatgcc 20940
acccctgttt tttgtttttt gggttttgtt tttttttttt ttttgagatg gttttttttgc 21000 taagttgccc aggttggcct agaactttct ataaggccca ggctaacttt aaatttacat 21060
tcatccttct gcctcggttt ccccagtgtt gagattacaa atgtgtgaca cctgcctgga 21120
cagttccaga tgacattttc cttctagatc ctaccaaatc ttcattggta gtggggaggt 21180
gaggtcagag ttgagaatgt agagcctaga gaaacagatg tgtatattca ctctgtggtg 21240
gagttcagag tacagacaac aacagcccaa gaggcaaggt gttcaagggt cctttgggcc 21300
tgtgctgagg gccctaccag ctctggcagg aagagcagaa tgggtgagtg gaagtagaga 21360
tgaccctggc tgtctttctc acctctagac caggtggaga tccgcgcctg cactaaacag 21420
cagaaccgag tgtgtgcttg cgaagctggc aggtactgcg ccttgaaaac ccattctggc 21480
agctgtcgac agtgcatgag gctgagcaag tgcggccctg gcttcggagt ggccagttca 21540
agtaaggatc cctcttcctc tccctgggaa aggatgtgaa catccctgag atgtcacagg 21600
cacttacctc tctaagcctt acctctaagc ctccagtagc tgccacatgc attacatgtc 21660
tcctggcacc cctggttaca ccaagccctt agctagtagg aaatcaggta ggacaggaag 21720
gtaaccctgg acagcaagtc catgtacatg tatggtcatg tgtgtccatg catgcatgca 21780
tgcgcgcgcg cgcgcgcgcg cgtgtgtgtg tgtgtgtgtg tgtgtgtgtg tgtgtgtgtg 21840
tgtgtgtgtg ttttaaggga gaggattaca aagtggcctc ccttgtggcc ccactgttaa 21900
gagactcccc acctggctac atgaagtgtt catattgtcg acaagctctg gattttctct 21960
tcaaggagcc ccaaatggaa atgtgctatg caaggcctgt gccccaggga cgttctctga 22020
caccacatca tccactgatg tgtgcaggcc ccaccgcatg tgagtgttga cttcctggct 22080
tctgaaggag cagggagggt gaccgcctag gggaactggg tcccaggata taggacagct 22140
tgtcactctt tgtctcttga cttgggttct gggacagaca atggatgact tgagcaggaa 22200
cctgacatag aggcaagatt ggatagagtg acactgggtg gaagttgagg agtatatgag 22260
ggggtagtgc taagaagccc atactcattg cttggctgtt aggatccttg tcctcaggcc 22320
tggctccctg aaattctgtg gtcttctatc ttctgtggtc tcctgattac aatcttcctc 22380
ccccagctgt agcatcctgg ctattcccgg aaatgcaagc acagatgcag tctgtgcgcc 22440
cgagtcccca actctaagtg ccatcccaag gacactctac gtatctcagc cagagcccac 22500
aagatcccaa cccctggatc aagagccagg gcccagccaa actccaagca tccttacatc 22560
gttgggttca acccccatta ttgaacaaag taccaagggt ggcatctctc ttccaattgg 22620
taagtcctca gtctcaagag tgacccaggc aggcttggaa gtgtgcagtc tgagctactg 22680
gggaagctga gacaagagaa ttgcaagttc aaggccaacc tgggctatag agtaagtttg 22740
aggtcaatct gggcaactta gtcagaccct gtctcaaaat agtactttta atgggagctg 22800
aggctgtagc ccattggtag aatgtctgac tagtttgggg ttaaatctgt aacaaaagta 22860
aattgaaaca taaaagggag gtgatccccc acccccaccc cctgtctctc ttgcctccct 22920
ttgggcagaa ctggggcctg gtctctgtct tttagaacag atgcaagtgt agaagagttg 22980
agtctccaaa gatgtgatat tgccataggg aatccctggg tggcatgaat gtgaacatag 23040
gttctggttg ctagttatga tgaacccgtt tgtctcacag actatggact gctggtgtct 23100
ctggcttccc tctggggtta ggatggtacc aagcccaagg ccctacactg tagccttctg 23160
actgcatgtg gtttgcagat gtgatctttg gtttgaccct gaatttgagg gcctaaggct 23220
ggacttgatc tcagcatcag caccagccac cctggaacct ttgtttctga gtaccctgcc 23280
gttttcctag gtctgattgt tggagtgaca tcactgggtc tgctgatgtt aggactggtg 23340
aactgcatca tcctggtgca gaggaaaagt aaggttctgc tctcgtcctg tttcccgccc 23400
cacgtcccta ccctaacact ttctcggagc cttgggtggc aggcctcgtt cagagctctg 23460
cactatcata gactcgggtg gatctggaga ctgtagcctc ttgctctcca ggaacttaga 23520
gcctggtgta gaaggtacat actctaacct ggctaccaga aggtagtgtc aaggctattc 23580
caggggattg aagttcagga tttttataca ggaagcctgg agtctctcgg attctgtgag 23640
ctggcctggg tctcagtggg tggagtgtgt tgaggcaggg ctacaacaca ggctgtactg 23700
gaggatggct ggggcaaagg ggtagtggct gaaagtagca tgggctcatc cgtgaacatg 23760
acaggcagct actccctggg ctgggtccac tctcctggct ctaccctagc catgctgtgc 23820
ccattaagac agctgttctg aagaagtcct gcctctgact tgttcccctc tcttcattgt 23880
agagaagccc tcctgcctac aaagagatgc caaggtggtg agtatccctc tgcggtcctc 23940 ctccccccttc tctcctccag ctctccctct tcctcctcct ctttctcctc ctcttccagt 24000
tcctttacta gggcatcata agcaacatca tataagcagg atctaatgta tatggtggtg 24060
catacctgcc atcccaatag ttaggggcag gtagaggctg gagggtcaga gtgtaaatac 24120
tccctcagag ccagctgatg tttagttcca ttacagttgg gaagaaaccg gcaaactctc 24180
ccctagctgg gcatagccag gctctttccc taggctatgt ccaactcctc actggtccta 24240
tgcataaggc accttggctc ctcattatat agatgaggaa atgtaggctt aacagataca 24300
gtcacccttg aaaggttgtg ttgtgtcctg gtggtcaaac cctctgcgca tgtgcatccg 24360
gcagctacac ccaaagctgt ctcaggctgg cctctcctag cagggactgc tcgccaagac 24420
tggtcaccag gatttggaga acctagatgc ccccctttgt ccagccctgt gccctgtcag 24480
ctacctgccc cagggcccta ctctggagcc cagtggacgg tgtcctcatg tgctagagtg 24540
aggaggctgt caggcaggag cagcagtgac tcagcttcta ctctgaggac tggggaagat 24600
gaggttatct ggaaaaacag cacgtgaatt catctacacc tcccccagtc atgcgcatgg 24660
ttcatgttta gtcgccggca gttactggtg gtggtggagg aaggacgtgc cagcactgtc 24720
tgagggctta ttcttccagc ttgactgtga cacaggctat gacacaggct gtggcacagg 24780
ctgtgacaga ggttattgcc cccaacgtta gacagagtct gggattatat ggctcagaca 24840

```
ctcttaagta attgtcctgt gtcctagctg tgtcctagac acagctaatg ggtatggcct  24900
ggaacacaaa cttagcatac aattactacc cagcatacaa ttactgtgcc actcttaggc  24960
atgcccacat gagcctgcac atataaatac ccttagctca gaggccgaca gaagccagcc  25020
atgcttctgc cagtcccagt tccatataac aggaccagac ccagaaccat aggaggtatc  25080
aggcaagcta agatttttg gtgttcattc agtggggtcc tagccagagt cacatgactc  25140
tgatagtgtc tgtacttgaa cactgtagct tgtggctttg aagaagctag ctgtgacctt  25200
tggggaggag gggaagatcg ggttctgtct ggctctagcc acaagcagaa agggggaggc  25260
ccagacagaa aagctccttc tctggggctg gtgtggtgtg acatttatga gtgcctctgt  25320
agagttacag ggtaaggcca gggccaaggt cagaccgtga gttcaggatg tttttcctct  25380
cttccatttt ggggtaccta gctgggagga ccccagggga gtcaggagga tgcagtgggc  25440
atgctcccac atcctagact gggtttgctt actgtggcca tcagccagct ctgtaactct  25500
gagctctgga ttcatcttct gtgggctttt gtggcctcat gaagacagct tgtataagat  25560
ccttccagtc cagagtcaga agctgtggac tgtgcaggaa acaaggcctc aaggccatgt  25620
atcatgacat acctgggcat ctaagaagac atagcaacag tgggcaggac ctggagatgg  25680
aagttttagt gactctctag agagcaccag ccacaggaag gatagcccaa ctattgtttc  25740
agcttagact acacctggca ttgtgcctcc ctggaaaagt gtggccactt ttccagctgc  25800
tgtcaacaga caatggcctt ggaatagatg tccttagcat aagttgccat gaacagggaa  25860
tttgtcttaa gcctcaagag ctgaacccca gacacccaga agaggcatgg tgagttttta  25920
gctcgactgc actgtatcca aaccatggcc tcaggcagaa agttccgttt ccatatttac  25980
agagctagga tggcactagg ctatattgag tgtctagaag agctgagacc aatgtgactc  26040
aggcacagga tttggcacta ggtgctcatg tcacatacag agtaagaagc cacagggaag  26100
ccacacgaca tcatctgggt gaactgtggg aacgggcagc tgagaagacc agtgaggaac  26160
cctgtgagtg gccctgtgag tggccctgag gaaaggaccc catgggccag ggtgattcat  26220
tgagcagaag gaatgaagag taaaggtgtt aagcttcaag caccaaggct ggcctctggg  26280
acagctactc tgatctgcca cccaccatca ggaagtctgt gctttgcaaa acattgatga  26340
cagctcaggt gcatcaaact tgtttattta cgaacactaa aacttgacct ttagatttga  26400
ggcattttgt attttagaca cggacttatg tagcctgtat tgaccctgaa cactaactga  26460
ggatggcttt gaatttatga tcctcctgcc tcaacctccc cagtgctggg attactacat  26520
acaccaccac accctgcttg tgtgatgctg gggactgaac ccctgagctc taggcagagt  26580
ctttagtccc ttctgttctt gcagaaaaca tgatttcagt tctcagcacc aagagaggtt  26640
aggtaacttt ttcaaggtca tctagccagt gagtggtaga gctatgaact ttagactcag  26700
gtgtctggtt cagaattcat ctcttagctg ccaggctggt gacacatctc cctatgctcc  26760
aaaaagtcac tttttccatt tccttgtgag gactgagatt gaaaaccttt ggtgccctgt  26820
gtggaaacgt gtggtgtggg cagaaatgtg taagctgtgg agtgtgggtg acaggggaga  26880
ctaggagagc aaaggcactt gcagatggat taatattctc tcttttcctc ccagcctcat  26940
gtgcctgatg agaaatccca ggatgcagta ggccttgagc agcagcacct gttgaccaca  27000
gcacccagtt ccagcagcag ctccctagag agctcagcca gcgctgggga ccgaagggcg  27060
ccccctgggg gccatcccca agcaagagtc atggcggagg cccaagggtt tcaggaggcc  27120
cgtgccagct ccaggatttc aggtgagagg ctgattccct cctgctctgg acagatagct  27180
ggccctccac ctactggttg aaaataaccc aagaggaaaa tgcctttaac acttggtggc  27240
```

```
tatgacaacg gacagaatgg ctctgatctg ctgcccagtg tcttgcgaga ggatcctatt  27300
gcaattcaat agttccgaaa aaggtccagg ctcacagtgc taaacacagc tcccatggaa  27360
tgcgtgtatc atgttcccac caacgtcaag ttgcaaaacc tcgagtcaga cttctgtagg  27420
taaagtcagg ttcatgtgta tcccttgcgt aatctctgct ggtgtcctgg agctgccctg  27480
tgaagccacc cttagctgag cctggctgac ttcctagttc tggctcatgt gcagtccagc  27540
cacggtaggt tcagcgccac ctgtgttggt tatctcacta gctcattcgt cttcagacac  27600
ccctgctttg tctttcaagg cttccatatc aggtggggag taatcctgaa cccctccacg  27660
ttgtcatctc tggccagctt ggcctttgtt cagggatccc caaggtcatg ccgcctttcc  27720
acaggattat ctgtcttctg cctttcgatg gcctgtgtga tttccccaaa gccacgttct  27780
gcttatatcc ctaggcccag cactggtctg gctagattgt ttgtttgttt gtgagacaag  27840
gtttctctgt gtagcctagg ctgtcctgga acttgctttg tagaccaggc tggcctggaa  27900
ctcagagctc cctctgcctt tgcctcctca gtactgggat taaaggcatg tgccaccatc  27960
cctcattggc ctgtccagtt ttataagcta atacttccta gggcattgta acacaccagt  28020
ctttgtcctg ggtgctttac atgaaccaaa cctgcctatc aatactaaga gatagttact  28080
attactaccc cattttccag atgaggaaat tgaggtccag gacaccttgt taagaggaca  28140
tagctagtgc acccaagctc caggagtcat cagctctgca gtatgagctt cagagccctg  28200
gaaatgggag atgaatgaaa tagttccttc agggttcttt aaaaatgttt tgtgtatggg  28260
tattttacct gcatgcattt ccatgtactg taggtgtgca tggtgtctat agaggccaga  28320
agagggtgtc agatctccta gaaatggagt tacagatggt tgtgaagtgc catgtgggtg  28380
ttgtgaatct aacctaactc ctctgaagga gcaacaagtg ctcttagcta ctgagccacc  28440
tctccagacc cattcttctg gggttctgc tcactgtagc tcactgatga tgatcacttt  28500
gagtcaaagg catgatgtgt gaccctgttg cctttacttg gtctgcatct taccctacat  28560
atatataatc tataatagag acactattgg tatctcttgt gcctacaatg gagtcagtcc  28620
cttgtaggtt tcccaagaac ccagagattc cctttggttt ggtttgtaga agaaagggca  28680
agactacagg cctttgtccc tctctcccgg cagcacaggc gagtggggca ataggaagta  28740
taaacatgaa cgtgaacttg gtcattcacc cagagcagcc caacagccct ggggccatga  28800
gaatccaagc aggctcctac atcccatttc ctcatctggt gatgagacat gctcttcctt  28860
agcacgtcaa tgagagactg tggctttgtg cccacattgg ctcctgacag gggattgaca  28920
gccaagacca cactgcctcc cacaccagcc tcctctaaca cccatgttct gttgctgcct  28980
tgacttccgt gccctgctct tactcctgcc tattcaagct tttctgcctg cagcactcct  29040
gctgtctccc tgcccgcagg agtcccggtg tctgctttgt gtttttcccg tcggaacccc  29100
agcctcacta gcacgtggta acttgtcagg gcccctggct ctgacctgag gattccctga  29160
gcctggcttg gaacagaaca ggtgtctctt aacattggtt gagtgaatac atgtgcttga  29220
atagaagcat gaattcatct ttcatggctt ccctcctccc atggtgttcc actgtggctc  29280
cttctttggt ccctgaggac ctaagttctt tctcctctga cctctgcccc ctcctctttc  29340
ttctcccagg tgtactgtac ctctcctcct ctcccattga cacctccctc tacccgtggg  29400
gcctgtaaac cccagaattg ccccactcac ccccacatgt tcatgacatg caaaggtcat  29460
ggtgacttca aatgacgttc gggtgctgtt gaggcccagg gtagaggttt ctttgtggtc  29520
ccttgattcc agttctccct ctgcttgata tatttgaggc tgctctgaat agactggttg  29580
```

-continued

```
gctctgtcct aacccaagct cccttgagtc ccaatttccg ggaggcagaa gccaggataa  29640
atagacagct gccactacta tgggccccgg ggggttctgc agatctagct gcagtcgcaa  29700
gagcaattgc catgcagttg acatttggga gtaacatatg tctaccctct gctagtctgg  29760
cattcactcc tcgccaactt agagaactta gaagcccaca gaggtcaggc aggatgatag  29820
atggactgtc cctgatattc gttctgtctg tgatttctgc ttctctatat cccagtggta  29880
gggatcaaaa tccacgtgtc tggtaggtga gctttaaact gccaacccct aaattttaag  29940
tgttgtcagt caattcactt aaaatgctat catcaccaaa accaaagtgt gcctaggctg  30000
gttttgatcc atttggtact tgccctttca gtggtcatgg ggaatattct ttgtagattt  30060
ggccataggc agtcttctgt aactgcttcc tgccacatcc tagcttctct gttccagcaa  30120
actgctctct ctctctctct ctctctctct ctctctctct ctctctctct ctcacacaca  30180
cacacacaca cacacacaca cacacaggtg tgctaatgag tccacgtgtc tatgtggaag  30240
ctagaggaca acctcaggtg gcatccttag gaaccccatc tgcctccttt aagacagttt  30300
ccccttggct tggtgtccac cagttagact tagttggttg gcctgaaaag acccagaaat  30360
ctccctttct ctgcctccca agtactgaga ttacaagtgt gtgccgccat gcccagcctc  30420
cttacatggg gtctcagggg ttgaatttag gtccttaagc ttgcaagaca aagtccttac  30480
taactgagcc atatcctcag cccaatgttt tgttcttctt ggagtacttt tgtctgcttt  30540
agaaaattgt ctccggtcaa cagcagggag cgttgggctg ggcagctggg aagtgagcac  30600
acaggcatgt aagggtgatg catctgccat cgtagtagag gtgagctagg gtctttagcc  30660
tcttggccct tggcctattg ctctaacctg cccctgggac aagaggcaaa ctgcaaagac  30720
accctgtctc caagatcccc agactcaccc tcccatcctg tgcttcacag attcttccca  30780
cggaagccac gggacccacg tcaacgtcac ctgcatcgtg aacgtctgta gcagctctga  30840
ccacagttct cagtgctctt cccaagccag cgccacagtg ggagacccag atgccaagcc  30900
ctcagcgtcc ccaaaggatg agcaggtccc cttctctcag gaggagtgtc cgtctcagtc  30960
cccgtgtgag actacagaga cactgcagag ccatgagaag cccttgcccc ttggtgtgcc  31020
ggatatgggc atgaagccca gccaagctgg ctggtttgat cagattgcag tcaaagtggc  31080
ctgacccctg acaggggtaa caccctgcaa agggaccccc gagaccctga acccatggaa  31140
cttcatgact tttgctggat ccatttccct tagtggcttc cagagcccca gttgcaggtc  31200
aagtgagggc tgagacagct agagtggtca aaaactgcca tggtgtttta tgggggcagt  31260
cccaggaagt tgttgctctt ccatgacccc tctggatctc ctgggctctt gcctgattct  31320
tgcttctgag aggccccagt attttttcct tctaaggagc taacatcctc ttccatgaat  31380
agcacagctc ttcagcctga atgctgacac tgcagggcgg ttccagcaag taggagcaag  31440
tggtggcctg gtagggcaca gaggcccttc aggttagtgc taaactctta ggaagtaccc  31500
tctccaagcc caccgaaatt cttttgatgc aagaatcaga ggccccatca ggcagagttg  31560
ctctgttata ggatggtagg gctgtaactc agtggtccag tgtgctttta gcatgccctg  31620
ggtttgatcc tcagcaacac atgcaaaacg taagtagaca gcagacagca gacagcacag  31680
ccagccccct gtgtggtttg cagcctctgc ctttgacttt tactctggtg ggcacacaga  31740
gggctggagc tcctcctcct gaccttctaa tgagcccttc caaggccacg ccttccttca  31800
gggaatctca gggactgtag agttcccagg cccctgcagc cacctgtctc ttcctacctc  31860
agcctggagc actccctcta actccccaac ggcttggtac tgtacttgct gtgaccccaa  31920
gtgcatgtcc gggttaggca ctgtgagttg gaacagctga tgacatcggt tgaaaggccc  31980
```

acccggaaac agctgaagcc agctcttttg ccaaaggatt catgccggtt ttctaatcaa 32040
cctgctcccc tagcatgcct ggaaggaaag ggttcaggag actcctcaag aagcaagttc 32100
agtctcaggt gcttggatgc catgctcacc gattccactg gatatgaact tggcagagga 32160
gcctagttgt tgccatggag acttaaagag ctcagcactc tggaatcaag atactggaca 32220
cttggggccg acttgttaag gctctgcagc atcagactgt agaggggaag gaacacgtct 32280
gccccctggt ggcccgtcct gggatgacct cgggcctcct aggcaacaaa agaatgaatt 32340
ggaaaggact gttcctgggt gtggcctcag ctcctgtgct tgtgtggatc cctaaagggt 32400
gtgctaagga gcaattgcac tgtgtgctgg acagaattcc tgcttataaa tgctttttgt 32460
tgttgttttg tacactgagc cctggctgag ccaccccacc ccacctccca tcccaccttt 32520
acagccactc ttgcagagaa cctggctgtc tcccacttgt agcctgtgga tgctgaggaa 32580
acacccagcc aagtagactc caggcttgcc cctatctcct gctctgagtc tggcctcctc 32640
attgtgttgt gggaaggaga cggttctgt catctcggaa gcccacaccg tggatgtgaa 32700
caatggctgt actagcttag accagcttag ggctctgcaa tcagaggagg gggagcaggg 32760
aacaatttga gtgctgacct ataacacatt cctaaaggat gggcagtcca gaatctccct 32820
ccttcagtgt gtgtgtgtgt gtgtgtgtgt gtgtgtgtgt gtgtgtgtcc atgtttgcat 32880
gtatgtgtgt gccagtgtgt ggaggccaga ggttggcttt gggtgtgttt gatcactctc 32940
agttactgag gcagggctct catctgtacc cagagcttgc acatttteta gtctaacttg 33000
cttcagggat ctctgtctgc ctatggagtg ctcaggttac aggcaggctg ccatacctgc 33060
ccgacattta catgaatact agagatctga attctggtcc tcacacttgt atacctgcat 33120
tttatccact aagacatctc tccaagggct ccccctteet atttaataag ttagttttga 33180
actggcaaga tggctcagtg ggtaaggcag tttgcggaca aacctgatga cctgagttgg 33240
atccctgacc ataaggtaga agagacctga ttcctgcaag ttgtcctctg accaccaccc 33300
catacatgct tctgcatatg tgcacacatc acattcttgc acacacactc acataccata 33360
aatgtaataa atttttttaa ataaattgat tttatctttt aatcattatt tttgcttatc 33420
tgtttgttca tacatggagt tttgctgtat acccagtctg gctgcatcct ccaggcacct 33480
tgaacttgga tattctcctg cctcagtttc gagagtgctg agttataggc atgtgcaacc 33540
gtgtcaggac ccttggcgtt acattatgtt ttcgaatctt atttttccat ctaagactga 33600
caaccacctt gccaaaggat gaccttgact tttgtatcct cttgcctcta cttcccaagt 33660
attgggatga caagtctgtc catcctatga tttgtgtggt gctggggctt gaacccaggg 33720
gcctcgtgaa tgctaggcaa acgcaatcag ctgcccaacc ccgaacttca cttttcacct 33780
gtgatttctt aacatggttc ctgagcagac agcatgatcc tgttgccttg aggagctctg 33840
ctcgttgctt tgacaatgct ctatttacta aagaatactt atagagttca agactccaaa 33900
gcagcagttc ccaacctgtg ggtatgacct cttgggtatc ccatatcaga tatttacatt 33960
aaacttataa cagaagcaaa attacagtta tggggtagca acaaaataat tttttttga 34020
ggcagggttt atctgtgtag ctcactttgt acagactagg ctggccttga acttaaagat 34080
ctgcctgcct ctgccttctg aatgctggga ttaaatgtgt gtgccaacat gcccagtgca 34140
gtgaaataat tttattgttg ggtcaccaaa acatgagaaa gagtattaaa aggtcatagc 34200
gttaggaagg ttgagaacca ctgccccaaa agatagtaga aataggtaat agcattttaa 34260
aaaaagatta atttcttttt ccgtgtgtgt gtgtgtgtgt gtgtgtgtgt gtgtgtgtgt 34320

-continued

```
gtgtgtgtgt gtgtgtgaag ggtgctgaat tccctaaatc tgggattaca gacaattgtg  34380

ccaaatgggt attgggaacc aaagttgggt tttctgaaag agcagcaagt gcccttaact  34440

gctgagccct ctctctagct ataataaact ttttttaaa aaaattaaaa aaatttagca  34500

ctc                                                               34503
```

<210> SEQ ID NO 16
<211> LENGTH: 4913
<212> TYPE: DNA
<213> ORGANISM: Mus musculus

<400> SEQUENCE: 16

```
agtcaccagc tagagcgcag ctgaggcact agagctccag gcacaagggc gggagccacc    60

gctgccccta tggcgcccgc cgccctctgg gtcgcgctgg tcttcgaact gcagctgtgg   120

gccaccgggc acacagtgcc cgcccaggtt gtcttgacac cctacaaacc ggaacctggg   180

tacgagtgcc agatctcaca ggaatactat gacaggaagg ctcagatgtg ctgtgctaag   240

tgtcctcctg gccaatatgt gaaacatttc tgcaacaaga cctcggacac cgtgtgtgcg   300

gactgtgagg caagcatgta tacccaggtc tggaaccagt ttcgtacatg tttgagctgc   360

agttcttcct gtaccactga ccaggtggag atccgcgcct gcactaaaca gcagaaccga   420

gtgtgtgctt gcgaagctgg caggtactgc gccttgaaaa cccattctgg cagctgtcga   480

cagtgcatga ggctgagcaa gtgcggccct ggcttcggag tggccagttc aagagcccca   540

aatggaaatg tgctatgcaa ggcctgtgcc ccagggacgt tctctgacac cacatcatcc   600

actgatgtgt gcaggcccca ccgcatctgt agcatcctgg ctattcccgg aaatgcaagc   660

acagatgcag tctgtgcgcc cgagtcccca actctaagtg ccatcccaag gacactctac   720

gtatctcagc cagagcccac aagatcccaa cccctggatc aagagccagg gcccagccaa   780

actccaagca tccttacatc gttgggttca acccccatta ttgaacaaag taccaagggt   840

ggcatctctc ttccaattgg tctgattgtt ggagtgacat cactgggtct gctgatgtta   900

ggactggtga actgcatcat cctggtgcag aggaaaaaga agccctcctg cctacaaaga   960

gatgccaagg tgcctcatgt gcctgatgag aaatcccagg atgcagtagg ccttgagcag  1020

cagcacctgt tgaccacagc acccagttcc agcagcagct ccctagagag ctcagccagc  1080

gctggggacc gaagggcgcc ccctgggggc catccccaag caagagtcat ggcggaggcc  1140

caagggtttc aggaggcccg tgccagctcc aggatttcag attcttccca cggaagccac  1200

gggacccacg tcaacgtcac ctgcatcgtg aacgtctgta gcagctctga ccacagttct  1260

cagtgctctt cccaagccag cgccacagtg ggagacccag atgccaagcc ctcagcgtcc  1320

ccaaaggatg agcaggtccc cttctctcag gaggagtgtc cgtctcagtc cccgtgtgag  1380

actacagaga cactgcagag ccatgagaag cccttgcccc ttggtgtgcc ggatatgggc  1440

atgaagccca gccaagctgg ctggtttgat cagattgcag tcaaagtggc ctgacccctg  1500

acaggggtaa caccctgcaa agggaccccc gagaccctga acccatggaa cttcatgact  1560

tttgctggat ccatttccct tagtggcttc cagagcccca gttgcaggtc aagtgagggc  1620

tgagacagct agagtggtca aaaactgcca tggtgtttta tgggggcagt cccaggaagt  1680

tgttgctctt ccatgacccc tctggatctc ctgggctctt gcctgattct tgcttctgag  1740

aggccccagt attttttcct tctaaggagc taacatcctc ttccatgaat agcacagctc  1800

ttcagcctga atgctgacac tgcagggcgg ttccagcaag taggagcaag tggtggcctg  1860

gtagggcaca gaggcccttc aggttagtgc taaactctta ggaagtaccc tctccaagcc  1920
```

```
caccgaaatt cttttgatgc aagaatcaga ggccccatca ggcagagttg ctctgttata   1980
ggatggtagg gctgtaactc agtggtccag tgtgctttta gcatgccctg ggtttgatcc   2040
tcagcaacac atgcaaaacg taagtagaca gcagacagca gacagcacag ccagccccct   2100
gtgtggtttg cagcctctgc ctttgacttt tactctggtg ggcacacaga gggctggagc   2160
tcctcctcct gaccttctaa tgagcccttc caaggccacg ccttccttca gggaatctca   2220
gggactgtag agttcccagg cccctgcagc cacctgtctc ttcctacctc agcctggagc   2280
actccctcta actccccaac ggcttggtac tgtacttgct gtgaccccaa gtgcatgtcc   2340
gggttaggca ctgtgagttg gaacagctga tgacatcggt tgaaaggccc acccggaaac   2400
agctgaagcc agctcttttg ccaaaggatt catgccggtt ttctaatcaa cctgctcccc   2460
tagcatgcct ggaaggaaag ggttcaggag actcctcaag aagcaagttc agtctcaggt   2520
gcttggatgc catgctcacc gattccactg gatatgaact tggcagagga gcctagttgt   2580
tgccatggag acttaaagag ctcagcactc tggaatcaag atactggaca cttggggccg   2640
acttgttaag gctctgcagc atcagactgt agaggggaag gaacacgtct gccccctggt   2700
ggcccgtcct gggatgacct cgggcctcct aggcaacaaa agaatgaatt ggaaaggact   2760
gttcctgggt gtggcctcag ctcctgtgct tgtgtggatc cctaaagggt gtgctaagga   2820
gcaattgcac tgtgtgctgg acagaattcc tgcttataaa tgctttttgt tgttgttttg   2880
tacactgagc cctggctgag ccaccccacc ccacctccca tcccaccttt acagccactc   2940
ttgcagagaa cctggctgtc tcccacttgt agcctgtgga tgctgaggaa acacccagcc   3000
aagtagactc caggcttgcc cctatctcct gctctgagtc tggcctcctc attgtgttgt   3060
gggaaggaga cgggttctgt catctcggaa gcccacaccg tggatgtgaa caatggctgt   3120
actagcttag accagcttag ggctctgcaa tcagaggagg gggagcaggg aacaatttga   3180
gtgctgacct ataacacatt cctaaaggat gggcagtcca gaatctccct ccttcagtgt   3240
gtgtgtgtgt gtgtgtgtgt gtgtgtgtgt gtgtgtgtcc atgtttgcat gtatgtgtgt   3300
gccagtgtgt ggaggccaga ggttggcttt gggtgtgttt gatcactctc agttactgag   3360
gcagggctct catctgtacc cagagcttgc acattttcta gtctaacttg cttcagggat   3420
ctctgtctgc ctatggagtg ctcaggttac aggcaggctg ccatacctgc ccgacattta   3480
catgaatact agagatctga attctggtcc tcacacttgt atacctgcat tttatccact   3540
aagacatctc tccaagggct ccccccttcct atttaataag ttagttttga actggcaaga   3600
tggctcagtg ggtaaggcag tttgcggaca aacctgatga cctgagttgg atccctgacc   3660
ataaggtaga agagacctga ttcctgcaag ttgtcctctg accaccaccc catacatgct   3720
tctgcatatg tgcacacatc acattcttgc acacacactc acataccata aatgtaataa   3780
attttttttaa ataaattgat tttatctttt aatcattatt tttgcttatc tgtttgttca   3840
tacatggagt tttgctgtat acccagtctg gctgcatcct ccaggcacct tgaacttgga   3900
tattctcctg cctcagtttc gagagtgctg agttataggc atgtgcaacc gtgtcaggac   3960
ccttggcgtt acattatgtt ttcgaatctt atttttccat ctaagactga caaccacctt   4020
gccaaaggat gaccttgact tttgtatcct cttgcctcta cttcccaagt attgggatga   4080
caagtctgtc catcctatga tttgtgtggt gctggggctt gaacccaggg gcctcgtgaa   4140
tgctaggcaa acgcaatcag ctgcccaacc ccgaacttca cttttcacct gtgatttctt   4200
aacatggttc ctgagcagac agcatgatcc tgttgccttg aggagctctg ctcgttgctt   4260
```

```
tgacaatgct ctatttacta aagaatactt atagagttca agactccaaa gcagcagttc   4320

ccaacctgtg ggtatgacct cttgggtatc ccatatcaga tatttacatt aaacttataa   4380

cagaagcaaa attacagtta tggggtagca acaaaataat ttttttttga ggcagggttt   4440

atctgtgtag ctcactttgt acagactagg ctggccttga acttaaagat ctgcctgcct   4500

ctgccttctg aatgctggga ttaaatgtgt gtgccaacat gcccagtgca gtgaaataat   4560

tttattgttg ggtcaccaaa acatgagaaa gagtattaaa aggtcatagc gttaggaagg   4620

ttgagaacca ctgccccaaa agatagtaga aataggtaat agcattttaa aaaaagatta   4680

atttcttttt ccgtgtgtgt gtgtgtgtgt gtgtgtgtgt gtgtgtgtgt gtgtgtgtgt   4740

gtgtgtgaag ggtgctgaat tccctaaatc tgggattaca gacaattgtg ccaaatgggt   4800

attgggaacc aaagttgggt tttctgaaag agcagcaagt gcccttaact gctgagccct   4860

ctctctagct ataataaact tttttttaaa aaaattaaaa aaatttagca ctc          4913
```

```
<210> SEQ ID NO 17
<211> LENGTH: 474
<212> TYPE: PRT
<213> ORGANISM: Mus musculus

<400> SEQUENCE: 17

Met Ala Pro Ala Ala Leu Trp Val Ala Leu Val Phe Glu Leu Gln Leu
1               5                   10                  15

Trp Ala Thr Gly His Thr Val Pro Ala Gln Val Val Leu Thr Pro Tyr
            20                  25                  30

Lys Pro Glu Pro Gly Tyr Glu Cys Gln Ile Ser Gln Glu Tyr Tyr Asp
        35                  40                  45

Arg Lys Ala Gln Met Cys Cys Ala Lys Cys Pro Pro Gly Gln Tyr Val
    50                  55                  60

Lys His Phe Cys Asn Lys Thr Ser Asp Thr Val Cys Ala Asp Cys Glu
65                  70                  75                  80

Ala Ser Met Tyr Thr Gln Val Trp Asn Gln Phe Arg Thr Cys Leu Ser
                85                  90                  95

Cys Ser Ser Ser Cys Thr Thr Asp Gln Val Glu Ile Arg Ala Cys Thr
            100                 105                 110

Lys Gln Gln Asn Arg Val Cys Ala Cys Glu Ala Gly Arg Tyr Cys Ala
        115                 120                 125

Leu Lys Thr His Ser Gly Ser Cys Arg Gln Cys Met Arg Leu Ser Lys
    130                 135                 140

Cys Gly Pro Gly Phe Gly Val Ala Ser Ser Arg Ala Pro Asn Gly Asn
145                 150                 155                 160

Val Leu Cys Lys Ala Cys Ala Pro Gly Thr Phe Ser Asp Thr Thr Ser
                165                 170                 175

Ser Thr Asp Val Cys Arg Pro His Arg Ile Cys Ser Ile Leu Ala Ile
            180                 185                 190

Pro Gly Asn Ala Ser Thr Asp Ala Val Cys Ala Pro Glu Ser Pro Thr
        195                 200                 205

Leu Ser Ala Ile Pro Arg Thr Leu Tyr Val Ser Gln Pro Glu Pro Thr
    210                 215                 220

Arg Ser Gln Pro Leu Asp Gln Glu Pro Gly Pro Ser Gln Thr Pro Ser
225                 230                 235                 240

Ile Leu Thr Ser Leu Gly Ser Thr Pro Ile Ile Glu Gln Ser Thr Lys
                245                 250                 255

Gly Gly Ile Ser Leu Pro Ile Gly Leu Ile Val Gly Val Thr Ser Leu
```

-continued

```
            260                 265                 270

Gly Leu Leu Met Leu Gly Leu Val Asn Cys Ile Ile Leu Val Gln Arg
        275                 280                 285

Lys Lys Lys Pro Ser Cys Leu Gln Arg Asp Ala Lys Val Pro His Val
    290                 295                 300

Pro Asp Glu Lys Ser Gln Asp Ala Val Gly Leu Glu Gln Gln His Leu
305                 310                 315                 320

Leu Thr Thr Ala Pro Ser Ser Ser Ser Ser Ser Leu Glu Ser Ser Ala
                325                 330                 335

Ser Ala Gly Asp Arg Arg Ala Pro Pro Gly Gly His Pro Gln Ala Arg
            340                 345                 350

Val Met Ala Glu Ala Gln Gly Phe Gln Glu Ala Arg Ala Ser Ser Arg
        355                 360                 365

Ile Ser Asp Ser Ser His Gly Ser His Gly Thr His Val Asn Val Thr
    370                 375                 380

Cys Ile Val Asn Val Cys Ser Ser Ser Asp His Ser Ser Gln Cys Ser
385                 390                 395                 400

Ser Gln Ala Ser Ala Thr Val Gly Asp Pro Asp Ala Lys Pro Ser Ala
                405                 410                 415

Ser Pro Lys Asp Glu Gln Val Pro Phe Ser Gln Glu Glu Cys Pro Ser
            420                 425                 430

Gln Ser Pro Cys Glu Thr Thr Glu Thr Leu Gln Ser His Glu Lys Pro
        435                 440                 445

Leu Pro Leu Gly Val Pro Asp Met Gly Met Lys Pro Ser Gln Ala Gly
    450                 455                 460

Trp Phe Asp Gln Ile Ala Val Lys Val Ala
465                 470
```

<210> SEQ ID NO 18
<211> LENGTH: 20
<212> TYPE: DNA
<213> ORGANISM: Artificial sequence
<220> FEATURE:
<223> OTHER INFORMATION: gRNA sequence

<400> SEQUENCE: 18
cggacagtca ctcaccaagt 20

<210> SEQ ID NO 19
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 19
gaacaattcc atctgctgca cc 22

<210> SEQ ID NO 20
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 20
ttcgaaatcc tgacctcctg g 21

<210> SEQ ID NO 21

<211> LENGTH: 20
<212> TYPE: DNA
<213> ORGANISM: Artificial sequence
<220> FEATURE:
<223> OTHER INFORMATION: gRNA sequence

<400> SEQUENCE: 21
gacactgcct gaggtaattc 20

<210> SEQ ID NO 22
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 22
tgagacaggg tttctctata cc 22

<210> SEQ ID NO 23
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 23
catggcattc gtctttgt 18

<210> SEQ ID NO 24
<211> LENGTH: 20
<212> TYPE: DNA
<213> ORGANISM: Artificial sequence
<220> FEATURE:
<223> OTHER INFORMATION: gRNA sequence

<400> SEQUENCE: 24
cggcttccca gaattacctc 20

<210> SEQ ID NO 25
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 25
agtgagagca gagaattgtc 20

<210> SEQ ID NO 26
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 26
gagcttgcat gtgcacgcat 20

<210> SEQ ID NO 27
<211> LENGTH: 20
<212> TYPE: DNA
<213> ORGANISM: Artificial sequence
<220> FEATURE:
<223> OTHER INFORMATION: gRNA sequence

<400> SEQUENCE: 27 atataccccct caggggttat 20

<210> SEQ ID NO 28
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 28
tctcacactc cctgcagtcc gt 22

<210> SEQ ID NO 29
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 29
cagattgtat ggccccaact gt 22

<210> SEQ ID NO 30
<211> LENGTH: 20
<212> TYPE: DNA
<213> ORGANISM: Artificial sequence
<220> FEATURE:
<223> OTHER INFORMATION: gRNA sequence

<400> SEQUENCE: 30
attggactgg tccctcacct 20

<210> SEQ ID NO 31
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 31
ttctgaagcg gtgaaggagc c 21

<210> SEQ ID NO 32
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 32
cagattgtat ggccccaact gt 22

<210> SEQ ID NO 33
<211> LENGTH: 20
<212> TYPE: DNA
<213> ORGANISM: Artificial sequence
<220> FEATURE:
<223> OTHER INFORMATION: gRNA sequence

<400> SEQUENCE: 33
tacttgtaca atgactgtcc 20

<210> SEQ ID NO 34
<211> LENGTH: 21
<212> TYPE: DNA

<213> ORGANISM: Artificial sequence
<220> FEATURE:
<223> OTHER INFORMATION: Single strand DNA oligonucleotide

<400> SEQUENCE: 34
tgccggtact ggttcttcct g 21

<210> SEQ ID NO 35
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 35
gggtgctgct tctttctctg ct 22

<210> SEQ ID NO 36
<211> LENGTH: 20
<212> TYPE: DNA
<213> ORGANISM: Artificial sequence
<220> FEATURE:
<223> OTHER INFORMATION: gRNA sequence

<400> SEQUENCE: 36
taatgtatcg ctaccaacgg 20

<210> SEQ ID NO 37
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 37
accacagtgc tgttgcc 17

<210> SEQ ID NO 38
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 38
tcacctccct ccacacat 18

<210> SEQ ID NO 39
<211> LENGTH: 20
<212> TYPE: DNA
<213> ORGANISM: Artificial sequence
<220> FEATURE:
<223> OTHER INFORMATION: gRNA sequence

<400> SEQUENCE: 39
cactccaata atgccggtac 20

<210> SEQ ID NO 40
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 40
atctcttctt gcacagtgga c 21

<210> SEQ ID NO 41
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 41
acggtgttct gtttctcctg 20

<210> SEQ ID NO 42
<211> LENGTH: 20
<212> TYPE: DNA
<213> ORGANISM: Artificial sequence
<220> FEATURE:
<223> OTHER INFORMATION: gRNA sequence

<400> SEQUENCE: 42
agaggtgcac ggtcccattg 20

<210> SEQ ID NO 43
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 43
gaagaaccag taccggcatt a 21

<210> SEQ ID NO 44
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 44
gttgtcagac ccacagaata c 21

<210> SEQ ID NO 45
<211> LENGTH: 20
<212> TYPE: DNA
<213> ORGANISM: Artificial sequence
<220> FEATURE:
<223> OTHER INFORMATION: gRNA sequence

<400> SEQUENCE: 45
ttggactggt ccctcaccta 20

<210> SEQ ID NO 46
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 46
tctcttgatg gtgtctcctc ta 22

<210> SEQ ID NO 47
<211> LENGTH: 22
<212> TYPE: DNA
<213> ORGANISM: Artificial sequence
<220> FEATURE:

-continued

```
<223> OTHER INFORMATION: Single strand DNA oligonucleotide

<400> SEQUENCE: 47

actggaagaa gcagagaaag aa                                    22
```

METHODS OF TREATING AN ISCHEMIC DISEASE

RELATED APPLICATIONS

This application is a National Phase of PCT Patent Application No. PCT/IL2018/051139 having International filing date of Oct. 24, 2018, which claims the benefit of priority under 35 USC § 119(e) of U.S. Provisional Patent Application No. 62/576,094 filed on Oct. 24, 2017. The contents of the above applications are all incorporated by reference as if fully set forth herein in their entirety.

SEQUENCE LISTING STATEMENT

The ASCII file, entitled 82162SequenceListing.txt, created on Apr. 23, 2020, comprising 187,480 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to methods of treating an ischemic disease.

Ischemic heart disease, such as acute myocardial infarctions, congestive heart failure, arrhythmias, and sudden cardiac death, is the leading cause of morbidity and mortality in all industrialized nations. In the United States, ischemic heart disease causes nearly 20% of all deaths (≈600,000 deaths each year). Over the past half a century conventional medicine and surgery have offered many breakthroughs, resulting in a dramatic decline in mortality [Mozaffarian et al. Circulation. (2015) 131(4):e29-322.) Despite the major advances in treatment, the prognosis for patients who are admitted to hospital with heart failure remains poor, with a 5 year survival of about 50% and a 10 year survival of about 10%. The approach of using stem or precursor cells has emerged in the last decade as a regenerative strategy to address cardiac disease, with pre-clinical and clinical trials showing beneficial effects of progenitor cell therapy in acute myocardial infarction and ischemic cardiomyopathy [e.g. Choudhury et al. Eur J Heart Fail. (2017) 19(1):138-147; and Karantalis et al. Circ Res. (2015) 116(8):1413-30].

Tumor necrosis factor alpha (TNFα) is a pro-inflammatory cytokine that has been implicated in mediating or exacerbating various mammalian conditions such as myocardial infarction, heart failure, septic shock, inflammatory disease, HIV infection and tissue transplant. However, in anti-cytokine clinical trials, the use of either a soluble TNF receptor, or an anti-TNF antibody was not beneficial to patients with heart failure. In addition, treatment with soluble TNF receptors significantly exacerbated ventricular dysfunction and remodeling with enhanced interstitial fibrosis after myocardial infarction (Monden et al [34]). These findings suggest that TNFα may not be exclusively toxic but may be partially protective in cardiovascular diseases. TNFα initiates its biological effects by binding to two distinct cell surface receptors expressed in most cell types: TNFR1 (TNFα receptor type 1, with approximate mass of 55 kDa) and TNFR2 (TNF-α receptor type 2, with approximate mass of 75 kDa). The specific roles of TNFR1 and TNFR2 signaling in ischemic damage remain unclear with several studies indicating that signaling via TNFR1 is deleterious and signaling via TNFR2 is protective against ischemic damage while others suggesting no difference in the function of the two receptors in protecting the heart from ischemia (see e.g. Kishore et al. [33], Monden et al [34], Moe et al 2004 [35] and Kurrelmeyer et al [37]).

Additional background art includes:

International Patent Application Publication Nos. WO2000000504, WO2015104322 and WO2011006914;

US Patent Application Publication Nos: US20120014879 and US20110189768;

European Patent No. EP2746396;

Chinese Patent No. CN101401930;

Bao et al. (2008) Scand. Cardiovasc. J. 42, 56-62;

Farhang et al. (2017) Tissue Eng Part A. 23(15-16):738-749;

Kelly et al. (2010) Shock. 33(6): 602-607; and

Tan et al. (2010) Shock. 34(3):236-42.

SUMMARY OF THE INVENTION

According to an aspect of some embodiments of the present invention there is provided a method of treating an ischemic disease in a subject in need thereof, the method comprising administering to the subject a therapeutically effective amount of mononuclear bone marrow cells (mnBMCs) comprising mesenchymal stem cells (MSCs) and lymphocytes or progenitors thereof with reduced level of expression and/or activity of TNFR1 as compared to control cells of the same origin not contacted with an agent which downregulates expression and/or activity of the TNFR1, thereby treating the ischemic disease in the subject.

According to an aspect of some embodiments of the present invention there is provided a method of treating an ischemic disease in a subject in need thereof, the method comprising administering to the subject a therapeutically effective amount of differentiated cells with reduced level of expression and/or activity of TNFR1 as compared to control cells of the same origin not contacted with an agent which downregulates expression and/or activity of the TNFR1, wherein the differentiated cells are of a same type of tissue affected in the ischemic disease, thereby treating the ischemic disease in the subject.

According to some embodiments of the invention, the method further comprising treating the cells with reduced expression and/or activity of TNFR1 with TNFα prior to the administering.

According to some embodiments of the invention, the method comprising cryopreserving the cells prior to the treating with the TNFα.

According to an aspect of some embodiments of the present invention there is provided a method of treating an ischemic disease in a subject in need thereof, the method comprising:

(i) treating with TNFα cells with reduced expression and/or activity of TNFR1 as compared to control cells of the same origin not contacted with an agent which downregulates expression and/or activity of the TNFR1, wherein the cells are selected from the group consisting of mononuclear bone marrow cells (mnBMCs), stem cells and differentiated cells of a same type of tissue affected in the ischemic disease; and (ii) administering to the subject a therapeutically effective amount of the cells with reduced level of expression and/or activity of TNFR1 following the (i), thereby treating the ischemic disease in the subject.

According to some embodiments of the invention, the cells comprise differentiated cells of a same type of tissue affected in the ischemic disease.

According to some embodiments of the invention, the cells with reduced level of expression and/or activity of TNFR1 have the same level of expression and/or activity of TNFR2 as compared to the control stem cells.

According to some embodiments of the invention, the cells with reduced expression and/or activity of TNFR1 are genetically modified cells.

According to some embodiments of the invention, the genetically modified comprises genetically modified with a CRISPR/Cas system, a Zinc finger nuclease (ZFN), transcription-activator like effector nuclease (TALEN) or meganuclease for downregulating expression of the TNFR1.

According to some embodiments of the invention, the genetically modified comprises genetically modified with a CRISPR/Cas system for downregulating expression of the TNFR1.

According to an aspect of some embodiments of the present invention there is provided a method of downregulating expression and/or activity of TNFR1 in differentiated cells or bone marrow stem cells, the method comprising:

(i) contacting ex-vivo or in-vitro differentiated cells or bone marrow stem cells with an agent which downregulates expression and/or activity of TNFR1; and (ii) contacting ex-vivo or in-vitro the cells with TNFα.

According to some embodiments of the invention, the (i) is effected prior to the (ii).

According to some embodiments of the invention, the agent does not downregulate expression and/or activity of TNFR2.

According to some embodiments of the invention, the agent is selected from the group consisting of CRISPR/Cas system, a Zinc finger nuclease (ZFN), transcription-activator like effector nuclease (TALEN), meganuclease, antisense and siRNA.

According to some embodiments of the invention, the agent comprises a CRISPR/Cas system.

According to some embodiments of the invention, there is provided a method of treating an ischemic disease in a subject in need thereof, the method comprising:

(i) obtaining cells according to the method of the present invention; and (ii) administering to the subject a therapeutically effective amount of the cells, thereby treating the ischemic disease in the subject.

According to some embodiments of the invention, the differentiated cells are of a same type of tissue affected in the ischemic disease.

According to some embodiments of the invention, the method comprising cryopreserving the cells following the (i) and prior to the (ii).

According to some embodiments of the invention, the cells are non-autologous to the subject.

According to an aspect of some embodiments of the present invention there is provided a method of treating an ischemic disease in a subject in need thereof, the method comprising administering to the subject a therapeutically effective amount of a CRISPR/Cas system for downregulating expression of TNFR1, thereby treating the ischemic disease in the subject.

According to an aspect of some embodiments of the present invention there is provided a pharmaceutical composition comprising as an active ingredient differentiated cells or bone marrow stem cells genetically modified with a CRISPR/Cas system for downregulating expression of TNFR1.

According to an aspect of some embodiments of the present invention there is provided a pharmaceutical composition comprising as active ingredients cells genetically modified with a CRISPR/Cas system for downregulating expression of TNFR1 and at least 2 ng/ml TNFα.

According to some embodiments of the invention, the CRISPR/Cas system does not downregulate expression of TNFR2.

According to some embodiments of the invention, the cells comprise differentiated cells.

According to some embodiments of the invention, the differentiated cells are cardiomyocytes.

According to some embodiments of the invention, the cells comprise stem cells.

According to some embodiments of the invention, the stem cells are selected from the group consisting of embryonic stem cells (ESCs), induced pluripotent stem cells (iPS), hematopoietic stem cells (HSCs) and mesenchymal stem cells (MSCs).

According to some embodiments of the invention, the stem cells comprise hematopoietic stem cells (HSCs).

According to some embodiments of the invention, the cells are comprised in mononuclear bone marrow cells (mnBMCs).

According to some embodiments of the invention, the mnBMCs comprise lymphocytes or progenitors thereof.

According to some embodiments of the invention, the cells are obtained by density gradient centrifugation of bone marrow cells.

According to some embodiments of the invention, the method comprising obtaining the cells by density gradient centrifugation of bone marrow cells.

According to some embodiments of the invention, the cells are human cells.

According to some embodiments of the invention, the cells are cryopreserved cells.

According to some embodiments of the invention, the ischemic disease is ischemic heart disease.

According to some embodiments of the invention, the ischemic heart disease is myocardial infarction.

According to some embodiments of the invention, the ischemic heart disease is ischemic cardiomyopathy.

According to some embodiments of the invention, the subject is not treated with TNFα.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-B demonstrate a middle sized infarct volume (FIG. 1A) and cellular infiltration surrounding injected round clear cells (arrow, FIG. 1B) in mouse no. 15. FIGS. 1C-D demonstrate middle sized infarct volume (FIG. 1C) and cellular infiltration surrounding injected round clear cells (arrow) and some adipocytes (FIG. 1D) in mouse no. 16. FIGS. 1E-F demonstrate middle sized infarct volume (FIG. 1E) and marked cellular infiltration in and few injected cells (arrow, FIG. 1F) in mouse no. 18.

FIGS. 2A-B demonstrate a small infarct volume (FIG. 2A) and mild cellular infiltration (FIG. 2B) in mouse no. 7. FIGS. 2C-D demonstrate middle sized infarct volume (FIG. 2C) and focal extensive infiltration with some cellular debris of the injected cells (arrow, FIG. 2D) in mouse no. 9. FIGS. 2E-F a transmural infarct with still intact left ventricle wall (FIG. 2E) and marked cellular infiltration in the inner part of the ventricle wall (FIG. 2F) in mouse no. 10.

FIGS. 3A-B demonstrate a transmural infarct with a marked reduced myocardium tissue (FIG. 3A) and minimal cellular infiltration (FIG. 3B) in mouse no. 3. FIGS. 3C-D, demonstrate a relative small infarct volume in the wall of the left ventricle (FIG. 3C) and loss of tissue, inflammatory reaction and some fibrin material in the epicardium (arrow, FIG. 3D) in mouse no. 5. FIGS. 3E-F demonstrate a transmural infarct with a marked reduced myocardium tissue (FIG. 3E) and mild infiltration of inflammatory cells (FIG. 3F) in mouse no. 3.

FIGS. 4A-B demonstrate a very large infarct volume (FIG. 4A) and severe inflammation and necrosis (N) in the affected myocardium (FIG. 4B) in mouse no. 13. FIGS. 4C-D demonstrate a very large infarct volume (FIG. 4C) and severe inflammation and necrosis (N) in the affected myocardium (FIG. 4D) in mouse no. 14.

FIGS. 5A-B demonstrate a very large infarct volume (FIG. 5A) and severe inflammation and necrosis in the affected myocardium (FIG. 5B) in mouse no. 11. FIGS. 5C-D demonstrate a very large infarct volume (FIG. 5C) and severe inflammation and necrosis (N) in the affected myocardium (FIG. 5D) in mouse no. 12.

FIGS. 6A-B demonstrate a very large infarct volume (FIG. 6A) and severe inflammation and necrosis in the affected myocardium (FIG. 6B) in mouse no. 1. FIGS. 6C-D demonstrate a very large infarct volume (FIG. 6C) and severe inflammation and necrosis in the affected myocardium (FIG. 6D) in mouse no. 2.

FIG. 7A demonstrate a mild to moderate TUNEL reaction in the infarct lesion in mouse no. 6 (Group 1M). FIGS. 7B-D demonstrate high TUNEL reaction in the infarct lesion in mice no. 7 (FIG. 7B), 9 (FIG. 7C) and 10 (FIG. 7D) (Group 2M). FIGS. 7E-F demonstrate moderate to high TUNEL reaction in the infarct lesion in mice no. 15 (FIG. 7E) and 16 (FIG. 7F) (Control mice, Group 3M).

FIGS. 8A-B demonstrate high TUNEL reaction in the infarct lesion in mouse no. 1 and mild to moderate TUNEL reaction in the infarct lesion in mouse no. 2 (Group 1M). FIGS. 8C-D demonstrates mild TUNEL reaction in the infarct lesion in mice no. 11 and 12 (Group 2M). FIGS. 8E-F demonstrate high TUNEL reaction in the infarct lesion in mouse no. 13 and moderate TUNEL reaction in the infarct lesion in mouse no. 14 (Control mice, Group 3M).

DESCRIPTION OF SPECIFIC EMBODIMENTS OF THE INVENTION

Figures 1A, 1B, 1C, 1D, 1E, 1F:
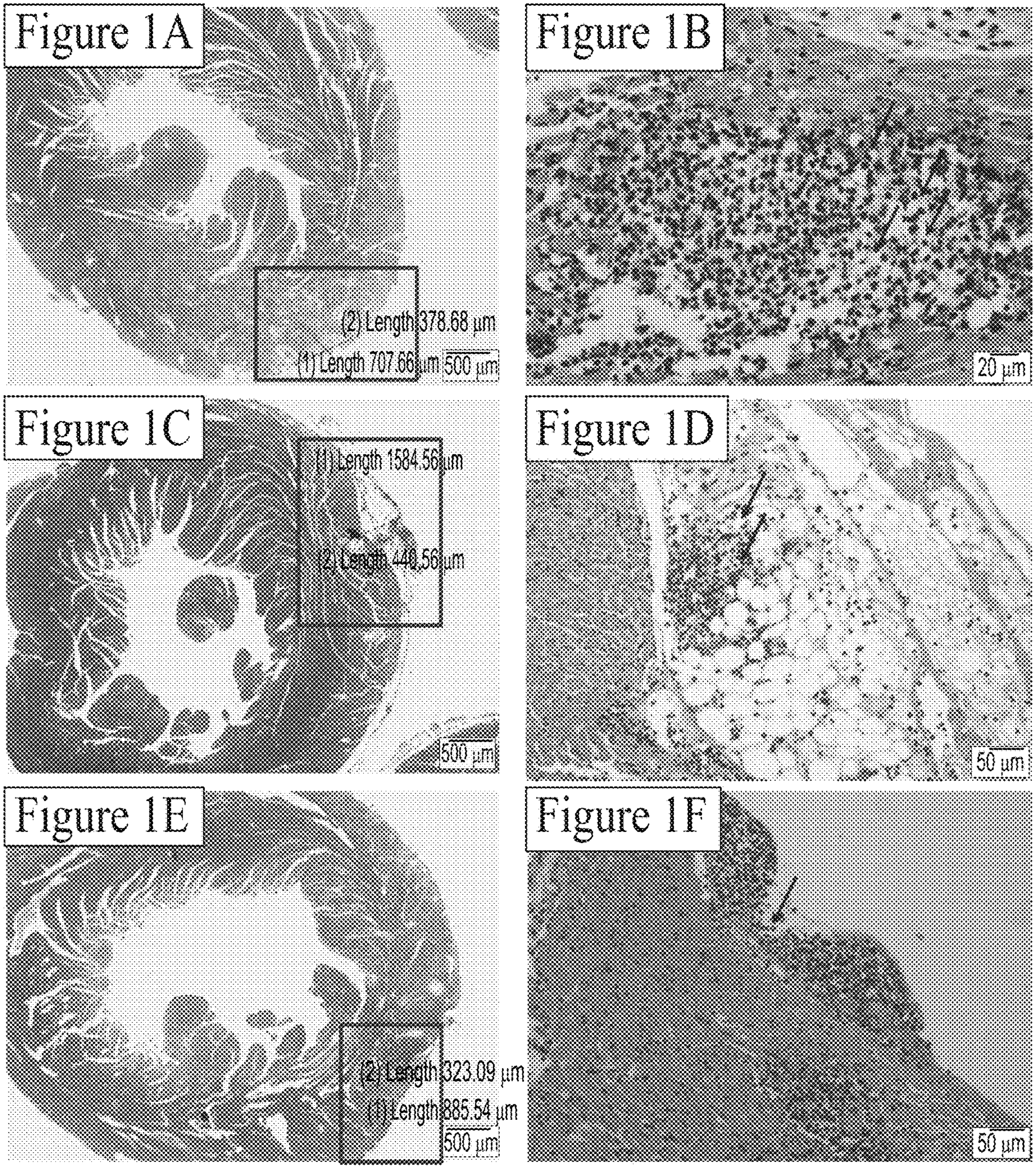
FIGS. 1A-F show representative photomicrographs of histological sections of hearts obtained from Control mice (Group 3M, see Table 2 hereinbelow) 24 hours following left anterior descending artery (LAD) occlusion and stained with Masson Trichrome (MT, FIGS. 1A, 1C, 1E) or Hematoxylin & Eosin (H&E, FIGS. 1B, 1D, 1F).
Figure 2A:
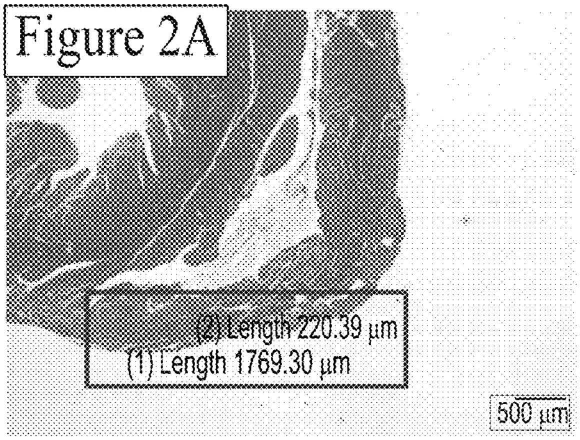
FIGS. 2A-F show representative photomicrographs of histological sections of hearts obtained from Group 2M mice (see Table 2 hereinbelow) 24 hours following LAD occlusion and stained with MT (FIGS. 2A, 2C, 2E) or H&E (FIGS. 2B, 2D, 2F).
Figure 2B:
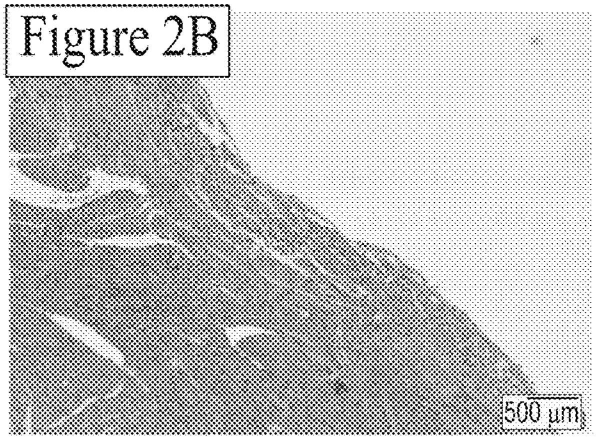
Figure 2C:
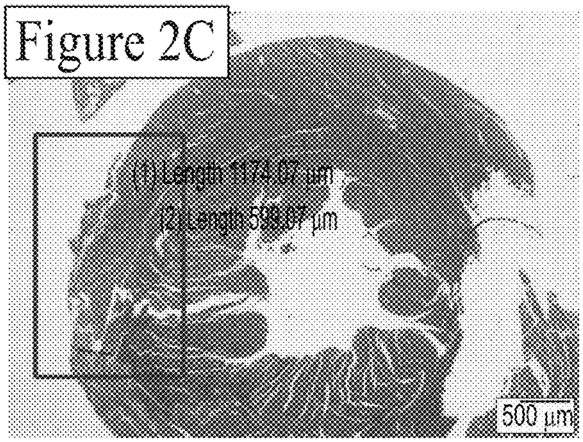
Figure 2D:
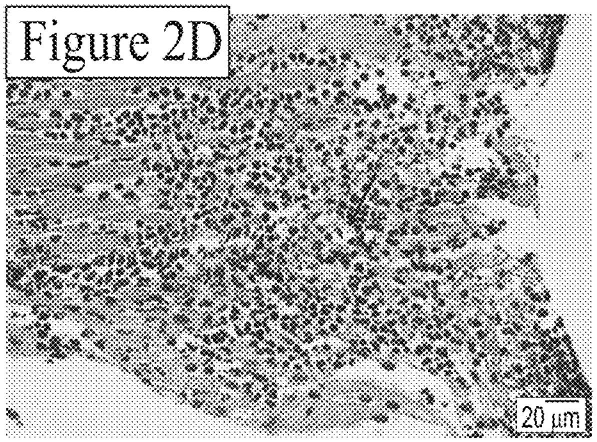
Figure 2E:
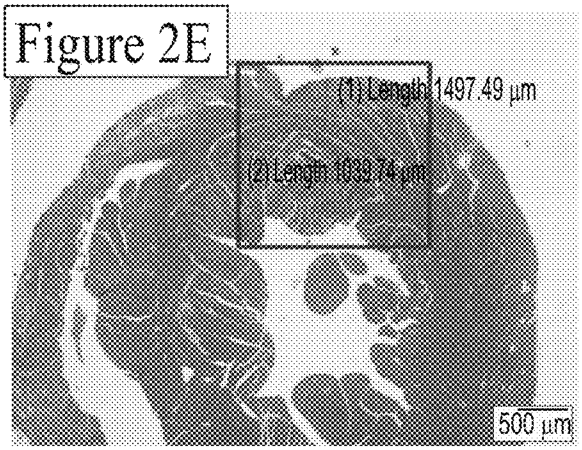
Figure 2F:
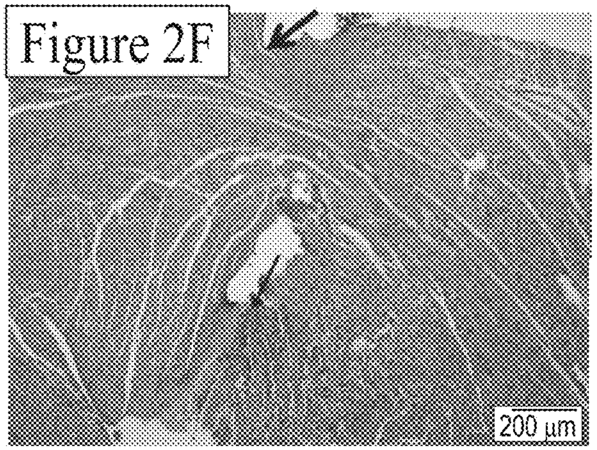
Figures 3A, 3B, 3C, 3D, 3E, 3F:
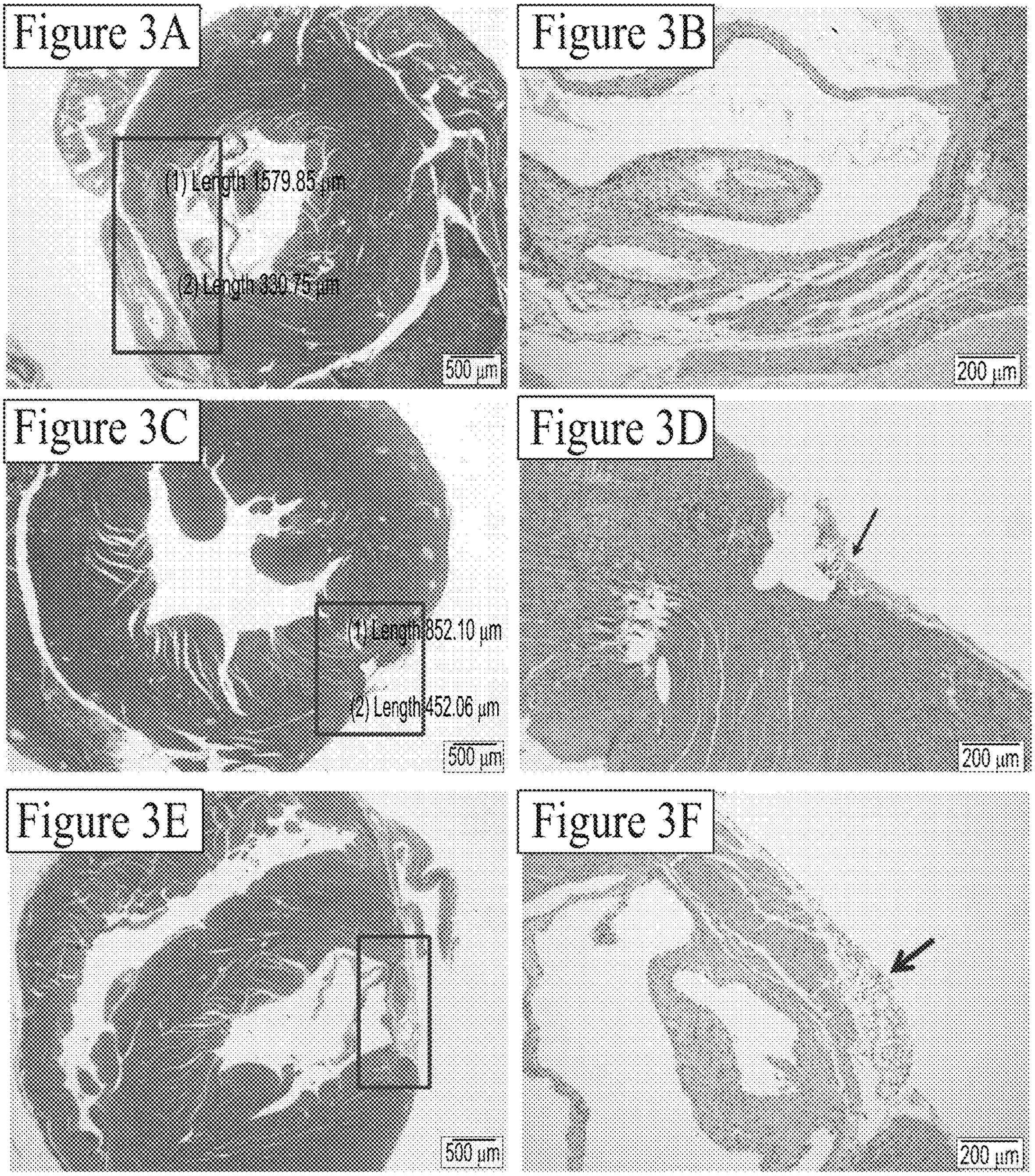
FIGS. 3A-F show representative photomicrographs of histological sections of hearts obtained from Group 1M mice (see Table 2 hereinbelow) 24 hours following LAD occlusion and stained with MT (FIGS. 3A, 3C, 3E) or H&E (FIGS. 3B, 3D, 3F).
Figures 4A, 4B, 4C, 4D:
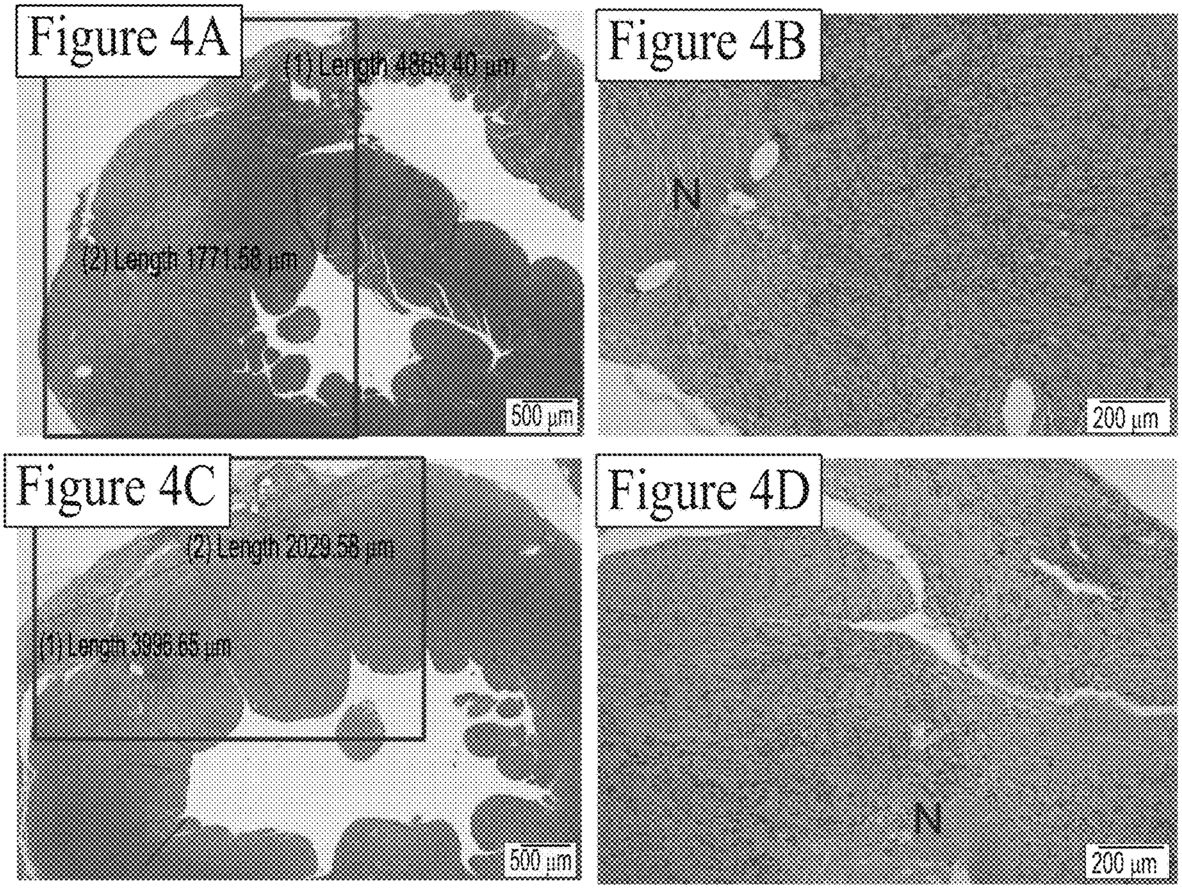
FIGS. 4A-D show representative photomicrographs of histological sections of hearts obtained from Control mice (Group 3M, see Table 2 hereinbelow) 4 days following LAD occlusion and stained with MT (FIGS. 4A, 4C) or H&E (FIGS. 4B, 4D).
Figures 5A, 5B, 5C, 5D:
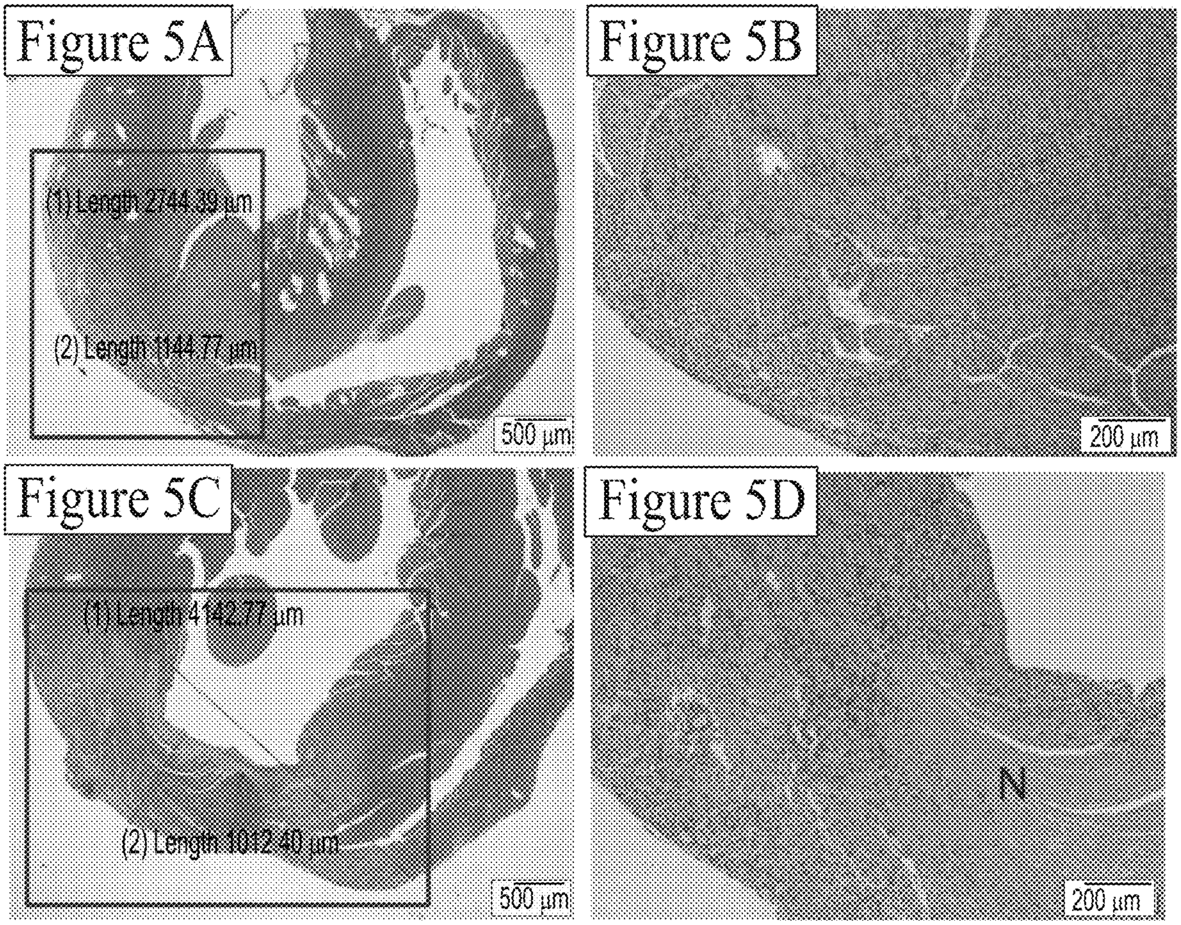
FIGS. 5A-D show representative photomicrographs of histological sections of hearts obtained from Group 2M mice (see Table 2 hereinbelow) 4 days following LAD occlusion and stained with MT (FIGS. 5A, 5C) or H&E (FIGS. 5B, 5D).
Figure 6A:
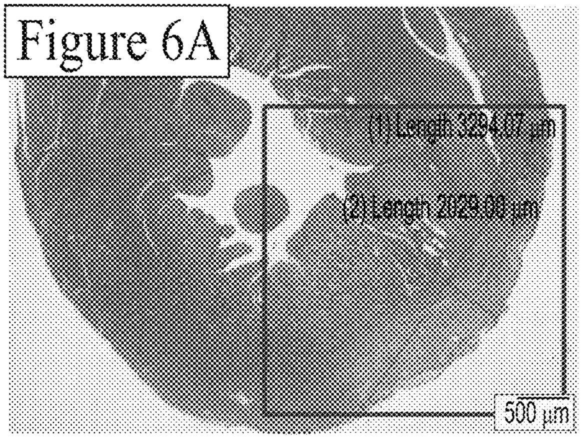
FIGS. 6A-D show representative photomicrographs of histological sections of hearts obtained from Group 1M mice (see Table 2 hereinbelow) 4 days following LAD occlusion and stained with MT (FIGS. 6A, 6C) or H&E (FIGS. 6B, 6D).
Figure 6B:
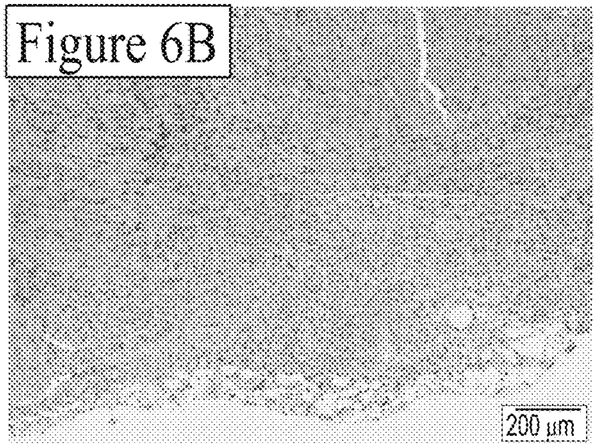
Figure 6C:
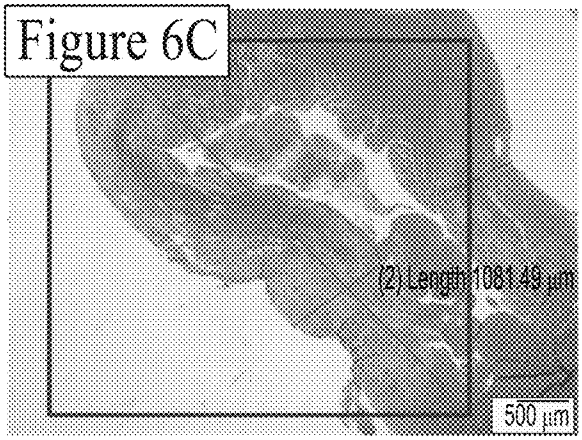
Figure 6D:
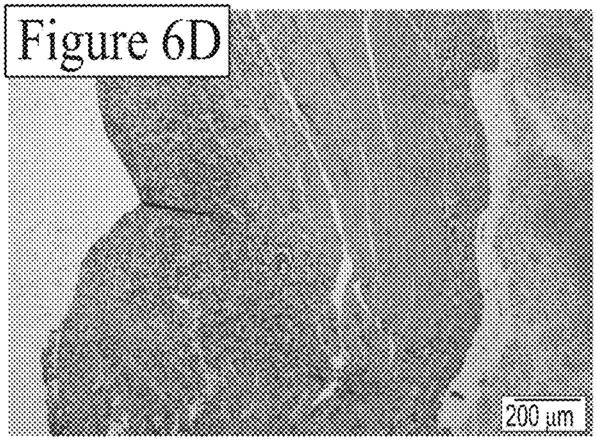
Figure 7A:
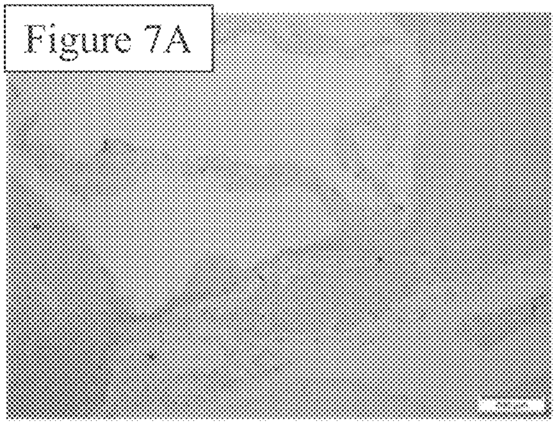
FIGS. 7A-F show representative photomicrographs of histological sections of hearts obtained from Control mice (Group 3M), Group 2M mice, and Group 1M mice (see Table 2 hereinbelow) 24 hours following LAD occlusion and stained with TUNEL.
Figure 7B:
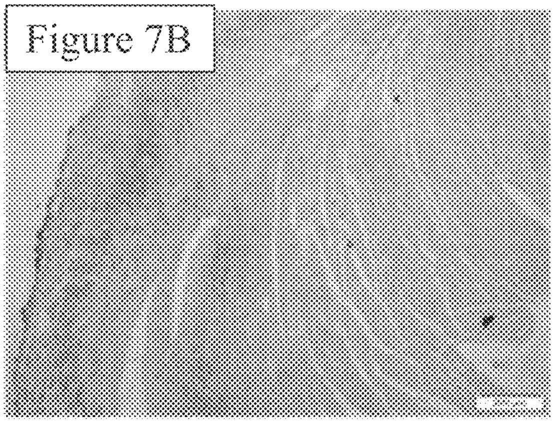
Figure 7C:
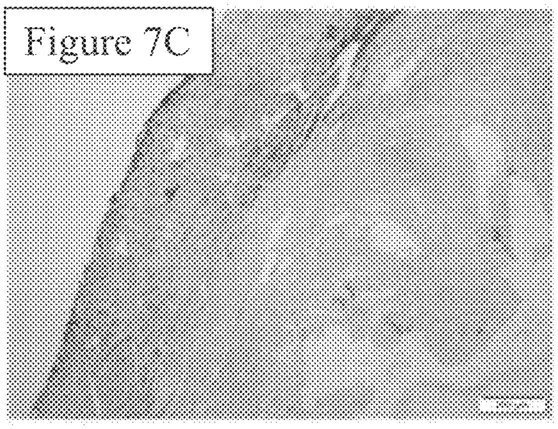
Figure 7D:
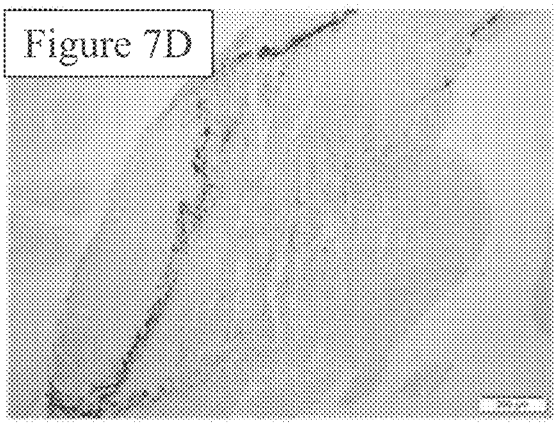
Figure 7E:
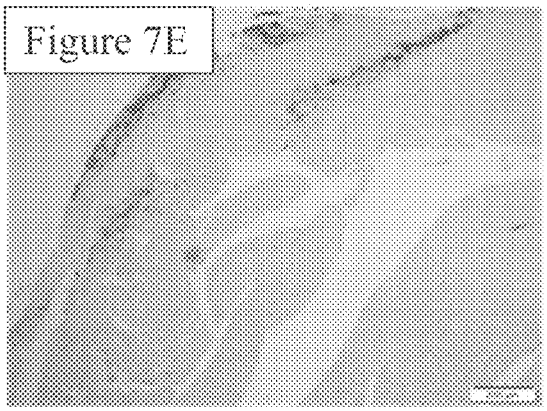
Figure 7F:
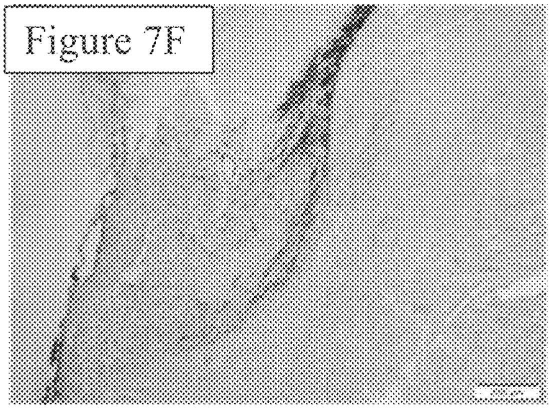
Figure 8A:
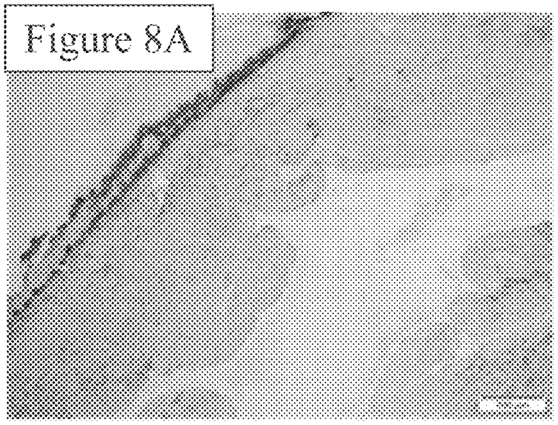
FIGS. 8A-F show representative photomicrographs of histological sections of hearts obtained from Control mice (Group 3M), Group 2M mice, and Group 1M mice (see Table 2 hereinbelow) 4 days following LAD occlusion and stained with TUNEL.
Figure 8B:
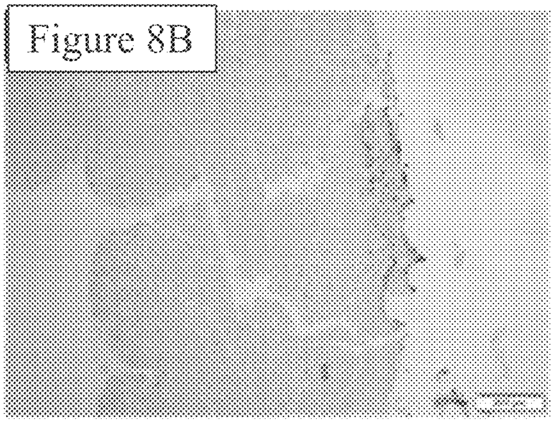
Figure 8C:
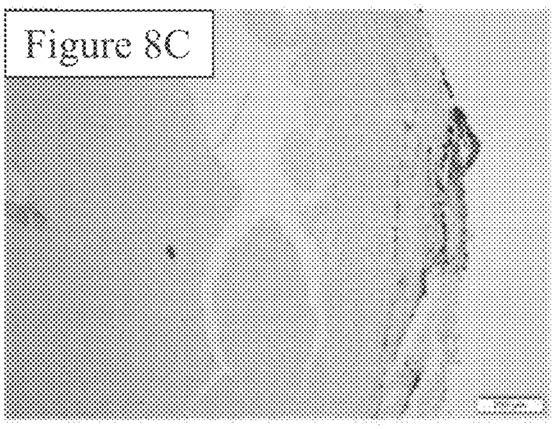
Figure 8D:
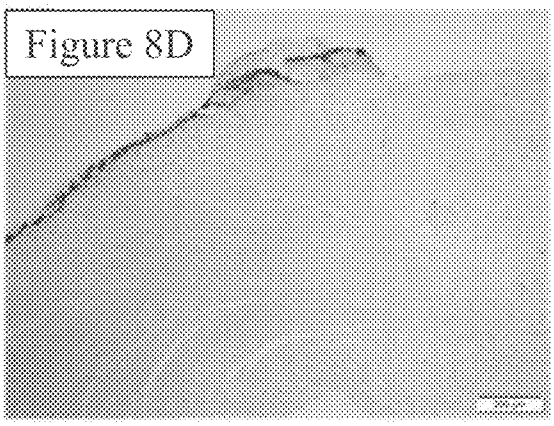
Figure 8E:
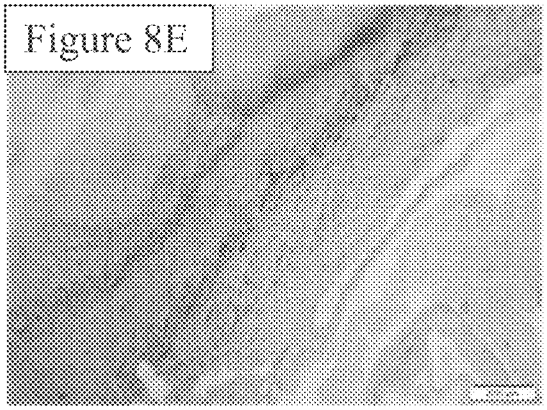
Figure 8F:
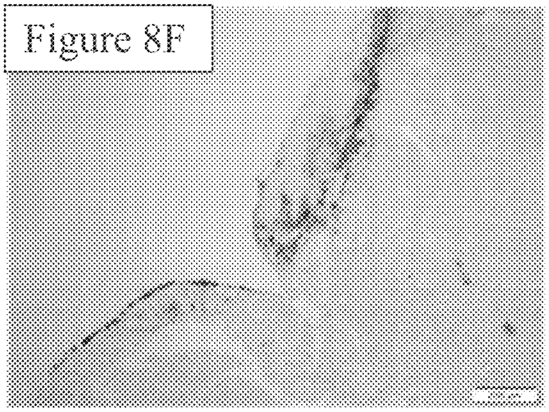
Figure 9A:
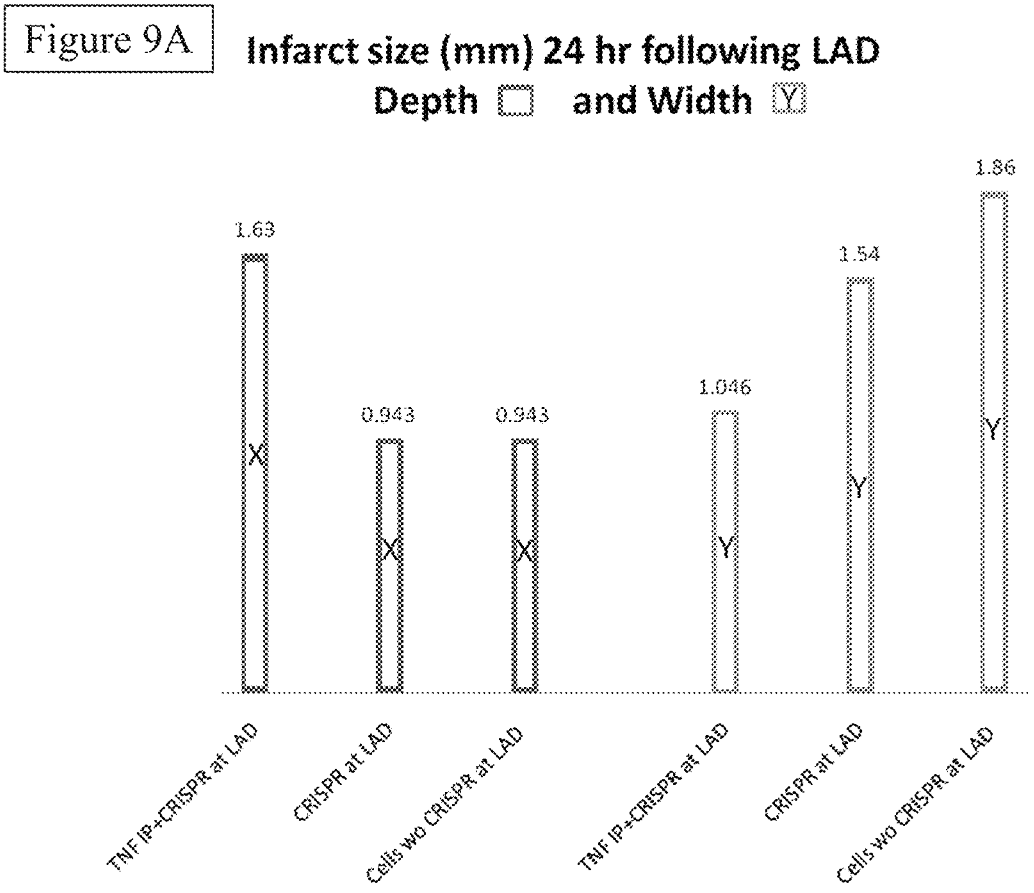
FIGS. 9A-B are bar graphs demonstrating that transplantation of mono-nuclear bone marrow cells (mnBMCs) transfected with TNFR1 CRISPR reduced infract size in the LAD occlusion mouse model compared to control mice transplanted with non-transfected mnBMCs, as determined by histological evaluation 24 hours (FIG. 9A) and 4 days (FIG. 9B) following LAD occlusion.
Figure 9B:
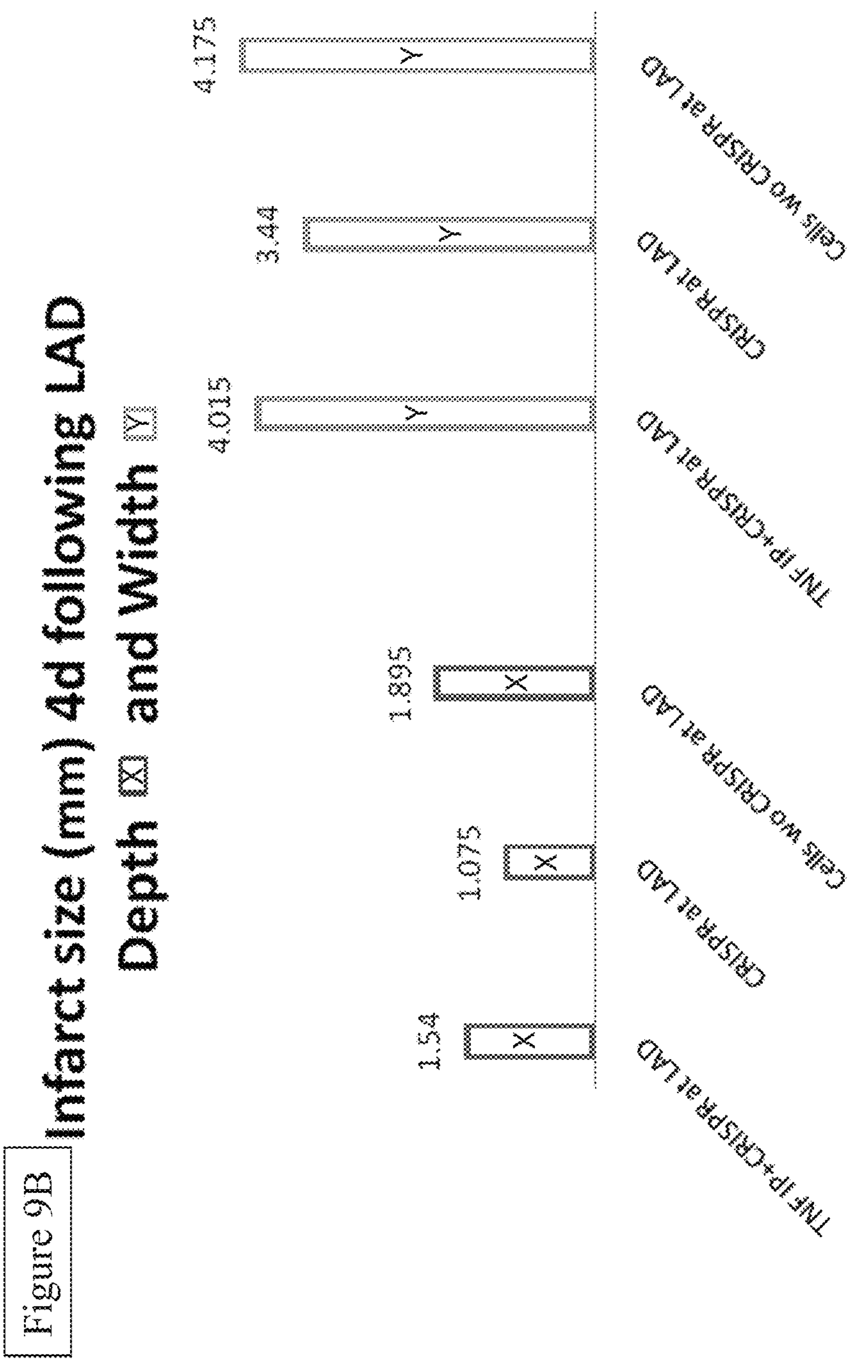

The present invention, in some embodiments thereof, relates to methods of treating an ischemic disease.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Ischemic heart disease is the leading cause of morbidity and mortality in all industrialized nations. Over the past half a century conventional medicine and surgery have offered many breakthroughs, resulting in a dramatic decline in mortality; however, despite the major advances in treatment, the prognosis for patients who are admitted to hospital with heart failure remains poor. The approach of using stem or precursor cells has emerged in the last decade as a regenerative strategy to address cardiac disease, with pre-clinical and clinical trials showing beneficial effects of progenitor cell therapy in acute myocardial infarction and ischemic cardiomyopathy.

Whilst reducing the present invention to practice, the present inventors have now uncovered in a left anterior descending artery (LAD) mouse model that transplantation of mononuclear MB cells (mnBMCs) transfected with TNFR1 CRISPR/Cas system and treated with TNFα provides a cardio-protective effect from ischemic damage, as demonstrated by reduced infarct depth and width (Examples section and FIGS. 1A-10).

Consequently, some embodiments of the present teachings suggest that therapeutic cells with reduced level of expression and/or activity of TNFR1 can be used for treating an ischemic disease.

Thus, according to a first aspect of the present invention, there is provided a method of treating an ischemic disease in a subject in need thereof, the method comprising administering to the subject a therapeutically effective amount of mononuclear bone marrow cells (mnBMCs) comprising mesenchymal stem cells (MSCs) and lymphocytes or progenitors thereof with reduced level of expression and/or activity of TNFR1 as compared to control cells of the same origin not contacted with an agent which downregulates expression and/or activity of said TNFR1, thereby treating the ischemic disease in the subject.

According to another aspect of the present invention, there is provided a method of treating an ischemic disease in a subject in need thereof, the method comprising administering to the subject a therapeutically effective amount of differentiated cells with reduced level of expression and/or activity of TNFR1 as compared to control cells of the same origin not contacted with an agent which downregulates expression and/or activity of said TNFR1, wherein said differentiated cells are of a same type of tissue affected in said ischemic disease, thereby treating the ischemic disease in the subject.

According to specific embodiments, the method further comprising treating said cells with reduced expression and/or activity of TNFR1 with TNFα prior to said administering.

According to another aspect of the present invention, there is provided a method of treating an ischemic disease in a subject in need thereof, the method comprising:

(i) treating with TNFα cells with reduced expression and/or activity of TNFR1 as compared to control cells of the same origin not contacted with an agent which downregulates expression and/or activity of said TNFR1, wherein said cells are selected from the group consisting of mononuclear bone marrow cells (mnBMCs), stem cells and differentiated cells of a same type of tissue affected in said ischemic disease; and (ii) administering to the subject a therapeutically effective amount of said cells with reduced level of expression and/or activity of TNFR1 following said (i), thereby treating the ischemic disease in the subject.

The term "treating" or "treatment" refers to inhibiting, preventing or arresting the development of a pathology (disease, disorder or medical condition e.g. ischemic disease e.g. ischemic heart disease) and/or causing the reduction, remission, or regression of a pathology or a symptom of a pathology. Those of skill in the art will understand that various methodologies and assays can be used to assess the development of a pathology, and similarly, various methodologies and assays may be used to assess the reduction, remission or regression of a pathology.

As used herein, the term "ischemic disease" refers to a disease characterized by reduced blood (and hence oxygen) supply to the diseased tissue/organ. According to specific embodiments, the ischemic disease is an acute ischemic disease. According to other specific embodiments, the ischemic disease is a chronic ischemic disease. Non-limiting Examples of ischemic diseases include trauma, ischemic cerebrovascular disorder (such as apoplexy or cerebral infarction), ischemic renal disease, ischemic pulmonary disease, infection-related ischemic disease, ischemic disease of limbs, and ischemic heart disease.

According to specific embodiments, the ischemic disease is not a rejection reaction following transplantation (e.g. GVHD).

According to specific embodiments, the ischemic disease is ischemic heart disease.

As used herein the term "ischemic heart disease" refers to a disease in which heart muscle is damaged or works inefficiently because of reduced blood (and hence oxygen) supply to the heart. Non-limiting Examples of ischemic heart diseases include ischemic cardiomyopathy, myocardial infarction or ischemic heart failure and chronic ischemic heart disease.

According to specific embodiments, the ischemic disease is myocardial infarction (also known as heart attack).

According to specific embodiments, the myocardial infarction is ST-segment elevation MI (STEMI) myocardial infarction (i.e. the coronary artery is completely blocked, thus virtually all of the heart muscle supplied by the affected artery becomes infarcted), as determined by ECG.

According to other specific embodiments, the myocardial infarction is non-ST-segment elevation MI (NSTEMI) myocardial infarction (i.e. the artery is only partially occluded thus only a portion of the heart muscle supplied by the artery becomes infarcted), as determined by ECG.

According to specific embodiments, the ischemic disease is ischemic cardiomyopathy.

As used herein, the term "subject" includes mammals, e.g., human beings at any age and of any gender who suffer from the pathology (medical condition). According to specific embodiments, this term encompasses individuals who are at risk to develop the pathology.

According to specific embodiments, the subject is not treated with TNFα.

"TNFα", a cytokine also known as Tumor necrosis factor alpha. TNFα can bind TNFR1 and TNFR2. According to specific embodiments, the TNFα protein refers to the human protein, such as provided in the following GenBank Number NP_000585 (SEQ ID NO: 1).

The term also encompasses functional homologues (naturally occurring or synthetically/recombinantly produced), orthologs (from other species) which exhibit the desired activity (i.e., binding TNFR1, binding TNFR2, activation of NFκB, activation of the MAPK pathway). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide SEQ ID NO: 1 or 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same (as further described hereinbelow).

Sequence identity or homology can be determined using any protein or nucleic acid sequence alignment algorithm such as Blast, ClustalW, and MUSCLE.

The functional homologs also refer to functional portions of TNFα which maintain the activity of the full length protein (i.e. binding TNFR1, binding TNFR2, activation of NFκB, activation of the MAPK pathway).

According to specific embodiments, the TNFα is a recombinant TNFα, which can be prepared by standard recombinant expression methods or purchased commercially.

TNFα can be commercially obtained from e.g. R&D Systems.

According to specific embodiments, the cells are treated (or contacted) with TNFα.

According to specific embodiments, the effect of treatment with TNFα is additive.

According to other specific embodiments, the effect of treatment with TNFα is synergistic.

According to specific embodiments, treatment (or contacting) with TNFα is effected at a concentration of at least 2 ng/ml, at least 5 ng/ml, at least 10 ng/ml, at least 20 ng/ml, at least 30 ng/ml, at least 40 ng/ml, at least 50 ng/ml or at least 60 ng/ml, each possibility represents a separate embodiment of the present invention.

According to specific embodiments, treatment (or contacting) with TNFα is effected at a concentration of 2-200 ng/ml or 20-200 ng/ml.

According to specific embodiments, treatment (or contacting) with TNFα is effected 1-72 hours, 1-48, 1-24, 1-10 or 1-5 hours prior to the administering, each possibility represents a separate embodiment of the present invention.

According to specific embodiments, treatment (or contacting) with TNFα comprises a single TNFα treatment.

According to other specific embodiments, treatment (or contacting) with TNFα comprises a plurality of TNFα treatments.

Several types of cells can be used and/or obtained according to specific embodiments of the present invention.

According to specific embodiments, the cells comprise differentiated cells.

Non-limiting examples of differentiated cells that can be used with some embodiments of the present invention include differentiated cells derived from heart, kidney, liver, lung and brain.

According to specific embodiments, the differentiated cells comprise differentiated cells of a same type of tissue affected in the ischemic disease.

Methods of obtaining such differentiated cells are well known in the art. For example a cell suspension may be obtained by any mechanical or chemical (e.g. enzymatic) means. Several methods exist for dissociating cell clusters to form cell suspensions (e.g. single cell suspension) from primary tissues, attached cells in culture, and aggregates, e.g., physical forces (mechanical dissociation such as cell scraper, trituration through a narrow bore pipette, fine needle aspiration, vortex disaggregation and forced filtration through a fine nylon or stainless steel mesh), enzymes (enzymatic dissociation such as trypsin, collagenase, Acutase and the like) or a combination of both. Thus, for example, enzymatic digestion of tissue/organ into isolate cells can be performed by subjecting the tissue to an enzyme such as type IV Collagenase (Worthington biochemical corporation, Lakewood, N.J., USA) and/or Dispase (Invitrogen Corporation products, Grand Island N.Y., USA). For example, the tissue may be enzyme digested by finely mincing tissue with a razor blade in the presence of e.g. collagenase, dispase and CaCl2 at 37° C. for about 1 hour. The method may further comprise removal of nonspecific debris from the resultant cell suspension by, for example, sequential filtration through filters (e.g. 70- and 40-μm filters), essentially as described under "General Materials and Experimental Methods" of the Examples section which follows. Furthermore, mechanical dissociation of tissue into isolated cells can be performed using a device designed to break the tissue to a predetermined size. Such a device can be obtained from CellArtis Goteborg, Sweden. Additionally or alternatively, mechanical dissociation can be manually performed using a needle such as a 27 g needle (BD Microlance, Drogheda, Ireland) while viewing the tissue/cells under an inverted microscope. Following enzymatic or mechanical dissociation of the tissue, the dissociated cells are further broken to small clumps using 200 μl Gilson pipette tips (e.g., by pipetting up and down the cells). Alternatively, such differentiated cells can be obtained by differentiation of stem cell. Hence, according to specific embodiments, the differentiated cells have been ex-vivo differentiated. Methods of inducing differentiation of stem cells are well known to the skilled in the art. Thus, for example approaches to differentiate pluripotent cells into cardiomyocytes are disclosed in e.g. Burridge et al. (2012) Cell Stem Cell 10:16-28; Mummery et al. Circ Res. 2012 Jul. 20; 111(3):344-58; WO2014200339, WO2011056416, WO2015004539, WO201202649 land WO2014078414 and U.S. Pat. No. 7,534,607, the contents of which are fully incorporated herein by reference.

It will be appreciated that commercially available differentiated cells can also be used according to some embodiments of the invention.

According to specific embodiments, the differentiated cells comprise cardiomyocytes.

According to specific embodiments, the differentiated cells comprise lymphocytes.

According to specific embodiments, the cells comprise bone marrow cells.

Methods of obtaining bone marrow cells are well known in the art. Thus, for example, bone marrow can be obtained from iliac crest, femora, tibiae, spine, rib or other medullar spaces. Following, the desired cellular fraction can be purified from the bone marrow aspirates.

According to specific embodiments, the cells comprise mononuclear bone marrow cells (mnBMCs).

According to specific embodiments, the cells are comprised in mononuclear bone marrow cells (mnBMCs).

According to specific embodiment, the cells comprise at least 50% at least 60%, at least 70%, at least 80%, at least 90% or at least 95% mnBMCs.

Thus, for example, the mononuclear fraction can be purified from the bone marrow aspirates. There are several methods and reagents known to those skilled in the art for purifying mnBMCs from bone marrow such as, density gradient centrifugation (e.g. ficoll), sedimentation (e.g. Hespan), centrifugal elutriation, fractionation, automated processes (e.g. Sepax® from Biosafe SA, Eysins, Switzerland and the AutoXpress Platform® (AXP) from Thermogenesis, Rancho Cordova, Calif. chemical lysis of e.g. red blood cells (e.g. by ACK), selection of specific cell types using cell surface markers (using e.g. FACS sorter or magnetic cell separation techniques such as are commercially available e.g. from Invitrogen, Stemcell Technologies, Cellpro, Advanced Magnetics, or Miltenyi Biotec.), and depletion of specific cell types by methods such as eradication (e.g.

killing) with specific antibodies or by affinity based purification based on negative selection (using e.g. magnetic cell separation techniques, FACS sorter and/or capture ELISA labeling). Such methods are described for example in THE HANDBOOK OF EXPERIMENTAL IMMUNOLOGY, Volumes 1 to 4, (D. N. Weir, editor) and FLOW CYTOMETRY AND CELL SORTING (A. Radbruch, editor, Springer Verlag, 2000).

According to specific embodiments, the bone marrow cells are obtained by density gradient centrifugation (e.g. ficoll) of bone marrow cells.

According to specific embodiments, the bone marrow cells comprise stem cells (e.g. hematopoietic stem cells, mesenchymal stem cells). Methods of obtaining bone marrow stem cells are well known in the art and are further described hereinbelow.

According to specific embodiments, the bone marrow cells comprise mesenchymal stem cells (MSCs) and lymphocytes or progenitors thereof.

According to specific embodiments, the bone marrow cells comprise lymphocytes or progenitors thereof.

As used herein the term "lymphocytes progenitors" refers to hematopoietic progenitor cells that can differentiate to lymphocytes.

According to a specific embodiment the lymphocytes progenitor cells are mobilized to the peripheral blood by agents such as G-CSF with or without chemotherapy.

According to specific embodiments, the cells comprise stem cells.

As used herein, the phrase "stem cells" refers to cells which are capable of remaining in an undifferentiated state (e.g., totipotent, pluripotent or multipotent stem cells) for extended periods of time in culture until induced to differentiate into other cell types having a particular, specialized function (e.g., fully differentiated cells). Totipotent cells, such as embryonic cells within the first couple of cell divisions after fertilization are the only cells that can differentiate into embryonic and extra-embryonic cells and are able to develop into a viable human being. Preferably, the phrase "pluripotent stem cells" refers to cells which can differentiate into all three embryonic germ layers, i.e., ectoderm, endoderm and mesoderm or remaining in an undifferentiated state. The pluripotent stem cells include embryonic stem cells (ESCs) and induced pluripotent stem cells (iPS). The multipotent stem cells include e.g. adult stem cells, hematopoietic stem cells and mesenchymal stem cells.

It will be appreciated that undifferentiated stem cells are of a distinct morphology, which is clearly distinguishable from differentiated cells of embryo or adult origin by the skilled in the art. Typically, undifferentiated stem cells have high nuclear/cytoplasmic ratios, prominent nucleoli and compact colony formation with poorly discernable cell junctions. Additional features of undifferentiated stem cells are further described hereinunder.

According to specific embodiments, the stem cells are selected from the group consisting of embryonic stem cells (ESCs), induced pluripotent stem cells (iPS), hematopoietic stem cells (HSCs) and mesenchymal stem cells (MSCs).

According to specific embodiments, the cells are embryonic stem cells (ESCs).

The phrase "embryonic stem cells (ESCs)" refers to ESCs which are capable of differentiating into cells of all three embryonic germ layers (i.e., endoderm, ectoderm and mesoderm), or remaining in an undifferentiated state. The phrase "embryonic stem cells (ESCs)" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763), embryonic germ (EG) cells which are obtained from the genital tissue of a fetus any time during gestation, preferably before 10 weeks of gestation, and cells originating from an unfertilized ova which are stimulated by parthenogenesis (parthenotes).

The ESCs of some embodiments of the invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ESCs the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

It will be appreciated that commercially available stem cells can also be used according to some embodiments of the invention. Human ESCs can be purchased from the NIH human embryonic stem cells registry [Hypertext Transfer Protocol://grants (dot) nih (dot) gov/stem_cells/registry/current (dot) htm]. Non-limiting examples of commercially available embryonic stem cell lines are BG01, BG02, BG03, BG04, CY12, CY30, CY92, CY10, TE03, TE32, CHB-4, CHB-5, CHB-6, CHB-8, CHB-9, CHB-10, CHB-11, CHB-12, HUES 1, HUES 2, HUES 3, HUES 4, HUES 5, HUES 6, HUES 7, HUES 8, HUES 9, HUES 10, HUES 11, HUES 12, HUES 13, HUES 14, HUES 15, HUES 16, HUES 17, HUES 18, HUES 19, HUES 20, HUES 21, HUES 22, HUES 23, HUES 24, HUES 25, HUES 26, HUES 27, HUES 28, CyT49, RUES3, WA01, UCSF4, NYUES1, NYUES2, NYUES3, NYUES4, NYUES5, NYUES6, NYUES7, UCLA 1, UCLA 2, UCLA 3, WA077 (H7), WA09 (H9), WA13 (H13), WA14 (H14), HUES 62, HUES 63, HUES 64, CT1, CT2, CT3, CT4, MA135, Eneavour-2, WIBR1, WIBR2, WIBR3, WIBR4, WIBR5, WIBR6, HUES 45, Shef 3, Shef 6, BJNhem19, BJNhem20, SA001, SA001.

In addition, ESCs can be obtained from other species as well, including mouse (Mills and Bradley, 2001), golden hamster [Doetschman et al., 1988, Dev Biol. 127: 224-7], rat [Iannaccone et al., 1994, Dev Biol. 163: 288-92] rabbit [Giles et al. 1993, Mol Reprod Dev. 36: 130-8; Graves & Moreadith, 1993, Mol Reprod Dev. 1993, 36: 424-33], several domestic animal species [Notarianni et al., 1991, J Reprod Fertil Suppl. 43: 255-60; Wheeler 1994, Reprod Fertil Dev. 6: 563-8; Mitalipova et al., 2001, Cloning. 3: 59-67] and non-human primate species (Rhesus monkey and marmoset) [Thomson et al., 1995, Proc Natl Acad Sci USA. 92: 7844-8; Thomson et al., 1996, Biol Reprod. 55: 254-9].

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, Mo., USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

Another method for preparing ESCs is described in Chung et al., Cell Stem Cell, Volume 2, Issue 2, 113-117, 7 Feb. 2008. This method comprises removing a single cell from an embryo during an in vitro fertilization process. The embryo is not destroyed in this process.

EG cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090,622.

ESCs (e.g., human ESCs) originating from an unfertilized ova stimulated by parthenogenesis (parthenotes) are known in the art (e.g., Zhenyu Lu et al., 2010. J. Assist Reprod. Genet. 27:285-291; "Derivation and long-term culture of human parthenogenetic embryonic stem cells using human foreskin feeders", which is fully incorporated herein by reference). Parthenogenesis refers to the initiation of cell division by activation of ova in the absence of sperm cells, for example using electrical or chemical stimulation. The activated ovum (parthenote) is capable of developing into a primitive embryonic structure (called a blastocyst) but cannot develop to term as the cells are pluripotent, meaning that they cannot develop the necessary extra-embryonic tissues (such as amniotic fluid) needed for a viable human fetus.

According to specific embodiments, the cells are embryonic stem cells Induced pluripotent stem cells (iPS).

Induced pluripotent stem cells (iPS; embryonic-like stem cells), are cells obtained by de-differentiation of adult somatic cells which are endowed with pluripotency (i.e., being capable of differentiating into the three embryonic germ cell layers, i.e., endoderm, ectoderm and mesoderm). According to some embodiments of the invention, such cells are obtained from a differentiated tissue (e.g., a somatic tissue such as skin) and undergo de-differentiation by genetic manipulation which re-program the cell to acquire embryonic stem cells characteristics. According to some embodiments of the invention, the induced pluripotent stem cells are formed by inducing the expression of Oct-4, Sox2, Kfl4 and c-Myc in a somatic stem cell.

Induced pluripotent stem cells (iPS) (embryonic-like stem cells) can be generated from somatic cells by genetic manipulation of somatic cells, e.g., by retroviral transduction of somatic cells such as fibroblasts, hepatocytes, gastric epithelial cells with transcription factors such as Oct-3/4, Sox2, c-Myc, and KLF4 [Yamanaka S, Cell Stem Cell. 2007, 1(1):39-49; Aoi T, et al., Generation of Pluripotent Stem Cells from Adult Mouse Liver and Stomach Cells. Science. 2008 Feb. 14. (Epub ahead of print); I H Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell (2007) 131:861-872]. Other embryonic-like stem cells can be generated by nuclear transfer to oocytes, fusion with embryonic stem cells or nuclear transfer into zygotes if the recipient cells are arrested in mitosis.

The phrase "adult stem cells" (also called "tissue stem cells" or a stem cell from a somatic tissue) refers to any stem cell derived from a somatic tissue [of either a postnatal or prenatal animal (especially the human)]. The adult stem cell is generally thought to be a multipotent stem cell, capable of differentiation into multiple cell types. Adult stem cells can be derived from any adult, neonatal or fetal tissue such as adipose tissue, skin, kidney, liver, prostate, pancreas, intestine, bone marrow and placenta.

Adult tissue stem cells can be isolated using various methods known in the art such as those disclosed by Alison, M. R. [J Pathol. (2003) 200(5): 547-50], Cai, J. et al., [Blood Cells Mol Dis. 2003 31(1): 18-27], Collins, A. T. et al., [J Cell Sci. 2001; 114(Pt 21): 3865-72], Potten, C. S. and Morris, R. J. [Epithelial stem cells in vivo. 1988. J. Cell Sci. Suppl. 10, 45-62], Dominici, M et al., [J. Biol. Regul. Homeost. Agents. 2001, 15: 28-37], Caplan and Haynesworth [U.S. Pat. No. 5,486,359] Jones E. A. et al., [Arthritis Rheum. 2002, 46(12): 3349-60]. Generally, isolation of adult tissue stem cells is based on the discrete location (or niche) of each cell type included in the adult tissue, i.e., the stem cells, the transit amplifying cells and the terminally differentiated cells [Potten, C. S. and Morris, R. J. (1988). Epithelial stem cells in vivo. J. Cell Sci. Suppl. 10, 45-62].

Hematopoietic stem cells (HSCs), which may also referred to as adult tissue stem cells, include stem cells obtained from blood or bone marrow tissue of an individual at any age or from cord blood of a newborn individual. According to specific embodiments, the cells comprise HSCs.

According to a specific embodiment, hematopoietic stem cell is a CD34+ cell.

As used herein the term "CD34+ cell" refers to a hematopoietic stem cell positive for the CD34 marker that can differentiate to each of the cell types in the blood, i.e.; the myeloid (monocyte, macrophage, neutrophil, basophil, eosinophil, erythrocyte, megakaryocyte, dendritic cell) or lymphoid (T cell, B cell, NK cell) lineages.

The HSCs may be a specific cell line, alternatively may be generated from iPS or embryonic stem cells [see for example Pick M et al. (2007) *Stem Cells,* 25(9): 2206-14; and Pick M et al. (2013) *PLoS One,* 8(2): e55530] or alternatively may be isolated using various methods known in the arts such as those disclosed by "Handbook of Stem Cells" edit by Robert Lanze, Elsevier Academic Press, 2004, Chapter 54, pp 609-614, isolation and characterization of hematopoietic stem cells, by Gerald J Spangrude and William B Stayton. Thus, for example, HSCs can be isolated from cord blood, peripheral blood or BM samples by means of density gradient centrifugation using for example Ficoll-Paque (can be obtained from GE Healthcare Bio-Science AB) followed by immunomagnetic or immunofluorescent methods (such as Diamond or Microbeads CD34+ isolation kit obtained from Miltenyi Biotech). Purity of the purified fraction can be assessed by flow cytometry for the specified markers (for example CD34).

According to a specific embodiment the HSCs are mobilized to the peripheral blood by agents such as G-CSF with or without chemotherapy.

Placental and cord blood stem cells may also be referred to as "young stem cells".

Fetal stem cells can be isolated using various methods known in the art such as those disclosed by Eventov-Friedman S, et al., PLoS Med. 2006, 3: e215; Eventov-Friedman S, et al., Proc Natl Acad Sci USA. 2005, 102: 2928-33; Dekel B, et al., 2003, Nat Med. 9: 53-60; and Dekel B, et al., 2002, J. Am. Soc. Nephrol. 13: 977-90.

According to specific embodiments, the cells comprise mesenchymal stem cells (MSCs).

Mesenchymal stem cells give rise to one or more mesenchymal tissues (e.g., adipose, osseous, cartilaginous, elastic and fibrous connective tissues, myoblasts) as well as to tissues other than those originating in the embryonic mesoderm (e.g., neural cells) depending upon various influences from bioactive factors such as cytokines. Although such cells can be isolated from embryonic yolk sac, placenta, umbilical cord, fetal and adolescent skin, blood and other tissues, their abundance in the bone marrow far exceeds their abundance in other tissues and as such isolation from bone marrow is presently preferred.

Methods of isolating, purifying and expanding MSCs are known in the art and include, for example, those disclosed by Caplan and Haynesworth in U.S. Pat. No. 5,486,359 and Jones E. A. et al., 2002, Isolation and characterization of bone marrow multipotential mesenchymal progenitor cells, Arthritis Rheum. 46(12): 3349-60.

According to specific embodiments, MSC cultures are generated by diluting bone marrow aspirates (usually 20 ml) with equal volumes of Hank's balanced salt solution (HBSS; GIBCO Laboratories, Grand Island, N.Y., USA) and layering the diluted cells over about 10 ml of a Ficoll column (Ficoll-Paque; Pharmacia, Piscataway, N.J., USA). Following 30 minutes of centrifugation at 2,500×g, the mononuclear cell layer is removed from the interface and suspended in HBSS. Cells are then centrifuged at 1,500×g for 15 minutes and resuspended in a complete medium (MEM, a medium without deoxyribonucleotides or ribonucleotides; GIBCO); 2-20% fetal calf serum (FCS) derived from a lot selected for rapid growth of MSCs (Atlanta Biologicals, Norcross, Ga.); 100 units/ml penicillin (GIBCO), 100 μg/ml streptomycin (GIBCO); and 2 mM L-glutamine (GIBCO). Resuspended cells are plated in about 25 ml of medium in a 10 cm culture dish (Corning Glass Works, Corning, N.Y.) and incubated at 37° C. with 5% humidified $CO_2$. Following 24 hours in culture, nonadherent cells are discarded, and the adherent cells are thoroughly washed twice with phosphate buffered saline (PBS). The medium is replaced with a fresh complete medium every 3 or 4 days for about 14 days. Adherent cells are then harvested with 0.25% trypsin and 1 mM EDTA (Trypsin/EDTA, GIBCO) for 5 min at 37° C., replated in a 6-cm plate and cultured for another 14 days. Cells are then trypsinized and counted using a cell counting device such as for example, a hemocytometer (Hausser Scientific, Horsham, Pa.). Cultured cells are recovered by centrifugation and resuspended with 5% DMSO and 30% FCS at a concentration of 1 to $2\times10^6$ cells per ml. Aliquots of about 1 ml each are slowly frozen and stored in liquid nitrogen.

To expand the MSC fraction, cells are resuspended in a complete medium and plated at a concentration of about 5,000 cells/$cm^2$. Following 24 hours in culture, nonadherent cells are removed and the adherent cells are harvested using Trypsin/EDTA, dissociated by passage through a narrowed Pasteur pipette, and preferably replated at a density of about 1.5 to about 3.0 cells/$cm^2$. Under these conditions, MSC cultures can grow for about 50 population doublings and be expanded for about 2000 fold [Colter D C., et al. Rapid expansion of recycling stem cells in cultures of plastic-adherent cells from human bone marrow. Proc Natl Acad Sci USA. 97: 3213-3218, 2000].

MSC cultures utilized by some embodiments of the invention include three groups of cells which are defined by their morphological features: small and agranular cells (referred to as RS-1, hereinbelow), small and granular cells (referred to as RS-2, hereinbelow) and large and moderately granular cells (referred to as mature MSCs, hereinbelow). The presence and concentration of such cells in culture can be assayed by identifying a presence or absence of various cell surface markers, by using, for example, immunofluorescence, in situ hybridization, and activity assays.

When MSCs are cultured under the culturing conditions of some embodiments of the invention they exhibit negative staining for the HSC markers CD34, CD11B, CD43 and CD45. A small fraction of cells (less than 10%) are dimly positive for CD31 and/or CD38 markers. In addition, mature MSCs are dimly positive for the HSC marker, CD117 (c-Kit), moderately positive for the osteogenic MSCs marker, Stro-1 [Simmons, P. J. & Torok-Storb, B. (1991). Blood 78, 5562] and positive for the thymocytes and peripheral T lymphocytes marker, CD90 (Thy-1). On the other hand, the RS-1 cells are negative for the CD117 and Stro1 markers and are dimly positive for the CD90 marker, and the RS-2 cells are negative for all of these markers.

The cells of some embodiments of the present invention can be a primary cell (non-cultured and alternatively or additionally non-immortalized cell) or a cell-line.

According to specific embodiments, the cells used and/or obtained according to the present invention can be freshly isolated, stored e.g., cryopreserved (i.e. frozen) at e.g. liquid nitrogen temperature at any stage (e.g. following their retrieval, following contacting with the agent, following treatment with TNFα) for long periods of time (e.g., months, years) for future use; and cell lines.

Thus, according to specific embodiments, the cells are cryopreserved cells.

According to specific embodiments, the cells are cryopreserved prior to contacting with the agent which down-regulates expression and/or activity of TNFR1.

According to specific embodiments, the cells are cryopreserved following contacting with the agent which down-regulates expression and/or activity of TNFR1.

According to specific embodiments, the cells are cryopreserved prior to treatment with TNFα.

According to specific embodiments, the cells are cryopreserved following treatment with TNFα.

According to specific embodiments, the cells are cryopreserved prior to administering to the subject.

Methods of cryopreservation are commonly known by one of ordinary skill in the art and are disclosed e.g. in International Patent Application Publication Nos. WO2007054160 and WO 2001039594 and US Patent Application Publication No. US20120149108.

According to specific embodiments, the cells obtained according to the present invention can be stored in a cell bank or a depository or storage facility.

According to specific embodiments, the cells are freshly isolated (i.e., not subjected to preservation processes).

The cells used according to specific embodiments of the present invention may be autologous or non-autologous; they can be syngeneic or non-syngeneic: allogeneic or xenogeneic to the subject; each possibility represents a separate embodiment of the present invention.

According to specific embodiments, the cells are autologous to said subject.

As used herein, the term "autologous" means that the donor subject is the recipient subject. Thus, in autologous transplantation the cells have been removed and re-introduced e.g., re-infused to the subject.

According to specific embodiments, the cells are non-autologous to said subject.

As used herein, the term "non-autologous" means that the donor subject is not the recipient subject.

As used herein, the term "syngeneic" means that the donor subject is essentially genetically identical with the recipient subject. Examples of syngeneic transplantation include transplantation of cells derived from the subject (also referred to in the art as "autologous"), a clone of the subject, or a homozygotic twin of the subject As used herein, the term "allogeneic" means that the donor is of the same species as the recipient, but which is substantially non-clonal with the recipient. Typically, outbred, non-zygotic twin mammals of the same species are allogeneic with each other. It will be appreciated that an allogeneic donor may be HLA identical or HLA non-identical with respect to the subject As used herein, the term "xenogeneic" means that the donor subject is from a different species relative to the recipient subject.

According to specific embodiments, the cells are mammalian cells.

According to specific embodiments, the cells are primate cells.

According to specific embodiments, the cells are human cells.

According to other specific embodiments, the cells are rodent cells (e.g. mouse, rat).

The cells of some embodiments of the present invention are characterized by reduced level of expression and/or activity of TNFR1.

As used herein, the term "TNFR1 (Tumor necrosis factor receptor 1)", also known as tumor necrosis factor receptor superfamily member 1A (TNFRSF1A), CD120a and p55 refers to the TNFR1 gene and to its polynucleotide or polypeptide expression product. According to specific embodiments, the TNFR1 refers to the human TNFR1, such as provided in Gene ID: 7132 (SEQ ID NO: 2) and the following Accession Numbers: NM_001065 (SEQ ID NO: 3), NM_001346091 (SEQ ID NO: 4), NM_001346092 (SEQ ID NO: 5), NP_001056 (SEQ ID NO: 6), NP_001333020 (SEQ ID NO: 7) and NP_001333021 (SEQ ID NO: 8). According to specific embodiments, the TNFR1 refers to the mouse TNFR1, such as provided in Gene ID: 21937 (SEQ ID NO: 9) and in the following Accession Numbers: NM_011609 (SEQ ID NO: 10) and NP_035739 (SEQ ID NO: 11).

According to specific embodiments, TNFR1 activity is at least one of (or two of or all of): binding TNFα, forming a trimer, activating the transcription factor NFκB and/or mediating apoptosis.

As used herein, "reduced level of expression and/or activity" refers to a decrease of at least 10% in TNFR1 expression or activity in comparison to a control cell of the same origin which was not contacted with an agent which downregulates expression and/or activity of TNFR1, as may be determined by e.g. PCR, ELISA, Western blot analysis, immunoprecipitation, flow cytometry, immuno-staining, TNFα signaling assays. According to a specific embodiment, the decrease is in at least 20%, 30%, 40% or even higher say, 50%, 60%, 70%, 80%, 90% or even 100%.

According to specific embodiments, the cell does not express TNFR1.

According to specific embodiments the cells with reduced expression and/or activity of TNFR1 are genetically modified cells. Methods and agents for genetically modifying cells are well known in the art and are further described in details hereinbelow.

According to specific embodiments, the cells are genetically modified with a CRISPR/Cas system, a Zinc finger nuclease (ZFN), transcription-activator like effector nuclease (TALEN) or meganuclease for downregulating expression of said TNFR1.

According to specific embodiments, the cells are genetically modified with a CRISPR/Cas system for downregulating expression of said TNFR1.

According to specific embodiments, the cells with reduced level of expression and/or activity of TNFR1 express similar levels and/or activity of TNFR2 in comparison to a control cell of the same origin which was not contacted with an agent which downregulates expression and/or activity of TNFR1, as may be determined by e.g. PCR, ELISA, Western blot analysis, immunoprecipitation, flow cytometry, immuno-staining, TNFα signaling assays.

As used herein, the term "TNFR2 (Tumor necrosis factor receptor 2)", also known as tumor necrosis factor receptor superfamily member 1B (TNFRSF1B) and CD120b and p75 refers to the TNFR2 gene and to its polynucleotide or polypeptide expression product. According to specific embodiments, the TNFR2 refers to the human TNFR2, such as provided in Gene ID: 7133 (SEQ ID NO: 12) and the following Accession Numbers: NM_001066 (SEQ ID NO: 13) and NP_001057 (SEQ ID NO: 14). According to specific embodiments, the TNFR1 refers to the mouse TNFR2, such as provided in Gene ID: 21938 (SEQ ID NO: 15) and in the following Accession Numbers: NM_011610 (SEQ ID NO: 16) and NP_035740 (SEQ ID NO: 17).

According to specific embodiments, TNFR2 activity is at least one of (or two of or all of): binding TNFα and/or mediating the recruitment of two anti-apoptotic proteins, c-IAP1 and c-IAP2.

As the cells of some embodiments of the present invention are characterized by reduced level of expression and/or activity of TNFR1, the present invention also contemplates methods of obtaining such cells.

Thus, according to an aspect of the present invention there is provided a method of downregulating expression and/or activity of TNFR1 in differentiated cells or bone marrow stem cells, the method comprising:

(i) contacting ex-vivo or in-vitro differentiated cells or bone marrow stem cells with an agent which downregulates expression and/or activity of TNFR1; and (ii) contacting ex-vivo or in-vitro said cells with TNFα.

According to another aspect of the present invention there is provided a method of downregulating expression and/or activity of TNFR1 in differentiated cells, the method comprising:

(i) inducing ex-vivo or in-vivo differentiation of stem cells;

(ii) contacting ex-vivo or in-vitro said cells with an agent which downregulates expression and/or activity of TNFR1; and (iii) contacting ex-vivo or in-vitro said cells with TNFα.

According to specific embodiments, inducing differentiation of the stem cells is effected prior to contacting with the agent. Methods of inducing differentiation of stem cells are known in the art and are further described hereinabove.

According to another aspect of the present invention there is provided a method of downregulating expression and/or activity of TNFR1 in differentiated cells or bone marrow stem cells, the method comprising genetically modifying ex-vivo or in-vitro differentiated cells or bone marrow stem cells with an agent which downregulates expression and/or activity of TNFR1.

According to specific embodiments, the method further comprising contacting the cells ex-vivo or in-vitro with TNFα.

According to specific embodiments, contacting the cells with the agent is effected prior to contacting the cells with the TNFα.

According to specific embodiments, contacting the cells with the agent is effected following contacting the cells with the TNFα.

Specific embodiments of the present invention contemplates a method of treating an ischemic disease in a subject in need thereof, the method comprising:

(i) obtaining cells according to the methods of downregulating expression and/or activity of TNFR1 described herein; and (ii) administering to the subject a therapeutically effective amount of said cells, thereby treating the ischemic disease in the subject.

As used herein, "downregulating expression and/or activity" and "downregulates expression and/or activity" refer to a decrease of at least 5% in expression and/or biological function in the presence of the agent in comparison to same in the absence of the agent, as determined by e.g. PCR, ELISA, Western blot analysis, immunoprecipitation, flow cytometry, immuno-staining, TNFα signaling assays. According to a specific embodiment, the decrease is in at least 10%, 30%, 40% or even higher say, 50%, 60%, 70%, 80%, 90% or even 100%. According to specific embodiments, the decrease is at least 1.5 fold, at least 2 fold, at least 3 fold, at least 5 fold, at least 10 fold, or at least 20 fold as compared to same in the absence of the agent.

According to specific embodiments, downregulating expression refers to the absence of mRNA and/or protein, as detected by RT-PCR or Western blot, respectively.

According to specific embodiments, "downregulating expression and/or activity of TNFR1" and "downregulates expression and/or activity of TNFR1" refer to the ability to specifically downregulate the expression and/or activity of TNFR1 and not to downregulate the expression and/or activity of TNFR2, as determined by e.g. PCR, ELISA, Western blot analysis, immunoprecipitation, flow cytometry, immuno-staining, TNFα signaling assays. This selective inhibition can be manifested as higher affinity (e.g., $K_d$) of the agent to TNFR1 than to TNFR2. Increased affinity can be of at least 5, 10, 100, 1000 or 10000 fold.

Hence, according to specific embodiments, the agent does not downregulate expression and/or activity of TNFR2.

Downregulating expression and/or activity can be effected at the genomic (e.g. homologous recombination and site specific endonucleases) and/or the transcript level using a variety of molecules which interfere with transcription and/or translation (e.g., RNA silencing agents) of a target expression product described herein, but may also be effected at the protein level (e.g., antibodies, small molecules, inhibitory peptides, enzymes that cleave the polypeptide, aptamers and the like).

According to specific embodiments, the agent directly binds TNFR1.

According to other specific embodiments, the agent indirectly binds TNFR1 by acting through an intermediary molecule, for example the agent binds to or modulates a molecule that in turn binds to or modulates the target.

According to specific embodiments, the agent does not bind TNFR2.

Non-limiting examples of down-regulating agents at the nucleic acid level are described in details hereinbelow.

Down-regulation at the nucleic acid level is typically effected using a nucleic acid agent, having a nucleic acid backbone, DNA, RNA, mimetics thereof or a combination of same. The nucleic acid agent may be encoded from a DNA molecule or provided to the cell per se.

Downregulation can be achieved by inactivating the gene (i.e. the TNFR1 gene) via introducing targeted mutations involving loss-of function alterations (e.g. point mutations, deletions and insertions) in the gene structure.

As used herein, the phrase "loss-of-function alterations" refers to any mutation in the DNA sequence of a gene which results in downregulation of the expression level and/or activity of the expressed product, i.e., the mRNA transcript and/or the translated protein. Non-limiting examples of such loss-of-function alterations include a missense mutation, i.e., a mutation which changes an amino acid residue in the protein with another amino acid residue and thereby abolishes the enzymatic activity of the protein; a nonsense mutation, i.e., a mutation which introduces a stop codon in a protein, e.g., an early stop codon which results in a shorter protein devoid of the enzymatic activity; a frame-shift mutation, i.e., a mutation, usually, deletion or insertion of nucleic acid(s) which changes the reading frame of the protein, and may result in an early termination by introducing a stop codon into a reading frame (e.g., a truncated protein, devoid of the enzymatic activity), or in a longer amino acid sequence (e.g., a readthrough protein) which affects the secondary or tertiary structure of the protein and results in a non-functional protein, devoid of the enzymatic activity of the non-mutated polypeptide; a readthrough mutation due to a frame-shift mutation or a modified stop codon mutation (i.e., when the stop codon is mutated into an amino acid codon), with an abolished enzymatic activity; a promoter mutation, i.e., a mutation in a promoter sequence, usually 5' to the transcription start site of a gene, which results in down-regulation of a specific gene product; a regulatory mutation, i.e., a mutation in a region upstream or downstream, or within a gene, which affects the expression of the gene product; a deletion mutation, i.e., a mutation which deletes coding nucleic acids in a gene sequence and which may result in a frame-shift mutation or an in-frame mutation (within the coding sequence, deletion of one or more amino acid codons); an insertion mutation, i.e., a mutation which inserts coding or non-coding nucleic acids into a gene sequence, and which may result in a frame-shift mutation or an in-frame insertion of one or more amino acid codons; an inversion, i.e., a mutation which results in an inverted coding or non-coding sequence; a splice mutation i.e., a mutation which results in abnormal splicing or poor splicing; and a duplication mutation, i.e., a mutation which results in a duplicated coding or non-coding sequence, which can be in-frame or can cause a frame-shift.

According to specific embodiments loss-of-function alteration of a gene may comprise at least one allele of the gene.

The term "allele" as used herein, refers to any of one or more alternative forms of a gene locus, all of which alleles relate to a trait or characteristic. In a diploid cell or organism, the two alleles of a given gene occupy corresponding loci on a pair of homologous chromosomes.

According to other specific embodiments loss-of-function alteration of a gene comprises both alleles of the gene. In such instances the TNFR1 may be in a homozygous form or in a heterozygous form.

Methods of introducing nucleic acid alterations to a gene of interest are well known in the art [see for example Menke D. Genesis (2013) 51:-618; Capecchi, Science (1989) 244: 1288-1292; Santiago et al. Proc Natl Acad Sci USA (2008) 105:5809-5814; International Patent Application Nos. WO 2014085593, WO 2009071334 and WO 2011146121; U.S. Pat. Nos. 8,771,945, 8,586,526, 6,774,279 and UP Patent Application Publication Nos. 20030232410, 20050026157, US20060014264; the contents of which are incorporated by reference in their entireties] and include targeted homologous recombination, site specific recombinases, PB transposases and genome editing by engineered nucleases. Agents for introducing nucleic acid alterations to a gene of interest can be designed publically available sources or obtained commercially from Transposagen, Addgene and Sangamo Biosciences.

Following is a description of various exemplary methods used to introduce nucleic acid alterations to a gene of interest and agents for implementing same that can be used according to specific embodiments of the present invention.

Genome Editing using engineered endonucleases—this approach refers to a reverse genetics method using artificially engineered nucleases to cut and create specific double-stranded breaks at a desired location(s) in the genome, which are then repaired by cellular endogenous processes such as, homology directed repair (HDR) and non-homologous end-joining (NHEJ). NHEJ directly joins the DNA ends in a double-stranded break, while HDR utilizes a homologous sequence as a template for regenerating the missing DNA sequence at the break point. In order to introduce specific nucleotide modifications to the genomic DNA, a DNA repair template containing the desired sequence must be present during HDR. Genome editing cannot be performed using traditional restriction endonucleases since most restriction enzymes recognize a few base pairs on the DNA as their target and the probability is very high that the recognized base pair combination will be found in many locations across the genome resulting in multiple cuts not limited to a desired location. To overcome this challenge and create site-specific single- or double-stranded breaks, several distinct classes of nucleases have been discovered and bioengineered to date. These include the meganucleases, Zinc finger nucleases (ZFNs), transcription-activator like effector nucleases (TALENs) and CRISPR/Cas system.

Meganucleases—Meganucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif. The four families of meganucleases are widely separated from one another with respect to conserved structural elements and, consequently, DNA recognition sequence specificity and catalytic activity. Meganucleases are found commonly in microbial species and have the unique property of having very long recognition sequences (>14 bp) thus making them naturally very specific for cutting at a desired location. This can be exploited to make site-specific double-stranded breaks in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence. Alternatively, DNA interacting amino acids of the meganuclease can be altered to design sequence specific meganucleases (see e.g., U.S. Pat. No. 8,021,867). Meganucleases can be designed using the methods described in e.g., Certo, M T et al. Nature Methods (2012) 9:073-975; U.S. Pat. Nos. 8,304,222; 8,021,867; 8,119,381; 8,124,369; 8,129,134; 8,133,697; 8,143,015; 8,143,016; 8,148,098; or 8,163,514, the contents of each are incorporated herein by reference in their entirety. Alternatively, meganucleases with site specific cutting characteristics can be obtained using commercially available technologies e.g., Precision Biosciences' Directed Nuclease Editor™ genome editing technology.

ZFNs and TALENs—Two distinct classes of engineered nucleases, zinc-finger nucleases (ZFNs) and transcription activator-like effector nucleases (TALENs), have both proven to be effective at producing targeted double-stranded breaks (Christian et al., 2010; Kim et al., 1996; Li et al., 2011; Mahfouz et al., 2011; Miller et al., 2010).

Basically, ZFNs and TALENs restriction endonuclease technology utilizes a non-specific DNA cutting enzyme which is linked to a specific DNA binding domain (either a series of zinc finger domains or TALE repeats, respectively). Typically a restriction enzyme whose DNA recognition site and cleaving site are separate from each other is selected. The cleaving portion is separated and then linked to a DNA binding domain, thereby yielding an endonuclease with very high specificity for a desired sequence. An exemplary restriction enzyme with such properties is Fokl. Additionally Fokl has the advantage of requiring dimerization to have nuclease activity and this means the specificity increases dramatically as each nuclease partner recognizes a unique DNA sequence. To enhance this effect, Fokl nucleases have been engineered that can only function as heterodimers and have increased catalytic activity. The heterodimer functioning nucleases avoid the possibility of unwanted homodimer activity and thus increase specificity of the double-stranded break.

Thus, for example to target a specific site, ZFNs and TALENs are constructed as nuclease pairs, with each member of the pair designed to bind adjacent sequences at the targeted site. Upon transient expression in cells, the nucleases bind to their target sites and the FokI domains heterodimerize to create a double-stranded break. Repair of these double-stranded breaks through the non-homologous end-joining (NHEJ) pathway most often results in small deletions or small sequence insertions. Since each repair made by NHEJ is unique, the use of a single nuclease pair can produce an allelic series with a range of different deletions at the target site. The deletions typically range anywhere from a few base pairs to a few hundred base pairs in length, but larger deletions have successfully been generated in cell culture by using two pairs of nucleases simultaneously (Carlson et al., 2012; Lee et al., 2010). In addition, when a fragment of DNA with homology to the targeted region is introduced in conjunction with the nuclease pair, the double-stranded break can be repaired via homology directed repair to generate specific modifications (Li et al., 2011; Miller et al., 2010; Urnov et al., 2005).

Although the nuclease portions of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers typically found in repeats that are 3 bp apart and are found in diverse combinations in a variety of nucleic acid interacting proteins. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs can also be designed and obtained commercially from e.g., Sangamo Biosciences™ (Richmond, Calif.).

Method for designing and obtaining TALENs are described in e.g. Reyon et al. Nature Biotechnology 2012 May; 30(5):460-5; Miller et al. Nat Biotechnol. (2011) 29: 143-148; Cermak et al. Nucleic Acids Research (2011) 39 (12): e82 and Zhang et al. Nature Biotechnology (2011) 29 (2): 149-53. A recently developed web-based program named Mojo Hand was introduced by Mayo Clinic for designing TAL and TALEN constructs for genome editing applications (can be accessed through www(dot)talendesign (dot)org). TALEN can also be designed and obtained commercially from e.g., Sangamo Biosciences™ (Richmond, Calif.).

CRISPR-Cas system—Many bacteria and archaea contain endogenous RNA-based adaptive immune systems that can degrade nucleic acids of invading phages and plasmids. These systems consist of clustered regularly interspaced short palindromic repeat (CRISPR) genes that produce RNA components and CRISPR associated (Cas) genes that encode protein components. The CRISPR RNAs (crRNAs) contain short stretches of homology to specific viruses and plasmids and act as guides to direct Cas nucleases to degrade the complementary nucleic acids of the corresponding pathogen. Studies of the type II CRISPR/Cas system of *Streptococcus pyogenes* have shown that three components form an RNA/protein complex and together are sufficient for sequence-specific nuclease activity: the Cas9 nuclease, a crRNA containing 20 base pairs of homology to the target sequence, and a trans-activating crRNA (tracrRNA) (Jinek et al. *Science* (2012) 337: 816-821). It was further demonstrated that a synthetic chimeric guide RNA (gRNA) composed of a fusion between crRNA and tracrRNA could direct Cas9 to cleave DNA targets that are complementary to the crRNA in vitro. It was also demonstrated that transient expression of Cas9 in conjunction with synthetic gRNAs can be used to produce targeted double-stranded brakes in a variety of different species (Cho et al., 2013; Cong et al., 2013; DiCarlo et al., 2013; Hwang et al., 2013a,b; Jinek et al., 2013; Mali et al., 2013).

The CRIPSR/Cas system for genome editing contains two distinct components: a gRNA and an endonuclease e.g. Cas9.

The gRNA is typically a 20 nucleotide sequence encoding a combination of the target homologous sequence (crRNA) and the endogenous bacterial RNA that links the crRNA to the Cas9 nuclease (tracrRNA) in a single chimeric transcript. The gRNA/Cas9 complex is recruited to the target sequence by the base-pairing between the gRNA sequence and the complement genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the Cas9 can cut both strands of the DNA causing a double-strand break. Just as with ZFNs and TALENs, the double-stranded brakes produced by CRISPR/Cas can undergo homologous recombination or NHEJ.

The Cas9 nuclease has two functional domains: RuvC and HNH, each cutting a different DNA strand. When both of these domains are active, the Cas9 causes double strand breaks in the genomic DNA.

A significant advantage of CRISPR/Cas is that the high efficiency of this system coupled with the ability to easily create synthetic gRNAs enables multiple genes to be targeted simultaneously. In addition, the majority of cells carrying the mutation present biallelic mutations in the targeted genes.

However, apparent flexibility in the base-pairing interactions between the gRNA sequence and the genomic DNA target sequence allows imperfect matches to the target sequence to be cut by Cas9.

Modified versions of the Cas9 enzyme containing a single inactive catalytic domain, either RuvC- or HNH-, are called ‘nickases’. With only one active nuclease domain, the Cas9 nickase cuts only one strand of the target DNA, creating a single-strand break or ‘nick’. A single-strand break, or nick, is normally quickly repaired through the HDR pathway, using the intact complementary DNA strand as the template. However, two proximal, opposite strand nicks introduced by a Cas9 nickase are treated as a double-strand break, in what is often referred to as a ‘double nick’ CRISPR system. A double-nick can be repaired by either NHEJ or HDR depending on the desired effect on the gene target. Thus, if specificity and reduced off-target effects are crucial, using the Cas9 nickase to create a double-nick by designing two gRNAs with target sequences in close proximity and on opposite strands of the genomic DNA would decrease off-target effect as either gRNA alone will result in nicks that will not change the genomic DNA.

Modified versions of the Cas9 enzyme containing two inactive catalytic domains (dead Cas9, or dCas9) have no nuclease activity while still able to bind to DNA based on gRNA specificity. The dCas9 can be utilized as a platform for DNA transcriptional regulators to activate or repress gene expression by fusing the inactive enzyme to known regulatory domains. For example, the binding of dCas9 alone to a target sequence in genomic DNA can interfere with gene transcription.

There are a number of publically available tools available to help choose and/or design target sequences as well as lists of bioinformatically determined unique gRNAs for different genes in different species such as the Feng Zhang lab's Target Finder, the Michael Boutros lab's Target Finder (E-CRISP), the RGEN Tools: Cas-OFFinder, the CasFinder: Flexible algorithm for identifying specific Cas9 targets in genomes and the CRISPR Optimal Target Finder.

Non-limiting examples of gRNA sequences that can be used with some embodiments of the present invention are described in Tables 1A and 1B hereinbelow.

According to specific embodiments, the gRNA sequence does not have a significant off target effect. Methods of determining off target effect are well known in the art, such as BGI Human Whole Genome Sequencing (described in Nature; 491:65-56.2012), next generation sequencing (NGS) using e.g. commercially available kits such as Alt- R-Genom Editing (IDT detection kit) or Sure select target enrich <1% variant allele frequency (Agilent).

In order to use the CRISPR system, both gRNA and Cas9 should be expressed in a target cell. The insertion vector can contain both cassettes on a single plasmid or the cassettes are expressed from two separate plasmids. CRISPR plasmids are commercially available such as the px330 plasmid from Addgene. Alternatively, the target cell can be transfected with both gRNA and Cas9 without plasmid using e.g. a transfection reagent such as CRISPRMAX [see e.g. Yu et al. (2016) JD1Biotechnol Lett. 38(6):919-29]. In some cells electroporation can improve the transfection of the gRNA and the Cas9 [see e.g. Liang et al. (2015) Journal of Biotechnology 208, 2015, Pages 44-53; and Liang et al. (2017) Journal of Biotechnology, Volume 241, 2017, pp. 136-146].

TABLE 1A

TNFR1 guide RNA sequences designed according to the mouse TNFR1

| | Sequence of gRNA | Forward | Reverse | GCD Band sizes |
|---|---|---|---|---|
| CRISPR1 | CGGACAGTCA CTCACCAAGT SEQ ID NO: 18 | GAACAATTCCAT CTGCTGCACC SEQ ID NO: 19 | TTCGAAATCCT GACCTCCTGG SEQ ID NO: 20 | 604 378 bp 226 bp |
| CRISPR2 | GACACTGCCT GAGGTAATTC SEQ ID NO: 21 | TGAGACAGGGT TTCTCTATACC SEQ ID NO: 22 | CATGGCATT CGTCTTTGT SEQ ID NO: 23 | 600 357 bp 243 bp |
| CRISPR3 | CGGCTTCCCA GAATTACCTC SEQ ID NO: 24 | AGTGAGAGCAG AGAATTGTC SEQ ID NO: 25 | GAGCTTGCATG TGCACGCAT SEQ ID NO: 26 | 608 417 bp 191 bp |

* Mouse tumor necrosis factor receptor superfamily, member 1a mRNA: NM_011609 (SEQ ID NO: 10) Total No. of Exons: 10, Targeted Exons: 2 (2, 3)

TABLE 1B

TNFR1 guide RNA sequences designed according to the human TNFR1

| | Sequence of gRNA | Forward | Reverse | GCD Band sizes |
|---|---|---|---|---|
| CRISPR1 | ATATACCCCT CAGGGGTTAT SEQ ID NO: 27 | TCTCACACTCC CTGCAGTCCGT SEQ ID NO: 28 | CAGATTGTATG GCCCCAACTGT SEQ ID NO: 29 | 625 415 bp 210 bp |
| CRISPR2 | ATTGGACTGG TCCCTCACCT SEQ ID NO: 30 | TTCTGAAGCGG TGAAGGAGCC SEQ ID NO: 31 | CAGATTGTATG GCCCCAACTGT SEQ ID NO: 32 | 648 420 bp 228 bp |
| CRISPR3 | TACTTGTACA ATGACTGTCC SEQ ID NO: 33 | TGCCGGTACTG GTTCTTCCTG SEQ ID NO: 34 | GGGTGCTGCTT CTTTCTCTGCT SEQ ID NO: 35 | 484 360 bp 124 bp |
| CRISPR4 | TAATGTATCG CTACCAACGG SEQ ID NO: 36 | ACCACAGTGCT GTTGCC SEQ IF NO: 37 | TCACCTCCCTC CACACAT SEQ ID NO: 38 | |
| CRISPR5 | CACTCCAATA ATGCCGGTAC SEQ ID NO: 39 | ATCTCTTCTTG CACAGTGGAC SEQ ID NO: 40 | ACGGTGTTCTG TTTCTCCTG SEQ ID NO: 41 | |

TABLE 1B-continued

TNFR1 guide RNA sequences designed according to the human TNFR1

| | Sequence of gRNA | Forward | Reverse | GCD Band sizes |
|---|---|---|---|---|
| CRISPR6 | AGAGGTGCAC GGTCCCATTG SEQ ID NO: 42 | GAAGAACCAG TACCGGCATTA SEQ ID NO: 43 | GTTGTCAGACC CACAGAATAC SEQ ID NO: 44 | |
| CRISPR7 | TTGGACTGGT CCCTCACCTA SEQ ID NO: 45 | TCTCTTGATGG TGTCTCCTCTA SEQ ID NO: 46 | ACTGGAAGAAG CAGAGAAAGAA SEQ ID NO: 47 | |

* Human tumor necrosis factor receptor superfamily, member 1a mRNA: NM_001065 (SEQ ID NO: 3)

"Hit and run" or "in-out"—involves a two-step recombination procedure. In the first step, an insertion-type vector containing a dual positive/negative selectable marker cassette is used to introduce the desired sequence alteration. The insertion vector contains a single continuous region of homology to the targeted locus and is modified to carry the mutation of interest. This targeting construct is linearized with a restriction enzyme at a one site within the region of homology, electroporated into the cells, and positive selection is performed to isolate homologous recombinants. These homologous recombinants contain a local duplication that is separated by intervening vector sequence, including the selection cassette. In the second step, targeted clones are subjected to negative selection to identify cells that have lost the selection cassette via intrachromosomal recombination between the duplicated sequences. The local recombination event removes the duplication and, depending on the site of recombination, the allele either retains the introduced mutation or reverts to wild type. The end result is the introduction of the desired modification without the retention of any exogenous sequences.

The "double-replacement" or "tag and exchange" strategy—involves a two-step selection procedure similar to the hit and run approach, but requires the use of two different targeting constructs. In the first step, a standard targeting vector with 3' and 5' homology arms is used to insert a dual positive/negative selectable cassette near the location where the mutation is to be introduced. After electroporation and positive selection, homologously targeted clones are identified. Next, a second targeting vector that contains a region of homology with the desired mutation is electroporated into targeted clones, and negative selection is applied to remove the selection cassette and introduce the mutation. The final allele contains the desired mutation while eliminating unwanted exogenous sequences.

Site-Specific Recombinases—The Cre recombinase derived from the P1 bacteriophage and Flp recombinase derived from the yeast *Saccharomyces cerevisiae* are site-specific DNA recombinases each recognizing a unique 34 base pair DNA sequence (termed "Lox" and "FRT", respectively) and sequences that are flanked with either Lox sites or FRT sites can be readily removed via site-specific recombination upon expression of Cre or Flp recombinase, respectively. For example, the Lox sequence is composed of an asymmetric eight base pair spacer region flanked by 13 base pair inverted repeats. Cre recombines the 34 base pair lox DNA sequence by binding to the 13 base pair inverted repeats and catalyzing strand cleavage and religation within the spacer region. The staggered DNA cuts made by Cre in the spacer region are separated by 6 base pairs to give an overlap region that acts as a homology sensor to ensure that only recombination sites having the same overlap region recombine.

Basically, the site specific recombinase system offers means for the removal of selection cassettes after homologous recombination. This system also allows for the generation of conditional altered alleles that can be inactivated or activated in a temporal or tissue-specific manner. Of note, the Cre and Flp recombinases leave behind a Lox or FRT "scar" of 34 base pairs. The Lox or FRT sites that remain are typically left behind in an intron or 3' UTR of the modified locus, and current evidence suggests that these sites usually do not interfere significantly with gene function.

Thus, Cre/Lox and Flp/FRT recombination involves introduction of a targeting vector with 3' and 5' homology arms containing the mutation of interest, two Lox or FRT sequences and typically a selectable cassette placed between the two Lox or FRT sequences. Positive selection is applied and homologous recombinants that contain targeted mutation are identified. Transient expression of Cre or Flp in conjunction with negative selection results in the excision of the selection cassette and selects for cells where the cassette has been lost. The final targeted allele contains the Lox or FRT scar of exogenous sequences.

Transposases—As used herein, the term "transposase" refers to an enzyme that binds to the ends of a transposon and catalyzes the movement of the transposon to another part of the genome.

As used herein the term "transposon" refers to a mobile genetic element comprising a nucleotide sequence which can move around to different positions within the genome of a single cell. In the process the transposon can cause mutations and/or change the amount of a DNA in the genome of the cell.

A number of transposon systems that are able to also transpose in cells e.g. vertebrates have been isolated or designed, such as Sleeping Beauty [Izsvák and Ivics Molecular Therapy (2004) 9, 147-156], piggyBac [Wilson et al. Molecular Therapy (2007) 15, 139-145], Tol2 [Kawakami et al. PNAS (2000) 97 (21): 11403-11408] or Frog Prince [Miskey et al. Nucleic Acids Res. Dec. 1, 2003 31(23): 6873-6881]. Generally, DNA transposons translocate from one DNA site to another in a simple, cut-and-paste manner. Each of these elements has their own advantages, for example, Sleeping Beauty is particularly useful in region-specific mutagenesis, whereas Tol2 has the highest tendency to integrate into expressed genes. Hyperactive systems are available for Sleeping Beauty and piggyBac. Most importantly, these transposons have distinct target site preferences, and can therefore introduce sequence alterations in overlapping, but distinct sets of genes. Therefore, to achieve the best possible coverage of genes, the use of more than one element is particularly preferred. The basic mechanism is shared between the different transposases, therefore we will describe piggyBac (PB) as an example.

PB is a 2.5 kb insect transposon originally isolated from the cabbage looper moth, *Trichoplusia ni*. The PB transposon consists of asymmetric terminal repeat sequences that flank a transposase, PBase. PBase recognizes the terminal repeats and induces transposition via a "cut-and-paste" based mechanism, and preferentially transposes into the host genome at the tetranucleotide sequence TTAA. Upon insertion, the TTAA target site is duplicated such that the PB transposon is flanked by this tetranucleotide sequence. When mobilized, PB typically excises itself precisely to reestablish a single TTAA site, thereby restoring the host sequence to its pretransposon state. After excision, PB can transpose into a new location or be permanently lost from the genome.

Typically, the transposase system offers an alternative means for the removal of selection cassettes after homologous recombination quit similar to the use Cre/Lox or Flp/FRT. Thus, for example, the PB transposase system involves introduction of a targeting vector with 3' and 5' homology arms containing the mutation of interest, two PB terminal repeat sequences at the site of an endogenous TTAA sequence and a selection cassette placed between PB terminal repeat sequences. Positive selection is applied and homologous recombinants that contain targeted mutation are identified. Transient expression of PBase removes in conjunction with negative selection results in the excision of the selection cassette and selects for cells where the cassette has been lost. The final targeted allele contains the introduced mutation with no exogenous sequences.

For PB to be useful for the introduction of sequence alterations, there must be a native TTAA site in relatively close proximity to the location where a particular mutation is to be inserted.

Genome editing using recombinant adeno-associated virus (rAAV) platform—this genome-editing platform is based on rAAV vectors which enable insertion, deletion or substitution of DNA sequences in the genomes of live mammalian cells. The rAAV genome is a single-stranded deoxyribonucleic acid (ssDNA) molecule, either positive- or negative-sensed, which is about 4.7 kb long. These single-stranded DNA viral vectors have high transduction rates and have a unique property of stimulating endogenous homologous recombination in the absence of double-strand DNA breaks in the genome. One of skill in the art can design a rAAV vector to target a desired genomic locus and perform both gross and/or subtle endogenous gene alterations in a cell. rAAV genome editing has the advantage in that it targets a single allele and does not result in any off-target genomic alterations. rAAV genome editing technology is commercially available, for example, the rAAV GENESIS™ system from Horizon™ (Cambridge, UK).

It will be appreciated that the agent can be a mutagen that causes random mutations and the cells exhibiting downregulation of the expression level and/or activity of the target may be selected.

The mutagens may be, but are not limited to, genetic, chemical or radiation agents. For example, the mutagen may be ionizing radiation, such as, but not limited to, ultraviolet light, gamma rays or alpha particles. Other mutagens may include, but not be limited to, base analogs, which can cause copying errors; deaminating agents, such as nitrous acid; intercalating agents, such as ethidium bromide; alkylating agents, such as bromouracil; transposons; natural and synthetic alkaloids; bromine and derivatives thereof; sodium azide; psoralen (for example, combined with ultraviolet radiation). The mutagen may be a chemical mutagen such as, but not limited to, ICR191, 1,2,7,8-diepoxy-octane (DEO), 5-azaC, N-methyl-N-nitrosoguanidine (MNNG) or ethyl methane sulfonate (EMS).

Methods for qualifying efficacy and detecting sequence alteration are well known in the art and include, but not limited to, DNA sequencing, electrophoresis, an enzyme-based mismatch detection assay and a hybridization assay such as PCR, RT-PCR, RNase protection, in-situ hybridization, primer extension, Southern blot, Northern Blot and dot blot analysis.

Sequence alterations in a specific gene can also be determined at the protein level using e.g. chromatography, electrophoretic methods, immunodetection assays such as ELISA and western blot analysis and immunohistochemistry.

In addition, one ordinarily skilled in the art can readily design a knock-in/knock-out construct including positive and/or negative selection markers for efficiently selecting transformed cells that underwent a homologous recombination event with the construct. Positive selection provides a means to enrich the population of clones that have taken up foreign DNA. Non-limiting examples of such positive markers include glutamine synthetase, dihydrofolate reductase (DHFR), markers that confer antibiotic resistance, such as neomycin, hygromycin, puromycin, and blasticidin S resistance cassettes. Negative selection markers are necessary to select against random integrations and/or elimination of a marker sequence (e.g. positive marker). Non-limiting examples of such negative markers include the herpes simplex-thymidine kinase (HSV-TK) which converts ganciclovir (GCV) into a cytotoxic nucleoside analog, hypoxanthine phosphoribosyltransferase (HPRT) and adenine phosphoribosytransferase (ARPT).

Downregulation can also be achieved by RNA silencing. As used herein, the phrase “RNA silencing” refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or “silencing” of the expression of a corresponding protein-coding gene. RNA silencing has been observed in many types of organisms, including plants, animals, and fungi.

As used herein, the term “RNA silencing agent” refers to an RNA which is capable of specifically inhibiting or “silencing” the expression of a target gene. In certain embodiments, the RNA silencing agent is capable of preventing complete processing (e.g., the full translation and/or expression) of an mRNA molecule through a post-transcriptional silencing mechanism. RNA silencing agents include non-coding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs.

In one embodiment, the RNA silencing agent is capable of inducing RNA interference.

In another embodiment, the RNA silencing agent is capable of mediating translational repression.

According to an embodiment of the invention, the RNA silencing agent is specific to the target RNA (i.e. TNFR1) and does not cross inhibit or silence other targets or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene; as determined by PCR, Western blot, Immunohistochemistry and/or flow cytometry.

RNA interference refers to the process of sequence-specific post-transcriptional gene silencing in animals mediated by short interfering RNAs (siRNAs).

Following is a detailed description on RNA silencing agents that can be used according to specific embodiments of the present invention.

DsRNA, siRNA and shRNA—The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplate use of dsRNA to downregulate protein expression from mRNA.

According to one embodiment dsRNA longer than 30 bp are used. Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

According to some embodiments of the invention, dsRNA is provided in cells where the interferon pathway is not activated, see for example Billy et al., PNAS 2001, Vol 98, pages 14428-14433; and Diallo et al, Oligonucleotides, Oct. 1, 2003, 13(5): 381-392. doi: 10.1089/154545703322617069.

According to an embodiment of the invention, the long dsRNA are specifically designed not to induce the interferon and PKR pathways for down-regulating gene expression. For example, Shinagwa and Ishii [*Genes & Dev.* 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly (A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term “siRNA” refers to small inhibitory RNA duplexes (generally between 18-30 base pairs) that induce the RNA interference (RNAi) pathway. Typically, siRNAs are chemically synthesized as 21 mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is suggested to result from providing Dicer with a substrate (27 mer) instead of a product (21 mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., a siRNA) may be connected to form a hairpin or stem-loop structure (e.g., a shRNA). Thus, as mentioned, the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-CAAGAGA-3' and 5'-UUACAA-3' (International Patent Application Nos. WO2013126963 and WO2014107763). It will be recognized by one of skill in the art that the resulting single chain oligonucleotide forms a stem-loop or hairpin structure comprising a double-stranded region capable of interacting with the RNAi machinery.

Synthesis of RNA silencing agents suitable for use with some embodiments of the invention can be effected as follows. First, the mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www(dot)ambion(dot)com/techlib/tn/91/912(dot)html).

Second, potential target sites are compared to an appropriate genomic database (e.g., human, mouse, rat etc.) using any sequence alignment software, such as the BLAST software available from the NCBI server (www(dot)ncbi(dot)nlm(dot)nih(dot)gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

It will be appreciated that, and as mentioned hereinabove, the RNA silencing agent of some embodiments of the invention need not be limited to those molecules containing only RNA, but further encompasses chemically-modified nucleotides and non-nucleotides.

miRNA and miRNA mimics—According to another embodiment the RNA silencing agent may be a miRNA.

The term "microRNA", "miRNA", and "miR" are synonymous and refer to a collection of non-coding single-stranded RNA molecules of about 19-28 nucleotides in length, which regulate gene expression. miRNAs are found in a wide range of organisms (viruses.fwdarw.humans) and have been shown to play a role in development, homeostasis, and disease etiology.

Below is a brief description of the mechanism of miRNA activity.

Genes coding for miRNAs are transcribed leading to production of an miRNA precursor known as the pri-miRNA. The pri-miRNA is typically part of a polycistronic RNA comprising multiple pri-miRNAs. The pri-miRNA may form a hairpin with a stem and loop. The stem may comprise mismatched bases.

The hairpin structure of the pri-miRNA is recognized by Drosha, which is an RNase III endonuclease. Drosha typically recognizes terminal loops in the pri-miRNA and cleaves approximately two helical turns into the stem to produce a 60-70 nucleotide precursor known as the pre-miRNA. Drosha cleaves the pri-miRNA with a staggered cut typical of RNase III endonucleases yielding a pre-miRNA stem loop with a 5' phosphate and ~2 nucleotide 3' overhang. It is estimated that approximately one helical turn of stem (~10 nucleotides) extending beyond the Drosha cleavage site is essential for efficient processing. The pre-miRNA is then actively transported from the nucleus to the cytoplasm by Ran-GTP and the export receptor Ex-portin-5.

The double-stranded stem of the pre-miRNA is then recognized by Dicer, which is also an RNase III endonuclease. Dicer may also recognize the 5' phosphate and 3' overhang at the base of the stem loop. Dicer then cleaves off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. miRNA* sequences may be found in libraries of cloned miRNAs but typically at lower frequency than the miRNAs.

Although initially present as a double-stranded species with miRNA*, the miRNA eventually becomes incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* is removed and degraded. The strand of the miRNA:miRNA* duplex that is loaded into the RISC is the strand whose 5' end is less tightly paired. In cases where both ends of the miRNA:miRNA* have roughly equivalent 5' pairing, both miRNA and miRNA* may have gene silencing activity.

The RISC identifies target nucleic acids based on high levels of complementarity between the miRNA and the mRNA, especially by nucleotides 2-7 of the miRNA.

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding.

Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al. (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut is typically between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

The term "microRNA mimic" or "miRNA mimic" refers to synthetic non-coding RNAs that are capable of entering the RNAi pathway and regulating gene expression. miRNA mimics imitate the function of endogenous miRNAs and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-O,4'-C-ethylene-bridged nucleic acids (ENA)). For mature, double stranded miRNA mimics, the length of the duplex region can vary between 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA.

Preparation of miRNAs mimics can be effected by any method known in the art such as chemical synthesis or recombinant methods.

It will be appreciated from the description provided herein above that contacting cells with a miRNA may be effected by transfecting the cells with e.g. the mature double stranded miRNA, the pre-miRNA or the pri-miRNA.

The pre-miRNA sequence may comprise from 45-90, 60-80 or 60-70 nucleotides.

The pri-miRNA sequence may comprise from 45-30,000, 50-25,000, 100-20,000, 1,000-1,500 or 80-100 nucleotides.

Antisense—Antisense is a single stranded RNA designed to prevent or inhibit expression of a gene by specifically hybridizing to its mRNA. Downregulation can be effected using an antisense polynucleotide capable of specifically hybridizing with an mRNA transcript encoding the target (i.e. TNFR1).

Design of antisense molecules which can be used to efficiently downregulate a target must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Jääskeläinen et al. Cell Mol Biol Lett. (2002) 7(2):236-7; Gait, Cell Mol Life Sci. (2003) 60(5):844-53; Martino et al. J Biomed Biotechnol. (2009) 2009:410260; Grijalvo et al. Expert Opin Ther Pat. (2014) 24(7):801-19; Falzarano et al, Nucleic Acid Ther. (2014) 24(1):87-100; Shilakari et al. Biomed Res Int. (2014) 2014: 526391; Prakash et al. Nucleic Acids Res. (2014) 42(13):8796-807 and Asseline et al. J Gene Med. (2014) 16(7-8):157-65].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)]. Such algorithms have been successfully used to implement an antisense approach in cells.

In addition, several approaches for designing and predicting efficiency of specific oligonucleotides using an in vitro system were also published (Matveeva et al., Nature Biotechnology 16: 1374-1375 (1998)].

Thus, the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

According to specific embodiments, the agent is selected from the group consisting of CRISPR/Cas system, a Zinc finger nuclease (ZFN), transcription-activator like effector nuclease (TALEN), meganuclease, antisense and siRNA.

According to specific embodiments, down-regulating expression and/or activity is effected at the genomic level.

According to specific embodiments, the agent comprises a CRISPR/Cas system.

Embodiments of the invention further contemplate the use of the CRISPR/Cas system per se (as the therapeutic agent and not as a cell therapy) for downregulating expression of TNFR1 for treating an ischemic disease.

Thus, according to an aspect of the present invention, there is provided a method of treating an ischemic disease in a subject in need thereof, the method comprising administering to the subject a therapeutically effective amount of a CRISPR/Cas system for downregulating expression of TNFR1, thereby treating the ischemic disease in the subject.

Such CRISPR/Cas systems are described in details hereinabove.

According to specific embodiments, the CRISPR/Cas system does not downregulate expression of TNFR2.

The cells or the agents (e.g. a CRISPR/Cas system for downregulating expression of TNFR1) of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the cell or the agent (e.g. a CRISPR/Cas system for downregulating expression of TNFR1) accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

According to specific embodiments, the cells or the agent (e.g. a CRISPR/Cas system for downregulating expression of TNFR1) or the pharmaceutical composition comprising same is administered intravenously.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the cells or the agent (e.g. a CRISPR/Cas system for downregulating expression of TNFR1) or the pharmaceutical composition comprising same in a local rather than systemic manner, for example, via injection of the pharmaceutical composition directly into a tissue region of a patient.

According to specific embodiments, the cells or the agent (e.g. a CRISPR/Cas system for downregulating expression of TNFR1) or the pharmaceutical composition comprising same is administered into the ischemic tissue.

According to specific embodiments, the cells or the agent (e.g. a CRISPR/Cas system for downregulating expression of TNFR1) or the pharmaceutical composition comprising same is administered by transendocardial injection.

According to specific embodiments, the cells or the agent (e.g. a CRISPR/Cas system for downregulating expression of TNFR1) or the pharmaceutical composition comprising same is administered intracoronary or intramyocardialy.

According to specific embodiments, the cells or the agent (e.g. a CRISPR/Cas system for downregulating expression of TNFR1) or the pharmaceutical composition comprising same is attached to an implantable device such as a stent, a valve, an intravascular device and a pacemaker.

According to some embodiments, the cells of the present invention are administered in a hydrated gel (hydrogel) such as a hyaluronic acid-based hydrogels (see the Examples section which follows). Such hydrogels are known in the art and disclosed e.g. in Xu et al. (2012) Soft Matter. 8(12): 3280-3294; Kim et al. (2012) Knee Surg Relat Res. September; 24(3): 164-172, the contents of which are fully incorporated herein by reference.

According to specific embodiments, the hyaluronic acid is provided at a concentration range of about 0.1-10%, e.g., about 0.5-10%, e.g., about 0.5-5, e.g., about 1-5%, e.g., about 2-5%, e.g., about 3-5%, e.g., about 3-4% in the composition e.g. hydrogel.

According to a specific embodiment, the hyaluronic acid is provided at a concentration range of about 3-4% in the composition e.g. hydrogel.

According to some embodiments, the cells of the present invention are administered in a biodegradable co-polymer or scaffold. Such scaffolds are known in the art and disclosed e.g. in Florian Weinberger et al. (2017) Circulation Research. 120:1487-1500; Rochkind S et al (2004) Neurol Res. 26(2):161-6; Rochkind S. et al. (2006) Eur Spine J. 15(2):234-45; and FSY Wong, A C Y Lo (2015) J Stem Cell Res Ther 5:267, the contents of which are fully incorporated herein by reference.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Alternative embodiments include depots providing sustained release or prolonged duration of activity of the active ingredient in the subject, as are well known in the art.

Pharmaceutical compositions suitable for use in context of some embodiments of the invention include compositions wherein the active ingredients are contained in an amount effective to achieve the intended purpose. More specifically, a therapeutically effective amount means an amount of active ingredients (the cells, the agent (e.g. a CRISPR/Cas system for downregulating expression of TNFR1) effective to prevent, alleviate or ameliorate symptoms of a disorder (e.g., ischemic disease, e.g., ischemic heart disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide the active ingredient in levels sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

According to specific embodiments, the cells, the agent (e.g. a CRISPR/Cas system for downregulating expression of TNFR1) or the pharmaceutical composition comprising same are administered within 1.5-24 hours following diagnosis of said ischemic disease.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

According to an aspect of the present invention, there is provided a pharmaceutical composition comprising as an active ingredient differentiated cells or bone marrow stem cells genetically modified with a CRISPR/Cas system for downregulating expression of TNFR1.

According to another aspect of the present invention, there is provided a pharmaceutical composition comprising as active ingredients cells genetically modified with a CRISPR/Cas system for downregulating expression of TNFR1 and at least 2 ng/ml TNFα.

According to another aspect of the present invention there is provided an article of manufacture comprising TNFα and the cells disclosed herein with reduced expression and/or activity of TNFR1 as compared to control cells of the same origin not contacted with an agent which downregulates expression and/or activity of said TNFR1.

According to specific embodiments, the TNFα and the cells are in a co-formulation.

According to specific embodiments, the TNFα and the cells are in separate containers.

According to another aspect of the present invention there is provided an article of manufacture comprising TNFα and a CRISPR/Cas system for downregulating expression of TNFR1.

According to specific embodiments, the TNFα and a CRISPR/Cas system are in a co-formulation.

According to specific embodiments, the TNFα and a CRISPR/Cas system are in separate containers.

According to specific embodiments, TNFα is provided at a concentration above its physiological concentration in the cells.

According to specific embodiments, TNFα is provided at a concentration of at least 2 ng/ml, at least 5 ng/ml, at least 10 ng/ml, at least 20 ng/ml, at least 30 ng/ml, at least 40 ng/ml or at least 50 ng/ml, each possibility represents a separate embodiment of the present invention.

According to specific embodiments, TNFα is provided at a concentration of 2-200 ng/ml or 20-200 ng/ml.

As used herein the term “about” refers to ±10%

The terms “comprises”, “comprising”, “includes”, “including”, “having” and their conjugates mean “including but not limited to”.

The term “consisting of” means “including and limited to”.

The term “consisting essentially of” means that the composition, method or structure may include additional ingredients, steps and/or parts, but only if the additional ingredients, steps and/or parts do not materially alter the basic and novel characteristics of the claimed composition, method or structure.

As used herein, the singular form “a”, “an” and “the” include plural references unless the context clearly dictates otherwise. For example, the term “a compound” or “at least one compound” may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases “ranging/ranges between” a first indicate number and a second indicate number and “ranging/ranges from” a first indicate number “to” a second indicate number are used herein interchangeably and are meant to include the first and second indicated numbers and all the fractional and integral numerals therebetween. As used herein the term “method” refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Mouse mnBMCs Transfected with Mouse TNFR1 CRISPR Reduce Infarct Size in a Myocaridal Nfarction Mouse Model Materials and Methods Isolation of mononuclear bone marrow cells—Seven 8 weeks old C57B1/6 (OldHsd) male mice weighing 20-23 gram were purchased from Envigo RMS (Israel) LTD. Bone marrow (BM) was flushed from tibiae and femurs of each mouse using 2 mL PBS supplemented with 2% fetal bovine serum (FBS). The suspension was resuspended and mashed through a 40-100 μM cell strainer. The sample was centrifuged at 300 g for 5 minutes and resuspended in 100 μL PBS. Following, 1 mL of red blood cell (RBC) lysis buffer (Roche) was added and the sample was incubated for 3 minutes at room temperature. 9 mL PBS (3 g/L glucose) supplemented with 2% FBS (3 g/L glucose) was added to stop the reaction and the sample was centrifuged at 300 g for 5 minutes and immediately resuspended in 1 mL of ice cold PBS supplemented with 2% fetal bovine serum (FBS). Mononuclear bone marrow cells (mnBMCs) were separated from the BM sample by Ficoll-Paque (Histopaque1077, Sigma), with 3 technical replicates. BM cells were resuspended in 2 mL PBS supplemented with 2% murine serum were layered on 1.5 ml Ficoll-Paque. The Ficoll-Paque gradients were centrifuged for 40 minutes at 400 g without brake. The mnBM layer was then collected, washed in PBS supplemented with 2% FBS. Viability and cell count was determined by trypan blue exclusion method using hemocytometer. A total of $100\times10^6$ mnBMCs was counted. $60\times10^6$ mnBMCs were frozen at −80° C. $40\times10^6$ cells were seeded in 24 wells plates (120,000 mnBMCs per well) in 1 mL/well DMEM medium containing—glutamine, sodium pyruvate, pen/strep and 3% mouse serum and cultured under standard culture conditions. Following 24 hours of incubation, the medium was replaced with optimem medium (Invitrogen) and cells were transfected with TNFR1 CRISPR for 2 days. Control cells, which were not transfected with TNFR1 CRISPR were cultured under the same culturing conditions: 120,000 mnBMCs per well in 24 wells plates in DMEM medium containing 2% FBS.

TNFR1 CRISPR transfection—For CRISPR transfection three different mouse TNFR1 guide RNA were designed and synthesized (Table 1A hereinabove) and mnBMCs were transfected with case 9 protein with the lipophilic transfection reagent CRISPRMAX as described before (Yu et al 2016).

mnBM Transplantation—750,000 cultured mnBMCs were treated with 30 ng/ml mouse TNFα (PeproTech) for 20 minutes and added to 50 μL gel containing 3.75% hyaluronic acid (HA), 20% non-activated murine serum (serum obtained from C57BL/6 mice and inactivated in 56° C.) in DMEM. Following ligation of the left anterior descending artery (LAD), 50 μL gel containing mnBMCs were injected to the heart as described in Toma et al 2002 and Kawada et al 2016.

Animal model—Animal experiments were conducted according to the guidelines of the Animal Care and Use Committee of Israel, and the Guide for the Care and Use of Laboratory Animals published by the US National Institute of Health. 18 C57BL/6 mice were purchased at 8 weeks (20-23 gr) from Ex-Vivo Israel. Following 1 week of acclimation the mice were intubated and anesthetized with 0.5% isoflurane gas. Permanent ligation of the left anterior descending artery (LAD) was performed as described in Kolk et al. (2009) JoVE. 32 (ref 41). The mice were randomly assigned into three groups, see table 2 hereinbelow:

Group 1M—on day 1, 2 hours prior to LAD mice were injected IP with 7.5 μg TNFα (PeproTech) and following LAD mice were injected to the LAD area (estimated area of the scar formation) with 750,000 mnBMCs transfected with TNFR1 CRISPR, n=6;

Group 2M—on day 1, following LAD, mice were injected to the LAD area with 750,000 mnBMCs transfected with TNFR1 CRISPR, n=12;

Group 3M—on day 1, following LAD, mice were injected to the LAD area with 750,000 mnBMCs that were not transfected with TNFR1 CRISPR, n=6.

Injected mnBMCs in all groups (1M, 2M, 3M) were treated for 20 minutes prior to injection with 30 ng/mL mouse TNFα (PeproTech) containing 1 mg/ml murine serum.

Body weight, mortality and morbidity were evaluated once a day. Mice were sacrificed 24 hours or 4 days following LAD occlusion and ~200 μl whole blood was collected from the retro-orbital sinus into yellow cap serum tubes. The collected blood was centrifuged (at 3000 rpm for 10 minutes) for serum preparation. Samples were frozen at (−60° C.)-(−90° C.) and stored in appropriately labeled test-tubes for further Creatin Kinase (CK) detection (Sigma). From each sacrificed mouse heart was dissected, weighed, fixated and sent for histological evaluation.

viability an apoptosis TUNEL kit stain was performed. The slides were photographed using a microscope (Olympus BX60), at magnifications of λ10, λ20 and λ40, equipped with an Olympus DP-73 camera.

The slides were examined by a pathologist, according to the following parameters:

H&E and MT stains:

Infarct diameter (mm);

Presence of injected mnBMCs (−, +, ++, +++);

Additional pathological changes

Scoring system for TUNEL evaluation:

Grade: −, no signs of positive TUNEL expression in all tissues and cells.

Grade: +, Only few cells (<10) per cross section are positive.

Grade ++, More cells (>10, >50) per cross section are positive.

Grade +++, Many cells (>50) per cross section are positive.

Results

The effect of transplantation of stem cells with reduced expression of TNFR1 on ischemic heart disease was assessed in a permanent ligation of the left anterior descending artery (LAD) mouse model, a known model of infarction and myocardial ischemia [Kolk et al. (2009) JoVE. 32]. To this end, mnBMCs transfected with TNFR1 CRISPR and treated with TNFα were injected to the LAD area and their effect on infract volume and cellular response was compared to the effect of injection of control mnBMCs (non-transfected and treated with TNFα).

Histological evaluation of hearts extracted from LAD occluded mice injected with mnBMCs transfected with TNFR1 CRISPR demonstrated reduced infarct size (both

TABLE 2

Experimental design:

| Group | Mouse No. | Time | Treatment |
|---|---|---|---|
| 1M | 3 | 24 hours | TNFα IP + Injection of mnBMCs transfected with TNFR1 CRISPR and treated with TNFα |
| | 5 | | |
| | 6 | | |
| 2M | 7 | | Injection of mnBMCs transfected with TNFR1 CRISPR and treated with TNFα |
| | 9 | | |
| | 10 | | |
| 3M | 15 | | Control: Injection of non-transfected mnBMCs treated with TNFα |
| | 16 | | |
| | 18 | | |
| 1M | 1 | 4 days | TNF IP + Injection of mnBMCs transfected with TNFR1 CRISPR and treated with TNFα |
| | 2 | | |
| 2M | 11 | | Injection of mnBMCs transfected with TNFR1 CRISPR and treated with TNFα |
| | 12 | | |
| 3M | 13 | | Control: Injection of non-transfected mnBMCs treated with TNFα |
| | 14 | | |

Histology—Hearts were harvested and fixed in 10% formaldehyde at Pharmaseed and transferred to Patho-Logica. All tissues were trimmed in the same manner into block cassettes. Transverse cross sections were performed in each heart producing four equal cross sections per organ. The tissues were embedded in paraffin, sectioned at no more than 5 micron thickness, and stained with Hematoxylin & Eosin (H&E) and Masson Trichrome (MT), to trace the injected cells, pathological changes and to evaluate the volume of the induced infarcts. Furthermore, to evaluated width and depth), as determined 24 hours and 4 days following LAD occlusion (Group 2M) compared to control mice that were injected with non-transfected mnBMCs (Group 3M) (FIGS. 1A-2F, 4A-5D and 9A-9B and Table 3 hereinbelow). Interestingly, moderate to high TUNEL reaction in the infarct lesion was demonstrated in these mice (FIGS. 7A-8F), mainly localized in the inner part of the ventricle wall.

Ischemic preconditioning (IP) has been recognized as one of the most potent mechanisms to protect against myocardial ischemic injury. In experimental animals and humans, a brief period of ischemia has been shown to protect the heart from more prolonged episodes of ischemia, reducing infarct size, attenuating the incidence, and severity of reperfusion-induced arrhythmias, and preventing endothelial cell dysfunction (e.g. 6). It has been shown that classical preconditioning can be mimicked by administration of TNFα [9-13].

In the present model, treatment of the mice with TNFα 2 hours prior to LAD occlusion followed by injection of the TNFR1 CRISPR transfected mnBMCs (Group 1M) did not have a beneficial effect on infarct size. On the contrary, histological evaluation of hearts extracted from these mice revealed a large infarct volume with a relative low cellular reaction and mild to moderate TUNEL reaction in the infarct lesion, as detected 24 hours and 4 days following LAD (FIGS. 3A-F, 6A-D, 7A-8F and Table 3 hereinbelow).

Figure 10:
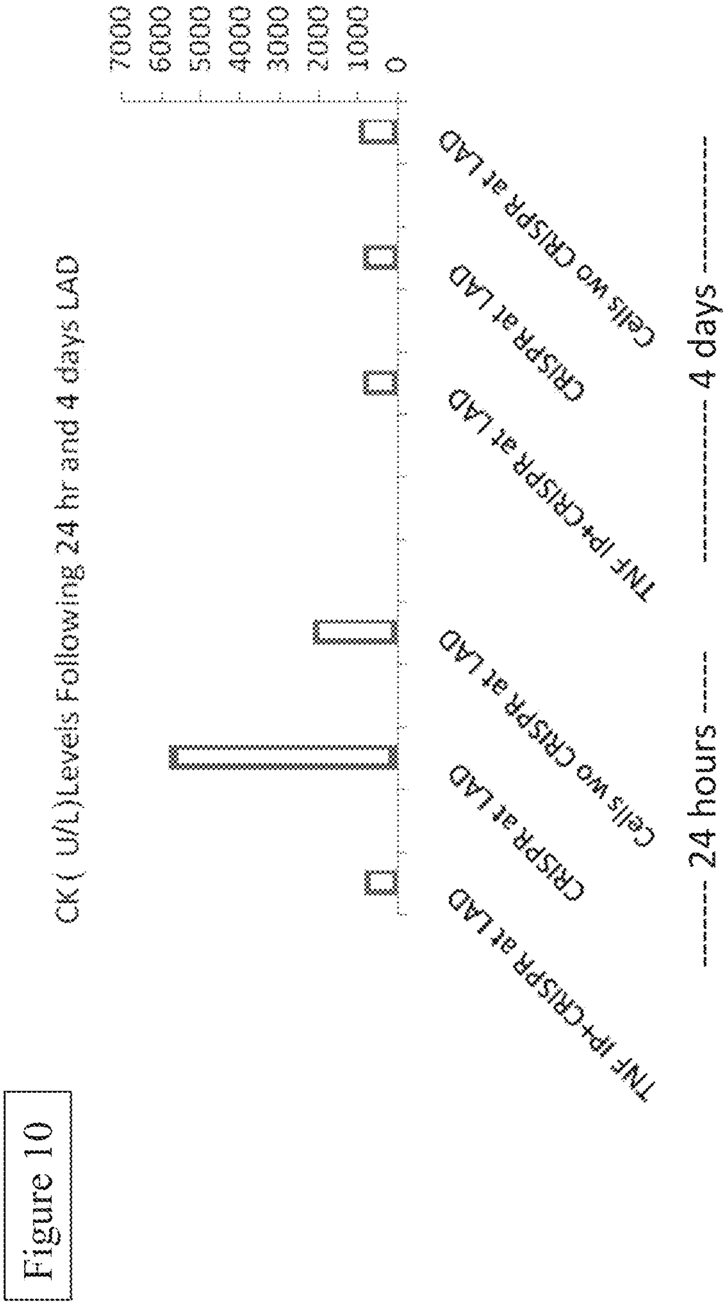
FIG. 10 is a bar graph demonstrating that transplantation of mnBMCs transfected with TNFR1 CRISPR had no toxic effect (such as severe muscle breakdown, acute kidney injury or autoimmune myositis) in the LAD occlusion mouse model compared to control mice transplanted with non-transfected mnBMCs, as determined by CK levels 4 days following LAD occlusion.

To evaluate toxicity, CK were determined in the serum of the transplanted mice. CK (made up of three enzyme forms, including CK-MB) levels can rise following heart attack, skeletal muscle injury and strenuous exercise. Importantly, detection of CK levels in the serum indicated that injection of the mnBMCs (either transfected or not transfected with TNFR1 CRISPR) did not have an effect of CK levels 4 days following LAD occlusion (FIG. 10).

Taken together, the results indicated a cardio-protective effect of transplantation of mnMB cells transfected with TNFR1 CRISPR against ischemic damage as demonstrated by reduced infarct depth and width in the mouse LAD model.

TABLE 3

Histological results of cardiac infarct parameters

| | Animal # | Group | Infarct volume mm (MT) Depth/width | BM cells in infarct | TUNNEL reaction | Additional pathological changes |
|---|---|---|---|---|---|---|
| 24 hours post LAD | 3 | 1M | Transmural/ 1.57 | − | − | Few neutrophils and lymphocytes |
| | 5 | 1M | 0.85/0.45 | − | − | Moderate infiltration of lymphocytes and few neutrophils. Fibrin on top of the infarct. |
| | 6 | 1M | Transmural/ 1.12 | − | ++ | Almost no reaction |
| | 7 | 2M | 0.22/1.76 | − | +++ | Mild infiltration of mainly lymphocytes and macrophages. |
| | 9 | 2M | 0.59/1.37 | + | +++ | Macrophages and neutrophils focally infiltrated next to injected cells debris |
| | 10 | 2M | Transmural/ 1.49 | − | +++ | Cellular infiltration of neutrophils and lymphocytes in the inner part of the ventricle wall |
| | 15 | 3M | 0.37/0.71 | ++ | ++ | Macrophages and neutrophils focally infiltrated next to injected cells debris |
| | 16 | 3M | 0.44/1.58 | ++ | +++ | Macrophages and neutrophils focally infiltrated next to injected cells debris and some adipocytes |
| | 18 | 3M | 0.32/0.88 | + | +++ | Macrophages and neutrophils focally infiltrated next to injected cells debris |
| 4 days post LAD | 1 | 1M | Transmural (2.02)/3.29 | − | +++ | A very large infarct with a central necrotic core, surrounded by many macrophages, lymphocytes and some fibrocytes. |
| | 2 | 1M | Transmural (1.06)/4.74 | − | ++ | A very large infarct with a central necrotic core, surrounded by many macrophages, lymphocytes and some fibrocytes. |
| | 11 | 2M | Transmural (1.14)/2.74 | − | ++ | A very large infarct with a central necrotic core, surrounded by many macrophages, lymphocytes and some fibrocytes. |
| | 12 | 2M | Transmural (1.01)/4.14 | − | ++ | A very large infarct with a central necrotic core, surrounded by many macrophages, lymphocytes and some fibrocytes. |

TABLE 3-continued

Histological results of cardiac infarct parameters

| Animal # | Group | Infarct volume mm (MT) Depth/width | BM cells in infarct | TUNNEL reaction | Additional pathological changes |
|---|---|---|---|---|---|
| 13 | 3M | 1.77/4.36 | – | +++ | A very large infarct with a central necrotic core, surrounded by many macrophages, lymphocytes and some fibrocytes. |
| 14 | 3M | 2.02/3.99 | – | ++ | A very large infarct with a central necrotic core, surrounded by many macrophages, lymphocytes and some fibrocytes. |

Example 2

Human mnBMCs Transfected with Human TNFR1 CRISPR Reduce Infarct Size in a Myocaridal Nfarction Mouse Model The effect of transplantation of human stem cells with reduced expression of TNFR1 on ischemic heart disease is assessed in a LAD occluded immune-deficient mouse model. To this end, human mnBMCs transfected with human TNFR1 CRISPR and treated with TNFα are injected to the LAD area and their effect on infract volume and cellular response is compared to the effect of injection of control human mnBMCs (non-transfected and treated with TNFα).

Materials and Methods

Isolation of human mnBMCs—Bone marrow (BM) is flushed from tibiae, femurs or from peripheral blood or taken from human blood bank or human umbilical cord blood bank. Each sample is handled using 2 mL PBS supplemented with 2% human serum. The suspension is resuspended and mashed through a 40-100 μM cell strainer. The sample is centrifuged at 300 g for 5 minutes and re-suspended in 100 μL PBS. Following, 1 mL of red blood cell (RBC) lysis buffer (Roche) is added and the sample is incubated for 3 minutes at room temperature. 9 mL PBS (3 g/L glucose) supplemented with 2% human serum (3 g/L glucose) is added to stop the reaction and the sample is centrifuged at 300 g for 5 minutes and immediately re-suspended in 1 mL of ice cold PBS supplemented with 2% human serum. Mononuclear bone marrow cells (mnBMCs) are separated from the BM sample by Ficoll-Paque (Histopaque1077, Sigma), with 3 technical replicates, as follows: BM cells re-suspended in 2 mL PBS supplemented with 2% human serum are ayered on 1.5 ml Ficoll-Paque. The Ficoll-Paque gradients are centrifuged for 40 minutes at 400 g without brake. Following, the mnBM layer is collected, washed in PBS supplemented with 2% human serum. Viability and cell count is determined by trypan blue exclusion method using hemocytometer. A fraction of the mnBMCs are frozen at −80° C. Another fraction is seeded in 24 wells plates (120,000 mnBMCs per well) in 1 mL/well DMEM medium containing—glutamine, sodium pyruvate, pen/strep and 3% human serum and cultured under standard culture conditions. Following 1-24 hours of incubation, the medium is replaced with optimem medium (Invitrogen) and cells are transfected with TNFR1 CRISPR for 5 minutes up to 2 days or immediately electroporated. Control cells, which are not transfected with TNFR1 CRISPR are cultured under the same culturing conditions.

TNFR1 CRISPR transfection—For CRISPR transfection seven different human TNFR1 guide RNA were designed and synthesized (Table 1B hereinabove). mnBMCs are transfected with case 9 protein with the lipophilic transfection reagent CRISPRMAX as described before (Yu et al 2016) or transfected immediately by electroporation.

mnBM Transplantation—As described in Example 1 hereinabove.

Animal model—As described in Example 1 hereinabove with Nude and/or SCID mice instead of C57BL/6 mice.

Histology—As described in Example 1 hereinabove

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1 Beutler, B. and van Huffel, C. (1994) Unraveling function in the TNF ligand and receptor families. Science. 264, 667-668

2 Kolesnick, R. and Golde, D. W. (1994) The sphingomyelin pathway in tumor-necrosis-factor and interleukin-1 signaling. Cell. 77, 325-328

3 Beyaert, R. and Fiers, W. (1994) Molecular mechanisms of tumor necrosis factor-induced cytotoxicity—What we do understand and what we do not. FEBS Lett. 340, 9-16

4 Valgimigli, M., Ceconi, C., Malagutti, P., Merli, E., Soukhomovskaia, O., Francolini, G., Cicchitelli, G., Olivares, A., Parrinello, G., Percoco, G., Guardigli, G., Mele, D., Pirani, R. and Ferrari, R. (2005) Tumor necrosis factor-alpha receptor 1 is a major predictor of mortality and new-onset heart failure in patients with acute myocardial infarction—The cytokine-activation and long-term prognosis in myocardial infarction (C-ALPHA) study. Circulation. 111, 863-870

5 Kleinbongard, P., Schulz, R. and Heusch, G. (2010) TNFalpha in myocardial ischemia/reperfusion, remodeling and heart failure. Heart Fail Rev. 16, 49-69

6 Murry, C. E., Jennings, R. B. and Reimer, K. A. (1986) Preconditioning with ischemia: a delay of lethal cell injury in ischemic myocardium. Circulation. 74, 1124-1136

7 Marber, M. S., Latchman, D. S., Walker, J. M. and Yellon, D. M. (1993) Cardiac stress protein elevation 24 hours after brief ischemia or heat stress is associated with resistance to myocardial infarction. Circulation. 88, 1264-1272

8 Schulz, R., Gres, P., Konietzka, I. and Heusch, G. (2005) Regional differences of myocardial infarct development and ischemic preconditioning. Basic Res. Cardiol. 100, 48-56

9 Smith, R. M., Suleman, N., McCarthy, J. and Sack, M. N. (2002) Classic ischemic but not pharmacologic preconditioning is abrogated following genetic ablation of the TNF alpha gene. Cardiovasc. Res. 55, 553-560

10 Ran, K., Duan, K. M., Zou, D. Q., Li, Z. J., Jin, L. Y. and Chang, Y. T. (2008) Effect of isoflurane delayed preconditioning on myocardial ischemia reperfusion injury in rabbits. Zhong Nan Da Xue Xue Bao Yi Xue Ban. 33, 146-150

11 Lecour, S., Smith, R. M., Woodward, B., Opie, L. H., Rochette, L. and Sack, M. N. (2002) Identification of a novel role for sphingolipid signaling in TNF alpha and ischemic preconditioning mediated cardioprotection. J. Mol. Cell. Cardiol. 34, 509-518

12 Lecour, S., Rochette, L. and Opie, L. (2005) Free radicals trigger TNF alpha-induced cardioprotection. Cardiovasc. Res. 65, 239-243

13 El-Ani, D., Zimlichman, R., Mashiach, Y. and Shainberg, A. (2007) Adenosine and TNF-alpha exert similar inotropic effect on heart cultures, suggesting a cardioprotective mechanism against hypoxia. Life Sci. 81, 803-813

14 Dorge, H., Schulz, R., Belosjorow, S., Post, H., van de Sand, A., Konietzka, I., Frede, S., Hartung, T., Vinten-Johansen, J., Youker, K. A., Entman, M. L., Erbel, R. and Heusch, G. (2002) Coronary microembolization: The role of TNF-alpha in contractile dysfunction. J. Mol. Cell. Cardiol. 34, 51-62

15 Reil, J. C., Gilles, S., Zahler, S., Brandl, A., Drexler, H., Hultner, L., Matrisian, L. M., Welsch, U. and Becker, B. F. (2007) Insights from knock-out models concerning postischemic release of TNF alpha from isolated mouse hearts. J. Mol. Cell. Cardiol. 42, 133-141

16 Skyschally, A., Gres, P., Hoffmann, S., Haude, M., Erbel, R., Schulz, R. and Heusch, G. (2007) Bidirectional role of tumor necrosis factor-alpha in coronary microembolization—Progressive contractile dysfunction versus delayed protection against infarction. Circul. Res. 100, 140-146

17 Heusch, P., Skyschally, A., Leineweber, K., Haude, M., Erbel, R. and Heusch, G. (2007) The interaction of coronary microembolization and ischemic preconditioning: A third window of cardioprotection through TNF-alpha. Archives of Medical Science. 3, 83-92

18 Thielmann, M., Dorge, H., Martin, C., Belosjorow, S., Schwanke, U., van de Sand, A., Konietzka, I., Buchert, A., Kruger, A., Schulz, R. and Heusch, G. (2002) Myocardial dysfunction with coronary microembolization—Signal transduction through a sequence of nitric oxide, tumor necrosis factor-alpha, and sphingosine. Circul. Res. 90, 807-813

19 El-Ani, D. and Zimlichman, R. (2003) TNFalpha stimulated ATP-sensitive potassium channels and attenuated deoxyglucose and Ca uptake of H9c2 cardiomyocytes. Ann. N. Y. Acad. Sci. 1010, 716-720

20 Meldrum, D. R., Dinarello, C. A., Shames, B. D., Cleveland, J. C., Cain, B. S., Banerjee, A., Meng, X. Z. and Harken, A. H. (1998) Ischemic preconditioning decreases postischemic myocardial tumor necrosis factor-alpha production—Potential ultimate effector mechanism of preconditioning. Circulation. 98, II214-II218

21 Mubagwa, K. and Flameng, W. (2001) Adenosine, adenosine receptors and myocardial protection: an updated overview. Cardiovasc. Res. 52, 25-39

22 Hutchinson, S. A. and Scammells, P. J. (2004) A(1) adenosine receptor agonists: medicinal chemistry and therapeutic potential. Curr.Pharm.Des. 10, 2021-2039

23 Lotz, C., Liem, D. and Ping, P. P. (2011) New frontiers in myocardial protection: A systems biology approach. Journal of Cardiovascular Pharmacology and Therapeutics. 16, 285-289

24 Hinkel, R., Trenkwalder, T. and Kupatt, C. (2011) Gene therapy for ischemic heart disease. Expert Opinion on Biological Therapy. 11, 723-737

25 Marais, E., Genade, S. and Lochner, A. (2008) CREB activation and ischaemic preconditioning. Cardiovasc. Drugs Ther. 22, 3-17

26 Qu, S., Zhu, H., Wei, X., Zhang, C., Jiang, L., Liu, Y. and Xiao, X. (2010) Oxidative stress-mediated up-regulation of myocardial ischemic preconditioning up-regulated protein 1 gene expression in H9c2 cardiomyocytes is regulated by cyclic AMP-response element binding protein. Free Radic. Biol. Med. 49, 580-586.

27 Muller, B. A. and Dhalla, N. S. (2010) Mechanisms of the beneficial actions of ischemic preconditioning on subcellular remodeling in ischemic-referfused heart. Curr. Cardiol. Rev. 6, 255-264

28 Schmitt, J. P., Ahmad, F., Lorenz, K., Hein, L., Schulz, S., Asahi, M., MacLennan, D. H., Seidman, C. E., Seidman, J. G. and Lohse, M. J. (2009) Alterations of phospholamban function can exhibit cardiotoxic effects independent of excessive sarcoplasmic reticulum $Ca^{2+}$-ATPase inhibition. Circulation. 119, 436-444

29 Cerra, M. C. and Imbrogno, S. (2012) Phospholamban and cardiac function: a comparative perspective in vertebrates. Acta Physiologica. 205, 9-25

30 Kranias, E. G. and Hajjar, R. J. (2012) Modulation of cardiac contractility by the phopholamban/SERCA2a regulatome. Circul. Res. 110, 1646-1660

31 Louch, W. E., Vangheluwe, P., Bito, V., Raeymaekers, L., Wuytack, F. and Sipido, K. R. (2012) Phospholamban ablation in hearts expressing the high affinity SERCA2b isoform normalizes global $Ca^{2+}$ homeostasis but not Ca2+-dependent hypertrophic signaling. American Journal of Physiology-Heart and Circulatory Physiology. 302, H2574-H2582

32 MacLennan, D. H. and Kranias, E. G. (2003) Phospholamban: A crucial regulator of cardiac contractility. Nature Reviews Molecular Cell Biology. 4, 566-577

33 Kishore, R., Tkebuchava, T., Sasi, S. P., Silver, M., Gilbert, H. Y., Yoon, Y. S., Park, H. Y., Thorne, T., Losordo, D. W. and Goukassian, D. A. (2011) Tumor necrosis factor-alpha signaling via TNFR1/p55 is deleterious whereas TNFR2/p75 signaling is protective in adult infarct myocardium. Advances in TNF Family Research. 691, 433-448

34 Monden, Y., Kubota, T., Inoue, T., Tsutsumi, T., Kawano, S., Ide, T., Tsutsui, H. and Sunagawa, K. (2007) Tumor necrosis factor-alpha is toxic via receptor 1 and protective via receptor 2 in a murine model of myocardial infarction. Am. J. Physiol. Heart Circ. Physiol. 293, H743-753

35 Moe, G. W., Marin-Garcia, J., Konig, A., Goldenthal, M., Lu, X. and Feng, Q. (2004) In vivo TNF-alpha inhibition ameliorates cardiac mitochondrial dysfunction, oxidative stress, and apoptosis in experimental heart failure. Am. J. Physiol. Heart Circ. Physiol. 287, H1813-1820

36 Bao, C., Guo, J., Lin, G., Hu, M. and Hu, Z. (2008) TNFR gene-modified mesenchymal stem cells attenuate inflammation and cardiac dysfunction following MI. Scand. Cardiovasc. J. 42, 56-62

37 Kurrelmeyer, K. M., Michael, L. H., Baumgarten, G., Taffet, G. E., Peschon, J. J., Sivasubramanian, N., Entman, M. L. and Mann, D. L. (2000) Endogenous tumor necrosis factor protects the adult cardiac myocyte against ischemic-induced apoptosis in a murine model of acute myocardial infarction. Proc. Nat. Acad. Sci. U.S.A. 97, 5456-5461

38 Wang, M., Crisostomo, P. R., Markel, T. A., Wang, Y. and Meldrum, D. R. (2008) Mechanisms of sex differences in TNFR2-mediated cardioprotection. Circulation. 118, S38-45

39 El-Ani, D., Stay, H., Guetta, V., Arad, M. and Shainberg, A. (2011) Rapamycin (sirolimus) protects against hypoxic damage in primary heart cultures via Na(+)/Ca(2+) exchanger activation. Life Sci. 89.

40 El-Ani D, Philipchik I, Stay H, Levi M, Zerbib J and Shainberg A. TNF alpha protects heart rat cultures Against hypoxic damage via activation of PKA and phospholamban to prevent calcium overload. 2014. Can J Physiol Pharmacol 92(11):917-25.2014.

41 Kolk M. V., Meyberg D., Deuse T., Tang-Quan K. R., Robbins R. C., Reichenspurner H., Schrepfer S. (2009). LAD-Ligation: A Murine Model of Myocardial Infarction. JoVE. 32.

---

What is claimed is:

1. A method of treating an ischemic heart disease in a subject in need thereof, the method comprising administering to the subject a therapeutically effective amount of cells with reduced level of expression and/or activity of TNFR1, wherein said cells are cardiomyocytes or mononuclear bone marrow cells (mnBMCs) comprising mesenchymal stem cells (MSCs) and lymphocytes or progenitors thereof, and wherein said reduced level of expression and/or activity of said TNFR1 is defined as compared to control cells of the same origin not contacted with an agent which downregulates expression and/or activity of said TNFR1, thereby treating the ischemic heart disease in the subject.

2. The method of claim 1, further comprising treating said cells with reduced expression and/or activity of TNFR1 with TNFα prior to said administering.

3. The method of claim 2, comprising cryopreserving said cells with reduced expression and/or activity of TNFR1 prior to said treating with said TNFα.

4. The method of claim 1, wherein said cells with reduced level of expression and/or activity of TNFR1 have the same level of expression and/or activity of TNFR2 as compared to said control cells.

5. The method of claim 1, wherein said cells with reduced expression and/or activity of TNFR1 are genetically modified cells.

6. The method of claim 5, wherein said genetically modified comprises genetically modified with a CRISPR/Cas system, a Zinc finger nuclease (ZFN), transcription-activator like effector nuclease (TALEN) or meganuclease for downregulating expression of said TNFR1.

7. The method of claim 5, wherein said genetically modified comprises genetically modified with a CRISPR/Cas system for downregulating expression of said TNFR1.

8. The method of claim 1, wherein said cells with reduced expression and/or activity of TNFR1 are non-autologous to said subject.

9. The method of claim 1, wherein said mnBMC are obtained by density gradient centrifugation of bone marrow cells.

10. The method of claim 1, comprising obtaining said mnBMC by density gradient centrifugation of bone marrow cells.

11. The method of claim 1, wherein said cells with reduced level of expression and/or activity of TNFR1 are human cells.

12. The method of claim 1, wherein said cells with reduced level of expression and/or activity of TNFR1 are cryopreserved cells.

13. The method of claim 1, wherein said ischemic heart disease is myocardial infarction.

14. The method of claim 1, wherein said ischemic heart disease is ischemic cardiomyopathy.

15. The method of claim 1, wherein said subject is not treated with TNFα.

16. The method of claim 1, wherein said mnBMCs are obtained from bone marrow, peripheral blood or umbilical cord blood.

17. The method of claim 1, comprising obtaining said mnBMCs from bone marrow, peripheral blood or umbilical cord blood.

18. The method of claim 1, wherein said cells with reduced level of expression and/or activity of TNFR1 are freshly isolated.

* * * * *